US006670463B1

(12) United States Patent
Mitcham et al.

(10) Patent No.: US 6,670,463 B1
(45) Date of Patent: Dec. 30, 2003

(54) COMPOSITIONS AND METHODS FOR THERAPY OF OVARIAN CANCER

(75) Inventors: Jennifer L. Mitcham, Redmond, WA (US); Tony N. Frudakis, Sarasota, FL (US); Gordon E. King, Seattle, WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/216,003

(22) Filed: Dec. 17, 1998

(51) Int. Cl.[7] ........................ C07H 21/04; C07H 21/02; C12P 21/06; C12N 15/00; C12N 15/09

(52) U.S. Cl. .................... 536/23.5; 536/23.1; 536/24.3; 536/24.33; 435/7.1; 435/7.23; 435/320.1; 435/325; 435/69.1; 424/64

(58) Field of Search .............................. 536/23.1, 23.5, 536/243, 24.31, 24.33; 435/7.1, 7.23, 320.1, 325, 69.1; 424/64

(56) References Cited

FOREIGN PATENT DOCUMENTS

| | | |
|---|---|---|
| WO | WO 99/25877 | 5/1999 |
| WO | WO 99/63088 | 12/1999 |
| WO | WO 00/12758 | 3/2000 |
| WO | WO 00/36107 | 6/2000 |

OTHER PUBLICATIONS

Hillier et al., Generation and Analysis of 280,000 Humans Expressed Sequence Tags, Genome Research, vol. 6, pp. 807–828, 1996*

Sambrook et al., Molecular Cloning vol. 3, pp. 16.68–16.81, 1989.*

Harris et al., Polycystic Kidney Disease 1: Identification and Analysis of the Primary Defect, Journl of the American Society of Nephrology, vol. 6, No. 4, pp. 1125–1133, 1995.*

Ahn et al., The structural and functional diversity of dystrophin, Nature Genetics, vol. 3, pp. 284–291, 1993.*

Cawthon et al.; cDNA Sequence and Genomic Structure of EV12B, a Gene Lying within an Intron of the Neurofibromatosis Type 1 Gene, vol. 9, pp. 446–460, 1991.*

Genbank Accession No. AA075632, Dec. 1997.*

Genbank Accession No. AA640762, Oct. 1997.*

Bookman et al., "Biological therapy of ovarian cancer: Current directions," *Seminars in Oncology*, 25(3):381–396. (1998).

Gillespie et al., "Mage, Bage and Gage: Tumour antigen expression in benign and malignant ovarian tissue," *British Journal of Cancer*, 78(6):816–821, Sep., 1998.

Heller et al., "Discovery and analysis of inflammatory disease–related genes using cDNA microarrays," *Proc. Natl. Acad. Sci. USA 94*:2150–2155, Mar., 1997.

Ishikawa et al., "Prediction of the coding sequence of unidentified human genes. The complete sequence of 100 new cDNA clones from brain which can code for large proteins in vitro," *DNA Res.*, 5:169–176, 1998.

Jin et al., "Human T cell leukemia virus type 1 oncoprotein tax targets the human mitotic checkpoint protein MAD1," *Cell 93*:81–91, Apr. 3, 1998.

(List continued on next page.)

*Primary Examiner*—Sheela Huff
(74) *Attorney, Agent, or Firm*—Seed Intellectual Property Law Group PLLC

(57) ABSTRACT

Compositions and methods for the therapy of cancer, such as ovarian cancer, are disclosed. Compositions may comprise one or more ovarian carcinoma proteins, immunogenic portions thereof, polynucleotides that encode such portions or antibodies or immune system cells specific for such proteins. Such compositions may be used, for example, for the prevention and treatment of diseases such as ovarian cancer. Methods are further provided for identifying tumor antigens that are secreted from ovarian carcinomas and/or other tumors.

12 Claims, 91 Drawing Sheets

11729.1 contg

TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC 11729-45.21.21.cons1

TAGGATGTGTTGGACCCTCTGTGTCAAAAAAAACCTCACAAAGAATCCCCTGCTCATTACAGAAGAAGATGCATTT
AAAATATGGGTTATTTTCAACTTTTTATCTGAGGACAAGTATCCATTAATTATTGTGTCAGAAGAGATTGAATACC
TGCTTAAGAAGCTTACAGAAGCTATGGAGGAGGTTGGCAGCAAGAACAATTTGAACATTATAAAATCAACTTTGA
TGACAGTAAAAATGGCCTTTCTGCATGGGAACTTATTGAGCTTATTGGAAATGGACAGTTTAGCAAAGGCATGGAC
CGGCAGACTGTGTCTATGGCAATTAATGAAGTCTTTAATGAACTTATATTAGATGTGTTAAAGCAGGGTTACATGA
TGAAAAAGGGCCACAGACGGAAAAACTGGACTGAAAGATGGTTTGTACTAAAACCCAACATAATTTCTTACTATGT
GAGTGAGGATCTGAAGGATAAGAAAGGAGACATTCTCTTGGATGAAAATTGCTGTGTAGAGTCCTTGCCTGACAAA
GATGGAAA 11729-45.21.21.cons2

TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC 11731.1contig TCTTTTTCTTTCGATTTCCTTCAATTTGTCACGTTTGATTTTATGAAGTTGTTCAAGGGCTAACTGCTGTGTATTA
TAGCTTTCTCTGAGTTCCTTCAGCTGATTGTTAAATGAATCCATTTCTGAGAGCTTAGATGCAGTTTCTTTTTCAA
GAGCATCTAATTGTTCTTTAAGTCTTTGGCATAATTCTTCCTTTTCTGATGACTTTTTATGAAGTAAACTGATCCC
TGAATCAGGTGTGTTACTGAGCTGCATGTTTTTAATTCTTTCGTTTAATAGCTGCTTCTCAGGGACCAGATAGATA
AGCTTATTTTGATATTCCTTAAGCTCTTGTTCAAGTTGTTTGATTTCCATAATTTCCAGGTCACACTGTTTATCCA
AAACTTCTAGCTCAGTCTTTTGTGTTTGCTTTCTGATTTGGACATCTTGTAGTCTGCCTGAGATCTGCTGATGXTT
TCCATTCACTGCTTCCAGTTCCAGGTGGAGACTTTXCTTTCTGGAGCTCAGCCTGACAATGCCTTCTTGXTCCCT

OTHER PUBLICATIONS

Köhler et al., "Immotherapy of Ovarian Carcinoma with the Monoclonal Anti–Idiotype Antibody ACA125—Results of the Phase LB Study," *Gebrutshilfe und Fraenheilkunde*, 58(4):180–186, Apr. 1998, + (English Abstract).

Ma et al., "Use of encapsulated single chain antibodies for induction of anti–idiotypic humoral and cellular immune responses," *Journal of Pharmaceutical Sciences*, 87(11):1375–1378, Nov. 1998.

Peoples et al., "Ovarian cancer–associated lymphocyte recognition of folate binding protein peptides," *Annals of Surgical Oncology*, 5(8):743–750, Dec., 1998.

Schena et al., "Parallel human genome analysis: Microarray–based expression monitoring of 1000 genes," *Proc. Natl. Acad. Sci.*, 93:10614–10619, Oct., 1996.

Hovig, E. et al., "CA125: The End of the Beginning," *Tumor Biology 22*: 345–347, 2001.

O'Brien, T.J. et al., "The CA125 Gene: A Newly Discovered Extension of the Glycosylated N–Terminal Domain Doubles the Size of This Extracellular Superstructure," *Tumor Biology 23*: 154–169, 2002.

O'Brien, T.J. et al., "The CA 125 Gene: An Extracellular Superstructure Dominated by Repeat Sequences," *Tumor Biology 22*: 348–366, 2001.

Schummer, M. et al., "Comparative hybridization of an array of 21 500 ovarian cDNAs for the discovery of genes overexpressed in ovarian carcinomas," *Gene 238*: 375–385, 1999.

Whitehouse, C. et al., "NBR1 interacts with fasciculation and elongation protein zeta–1 (FEZ1) and calcium and integrin binding protein (CIB) and shows developmentally restricted expression in the neural tube," *Eur. J. Biochem. 269*: 538–545, 2002.

Yin and Lloyd, "Molecular Cloning of the CA125 Ovarian Cancer Antigen. Identification as a new mucin, MUC16," *Journal of Biological Chemistry 276*(29): 27371–27375, Jul. 20, 2001.

Yin, B.W.T. et al., "Ovarian cancer antigen CA125 is encoded by the *MUC16* mucin gene," *International Journal of Cancer 98*: 737–740, 2002.

* cited by examiner 11729.1 contg

TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC 11729-45.21.21.cons1

TAGGATGTGTTGGACCCTCTGTGTCAAAAAAAACCTCACAAAGAATCCCCTGCTCATTACAGAAGAAGATGCATTT
AAAATATGGGTTATTTTCAACTTTTTATCTGAGGACAAGTATCCATTAATTATTGTGTCAGAAGAGATTGAATACC
TGCTTAAGAAGCTTACAGAAGCTATGGGAGGAGGTTGGCAGCAAGAACAATTTGAACATTATAAAATCAACTTTGA
TGACAGTAAAAATGGCCTTTCTGCATGGGAACTTATTGAGCTTATTGGAAATGGACAGTTTAGCAAAGGCATGGAC
CGGCAGACTGTGTCTATGGCAATTAATGAAGTCTTTAATGAACTTATATTAGATGTGTTAAAGCAGGGTTACATGA
TGAAAAAGGGCCACAGACGGAAAAACTGGACTGAAAGATGGTTTGTACTAAAACCCAACATAATTTCTTACTATGT
GAGTGAGGATCTGAAGGATAAGAAAGGAGACATTCTCTTGGATGAAAATTGCTGTGTAGAGTCCTTGCCTGACAAA
GATGGAAA 11729-45.21.21.cons2

TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC 11731.1contig TCTTTTTCTTTCGATTTCCTTCAATTTGTCACGTTTGATTTTATGAAGTTGTTCAAGGGCTAACTGCTGTGTATTA
TAGCTTTCTCTGAGTTCCTTCAGCTGATTGTTAAATGAATCCATTTCTGAGAGCTTAGATGCAGTTTCTTTTTCAA
GAGCATCTAATTGTTCTTTAAGTCTTTGGCATAATTCTTCCTTTTCTGATGACTTTTTATGAAGTAAACTGATCCC
TGAATCAGGTGTGTTACTGAGCTGCATGTTTTTAATTCTTTCGTTTAATAGCTGCTTCTCAGGGACCAGATAGATA
AGCTTATTTTGATATTCCTTAAGCTCTTGTTGAAGTTGTTTGATTTCCATAATTTCCAGGTCACACTGTTTATCCA
AAACTTCTAGCTCAGTCTTTTGTGTTTGCTTTCTGATTTGGACATCTTGTAGTCTGCCTGAGATCTGCTGATGXTT
TCCATTCACTGCTTCCAGTTCCAGGTGGAGACTTTXCTTTCTGGAGCTCAGCCTGACAATGCCTTCTTGXTCCCT

*Fig. 1A*

11731.2contig

AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTA 11734.1contig AATAGATTTAATGCAGAGTGTCAACTTCAATTGATTGATAGTGGCTGCCTAGAGTGCTGTGTTGAGTAGGTTTCTG
AGGATGCACCCTGGCTTGAAGAGAAAGACTGGCAGGATTAACAATATCTAAAATCTCACTTGTAGGAGAAACCACA
GGCACCAGAGCTGCCACTGGTGCTGGCACCAGCTCCACCAAGGCCAGCGAAGAGCCCAAATGTGAGAGTGGCGGTC
AGGCTGGCACCAGCACTGAAGCCACCACTGGTGCTGGCACTGGCACTGGCACTGTTATTGGTACTGGTACTGGCAC
CAGTGCTGGCACTGCCACTCTCTTGGGCTTTGGCTTTAGCTTCTGCTCCCGCCTGGATCCGGGCTTTGGCCCAGGG
TCCGATATCAGCTTCGTCCCAGTTGCAGGGCCCGGCAGCATTCTCCGAGCCGAGCCCAATGCCCATTCGAGCTCTA
ATCTCGGCCCTAGCCTTGGCTTCAGCTGCAGCCTCAGCTGCAGCCTTCAAATCCGCTTCCATCGCCTCTCGGTAC 11734.2contig GCCAAGAAAGCCCGAAAGGTGAAGCATCTGGATGGGGAAGAGGATGGCAGCAGTGATCAGAGTCAGGCTTCTGGAA
CCACAGGTGGCCGAAGGGTCTCAAAGGCCCTAATGGCCTCAATGGCCCGCAGGGCTTCAAGGGGTCCCATAGCCTT
TTGGGCCCGCAGGGCATCAAGGACTCGGTTGGCTGCTTGGGCCCGGAGAGCCTTGCTCTCCCTGAGATCACCTAAA
GCCCGTAGGGGCAAGGCTCGCCGTAGAGCTGCCAAGCTCCAGTCATCCCAAGAGCCTGAAGCACCACCACCTCGGG
ATGTGGCCCTTTTGCAAGGGAGGGCAAATGATTTGGTGAAGTACCTTTTGGCTAAAGACCAGACGAAGATTCCCAT
CAAGCGCTCGGACATGCTGAAGGACATCATCAAAGAATACACTGATGTGTACCCCGAAATCATTGAACGAGCAGGC
TATTCCTTGGAGAAGGTATTTGGGATTCAATTGAAGGAAATTGATAAGAATGACCACTTGTACATTCTTCTCAGC 11736.1contg GAGGTCTCACTATGTTGCCCAGGCTGTTCTTGAACTCCTGGGATCAAGCAATCCACCCATGTTGGTCTCCAAAAGT
GCTGGGATCATAGGCGTGAGCCACCTCACCCAGCCACCAATTTTCAATCAGGAAGACTTTTTCCTTCTTCAAGAAG
TGAAGGGTTTCCAGAGTATAGCTACACTATTGCTTGCCTGAGGGTGACTACAAAATTGCTTGCTAAAAGGTTAGGA
TGGGTAAAGAATTAGATTTTCTGAATGCAAAAATAAAATGTGAACTAATGAACTTTAGGTAATACATATTCATAAA
ATAATTATTCACATATTTCCTGATTTATCACAGAAATAATGTATGAAATGCTTTGAGTTTCTTGGAGTAAACTCCA
TTACTCATCCCAAGAAACCATATTATAAGTATCACTGATAATAAGAACAACAGGACCTTGTCATAAATTCTGGATA
AGAGAAATAGTCTCTGGGTGTTTGXTCTTAATTGATAAAATTTACTTGTCCATCTTTTAGTTCAGAATCACAAAA

*Fig. 1B*

11736.2contig

AAGCGGAAATGAGAAAGGAGGGAAAATCATGTGGTATTGAGCGGAAAACTGCTGGATGACAGGGCTCAGTCCTGTT
GGAGAACTCTGGGTGGTGCTGTAGAACAGGGCCACTCACAGTGGGGTGCACAGACCAGCACGGCTCTGTGACCTGT
TTGTTACAGGTCCATGATGAGGTAAACAATACACTGAGTATAAGGGTTGGTTTAGAAACTCTTACAGCAATTTGAC
AAAGTAATCTTCTGTGCAGTGAATCTAAGAAAAAAATTGGGGCTGTATTTGTATGTTCCTTTTTTTCATTTCATGT
TCTGAGTTACCTATTTTTATTGCATTTTACAAAAGCATCCTTCCATGAAGGACCGGAAGTTAAAAACAAAGCAGGT
CCTTTATCACAGCACTGTCGTAGAACACAGTTCAGAGTTATCCACCCAAGGAGCCAGGGAGCTGGGCTAAACCAAA
GAATTTTGCTTTTGGTTAATCATCAGGTACTTGAGTTGGAATTGTTTTAATCCCATCATTACCAGGCTGGAXGTG 11739-1&2

CCGCGGCTCCTGTCCAGACCCTGACCCTCCCTCCCAAGGCTCAACCGTCCCCCAACAACCGCCAGCCTTGTACTGA
TGTCGGCTGCGAGAGCCTGTGCTTAAGTAAGAATCAGGCCTTATTGGAGACATTCAAGCAAAGGTTGGACAACTAC
TTTTCCAGAACAGAAAGGAAACTCATGCATCAGAAAAGGTGACTAATAAAGGTACCAGAAGAATATGGCTGCACAA
ATACCAGAATCTGATCAGATAAAACAGTTTAAGGAATTTCTGGGGACCTACAATAAACTTACAGAGACCTGCTTTT
TGGACTGTGTTAGAGACTTCACAACAAGAGAAGTAAAACCTGAAGAGACCACCTGTTCAGAACATTGCTTACAGAA
ATATTTAAAAATGACACAAAGAATATCCATGAGATTTCAGGAATATCATATTCAGCAGAATGAAGCCCTGGCAGCC
AAAGCAGGACTCCTTGGCCAACCACGATAGAGAAGTCCTGATGGATGAACTTTTGATGAAAGATTGCCAACAGCTG
CTTTATTGGAAATGAGGACTCATCTGATAGAATCCCCTGAAAGCAGTAGCCACCATGTTCAACCATCTGTCATGAC
TGTTTGGCAAATGGAAACCGCTGGAGAAACAAAATTGCTATTTACCAGGAATAATCACAATAGAAGGTCTTATTGT
TCAGTGAAATAATAAGATGCAACATTTGTTGAGGCCTTATGATTCAGCAGCTTGGTCACTTGATTAGAAAAATAAA
CCATTGTTTCTTCAATTGTGACTGTTAATTTTAAAGCAACTTATGTGTTCGATCATGTATGAGATAGAAAAATTTT
TATTACTCAAAGTAAAATAAATGGA 11740.1.contig GAAAAAAAATATAAAACACACTTTTGCGAAAACGGTGGCCCTAAAAGAGGAAAAGAATTTCACCAATATAAATCCA
ATTTTATGAAAACTGACAATTTAATCCAAGAATCACTTTTGTAAATGAAGCTAGCAAGTGATGATATGATAAAATA
AACGTGGAGGAAATAAAAACACAAGACTTGGCATAAGATATATCCACTTTTGATATTAAACTTGTGAAGCATATTC
TTCGACAAATTGTGAAAGCGTTCCTGATCTTGCTTGTTCTCCATTTCAAATAAGGAGGCATATCACATCCCAAGAG
TAACAGAAAAAGAAAAAAGACATTTTTGCATTTTGAGATGAACCAAAGACACAAAACAAAACGAACAAAGTGTCAT
GTCTAATTCTAGCCTCTGAAATAAACCTTGAACATCTCCTACAAGGCACCGTGATTTTTGTAATTCTAACCTGAAG
AAATGTGATGACTTTTGTGGACATGAAAATCAGATGAGAAAACTGTGGTCTTTCCAAAGCCTGAACTCCCCTGAAA
ACCTTTGCA

*Fig. 1C*

11766.1.contig

CTGGGATCATTTCTCTTGATGTCATAAAAGACTCTTCTTCTTCCTCTTCATCCTCTTCTTCATCCTCTTCTGTACA
GTGCTGCCGGGTACAACGGCTATCTTTGTCTTTATCCTGAGATGAAGATGATGCTTCTGTTTCTCCTACCATAACT
GAAGAAATTTCGCTGGAAGTCGTTTGACTGGCTGTTTCTCTGACTTCACCTTCTTTGTCAAACCTGAGTCTTTTTA
CCTCATGCCCCTCAGCTTCCACAGCATCTTCATCTGGATGTTTATTTTTCAAAGGGCTCACTGAGGAAACTTCTGA
TTCAGAGGTCGAAGAGTCACTGTGATTTTTCTCCTCATTTTGCTGCAAATTTGCCTCTTTGCTGTCTGTGCTCTCA
GGCAACCCATTTGTTGTCATGGGGGCTGACAAAGAAACCTTTGGTCGATTAAGTGGCCTGGGTGTCCCAGGCCCAT
TTATATTAGACCTCTCAGTATAGCTTGGTGAATTTCCAGGAAACATAACACCATTCATTCGATTTAAACTATTGGA
ATTGGTTTT 11766.2.contig GAGGGTTGGTGGTAGCGGCTTGGGGAGGTGCTCGCTCTGTCGGTCTTGCTCTCTCGCACGCTTCCCCCGGCTCCCT
TCGTTTCCCCCCCCCGGTCGCCTGCGTGCCGGAGTGTGTGCGAGGGAGGGGGAGGGCGTCGGGGGGGTGGGGGGAG
GCGTTCCGGTCCCCAAGAGACCCGCGGAGGGAGGCGGAGGCTGTGAGGGACTCCGGGAAGCCATGGACGTCGAGAG
GCTCCAGGAGGCGCTGAAAGATTTTGAGAAGAGGGGGAAAAAGGAAGTTTGTCCTGTCCTGGATCAGTTTCTTTGT
CATGTAGCCAAGACTGGAGAAACAATGATTCAGTGGTCCCAATTTAAAGGCTATTTTATTTTCAAACTGGAGAAAG
TGATGGATGATTTCAGAACTTCAGCTCCTGAGCCAAGAGGTCCTCCCAACCCTAATGTCGA 11773.2.contig AAGCAGGCGGCTCCCGCGCTCGCAGGGCCGTGCCACCTGCCCGCCCGCCCGCTCGCTCGCTCGCCCGCCGCGCCGC
GCTGCCGACCGCCAGCATGCTGCCGAGAGTGGGCTGCCCCGCGCTGCCGXTGCCG 11775-1&2

ATCTCTTGTATGCCAAATATTTAATATAAATCTTTGAAACAAGTTCAGATGAAATAAAAATCAAAGTTTGCAAAAA
CGTGAAGATTAACTTAATTGTCAAATATTCCTCATTGCCCCAAATCAGTATTTTTTTTATTTCTATGCAAAAGTAT
GCCTTCAAACTGCTTAAATGATATATGATATGATACACAAACCAGTTTTCAAATAGTAAAGCCAGTCATCTTGCAA
TTGTAAGAAATAGGTAAAAGATTATAAGACACCTTACACACACACACACACACACACACACGTGTGCACGCCAATGAC
AAAAAACAATTTGGCCTCTCCTAAAATAAGAACATGAAGACCCTTAATTGCTGCCAGGAGGGAACACTGTGTCACC
CCTCCCTACAATCCAGGTAGTTTCCTTTAATCCAATAGCAAATCTGGGCATATTTGAGAGGAGTGATTCTGACAGC
CACGTTGAAATCCTGTGGGGAACCATTCATGTCCACCCACTGGTGCCCTGAAAAAATGCCAATAATTTTTCGCTCC
CACTTCTGCTGCTGtCTCTTCCACATCCTCACATAGACCCCAGACCCGCTGGCCCCTGGCTGGGCATCGCATTGCT
GGTAGAGCAAGTCATAGGTCTCGTCTTTGACGTCACAGAAGCGATACACCAAATTGCCTGGTCGGTCATTGTCATA
ACCAGAGA

*Fig. 1D*

11777.1&2.cons

CAGACGGGGTTTCACTATGTTGGCTAGGCTGGTCTTGAACTCCTGACTTCAGGTGATCTGCCTGCCTTGGCCTCCC
AAAGTGCTGGGATTACAGGCATAAGCCACTGCGCCCGGCTGATCTGATGGTTTCATAAGGCTTTTCCCCCTTTTGC
TCAGCACTTCTCCTTCCTGCCGCCATGTGAAGAAGGACATGTTTGCTTCCCCTTCCACCACGATTGTAAGTTGTTT
CCTGAGGCCTCCCCGGCCATGCTGAACTGTGAGTCAATTAAACCTCTTTCCTTTATAAATTATCCAGTTTTGGGTA
TGTCTTTATTAGTAGAATGAGAACAGACTAATACAACCCTTAAAGGAGACTGACGGAGAGGATTCTTCCTGGATCC
CAGCACTTCCTCTGAATGCTACTGACATTCTTCTTGAGGACTTTAAACTGGGAGATAGAAAACAGATTCCATGGCT
CAGCAGCCTGAGAGCAGGGAGGGAGCCAAGCTATAGATGACATGGGCAGCCTCCCCTGAGGCCAGGTGTGGCCGAA
CCTGGGCAGTGCTGCcACCCACCCCACCAGGGCCAAGTCCTGTCCTTGGAGAGCCAAGCCTCAATCACTGCTAGCC
TCAAGTGTCCCCAAGCCACAGTGGCTAGGGGGACTCAGGGAACAGTTCCCAGTCTGCCCTACTTCTCTTACCTTTA
CCCCTCATACCTCCAAAGTAGACCATGTTCATGAGGTCCAAAGG 11779.2.contig AAGCGAGGAAGCCACTGCGGCTCCTGGCTGAAAAGCGGCGCCAGGCTCGGGAACAGAGGGAACGCGAAGAACAGGA
GCGGAAGCTGCAGGCTGAAAGGGACAAGCGAATGCGAGAGGAGCAGCTGGCCCGGGAGGCTGAAGCCCGGGCTGAA
CGTGAGGCCGAGGCGCGGAGACGGGAGGAGCAGGAGGCTCGAGAGAAGGCGCAGGCTGAGCAGGAGGAGCAGGAGC
GACTGCAGAAGCAGAAAGAGGAAGCCGAAGCCCGGTCCCGGGAAGAAGCTGAGCGCCAGCGCCAGGAGCGGGAAAA
GCACTTTCAGAAGGAGGAACAGGAGAGACAAGAGCGAAGAAAGCGGCTGGAGGAGATAATGAAGAGGACTCGGAAA
TCAGAAGCCGCCGAAACCAAGAAGCAGGATGCAAAGGAGACCGCAGCTAACAATTCCGGCCCAGACCCTTGTGAAA
GCTGTAGAGACTCGGCCCTCTGGGCTTCCAGAAAGGATTCTATTGCAGAAAGGAAGGAGCTXGGCCCCCCAXGGA 11781 & 37.cons CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACXTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAAT

CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACCTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAATTA 11784-1 & 2

GGACGACAAGGCCATGGCGATATCGGATCCGAATTCAAGCCTTTGGAATTAAATAAACCTGGAACAGGGAAGGTGA
AAGTTGGAGTGAGATGTCTTCCATATCTATACCTTTGTGCACAGTTGAATGGGAACTGTTTGGGTTTAGGGCATCT
TAGAGTTGATTGATGGAAAAAGCAGACAGGAACTGGTGGGAGGTCAAGTGGGGAAGTTGGTGAATGTGGAATAACT
TACCTTTGTGCTCCACTTAAACCAGATGTGTTGCAGCTTTCCTGACATGCAAGGATCTACTTTAATTCCACACTCT
CATTAATAAATTGAATAAAAGGGAATGTTTTGGCACCTGATATAATCTGCCAGGCTATGTGACAGTAGGAAGGAAT
GGTTTCCCCTAACAAGCCCAATGCACTGGTCTGACTTTATAAATTATTTAATAAAATGAACTATTATC 11785.2.contig GGCAGTGACATTCACCATCATGGGAACCACCTTCCCTTTTCTTCAGGATTCTCTGTAGTGGAAGAGAGCACCCAGT
GTTGGGCTGAAAACATCTGAAAGTAGGGAGAAGAACCTAAAATAATCAGTATCTCAGAGGGCTCTAAGGTGCCAAG
AAGTCTCACTGGACATTTAAGTGCCAACAAAGGCATACTTTCGGAATCGCCAAGTCAAAACTTTCTAACTTCTGTC
TCTCTCAGAGACAAGTGAGACTCAAGAGTCTACTGCTTTAGTGGCAACTACAGAAAACTGGTGTTACCCAGAAAAA
CAGGAGCAATTAGAAATGGTTCCAATATTTCAAAGCTCCGCAAACAGGATGTGCTTTCCTTTGCCCATTTAGGGTT
TCTTCTCTTTCCTTTCTCTTTATTAACCACT

*Fig. 1F*

11718-1&2 cons

TGCGCTGAAAACAACGGCCTCCTTTACTGTTAAAATGCAGCCACAGGTGCTTAGCCGTGGGCATCTCAACCACCAG
CCTCTGTGGGGGGCAGGTGGGCGTCCCTGTGGGCCTCTGGGCCCACGTCCAGCCTCTGTCCTCTGCCTTCCGTTCT
TCGACAGTGTTCCCGGCATCCCTGGTCACTTGGTACTTGGCGTGGGCCTCCTGTGCTGCTCCAGCAGCTCCTCCAG
GXGGTCGGCCCGCTTCACCGCAGCCTCATGTTGTGTCCGGAGGCTGCTCACGGCCTCCTCCTTCCTCGCGAGGGCT
GTCTTCACCCTCCGGXGCACCTCCTCCAGCTCCAGCTGCTGGCGGGCCTGCAGCGTGGCCAGCTCGGCCTTGGCCT
GCCGCGTCTCCTCCTCARAGGCTGCCAGCCGGTCCTCGAACTCCTGGCGGATCACCTGGGCCAGGTTGCTGCGCTC
GCTAGAAAGCTGCTCGTTCACCGCCTGCGCATCCTCCAGCGCCCGCTCCTTCTGCCGCACAAGGCCCTGCAGACGC
AGATTCTCGCCCTCGGCcTCCCCAAGCTGGCCCTTCAGCTCCGAGCACCGCTCCTGAAGCTTCCGCTCCGACTGCT
CCAGCTCGGAGAGCTCGGCCTCGTACTTGTCCCGTAAGCGCTTGATGCGGCTCTCGGCAGCCTTCTCACTCTCCTC
CTTGGCCAGCGCCATGTCGGCCTCCAGCCGGTGAATGACCAGCTCAATCTCCTTGTCCCGGCCTTTCCGGATTTCT
TCCCTCAGCTCCTGTTCCCGGTTCAGCAGCCACGCCTCCTCCTTCCTGGTGCGGCCGGCCTCCCACGCCTGCCTCT
CCAGCTCCAGCTGCTGCTTCAGGGTATTCAGCTCCATCTGGCGGGCCTGCAGCGTGGCCA 13690.4

CAACTTATTACTTGAAATTATAATATAGCCTGTCCGTTTGCTGTTTCCAGGCTGTGATATATTTTCCTAGTGGTTT
GACTTTAAAAATAAATAAGGTTTAATTTTCTCCCC 13693.1

TGCAAGTCACGGGAGTTTATTTATTTAATTTTTTTCCCCAGATGGAGACTCTGTCGCCCAGGCTGGAGTGCAATGG
TGTGATCTTGGCTCACTGCAACCTCCACCTCCTGGGTTCAAGCGATTCTCCTGCCACAGCCTCCCGAGTAGCTGGG
ATTACAGGTGCCCGCCACCACACCCAGCTAATTTTTATATTTTTAGTAAAGACAGGGTTTCCCCATGTTGGCCAGG
CTGGTCTTGAACTTCTGACCTCAGGTGATCCACCTGCCTCGGCCTCCCAAAGTGTTGGGATTACAGGCGTGAGCTA
CCCGTGCCTGGCCAGCCACTGGAGTTTAAAGGACAGTCATGTTGGCTCCAGCCTAAGGCGGCATTTTCCCCCATCA
GAAAGCCCGCGGCTCCTGTACCTCAAAATAGGGCACCTGTAAAGTCAGTCAGTGAAGTCTCTGCTCTAACTGGCCA
CCCGGGGCCATTGGCNTCTGACACAGCCTTGCCAGGANGCCTGCATCTGCAAAAGAAAAGTTCACTTCCTTTCCG 13694.1

CAGAGAATCTKAGAAAGATGTCGCGTTTTCTTTTAATGAATGAGAGAAGCCCATTTGTATCCCTGAATCATTGAGA
AAAGGCGGCGGTGGCGACAGCGGCGACCTAGGGATCGATCTGGAGGGACTTGGGGAGCGTGCAGAGACCTCTAGCT
CGAGCGCGAGGGACCTCCCGCCGGGATGCCTGGGGAGCAGATGGACCCTACTGGAAGTCAGTTGGATTCAGATTTC
TCTCAGCAAGATACTCCTTGCCTGATAATTGAAGATTCTCAGCCTGAAAGCCAGGTTCTAGAGGATGATTCTGGTT
CTCACTTCAGTATGCTATCTCGACACCTTCCTAATCTCCAGACGCACAAAGAAAATCCTGTGTTGGATGTTGNGTC
CAATCCTTGAACAAACAGCTGGAGAAGAACGAGGAGACCGGTAATAGTGGGTTCAATGAACATTTGAAAGAAAACC
AGGTTGCAGACCCTG

GACTGTCCTGAACAAGGGACCTCTGACCAGAGAGCTGCAGGAGATGCAGAGTGGTGGCAGGAGTGGAAGCCAAAGA
ACACCCACCTTCCTCCCTTGAAGGAGTAGAGCAACCATCAGAAGATACTGTTTTATTGCTCTGGTCAAACAAGTCT
TCCTGAGTTGACAAAACCTCAGGCTCTGGTGACTTCTGAATCTGCAGTCCACTTTCCATAAGTTCTTGTGCAGACA
ACTGTTCTTTTGCTTCCATAGCAGCAACAGATGCTTTGGGGCTAAAAGGCATGTCCTCTGACCTTGCAGGTGGTGG
ATTTTGCTCTTTTACAACATGTACATCCTTACTGGGCTGTGCTGTCACAGGGATGTCCTTGCTGGACTGTTCTGCT
ATGGGGATATCTTCGTTGGACTGTTCTTCATGCTTAATTGCAGTATTAGCATCCACATCAGACAGCCTGGTATAAC
CAGAGTTGGTGGTTACTGATTGTAGCTGCTCTTTGTCCACTTCATATGGCACAAGTATTTTCCTCAACATCCTGGC
TCTGGGAAG 13695.1

GAAATGTATATTTAATCATTCTCTTGAACGATCAGAACTCTRAAATCAGTTTTCTATAACARCATGTAATACAGTC
ACCGTGGCTCCAAGGTCCAGGAAGGCAGTGGTTAACACATGAAGAGTGTGGGAAGGGGGCTGGAAACAAAGTATTC
TTTTCCTTCAAAGCTTCATTCCTCAAGGCCTCAATTCAAGCAGTCATTGTCCTTGCTTTCAAAAGTCTGTGTGTGC
TTCATGGAAGGTATATGTTTGTTGCCTTAATTTGAATTGTGGCCAGGAAGGGTCTGGAGATCTAAATTCAGAGTAA
GAAAACCTGAGCTAGAACTCAGGCATTTCTCTTACAGAACTTGGCTTGCAGGGTAGAATGAANGGAAAGAAACTTA
GAAGCTCAACAAGCTGAAGATAATCCCATCAGGCATTTCCCATAGGCCTTGCAACTCTGTTCACTGAGAGATGTTA
TCCTG 13695.2

AGTCTGGAGTGAGCAAACAAGAGCAAGAAACAARRAGAAGCCAAAAGCAGAAGGCTCCAATATGAACAAGATAAAT
CTATCTTCAAAGACATATTAGAAGTTGGGAAAATAATTCATGTGAACTAGACAAGTGTGTTAAGAGTGATAAGTAA
AATGCACGTGGAGACAAGTGCATCCCCAGATCTCAGGGACCTCCCCCTGCCTGTCACCTGGGGAGTGAGAGGACAG
GATAGTGCATGTTCTTTGTCTCTGAATTTTTAGTTATATGTGCTGTAATGTTGCTCTGAGGAAGCCCCTGGAAAGT
CTATCCCAACATATCCACATCTTATATTCCACAAATTAAGCTGTAGTATGTACCCTAAGACGCTGCTAATTGACTG
CCACTTCGCAACTCAGGGGCGGCTGCATTTTAGTAATGGGTCAAATGATTCACTTTTTATGATGCTTCCCAAGGTG
CCTTGGCTTCTCTTCCCAACTGACAAATGCCCAAGTTGAGAAAAATGATCATAATTTTAGCATAAACCGAGCAATC
GGCGACCCC 13697.1

TAGCTGTCTTCCTCACTCTTATGGCAATGACCCCATATCTTAATGGATTAAGATAATGAAAGTGTATTTCTTACAC
TCTGTATCTATCACCAGAAGCTGAGGTGATAGCCCGCTTGTCATTGTCATCCATATTCTGGGACTCAGGCGGGAAC
TTTCTGGAATATTGCCAGGGAGCATGGCAGAGGGGCACAGTGCATTCTGGGGGAATGCACATTGGCTCAGCCTGGG
TAATGAGTGATATACATTACCTCTGTTCACAACTCATTGCCCAGCACCAGTCACAAGGCCCCACCAAATACCAGAG
CCCAAGAAATGTAGTCCTGTTGATATGGTTTTGCTGTGTCCCAACCCAAATCTCATCTTGAATTGTAAGCTCCCAT
AATTCCCATGTGTTGTGGGAGGGACCTGGTG

ATCATGAGGATGTTACCAAAGGGATGGTACTAAACCATTTGTATTCGTCTGTTTTCACACTGCTTTGAAGATACTA
CCTGAGACTGGGTAATTTATAAACAAAAGAGATTTAATTGACTCACAGTTCTGCATGGCTGAAGAGGCCTCAGGAA
ACTTACAGTCATGGTGGAAGGCAAAGGAGGAGCAAGGCATGTCTTACATGTCAGTAGGAGAGAGAGCGAGAGCAGG
AGAACCTGCCACTTATAAACCATTCAGATCTCATAACTCCCTATCATGAGAAAAACATGGAGGAAACCACCCTCAT
GATCCAATCACCTCCCGCCAGGTCCCTCCCTCGACACGTGGGGATTATAATTCAGGATTAGAGGGACACAGAGACA
AACCATATCATCATTCATGAGAAATCCACCCTCATAGTCCAATCAGCTCCTACCAGGCCCCACCTCCAACACTGGG
GATTGCAATTCAACATGAGATTTGGATGGGGACACAGATTCAAACCATATCATAC 13699.1&2

CATGGCCTTTCTCCTTAGAGGCCAGAGGTGCTGCCCTGGCTGGGAGTGAAGCTCCAGGCACTACCAGCTTTCCTGA
TTTTCCCGTTTGGTCCATGTGAAGAGCTACCACGAGCCCCAGCCTCACAGTGTCCACTCAAGGGCAGCTTGGTCCT
CTTGTCCTGCAGAGGCAGGCTGGTGTGACCCTGGGAACTTGACCCGGGAACAACAGGTGGCCCAGAGTGAGTGTGG
CCTGGCCCCTCAACCTAGTGTCCGTCCTCCTCTCTCCTGGAGCCAGTCTTGAGTTTAAAGGCATTAAGTGTTAGAT
ACAAGCTCCTTGTGGCTGGAAAAACACCCCTCTGCTGATAAAGCTCAGGGGGCACTGAGGAAGCAGAGGCCCCTTG
GGGGTGCCCTCCTGAAGAGAGCGTCAGGCCATCAGCTCTGTCCCTCTGGTGCTCCCACGTCTGTTCCTCACCCTCC
ATCTCTGGGAGCAGCTGCACCTGACTGGCCACGCGGGGGCAGTGGAGGCACAGGCTCAGGGTGGCCGGGCTACCTG
GCACCCTATGGCTTACAAAGTAGAGTTGGCCCAGTTTCCTTCCACCTGAGGGGAGCACTCTGACTCCTAACAGTCT
TCCTTGCCCTGCCATCATCTGGGGTGGCTGGCTGTCAAGAAAGGCCGGGCATGCTTTCTAAACACAGCCACAGGAG
GCTTGTAGGGCATCTTCCAGGTGGGGAAACAGTCTTAGATAAGTAAGGTGACTTGCCTAAGGCCTCCCAGCACCCT
TGATCTTGGAGTCTCACAGCAGACTGCATGTSAACAACTGGAACCGAAAACATGCCTCAGTATAAAA 13703.3

CCAGAACCTCCTTCTCTTTGGAGAATGGGGAGGCCTCTTGGAGACACAGAGGGTTTCACCTTGGATGACCTCTAGA
GAAATTGCCCAAGAAGCCCACCTTCTGGTCCCAACCTGCAGACCCCACAGCAGTCAGTTGGTCAGGCCCTGCTGTA
GAAGGTCACTTGGCTCCATTGCCTGCTTCCAACCAATGGGCAGGAGAGAAGGCCTTTATTTCTCGCCCACCCATTC
TCCTGTACCAGCACCTCCGTTTTCAGTCAGYGTTGTCCAGCAACGGTACCGTTTACACAGTCA 13705.1

TGCATGTAGTTTTATTTATGTGTTTTSGTCTGGAAAACCAAGTGTCCCAGCAGCATGACTGAACATCACTCACTTC
CCCTACTTGATCTACAAGGCCAACGCCGAGAGCCCAGACCAGGATTCCAAACACACTGCACGAGAATATTGTGGAT
CCGCTGTCAGGTAAGTGTCCGTCACTGACCCARACGCTGTTACGTGGCACATGACTGTACAGTGCCACGTAACAGC
ACTGTACTTTTCTCCCATGAACAGTTACCTGCCATGTATCTACATGATTCAGAACATTTTGAACAGTTAATTCTGA
CACTTGAATAATCCCATCAAAAACCGTAAAATCACTTTGATGTTTGTAACGACAACATAGCATCACTTTACGACAG
AATCATCTGGAAAAACAGAACAACGAATACATACATCTTAAAAAATGCTGGGGTGGGCCAGGCACAGCTTCACGCC
TGTAATCCCAGCACTTTGGGAGGCTTAAGCGGGTG

*Fig. 1I*

```
TGGGGCGGAAAGAAGCCAAGGCCAAGGAGCTGGTGCGGCAGCTGCAGCTGGAGGCCGAGGAGCAGAGGAAGCAGAA
GAAGCGGCAGAGTGTGTCGGGCCTGCACAGATACCTTCACTTGCTGGATGGAAATGAAAATTACCCGTGTCTTGTG
GATGCAGACGGTGATGTGATTTCCTTCCCACCAATAACCAACAGTGAGAAGACAAAGGTTAAGAAAACGACTTCTG
ATTTGTTTTTGGAAGTAACAAGTGCCACCAGTCTGCAGATTTGCAAGGATGTCATGGATGCCCTCATTCTGAAAAT
GGCAAGAAATGAAAAAGTACACTTTAGAAAATAAAGAGGAAGGATCACTCTCAGATACTGAAGCCGATGCAGTCTC
TGGACAACTTCCAGATCCCACAACGAATCCCAGTGCTGGAAAGGACGGGCCCTTCCTTCTGGTGGTGGAACANGTC
CCGGTGGTGGATCTTGGAANGGAACCTGAANGTGGTGTACCCCGTCCAAGGCCGACCTTGGCCAC
```

13707.4

```
TCCCGCGCTCGCAGGGCNCGTGCCACCTGCCYGTCCGCCCGCTCGCTCGCTCGCCCGCCGCGCCGCGCTGCCGACC
GYCAGCATGCTGCCGAGAGTGGGCTGCCCCGCGCTGCCGCTGCCGCCGCCGCCGCTGCTGCCGCTGCTGCCGCTGC
TGCTGCTGC
```

13708.1&2

```
GGCGGGTAGGCATGGAACTGAGAAGAACGAAGAAGCTTTCAGACTACGTGGGGAAGAATGAAAAAACCAAAATTAT
CGCCAAGATTCAGCAAAGGGGACAGGGAGCTCCAGCCCGAGAGCCTATTATTAGCAGTGAGGAGCAGAAGCAGCTG
ATGCTGTACTATCACAGAAGACAAGAGGAGCTCAAGAGATTGGAAGAAAATGATGATGATGCCTATTTAAACTCAC
CATGGGCGGATAACACTGCTTTGAAAAGACATTTTCATGGAGTGAAAGACATAAAGTGGAGACCAAGATGAAGTTC
ACCAGCTGATGACACTTCCAAAGAGATTAGCTCACCT
```

13709.1

```
TCTGAAGGTTAAATGTTTCATCTAAATAGGGATAATGRTAAACACCTATAGCATAGAGTTGTTTGAGATTAAATGA
GATAATACATGTAAAATTATGTGCCTGGCATACAGCAAGATTGTTGTTGTTGATGATGATGATGATGATGATA
ATATTTTTCTATCCCCAGTGCACAACTGCTTGAACCTATTAGATAATCAATACATGTTTCTTGAACTGAGATCAAT
TTCCCCATGTTGTCTGACTGATGAAGCCCTACATTTTCTTCTAGAGGAGATGACATTTGAGCAAGATCTTAAAGAA
AATCAGATGCCTTCACCTGACCACTGCTTGGTGATCCCATGGCACTTTGTACATCTCTCCATTAGCTCTCATCTCA
CCAGCCCATCATTATTGTATGTGCTGCCTTCTGAAGCTTGCAGCTGGCTACCATCMGGTAGAATAAAAATCATCCT
TTCATAAAATAGTGACCCTCCTTTTTTATTTGCATTTCCCAAAGCCAAGCACCGTGGGANGGTAG
```

13709.2

TATGAAGAAGGGAAAAGAAGATAATTTGTGAAAGAAATGGGTCCAGTTACTAGTCTTTGAAAAGGGTCAGTCTGTA
GCTCTTCTTAATGAGAATAGGCAGCTTTCAGTTGCTCAGGGTCAGATTTCCTTAGTGGTGTATCTAATCACAGGAA
ACATCTGTGGTTCCCTCCAGTCTCTTTCTGGGGGACTTGGGCCCACTTCTCATTTCATTTAATTAGAGGAAATAGA
ACTCAAAGTACAATTTACTGTTGTTTAACAATGCCACAAAGACATGGTTGGGAGCTATTTCTTGATTTGTGTAAAA
TGCTGTTTTTGTGTGCTCATAATGGTTCCAAAAATTGGGTGCTGGCCAAAGAGAGATACTGTTACAGAAGCCAGCA
AGAAGACCTCTGTTCATTCACACCCCCGGGGATATCAGGAATTGACTCCAGTGTGTGCAAATCCAGTTTGGCCTAT
CTTCT 13712.1&2

TGAGGGACTGATTGGTTTGCTCTCTGCTATTCAATTCCCCAAGCCCACTTGTTCCTGCAGCGTCCTCCTTCTCATT
CCCTTTAGTTGTACCCTCTCTTTCATCTGAGACCTTTCCTTCTTGATGTCGCCTTTTCTTCTTCTTGCTTTTTCTG
ATGTTCTGCTCAGCATGTTCTGGGTGCTTCTCATCTGCATCATTCCTTTCAGATGCTGTAGCTTCTTCCTCCTCTT
TCTGCCTCCTTTTCTTTTTCTTTTTTTTGGGGGGCTTGCTCTCTGACTGCAGTTGAGGGGCCCCAGGGTCCTGGCC
TTTGAGACGAGCCAGGAAGGCCTGCTCCTGGGCCTCTAGGCGAGCAAGCTTGGCCTTCATTGTGATCCCAAGACGG
GCAGCCTTGTGTGCTGTTCGCCCCTCACAGGCTTGGAGCAGCATCTCATCAGTCAGAATCTTTGGGGACTTGGACC
CCTGGTTGTCGTCATCACTGCAGCTCTCCAAGTCTTTGTTTGGCTTCTCTCCACCTGAAGTCAATGTAGCCATCTT
CACAAACTTCTGATACAGCAAGTTGGGCTTGGGATGATTATAACGGGTGGTCTCCTTAGAAAGGCTCCTTATCTGT
ACTCCATCCTGCCCAGTTTCCACTACCAAGTTGGCCGCAGTCTTGTTGAAGAGCTCATTCCACCAGTGGTTTGTGA
ACTCCTTGGCAGGGTCATGTCCTACCCCATGAGTGTCTTGCTTCAGYGTCACCCTGAGAGCCTGAGTGATACCATT
CTCCTTCCG 13714.1&2

GACAACATGAAATAAATCCTAGAGGACAAAATTAAACTCAATAGAGTGTAGTCTAGTTAAAAACTCGAAAAATGAG
CAAGTCTGGTGGGAGTGGAGGAAGGGCTATACTATAAATCCAAGTGGGCCTCCTGATCTTAACAAGCCATGCTCAT
TATACACATCTCTGAACTGGACATACCACCTTTACGCAGGAAACAGGGCTTGGAACTTCTAAGGGAAATTAACATG
CACCACCCACATCTAACCTACCTGCCGGGTAGGTACCATCCCTGCTTCGCTGAAATCAGTGCTC 13716.1&2

TTGGAATTAAATAAACCTGGAACAGGGAAGGTGAAAGTTGGAGTGAGATGTCTTCCATATCTATACCTTTGTGCAC
AGTTGAATGGGAACTGTTTGGGTTTAGGGCATCTTAGAGTTGATTGATGGAAAAAGCAGACAGGAACTGGTGGGAG
GTCAAGTGGGGAAGTTGGTGAATGTGGAATAACTTACCTTTGTGCTCCACTTAAACCAGATGTGTTGCAGCTTTCC
TGACATGCAAGGATCTACTTTAATTCCACACTCTCATTAATAAATTGAATAAAAGGGAATGTTTTGGCACCTGATA
TAATCTGCCAGGCTATGTGACAGTAGGAAGGAATGGTTTCCCCTAACAAGCCCAATGCACTGGTCTGACTTTATAA
ATTATTTAATAAAATGAACTATTATC

AAACTGGACCTGCAACAGGGACATGAATTTACTGCARGGTCTGAGCAAGCTCAGCCCCTCTACCTCAGGGCCCCAC
AGCCATGACTACCTCCCCCAGGAGCGGGAGGGTGAAGGGGGCCTGTCTCTGCAAGTGGAGCCAGAGTGGAGGAATG
AGCTCTGAAGACACAGCACCCAGCCTTCTCGCACCAGCCAAGCCTTAACTGCCTGCCTGACCCTGAACCAGAACCC
AGCTGAACTGCCCCTCCAAGGGACAGGAAGGCTGGGGGAGGGAGTTTACAACCCAAGCCATTCCACCCCCTCCCCT
GCTGGGGAGAATGACACATCAAGCTGCTAACAATTGGGGGAAGGGGAAGGAAGAAAACTCTGAAAACAAAATCTTG
T 13722.3

CATGCGTTTCACCACTGTTGGCCAGGCTGGTCTCGAACTCCTGGCCTCAAGCAATCCACCCGCCTCAGCCTCCAAA
AGTGCTGGGATTACAGATGTGAGCCATGGCACCATGCCAAAAGGCTATATTCCTGGCTCTGTGTTTCCGAGACTGC
TTTTAATCCCAACTTCTCTACATTTAGATTAAAAAATATTTTATTCATGGTCAATCTGGAACATAATTACTGCATC
TTAAGTTTCCACTGATGTATATAGAAGGCTAAAGGCACAATTTTTATCAAATCTAGTAGAGTAACCAAACATAAAA
TCATTAATTACTTTCAACTTAATAACTAATTGACATTCCTCAAAAGAGCTGTTTTCAATCCTGATAGGTTCTTTAT
TTTTTCAAAATATATTTGCCATGGGATGCTAATTTGCAATAAGGCGCATAATGAGAATACCCCAAACTGGA 13722.4

GTTGGACCCCCAGGGACTGGAAAGACACTTCTTGCCCGAGCTGTGGCGGGAGAAGCTGATGTTCCTTTTTATTATG
CTTCTGGATCCGAATTTGATGAGATGTTTGTGGGTGTGGGAGCCAGCCGTATCAGAAATCTTTTTAGGGAAGCAAA
GGCGAATGCTCCTTGTGTTATATTTATTGATGAATTAGATTCTGTTGGTGGGAAGAGAATTGAATCTCCAATGCAT
CCATATTCAAGGCAGACCATAAATCAACTTCTTGCTGAAATGGATGGTTTTAAACCCAATGAAGGAGTTATCATAA
TAGGAGCCACAAACTTCCCAGAGGCATTAGATAATGCCTTAATACCGTCCTGGTCGTTTTGACATGCAAGTTACAG
TTCCAAGGCCAGATGTAAAAGGTCGAACAGAAATTTTGAAATGGTATCTCAATAAAATAAAGTTTGATCAATCCCG
TTGATCCAGAAATTATAGCCTCGAGGTACTGGTGGCTTTTCCGGAAGCAGAGTTGGGAGAATCTT 13724-13698-13748

GCCTACAACATCCAGAAAGAGTCTACCCTGCACCTGGTGCTSCGTCTCAGAGGTGGGATGCAGATCTTCGTGAAGA
CCCTGACTGGTAAGACCATCACTCTCGAAGTGGAGCCGAGTGACACCATYGAGAACGTCAAAGCAAAGATCCARGA
CAAGGAAGGCRTYCCTCCTGACCAGCAGAGGTTGATCTTTGCCGGAAAGCAGCTGGAAGATGGDCGCACCCTGTCT
GACTACAACATCCAGAAAGAGTCYACCCTGCACCTGGTGCTCCGTCTCAGAGGTGGGATGCARATCTTCGTGAAGA
CCCTGACTGGTAAGACCATCACCCTCGAGGTGGAGCCCAGTGACACCATCGAGAATGTCAAGGCAAAGATCCAAGA
TAAGGAAGGCATCCCTCCTGATCAGCAGAGGTTGATCTTTGCTGGGAAACAGCTGGAAGATGGACGCACCCTGTCT
GACTACAACATCCAGAAAGAGTCCACTCTGCACTTGGTCCTGCGCTTGAGGGGGGGTGTCTAAGTTTCCCCTTTTA
AGGTTTCMACAAATTTCATTGCACTTTCCTTTCAATAAAGTTGTTGCATTCCC

GAACTGGGCCCTGAGCCCAAGTCATGCCTTGTGTCCGCATCTGCCGTGTCACCTCTGTKCCTGCCCCTCACCCCTC
CCTCCTGGTCTTCTGAGCCAGCACCATCTCCAAATAGCCTATTCCTTCCTGCAAATCACACACACATGCGGGCCAC
ACATACCTGCTGCCCTGGAGATGGGGAAGTAGGAGAGATGAATAGAGGCCCATACATTGTACAGAAGGAGGGGCAG
GTGCAGATAAAAGCAGCAGACCCAGCGGCAGCTGAGGTGCATGGAGCACGGTTGGGGCCGGCATTGGGCTGAGCAC
CTGATGGGCCTCATCTCGTGAATCCTCGAGGCAGCGCCACAGCAGAGGAGTTAAGTGGCACCTGGGCCGAGCAGAG
CAGGAGACTGAGGGTCAGAGTGGAGGCTAAGCTGCCCTGGAACTCCTCAATCTTGCCTGCCCCCTAGTATGAAGCC
CCCTTCCTGCCCCTACAATTCCTGA 13732.1

ATGGATCTTACTTTGCCACCCAGGTTGGAGTGCAGTGCTGCAATCTTGGCTCACTGCAGCCTTAACCTCCCAGGCT
CAAGCTATCCTCCTGCCAAAGCCTTCCACATAGCTGGGACTACAGGTACACNGCCACCACACCCAGCTAAAATTTT
TGTATTTTTTGTAGAGACGGGATCTCGCCACGTTGCCCAGGCTGGTCCCATCCTGACCTCAAGCAGATCTGCCCAC
CTCAGCCCCCCAACGTGCTAGGATTACAGGCGTGAGCCACCGCACCCAGCCTTTGTTTTGCTTTTAATGGAATCAC
CAGTTCCCCTCCGTGTCTCAGCAGCAGCTGTGAGAAATGCTTTGCATCTGTGACCTTTATGAAGGGGAACTTCCAT
GCTGAATGAGGGTAGGATTACATGCTCCTGTTTCCCGGGGGTCAAGAAAGCCTCAGACTCCAGCATGATAAGCAGG
GTGAG 13732.2

ATAGGGGCTTTAAGGAGGGAATTCAGGTTCAATGAGGTCGTAAGGCCAGGGCTCTTATCCAGTAAGACTGGGGTCC
TTAGATGAGAAAGAGACACCCGAGGTCCTTCTCTCTGCCGTGTGAGGATGCATCAAGAAGGCGGCCGTCTGCAAGC
GAAGGAGAGGCCGCACCAGAAACCGACACCTTCATCTTGGACTTGCAGCCTCTAGAACTGAGAAAATAACTGTCTG
TTGGTTAAGCCACCCAGTTTGTAGTATTCTCTTATGGCTTCCTAAGCAGACTAACAAACAAACACCCAAAATTAAC
TGATGGCTTCGCTGTCTTCTGTAAAAATTGCTATGAGAGAACTTTTCACTCACTGTTTTGCAGTTTCTCCCTCAGT
CCCTGGTTCTTTCTTCTCACATAATCCCAATTTCAATTTATAGTTCATGGCCCAGGCAGAGTCATTCATCACGGCA
TCTCCTGAGCTAAACCAGCACCTGCTCTGCTCACTTCTTGACTGGCTGCTCATCATCAGCCCTCTTGCAGAGATTT
CATTTCCTCCCGTGCCAGGTACTTCACGCACCAAGCTCA

GGATAATGAAGTTGTTTTATTTAGCTTGGACAAAAAGGCATATTCCTCTATTTTCTTATACAACAAATATCCCCAA
AATAAAGCAAGCATATATATCTTGAATGTGTAATAATCCAGTGATAAACAAGAGCAGTACTTTAAAAGAAAAAAAA
ATATGTATTTCTGTCAGGTTAAAATGAGAATCAAAACCATTTACTCTGCTAACTCATTATTTTTTGCTTTCTTTTT
GGTTAAGAGAGGCAATGCAATACACTGAAAAAGGTTTTTATCTTATCTGGCATTGGAATTAGACATATTCAAACCC
CAGCCCCCATTTCCAAACTTTAAGACCACAAACAAGTAATTTACTTTTCTGAACATTGGTTTTTTCTGGAAAATGG
GAATTATAAAATAGACTTTGCAGACTCTTATGAGATTAAATAAGATAATGTATGAAATTCTTTCTTCTTTTTTACT
TCTTTTTCCTTTTTGAGATGGAGTCTCACCCCGTCACCCAGGCTGGAGTACAGTG 13735.2

CCACTGCACTCCAGCCTGGGTGACGGAGTGAGACTCTGTCTCAAAAAAACAAACAAACAAACAAACAAAAAACTGA
AAAGGAAATAGAGTTCCTCTTTCCTCATATATGAATATATTATTTCAACAGATTGTTGATCACCTACCATATGCTT
GGTATTGTTCTAATTGCTGGGGATACAGCAAGAGGTTCTGCAGAACTTCATGGAGCATGAAAGTAAATAAACAAAG
TTAATTTCAAGGCCAGGCATGGTTGCTCACACCTTTAGTCCCAGCACTTTGGGAGGCTGAGGCAGGTGGATCACTT
GGGCCCAGGAGTTCAAGGCTGCAGTGAGCCAAGATTGTGCCACTACTCTCCAGGCTGGGCAACAGAGCAAGACCCT
GTCTCAGGGGGAACAAAAAGTTAATTTCAGATTTTGTTAAGTGCTGTAAAGGAAGTAAATAGGTTGATATTCAAGA
GAGCACCTGAAGGCCAGGCGTGGTGGCTCACGCCTGTGGTCTAACGCTTTGGGAAGCCCGAGCGGGCGGATCACAA
GGTCAGGAGAATTTTGGCCAGGCATGGTG 13736.1

AGAATCCATTTATTGGGTTTTAAACTAGTTACACAACTGAAATCAGTTTGGCACTACTTTATACAGGGATTACGCC
TGTGTATGCCGACACTTAAATACTGTACCAGGACCACTGCTGTGCTTAGGTCTGTATTCAGTCATTCAGCATGTAG
ATACTAAAAATATACTGTAGTGTTCCTTTAAGGAAGACTGTACAGGGTGTGTTGCAAGATGACATTCACCAATTTG
TGAATTATTTCAACCCAGAAGATACCTTTCACTCTATAAACTTGTCATAGGCAAACATGTGGTGTTAGCATTGAGA
GATGCACACAAAAATGTTACATAAAAGTTCAGACATTCTAATGATAAGTGAACTGAAAAAAAAAAAAACCCCACAT
CTCAATTTTTGTAACAAGATAAAGAAAATAATTTAAAAACACAAAAAATGGCATTCAGTGGGTACAAAGCC 13737.1&2

CAAATATTTAATATAAATCTTTGAAACAAGTTCAGAKGAAATAAAAATCAAAGTTTGCAAAAACGTGAAGATTAAC
TTAATTGTCAAATATTCCTCATTGCCCCAAATCAGTATTTTTTTTATTTCTATGCAAAAGTATGCCTTCAAACTGC
TTAAATGATATATGATATGATACACAAACCAGTTTTCAAATAGTAAAGCCAGTCATCTTGCAATTGTAAGAAATAG
GTAAAAGATTATAAGACACCTTACACACACACACACACACACACACACACGTGTGCACcGCCAATGACAAAAAACA
ATTTGGCCTCTCCTAAAATAAGAACATGAAGACCCTTAATTGCTGCCAGGAGGGAACACTGTGTCACCCCTCCCTA
CAATCCAGGTAGTTTCCTTTAATCCAATAGCAAATCTGGGCATATTTGAGAGGAGTGATTCTGACAGCCACSGTTG
AAATCCTGTGGGGAACCATTCATGTCCACCCACTGGTGCCCTGAAAAAATGCCAATAATTTTTCGCTCCCACTTCT
GCTGCTGTCTCTTCCACATCCTCACATAGACCCCAGACCCGCTGGCCCCTGGCTGGGCATCGCATTGCTGGTAGAG
CAAGTCATAGGTCTCGTCTTTGACGTCACAGAAGCGATACACCAAATTGCCTGGTCGGTCATTGTCATAACCAG

TTTGACTTTAGTAGGGGTCTGAACTATTTATTTTACTTTGCCMGTAATATTTARACCYTATATATCTTTCATTATG
CCATCTTATCTTCTAATGBCAAGGGAACAGWTGCTAAMCTGGCTTCTGCATTWATCACATTAAAAATGGCTTTCTT
GGAAAATCTTCTTGATATGAATAAAGGATCTTTTAVAGCCATCATTTAAAGCMGGNTTCTCTCCAACACGAGTCTG
CTSASGGGGGGKGAGCTGTGAACTCTGGCTGAAGGCTTTCCCATACACACTGCAATGACMTGGTTTCTGACCAGBG
TGAGTTA 13738.2

AGAGAAGCCCCATAAATGCAATCAGTGTGGGAAGGCCTTCAGTCAGAGCTCAAGCCTTTTCCTCCATCATCGGGTT
CATACTGGAGAGAAACCCTATGTATGTAATGAATGCGGCAGAGCCTTTGGTTTTAACTCTCATCTTACTGAACACG
TAAGGATTCACACAGGAGAAAAACCCTATGTTTGTAATGAGTGCGGCAAAGCCTTTCGTCGGAGTTCCACTCTTGT
TCAGCATCGAAGAGTTCACACTGGGGAGAAGCCCTACCAGTGCGTTGAATGTGGGAAAGCTTTCAGCCAGAGCTCC
CAGCTCACCCTACATCAGCCGAGTTCACACTGGAGAGAAGCCCTATGACTGTGGTGACTGTGGGAAGGCCTTCAGC
CGGAGGTCAACCCTCATTCAGCATCAGAAAGTTCACAGCGGAGAGACTCGTAAGTGCAGAAAACATGGTCCAGCCT
TTGTTCATGGCTCCAGCCTCACAGCAGATGGACAGATTCCCACTGGAGAGAAGCACGGCAGAACCTTTAACCATGG
TGCAAATCTCATTCTGCGCTGGACAGTTC 13739.1&2

GAGACAGGGTCTCACTTTGTCACCCAGGCTGGAATGCAGTGGTGCGATCTTACGTAGCTCACTGCAGCCCTGACCT
CCTGGACTCAAACAATTCTCCTGCCTCAGCCCTGCAAGTAGCTGGGACTGTGGGTGCATGCCACCATGCCTGGCTA
ACTTTTGTAGTTTTTGTAAAGATGGGGTTTTGCCATGTTGCACATGCTGGTCTTGAACTCCTGAGCTCAAACGATC
TGCCCACCTCGGCCTCCCAGAATGTTGGGATTACAGGGGTAAACCACCACGCCTGGCCCCATTAGGGTATTCTTAG
CATCCACTTGCTCACTGAGATTAATCATAAGAGATGATAAGCACTGGAAGAAAAAAATTTTTACTAGGCTTTGGAT
ATTTTTTTCCTTTTTCAGCTTTATACAGAGGATTGGATCTTTAGTTTTCCTTTAACTGATAATAAAACATTGAAAG
GAAATAAGTTTACCTGAGATTCACAGAGATAACCGGCATCACTCCCTTGCTCAATTCCAGTCTTTACCACATCAAT
TATTTTCAGAGGTGCAGGATAAAGGCCTTTAGTCTGCTTTCGCACTTTTTCTTCCACTTTTTTGTAAACCTGTTGC
CTGACAAATGGAATTGACAGCGTATGCCATGACTATTCCATTTGTCAGGCATACGCTGTCAATTTTTCCACCAATC
CCTTGTCTCTCTTTGGAGAGATCTTCTTATCAGCTAGTCCTTTGGCAAAAGTAATTGCAACTTCTTCTAGGTATTC
TATTGTCCGTTCCACTGGTGGAACCCCTGGGACCAGGACTAAAACCTCCAG 13741.1

ATCTCATATATATATTTCTTCCTGACTTTATTTGCTTGCTTCTGNCACGCATTTAAAATATCACAGAGACCAAAAT
AGAGCGGCTTTCTGGTGGAACGCATGGCAGTCACAGGACAAAATACAAAACTAGGGGGCTCTGTCTTCTCATACAT
CATACAATTTTCAAGTATTTTTTTTATGTACAAAGAGCTACTCTATCTGAAAAAAAATTAAAAAATAAATGAGACA
AGATAGTTTATGCATCCTAGGAAGAAAGAATGGGAAGAAAGAACGGGGCAGTTGGGTACAGATTCCTGTCCCCTGT
TCCCAGGGACCACTACCTTCCTGCCACTGAGTTCCCCCACAGCCTCACCCATCATGTCACAGGGCAAGTGCCAGGG
TAGGTGGGGACCAGTGGAGACAGGAACCAGCAACATACTTTGGCCTGGAAGATAAGGAGAAAGTCTCAGAAACACA
CTGGTGGGAAGCAATCCCACNGGCCGTGCCCCANGAGCTTCCCACCTGCTGCTGGCTCCCTGGGTGGCTTTGGGAA
CAGCTTGGGCAGGCCCTTTTGGGTGGGGNCCAACTGGGCCTTTGGGCCCGTGTGGAAAG

AAACATTGAGATGGAATGATAGGGTTTCCCAGAATCAGGTCCATATTTTAACTAAATGAAAATTATGATTTATAGC
CTTCTCAAATACCTGCCATACTTGATATCTCAACCAGAGCTAATTTTACCTCTTTACAAATTAAATAAGCAAGTAA
CTGGATCCACAATTTATAATACCTGTCAATTTTTTCTGTATTAAACCTCTATCATAGTTTAAGCCTATTAGGGTAC
TTAATCCTTACAAATAAACAGGTTTAAAATCACCTCAATAGGCAACTGCCCTTCTGGTTTTCTTCTTTGACTAAAC
AATCTGAATGCTTAAGATTTTCCACTTTGGGTGCTAGCAGTACACAGTGTTACACTCTGTATTCCAGACTTCTTAA
ATTATAGAAAAAGGAATGTACACTTTTTGTATTCTTTCTGAGCAGGGCCGGGAGGCAACATCATCTACCATGGTAG
GGACTTGTATGCATGGACTACTTTA 14351.1

ACTCTGTCGCCCAGGCTGGAGCCCABTGGMGCGATCTCGACTCCCTGCAAGCTMCGCCTCACAGGWTCATGCCATT
CTCCTGCCTCAGCATCTGGAGTAGCTGGGACTACAGGCGCCAGCCACCATGCCCAGCTAATTTTT 14351.2

ACCTTAAAGACATAGGAGAATTTATACTGGGAGAGAAAGCTTACAAATGTAAGGTTTCTGACAAGACTTGGGAGTG
ATTCACACCTGGAACAACATACTGGACTTCACACTGGABAGAAACCTTACAAGTGTAATGAGTGTGGCAAAGCCTT
TGGCAAGCAGTCAACACTTATTCACCATCAGGCAATTCA 14354.2

AGTCAGGATCATGATGGCTCAGTTTCCCACAGCGATGAATGGAGGGCCAAATATGTGGGCTATTACATCTGAAGAA
CGTACTAAGCATGATAAACAGTTTGATAACCTCAAACCTTCAGGAGGTTACATAACAGGTGATCAAGCCCGTACTT
TTTTCCTACAGTCAGGTCTGCCGGCCCCGGTTTTAGCTGAAATATGGGCCTTATCAGATCTGAACAAGGATGGGAA
GATGGACCAGCAAGAGTTCTCTATAGCTATGAAACTCATCAAGTTAAAGTTGCAGGGCCAACAGCTGCCTGTAGTC
CTCCCTCCTATCATGAAACAACCCCCTATGTTCTCTCCACTAATCTCTGCTCGTTTTGGGATGGGAAGCATGCCCA
ATCTGTCCATTCATCAGCCATTGCCTCCAGTTGCACCTATAGCAACACCCTTGTCTTCTGCTACTTCAGGGACCAG
TATTCCTCCCTAATGATGCCTGCT 14354.1

CTTTCGATTTCCTTCAATTTGTCACGTTTGATTTTATGAAGTTGTTCAAGGGCTAACTGCTGTGTATTATAGCTTT
CTCTGAGTTCCTTCAGCTGATTGTTAAATGAATCCATTTCTGAGAGCTTAGATGCAGTTTCTTTTTCAAGAGCATC
TAATTGTTCTTTAAGTCTTTGGCATAATTCTTCCTTTTCTGATGACTTTCTATGAAGTAAACTGATCCCTGAATCA
GGTGTGTTACTGAGCTGCATGTTTTTAATTCTTTCGTTTAATAGCTGCTTCTCAGGGACCAGATAGATAAGCTTAT
TTTGATATTCCTTAAGCTCTTGGTGAAGTTGTTCGATTTCCATAATTTCCAGGTCACACTGGTTATCCCAAACTTC
T

TGGAGGTGAAACGGAGGCAAGAAAGGGGGCTACCTCAGGAGCGAGGGACAAAGGGGGCGTGAGGCACCTAGGCCGC
GGCACCCCGGCGACAGGAAGCCGTCCTGAACCGGGCTACCGGGTAGGGGAAGGGCCCGCGTAGTCCTCGCAGGGCC
CCAGAGCTGGAGTCGGCTCCACAGCCCCGGGCCGTCGGCTTCTCACTTCCTGGACCTCCCCGGCGCCCGGGCCTGA
GGACTGGCTCGGCGGAGGGAGAAGAGGAAACAGACTTGAGCAGCTCCCCGTTGTCTCGCAACTCCACTGCCGAGGA
ACTCTCATTTCTTCCCTCGCTCCTTCACCCCCCACCTCATGTAGAAAGGTGCTGAAGCGTCCGGAGGGAAGAAGAA
CCTGGGCTACCGTCCTGGCCTTCCCMCCCCCTTCCCGGGGCGCTTTGGTGGGCGTGGAGTTGGGGTTGGGGGGGTG
GGTGGGGGTTCTTTTTTGGAGTGCTGGGGAACTTTTTTCCCTTCTTCAGGTCAGGGGAAAGGGAATGCCCAATTCA
GAGAGACATGGGGGCAAGAAGGACGGGAGTGGAGGAGCTTCTGGAACTTTGCAGCCGTCATCGGGAGGCGGCAGCT
CTAACAGCAGAGAGCGTCACCGCTTGGTATCGAAGCACAAGCGGCATAAGTCCAAACACTCCAAAGACATGGGGTT
GGTGACCCCCGAAGCAGCATCCCTGGGCACAGTTATCAAACCTTTGGTGGAGTATGATGATATCAGCTCTGATTCC
GACACCTTCTCCGATGACATGGCCTTCAAACTAGACCGAAGGGAGAACGACGAACGTCGTGGATCAGATCGGAGCG
ACCGCCTGCACAAACATCGTCACCACCAGCACAGGCGTTCCCGGGACTTACTAAAAGCTAAACAGACCG 16432-1

GACATGTTTGCCTGCAGGGGACCAGAGACAATGGGATTAGCCAGTGCTCACTGTTCTTTATGCTTCCAGAGAGGAT
GGGGACAGCTCTCAGGTCAGAATCCAGGCTGAGAAGGCCATGCTGGTTGGGGGCCCCCGGAAGCACGGTCCGGATC
CTCCCTGGCATCAGCGTAGACCCGCTGCTCAGGCTTGGGGTACCAAACTCATGCTCTGTACTGTTTTGGCCCCATG
CGGTGAGAGGAAAACCTAGAAAAAGATTGGTCGTGCTAAGGAATCAGCTGCCCCCTCATCCTCCGCATCCAATGCT
GGTGACAACATATTCCCTCTCCCAGGACACAGACTCGGTGACTCCACACTGGGCTGAGTGGCCTCTGGAGGCTCGT
GGCCTAAGGCAGGGCTCCGTAAGGCTGATCGGCTGAACTGGGTGGGGTGAGGGTTTCTGACCCTTCGCTTCCCATC
CCATAACCGCTGTCAATGAGCTCACACTGTGGTCA 16432-2

GATGGCATGGTCGTTGCTAATGTGCCTGCTGGGATGGAGCACTTCCTCCTGTGAGCCCAGGGGACCCGCCTGTCCC
TGGAGCTTGGGGCAAGGAGGGAAGAGTGATACCAGGAAGGTGGGGCTGCAGCCAGGGGCCAGAGTCAGTTCAGGGA
GTGGTCCTCGGCCCTCAAAGCTCCTCCGGGGACTGCTCAGGAGTGATGGTGCCCTGGAGTTTGCCCCAACTTCCCT
GGCCACCCTGGAAGGTGCCTGGCTGCTCCAGGCCTCTAGGCTGGGCTGATGGGTTTCTCCAGGACACAAGTATCAT
TAAAGCCACCCTCTCCTCAGCTTGTCAGGCCGCACATGTGGGACAGGCTGTGCTCACAACCCCCTCGCCTGCCCTG
CCCTCCATCAGGAGGAGCCAGTGGAACCTTCGGAAAGCTCCCAGCATCTCAGCAGCCCTCAAAAGTCGTCCTGGGG
CAAGCTCTGGTTCTCCTGACTGGAGGTCATCTGGGCTTGGCCTGCTCTCTCTCGC 17184.3

TAAAAAAGTGTAACAAAGGTTTATTTAGACTTTCTTCATGCCCCCAGATCCAGGATGTCTATGTAAACCGTTATCT
TACAAAGAAAGCACAATATTTGGTATAAACTAAGTCAGTGACTTGCTTAACTGAAATAGCGTCCATCCAAAAGTGG
GTTTAAGGTAAAACTACCTGACGATATTGGCGGGGATCCTGCAGTTTGGACTGCTTGCCGGGTTTGTCCAGGGTTC
CGGGTCTGTTCTTGGCACTCATGGGGACAGGCATCCTGCTCGTCTGTGGGGCCCCGCTGGAGCCCTTACGTGAAGC
TGAAGGTATCGACCSTAGGGGGCTCTAGGGCAGTGGGACCTTCATCCGGAACTAACAAGGGTCGGGGAGAGGCCTC
TTGGGCTATGTGGG

CAAGCGTTCCTTTATGGATGTAAATTCAAACAGTCATGCTGAGCCATCCCGGGCTGACAGTCACGTTWAAGACACT
AGGTCGGGCGCCACAGTGCCACCCAAGGAGAAGAAGAATTTGGAATTTTTCCATGAAGATGTACGGAAATCTGATG
TTGAATATGAAAATGGCCCCCAAATGGAATTCCAAAAGGTTACCACAGGGGCTGTAAGACCTAGTGACCCTCCTAA
GTGGGAAAGAGGAATGGAGAATAGTATTTCTGATGCATCAAGAACATCAGAATATAAAACTGAGATCATAATGAAG
GAAAATTCCATATCCAATATGAGTTTACTCAGAGACAGTAGAAACTATTCCCAGG 17185.1

TAGGAATAACAAATGTTTATTCAGAAATGGATAAGTAATACATAATCACCCTTCATCTCTTAATGCCCCTTCCTCT
CCTTCTGCACAGGAGACACAGATGGGTAACATAGAGGCATGGGAAGTGGAGGAGGACACAGGACTAGCCCACCACC
TTCTCTTCCCGGTCTCCCAAGATGACTGCTTATAGAGTGGAGGAGGCAAACAGGTCCCCTCAATGTACCAGATGGT
CACCTATAGCACCAGCTCCAGATGGCCACGTGGTTGCAGCTGGACTCAATGAAACTCTGTGACAACCAGAAGATAC
CTGCTTTGGGATGAGAGGGAGGATAAAGCCATGCAGGGAGGATATTTACCATCCCTACCCTAAGCACAGTGCAAGC
AGTGAGCCCCCGGCTCCCAGTACCTGAAAAACCAAGGCCTACTGNCTTTTGGATGCTCTCTTGGGCCACG 17188.2

AAGCCTCCTGCCCTGGAAATCTGGAGCCCCTTGGAGCTGAGCTGGACGGGGCAGGGAGGGGCTGAGAGGCAAGACC
GTCTCCCTCCTGCTGCAGCTGCTTCCCCAGCAGCCACTGCTGGGCACAGCAGAAACGCCAGCAGAGAAAATGGGAG
CCGAGAGTCCTTAGCCCTGGAGCTGAGGCTGCCTCTGGGCTGACCCGCTGGCTGTACGTGGCCAGAACTGGGGTTG
GCATCTGGCATCCATTTGAGGCCAGGGTGGAGGAAAGGGAGGCCAACAGAGGAAAACCTATTCCTGCTGTGACAAC
ACAGCCCTTGTCCCACGCAGCCTAAGTGCAGGGAGCGTGATGAAGTCAGGCAGCCAGTCGGGGAGGACGAGGTAAC
TCAGCAGCAATGTCACCTTGTAGCCTATGCGCTCAATGGCCCGGAGGGGCAGCAACCCCCCGCACACGTCAGCCAA
CAGCAGTGCCTCTGCAGGCACCAAGAGAGCGATGATGGACTTGAGCGCCGTGTTC 17190.1

GTTTGGCAGAAGACATGTTTAATAACATTTTCATATTTAAAAAATACAGCAACAATTCTCTATCTGTCCACCATCT
TGCCTTGCCCTTCCTGGGGCTGAGGCAGACAAAGGAAAGGTAATGAGGTTAGGGCCCCCAGGCGGGCTAAGTGCTA
TTGGCCTGCTCCTGCTCAAAGAGAGCCATAGCCAGCTGGGCACGGCCCCCTAGCCCCTCCAGGTTGCTGAGGCGGC
AGCGGTGGTAGAGTTCTTCACTGAGCCGTGGGCTGCAGTCTCGCAGGGAGAACTTCTGCACCAGCCCTGGCTCTAC
GGCCCGAAAGAGGTGGAGCCCTGAGAACCGGAGGAAAACATCCATCACCTCCAGCCCCTCCAGGGCTTCCTCCTCT
TCCTGGCCTGCCAGTTCACCTGCCAGCCGGGCTCGGGCCGCCAGGTAGTCAGCGTTGTAGAAGCAGCCCTCCGCAG
AAGCCTGCCGGTCAAATCTCCCCGCTATAGGAGCCCCCCGGGAGGGGTCAGCACC

CAAGTTGAACGTCAGGCTTGGCAGAGGTGGAGTGTAGATGAAAACAAAGGTGTGATTATGAAGAGGATGTGAGTCC
TTTGGGTGTAGGAGAGAAAGGCTGTTGAGCTTCTATTTCAAGATACTTTTACCTGTGCAAAAAGCACATTTTCCAC
CTCCTTCTCATGGCATTTGTGTAAGGTGAGTATGATTCCTATTCCATCTGCATTTTAGAGGTGAAGAATAACGTAC
AAGGGATTCAGTGATTAGCAAGGGACCCCTCACTAAGTGTTGATGGAGTTAGGACAGAGCTCAGCTGTTTGAATCT
CAGAGCCCAGGCAGCTGGAGCTGGGTAGGATCCTGGAGCTGGCACTAATGTGAGGTGCATTCCCTCCAACCCAGGC
TCAGATCCGGAACCTGACCGTGCTGACCCCCGAAGGGGAGGCAGGGCTGAGCTGGCCCGTTGGGCTCCCTGCTCCT
TTCACACCACACTCTCGCTTTGAGGTGCTGGGCTGGGACTACTTCACAGAGCAGC 17191.2&89.2

TGGCCTGGGCAGGATTGGGAGAGAGGTAGCTACCCGGATGCAGTCCTTTGGGATGAAGACTATAGGGTATGACCCC
ATCATTTCCCCAGAGGTCTCGGCCTCCTTTGGTGTTCAGCAGCTGCCCCTGGAGGAGATCTGGCCTCTCTGTGATT
TCATCACTGTGCACACTCCTCTCCTGCCCTCCACGACAGGCTTGCTGAATGACAACACCTTTGCCCAGTGCAAGAA
GGGGGTGCGTGTGGTGAACTGTGCCCGTGGAGGGATCGTGGACGAAGGCGCCCTGCTCCGGGCCCTGCAGTCTGGC
CAGTGTGCCGGGGCTGCACTGGACGTGTTTACGGAAGAGCCGCCACGGGACCGGGCCTTGGTGGACCATGAGAATG
TCATCAGCTGTCCCCACCTGGGTGCCAGCACCAAGGAGGCTCAGAGCCGCTGTGGGGAGGAAATTGCTGTTCAGTT
CGTGGACATGGTGAAGGGGAAATCTCTCACGGGGGTTGTGAATGCCCAGGCCCTT

*Fig. 1S*

AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTAC
ATCCTCATTACCAAATGGAACTGCCAGTCTCATTCAGCCTTTATCCATTCCTTATTCTTCTTCAACATTGCCTCAT
GCATCATCTTACAGCCTGATGATGGGAGGATTTGGTGGTGCTAGTATCCAGAAGGCCCAGTCTCTGATTGATTTAG
GATCTAGTAGCTCAACTTCCTCAACTGCTTCCCTCTCAGGGAACTCACCTAAGACAGGGACCTCAGAGTGGGCAGT
TCCTCAGCCTTCAAGATTAAAGTATCGGCAAAAATTTAATAGTCTAGACAAAGGCATGAGCGGATACCTCTCAGGT
TTTCAAGCTAGAAATGCCCTTCTTCAGTCAAATCTCTCTCAAACTCAGCTAGCTACTATTTGGACTCTGGCTGACA
TCGATGGTGACGGACAGTTGAAAGCTGAAGAATTTATTCTGGCGATGCACCTCACTGACATGGCCAAAGCTGGACA
GCCACTACCACTGACGTTGCCTCCCGAGCTTGTCCCTCCATCTTTCAGAGGGGGAAAGCAAGTTGATTCTGTTAAT
GGAACTCTGCCTTCATATCAGAAAACACAAGAAGAAGAGCCTCAGAAGAAACTGCCAGTTACTTTTGAGGACAAAC
GGAAAGCCAACTATGAACGAGGAAACATGGAGCTGGAGAAGCGACGCCAAGTGTTGATGGAGCAGCAGCAGAGGGA
GGCTGAACGCAAAGCCCAGAAAGAGAAGGAAGAGTGGGAGCGGAAACAGAGAGAACTGCAAGAGCAAGAATGGAAG
AAGCAGCTGGAGTTGGAGAAACGCTTGGAGAAACAGAGAGAGCTGGAGAGACAGCGGGAGGAAGAGAGGAGAAAGG
AGATAGAAAGACGAGAGGCAGCAAAACAGGAGCTTGAGAGACAACGCCGTTTAGAATGGGAAAGACTCCGTCGGCA
GGAGCTGCTCAGTCAGAAGACCAGGGAACAAGAAGACATTGTCAGGCTGAGCTCCAGAAAGAAAAGTCTCCACCTG
GAACTGGAAGCAGTGAATGGAAAACATCAGCAGATCTCAGGCAGACTACAAGATGTCCAAATCAGAAAGCAAACAC
AAAAGACTGAGCTAGAAGTTTTGGATAAACAGTGTGACCTGGAAATTATGGAAATCAAACAACTTCAACAAGAGCT
TAAGGAATATCAAAATAAGCTTATCTATCTGGTCCCTGAGAAGCAGCTATTAAACGAAAGAATTAAAAACATGCAG
CTCAGTAACACACCTGATTCAGGGATCAGTTTACTTCATAAAAAGTCATCAGAAAAGGAAGAATTATGCCAAAGAC
TTAAAGAACAATTAGATGCTCTTGAAAAAGAAACTGCATCTAAGCTCTCAGAAATGGATTCATTTAACAATCAGCT
GAAGGAACTCAGAGAAAGCTATAATACACAGCAGTTAGCCCTTGAACAACTTCATAAAATCAAACGTGACAAATTG
AAGGAAATCGAAAGAAAAAGATTAGAGCAAAAAAAAAAAAA

*Fig. 2A*

ATGGCAGTGACATTCACCATCATGGGAACCACCTTCCCTTTTCTTCAGGATTCTCTGTAGTGGAAGAGAGCACCCA
GTGTTGGGCTGAAAACATCTGAAAGTAGGGAGAAGAACCTAAAATAATCAGTATCTCAGAGGGCTCTAAGGTGCCA
AGAAGTCTCACTGGACATTTAAGTGCCAACAAAGGCATACTTTCGGAATCGCCAAGTCAAAACTTTCTAACTTCTG
TCTCTCTCAGAGACAAGTGAGACTCAAGAGTCTACTGCTTTAGTGGCAACTACAGAAAACTGGTGTTACCCAGAAA
AACAGGAGCAATTAGAAATGGTTCCAATATTTCAAAGCTCCGCAAACAGGATGTGCTTTCCTTTGCCCATTTAGGG
TTTCTTCTCTTTCCTTTCTCTTTATTAACCACTA

*Fig. 2B*

ATATCTAGAAGTCTGGAGTGAGCAAACAAGAGCAAGAAACAAAAAGAAGCCAAAAGCAGAAGGCTCCAATATGAAC
AAGATAAATCTATCTTCAAAGACATATTAGAAGTTGGGAAAATAATTCATGTGAACTAGACAAGTGTGTTAAGAGT
GATAAGTAAAATGCACGTGGAGACAAGTGCATCCCCAGATCTCAGGGACCTCCCCCTGCCTGTCACCTGGGGAGTG
AGAGGACAGGATAGTGCATGTTCTTTGTCTCTGAATTTTTAGTTATATGTGCTGTAATGTTGCTCTGAGGAAGCCC
CTGGAAAGTCTATCCCAACATATCCACATCTTATATTCCACAAATTAAGCTGTAGTATGTACCCTAAGACGCTGCT
AATTGACTGCCACTTCGCAACTCAGGGGCGGCTGCATTTTAGTAATGGGTCAAATGATTCACTTTTTATGATGCTT
CCAAAGGTGCCTTGGCTTCTCTTCCCAACTGACAAATGCCAAAGTTGAGAAAAATGATCATAATTTTAGCATAAAC
AGAGCAGTCGGCGACACCGATTTTATAAATAAACTGAGCACCTTCTTTTTAAACAAACAAATGCGGGTTTATTTCT
CAGATGATGTTCATCCGTGAATGGTCCAGGGAAGGACCTTTCACCTTGACTATATGGCATTATGTCATCACAAGCT
CTGAGGCTTCTCCTTTCCATCCTGCGTGGACAGCTAAGACCTCAGTTTTCAATAGCATCTAGAGCAGTGGGACTCA
GCTGGGGTGATTTCGCCCCCCATCTCCGGGGGAATGTCTGAAGACAATTTTGTTACCTCAATGAGGGAGTGGAGGA
GGATACAGTGCTACTACCAACTAGTGGATAAAGGCCAGGGATGCTGCTCAACCTCCTACCATGTACAGGACGTCTC
CCCATTACAACTACCCAATCCGAAGTGTCAACTGTGTCAGGACTAAGAAACCCTGGTTTTGAGTAGAAAAGGGCCT
GGAAAGAGGGGAGCCAACAAATCTGTCTGCTTCCTCACATTAGTCATTGGCAAATAAGCATTCTGTCTCTTTGGCT
GCTGCCTCAGCACAGAGAGCCAGAACTCTATCGGGCACCAGGATAACATCTCTCAGTGAACAGAGTTGACAAGGCC
TATGGGAAATGCCTGATGGGATTATCTTCAGCTTGTTGAGCTTCTAAGTTTCTTTCCCTTCATTCTACCCTGCAAG
CCAAGTTCTGTAAGAGAAATGCCTGAGTTCTAGCTCAGGTTTTCTTACTCTGAATTTAGATCTCCAGACCCTTCCT
GGCCACAATTCAAATTAAGGCAACAAACATATACCTTCCATGAAGCACACACAGACTTTTGAAAGCAAGGACAATG
ACTGCTTGAATTGAGGCCTTGAGGAATGAAGCTTTGAAGGAAAAGAATACTTTGTTTCCAGCCCCCTTCCCACACT
CTTCATGTGTTAACCACTGCCTTCCTGGACCTTGGAGCCACGGTGACTGTATTACATGTTGTTATAGAAAACTGAT
TTTAGAGTTCTGATCGTTCAAGAGAATGATTAAATATACATTTCCTA

*Fig. 2C*

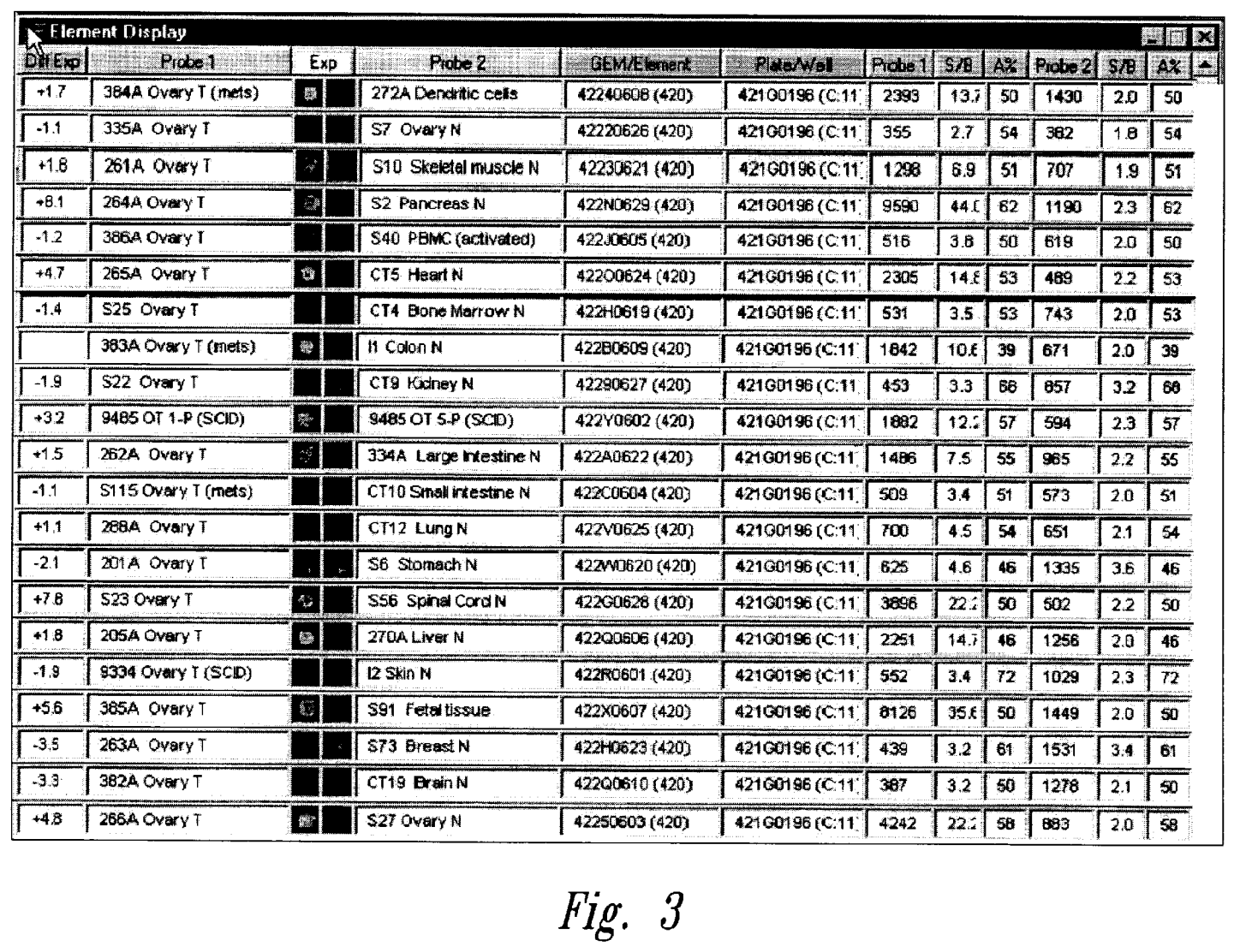

Element Display

| Diff Exp | Probe 1 | Exp | Probe 2 | GEM/Element | Plate/Well | Probe 1 | S/B | A% | Probe 2 | S/B | A% |
|---|---|---|---|---|---|---|---|---|---|---|---|
| +1.7 | 384A Ovary T (mets) | | 272A Dendritic cells | 42240608 (420) | 421G0196 (C:11 | 2393 | 13.7 | 50 | 1430 | 2.0 | 50 |
| -1.1 | 335A Ovary T | | S7 Ovary N | 42220626 (420) | 421G0196 (C:11 | 355 | 2.7 | 54 | 382 | 1.8 | 54 |
| +1.8 | 261A Ovary T | | S10 Skeletal muscle N | 42230621 (420) | 421G0196 (C:11 | 1298 | 6.9 | 51 | 707 | 1.9 | 51 |
| +8.1 | 264A Ovary T | | S2 Pancreas N | 422N0629 (420) | 421G0196 (C:11 | 9590 | 44. | 62 | 1190 | 2.3 | 62 |
| -1.2 | 386A Ovary T | | S40 PBMC (activated) | 422J0605 (420) | 421G0196 (C:11 | 516 | 3.8 | 50 | 619 | 2.0 | 50 |
| +4.7 | 265A Ovary T | | CT5 Heart N | 422O0624 (420) | 421G0196 (C:11 | 2305 | 14. | 53 | 489 | 2.2 | 53 |
| -1.4 | S25 Ovary T | | CT4 Bone Marrow N | 422H0619 (420) | 421G0196 (C:11 | 531 | 3.5 | 53 | 743 | 2.0 | 53 |
| | 383A Ovary T (mets) | | I1 Colon N | 422B0609 (420) | 421G0196 (C:11 | 1642 | 10. | 39 | 671 | 2.0 | 39 |
| -1.9 | S22 Ovary T | | CT9 Kidney N | 42290627 (420) | 421G0196 (C:11 | 453 | 3.3 | 66 | 857 | 3.2 | 66 |
| +3.2 | 9485 OT 1-P (SCID) | | 9485 OT 5-P (SCID) | 422Y0602 (420) | 421G0196 (C:11 | 1882 | 12. | 57 | 594 | 2.3 | 57 |
| +1.5 | 262A Ovary T | | 334A Large Intestine N | 422A0622 (420) | 421G0196 (C:11 | 1486 | 7.5 | 55 | 965 | 2.2 | 55 |
| -1.1 | S115 Ovary T (mets) | | CT10 Small intestine N | 422C0604 (420) | 421G0196 (C:11 | 509 | 3.4 | 51 | 573 | 2.0 | 51 |
| +1.1 | 288A Ovary T | | CT12 Lung N | 422V0625 (420) | 421G0196 (C:11 | 700 | 4.5 | 54 | 651 | 2.1 | 54 |
| -2.1 | 201A Ovary T | | S6 Stomach N | 422W0620 (420) | 421G0196 (C:11 | 625 | 4.6 | 46 | 1335 | 3.6 | 46 |
| +7.8 | S23 Ovary T | | S56 Spinal Cord N | 422G0628 (420) | 421G0196 (C:11 | 3896 | 22. | 50 | 502 | 2.2 | 50 |
| +1.8 | 205A Ovary T | | 270A Liver N | 422Q0606 (420) | 421G0196 (C:11 | 2251 | 14.7 | 46 | 1256 | 2.0 | 46 |
| -1.9 | 9334 Ovary T (SCID) | | I2 Skin N | 422R0601 (420) | 421G0196 (C:11 | 552 | 3.4 | 72 | 1029 | 2.3 | 72 |
| +5.6 | 385A Ovary T | | S91 Fetal tissue | 422X0607 (420) | 421G0196 (C:11 | 8126 | 35. | 50 | 1449 | 2.0 | 50 |
| -3.5 | 263A Ovary T | | S73 Breast N | 422H0623 (420) | 421G0196 (C:11 | 439 | 3.2 | 61 | 1531 | 3.4 | 61 |
| -3.3 | 382A Ovary T | | CT19 Brain N | 422Q0610 (420) | 421G0196 (C:11 | 387 | 3.2 | 50 | 1278 | 2.1 | 50 |
| +4.8 | 266A Ovary T | | S27 Ovary N | 42250603 (420) | 421G0196 (C:11 | 4242 | 22. | 58 | 883 | 2.0 | 58 |

*Fig. 3*

TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT

*Fig. 4*

TAGCGYGGTCGCGGCCGAGGYCTGCTTYTCTGTCCAGCCCAGGGCCTGTGGGGTCAGGGCGGTGGGTGCAGATGGC
ATCCACTCCGGTGGCTTCCCCATCTTTCTCTGGCCTGAGCAAGGTCAGCCTGCAGCCAGAGTACAGAGGGCCAACA
CTGGTGTTCTTGAACAAGGGCCTTAGCAGGCCCTGAAGGRCCCTCTCTGTAGTGTTGAACTTCCTGGAGCCAGGCC
ACATGTTCTCCTCATACCGCAGGYTAGYGATGGTGAAGTTGAGGGTGAAATAGTATTMANGRAGATGGCTGGCARA
CCTGCCCGGGCGGCCGCTCSAAATCC

*Fig. 5*

AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA

*Fig. 6*

TTGGGGNTTTMGAGCGGCCGCCCGGGCAGGTACCGGGGTGGTCAGCGAGGAGCCATTCACACTGAACTTCACCATC
AACAACCTGCGGTATGAGGAGAACATGCAGCACCCTGGCTCCAGGAAGTTCAACACCACGGAGAGGGTCCTTCAGG
GCCTGCTCAGGTCCCTGTTCAAGAGCACCAGTGTTGGCCCTCTGTACTCTGGCTGCAGACTGACTTTGCTCAGACT
TGAGAAACATGGGGCAGCCACTGGAGTGGACGCCATCTGCACCCTCCGCCTTGATCCCACTGGTCCTGGACTGGAC
AGAGAGCGGCTATACTGGGAGCTGAGCCAGTCCTCTGGCGGNGACNCCNCTT

*Fig. 7A*

AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA

*Fig. 7B*

TGTGGTGTTGAACTTCCTGGAGNCAGGGTGACCCATGTCCTCCCCATACTGCAGGTTGGTGATGGTGAAGTTGAGG
GTGAATGGTACCAGGAGAGGGCCAGCAGCCATAATTGTSGRGCKGSMGMSSGAGGMWGGWGTYYCWGAGGTTCYRA
RRTCCACTGTGGAGGTCCCAGGAGTGCTGGTGGTGGGCACAGAGSTCYGATGGGTGAAACCATTGACATAGAGACT
GTTCCTGTCCAGGGTGTAGGGGCCCAGCTCTTYRATGYCATTGGYCAGTTKGCTYAGCTCCCAGTACAGCCRCTCT
CKGYYGMGWCCAGSGCTTTTGGGGTCAAGATGATGGATGCAGATGGCATCCACTCCAGTGGCTGCTCCATCCTTCT
CGGACCTGAGAGAGGTCAGTCTGCAGCCAGAGTACAGAGGGCCAACACTGGTGTTCTTTGAATA

*Fig. 8*

TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG

*Fig. 9*

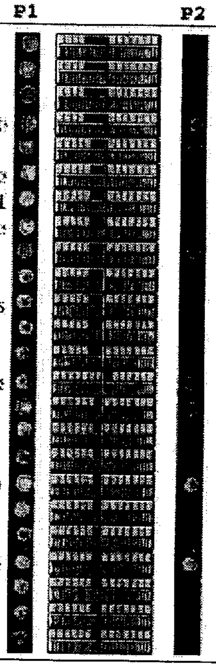

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 42IO0188 {D3} | +7.0 | 205A Ovary T | | | 270A Liver N | 422Q0606 | 8620 | 1240 | 57.7 | 65 | 2.2 | 65 |
| 42IO0188 {D3} | +5.9 | S23 Ovary T | | | S56 Spinal Cord N | 422G0628 | 5894 | 1002 | 35.3 | 89 | 3.9 | 89 |
| 42IO0188 {D3} | +5.7 | 385A Ovary T | | | S91 Fetal tissue | 422X0607 | 12151 | 2121 | 54.3 | 73 | 2.8 | 73 |
| 42IO0188 {D3} | +5.1 | 426A Ovary T (mets | | | 415A Aorta N | 422X0611 | 7487 | 1480 | 53.0 | 73 | 9.7 | 73 |
| 42IO0188 {D3} | +3.5 | 263A Ovary T | | | S73 Breast N | 422H0623 | 7302 | 2116 | 39.2 | 84 | 4.5 | 84 |
| 42IO0188 {D3} | +3.3 | 383A Ovary T (mets | | | I1 Colon N | 422B0609 | 3714 | 1113 | 20.4 | 83 | 2.6 | 83 |
| 42IO0188 {D3} | +3.0 | 9334 Ovary T (SCII | | | I2 Skin N | 422R0601 | 2435 | 814 | 12.1 | 75 | 2.1 | 75 |
| 42IO0188 {D3} | +2.6 | 384A Ovary T (mets | | | 272A Dendritic cell | 42240608 | 4578 | 1754 | 25.0 | 69 | 2.3 | 69 |
| 42IO0188 {D3} | +2.2 | 264A Ovary T | | | S2 Pancreas N | 422N0629 | 7904 | 3596 | 38.5 | 81 | 5.6 | 81 |
| 42IO0188 {D3} | +2.0 | 386A Ovary T | | | S40 PBMC (activat | 422J0605 | 2191 | 1081 | 14.0 | 90 | 2.9 | 90 |
| 42IO0188 {D3} | +2.0 | S115 Ovary T (mets | | | CT10 Small intestin | 422C0604 | 1979 | 971 | 10.4 | 80 | 2.7 | 80 |
| 42IO0188 {D3} | +2.0 | 265A Ovary T | | | CT5 Heart N | 422O0624 | 1911 | 964 | 13.9 | 93 | 3.4 | 93 |
| 42IO0188 {D3} | +2.0 | 335A Ovary T | | | S7 Ovary N | 42220626 | 1666 | 817 | 9.8 | 100 | 3.0 | 100 |
| 42IO0188 {D3} | -1.9 | 428A Ovary T (mets | | | 243A Esophagus N | 42240612 | 1827 | 3480 | 13.4 | 97 | 9.5 | 97 |
| 42IO0188 {D3} | +1.6 | 261A Ovary T | | | S10 Skeletal muscl | 42230621 | 5914 | 3653 | 30.4 | 86 | 6.0 | 86 |
| 42IO0188 {D3} | +1.6 | 266A Ovary T | | | S27 Ovary N | 42250603 | 2039 | 1274 | 11.9 | 50 | 2.6 | 50 |
| 42IO0188 {D3} | +1.6 | S22 Ovary T | | | CT9 Kidney N | 42290627 | 1736 | 1072 | 11.0 | 92 | 4.0 | 92 |
| 42IO0188 {D3} | +1.4 | 9485 OT 1-P (SCID | | | 9485 OT 5-P (SCID | 422Y0602 | 4204 | 3074 | 23.0 | 93 | 7.7 | 93 |
| 42IO0188 {D3} | +1.4 | 262A Ovary T | | | 334A Large Intestir | 422A0622 | 3002 | 2101 | 16.6 | 89 | 4.0 | 89 |
| 42IO0188 {D3} | +1.3 | S25 Ovary T | | | CT4 Bone Marrow | 422H0619 | 1643 | 1297 | 9.6 | 90 | 3.1 | 90 |
| 42IO0188 {D3} | +1.2 | 429A Ovary T (mets | | | 364A Ovary N | 422I0614 | 2521 | 2084 | 22.0 | 65 | 23.9 | 65 |
| 42IO0188 {D3} | +1.2 | 382A Ovary T | | | CT19 Brain N | 422Q0610 | 2072 | 1663 | 10.9 | 88 | 2.3 | 88 |
| 42IO0188 {D3} | +1.2 | 288A Ovary T | | | CT12 Lung N | 422V0625 | 1840 | 1473 | 10.7 | 87 | 3.8 | 87 |
| 42IO0188 {D3} | +1.1 | 201A Ovary T | | | S6 Stomach N | 422W0620 | 1329 | 1204 | 9.1 | 90 | 3.5 | 90 |

*Fig. 10*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421B0181 {C3} | +18.8 | 385A Ovary T | | | S91 Fetal tissue | 422X0607 | 26711 | 1424 | 103.3 | 54 | 2.0 | 54 |
| 421B0181 {C3} | +11.5 | S23 Ovary T | | | S56 Spinal Cord N | 422G0628 | 13559 | 1179 | 65.3 | 68 | 3.9 | 68 |
| 421B0181 {C3} | +11.1 | 426A Ovary T (mets) | | | 415A Aorta N | 422X0611 | 14125 | 1273 | 67.3 | 61 | 5.6 | 61 |
| 421B0181 {C3} | +10.8 | 205A Ovary T | | | 270A Liver N | 422Q0606 | 16121 | 1488 | 93.1 | 43 | 2.3 | 43 |
| 421B0181 {C3} | +5.1 | 263A Ovary T | | | S73 Breast N | 422H0623 | 11326 | 2235 | 58.2 | 68 | 4.4 | 68 |
| 421B0181 {C3} | +4.6 | 384A Ovary T (mets) | | | 272A Dendritic cells | 42240608 | 6583 | 1424 | 24.5 | 40 | 2.1 | 40 |
| 421B0181 {C3} | +4.4 | 264A Ovary T | | | S2 Pancreas N | 422N0629 | 9865 | 2245 | 40.9 | 64 | 3.6 | 64 |
| 421B0181 {C3} | +4.4 | 429A Ovary T (mets) | | | 364A Ovary N | 422I0614 | 2803 | 638 | 22.6 | 60 | 7.4 | 60 |
| 421B0181 {C3} | +4.2 | 261A Ovary T | | | S10 Skeletal muscle | M42230621 | 8271 | 1949 | 39.5 | 68 | 3.6 | 68 |
| 421B0181 {C3} | +3.8 | S115 Ovary T (mets) | | | CT10 Small intestine | M422C0604 | 2281 | 607 | 11.6 | 60 | 2.1 | 60 |
| 421B0181 {C3} | +2.5 | 265A Ovary T | | | CT5 Heart N | 422O0624 | 3192 | 1293 | 19.2 | 68 | 4.0 | 68 |
| 421B0181 {C3} | -2.3 | S22 Ovary T | | | CT9 Kidney N | 42290627 | 565 | 1276 | 3.6 | 70 | 3.9 | 70 |
| 421B0181 {C3} | +2.2 | 266A Ovary T | | | S27 Ovary N | 42250603 | 2774 | 1260 | 14.3 | 46 | 2.7 | 46 |
| 421B0181 {C3} | +2.1 | 9334 Ovary T (SCID) | | | I2 Skin N | 422R0601 | 1774 | 837 | 8.4 | 56 | 2.1 | 56 |
| 421B0181 {C3} | +1.9 | 9485 OT 1-P (SCID) | | | 9485 OT 5-P (SCID) | 422Y0602 | 6967 | 3726 | 41.5 | 70 | 9.2 | 70 |
| 421B0181 {C3} | +1.6 | 382A Ovary T | | | CT19 Brain N | 422Q0610 | 2313 | 1471 | 6.2 | 50 | 1.9 | 50 |
| 421B0181 {C3} | +1.6 | 288A Ovary T | | | CT12 Lung N | 422V0625 | 1657 | 1054 | 9.7 | 69 | 2.9 | 69 |
| 421B0181 {C3} | -1.5 | S25 Ovary T | | | CT4 Bone Marrow N | 422H0619 | 848 | 1243 | 4.5 | 65 | 2.7 | 65 |
| 421B0181 {C3} | +1.4 | 262A Ovary T | | | 334A Large Intestine | 422A0622 | 3171 | 2214 | 16.8 | 69 | 3.8 | 69 |
| 421B0181 {C3} | +1.2 | 386A Ovary T | | | S40 PBMC (activated | 422J0605 | 630 | 544 | 4.2 | 53 | 1.9 | 53 |
| 421B0181 {C3} | -1.2 | 335A Ovary T | | | S7 Ovary N | 42220626 | 592 | 730 | 3.7 | 75 | 2.6 | 75 |
| 421B0181 {C3} | -1.0 | 201A Ovary T | | | S6 Stomach N | 422W0620 | 1197 | 1237 | 7.8 | 65 | 3.5 | 65 |
| 421B0181 {C3} | -1.0 | 428A Ovary T (mets) | | | 243A Esophagus N | 42240612 | 783 | 797 | 4.5 | 95 | 2.4 | 95 |
| 421B0181 {C3} | | 383A Ovary T (mets) | | | I1 Colon N | 422B0609 | 3470 | 862 | 8.9 | 24 | 1.7 | 24 |

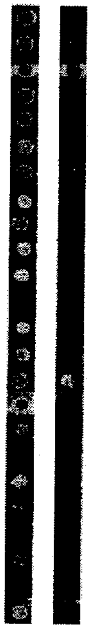

*Fig. 11*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 42110182 {H7} | +16.7 | 426A Ovary T (mets | 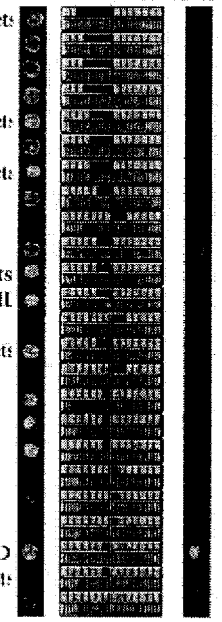 | | 415A Aorta N | 422X0611 | 7706 | 462 | 46.3 | 75 | 3.5 | 75 |
| 42110182 {H7} | +10.7 | 205A Ovary T | | | 270A Liver N | 422Q0606 | 10171 | 950 | 61.2 | 41 | 1.8 | 41 |
| 42110182 {H7} | +9.9 | 385A Ovary T | | | S91 Fetal tissue | 422X0607 | 14415 | 1459 | 62.1 | 48 | 2.2 | 48 |
| 42110182 {H7} | +8.8 | S23 Ovary T | | | S56 Spinal Cord N | 422G0628 | 7781 | 880 | 47.3 | 73 | 3.4 | 73 |
| 42110182 {H7} | +6.4 | 383A Ovary T (mets | | | I1 Colon N | 422B0609 | 4807 | 748 | 27.6 | 47 | 2.2 | 47 |
| 42110182 {H7} | +5.1 | 263A Ovary T | | | S73 Breast N | 422H0623 | 9815 | 1909 | 57.1 | 74 | 4.2 | 74 |
| 42110182 {H7} | +4.9 | 429A Ovary T (mets | | | 364A Ovary N | 422I0614 | 2661 | 543 | 20.3 | 61 | 6.7 | 61 |
| 42110182 {H7} | +3.5 | 264A Ovary T | | | S2 Pancreas N | 422N0629 | 7934 | 2274 | 38.8 | 71 | 3.9 | 71 |
| 42110182 {H7} | -2.9 | S25 Ovary T | | | CT4 Bone Marrow | 422H0619 | 480 | 1375 | 3.5 | 80 | 3.0 | 80 |
| 42110182 {H7} | +2.8 | 261A Ovary T | | | S10 Skeletal muscle | 42230621 | 8993 | 3245 | 34.6 | 69 | 5.1 | 69 |
| 42110182 {H7} | +2.5 | S115 Ovary T (mets | | | CT10 Small intestin | 422C0604 | 1864 | 738 | 8.1 | 67 | 2.2 | 67 |
| 42110182 {H7} | +2.3 | 9334 Ovary T (SCII | | | I2 Skin N | 422R0601 | 2552 | 1113 | 12.7 | 41 | 2.6 | 41 |
| 42110182 {H7} | -2.3 | S22 Ovary T | | | CT9 Kidney N | 42290627 | 386 | 889 | 3.2 | 69 | 3.4 | 69 |
| 42110182 {H7} | +2.2 | 384A Ovary T (mets | | | 272A Dendritic cells | 42240608 | 3516 | 1567 | 18.7 | 55 | 2.2 | 55 |
| 42110182 {H7} | -2.2 | 382A Ovary T | | | CT19 Brain N | 422Q0610 | 608 | 1320 | 4.2 | 60 | 2.3 | 60 |
| 42110182 {H7} | +1.9 | 265A Ovary T | | | CT5 Heart N | 42200624 | 2063 | 1080 | 13.6 | 87 | 3.5 | 87 |
| 42110182 {H7} | +1.8 | 266A Ovary T | | | S27 Ovary N | 42250603 | 1550 | 847 | 7.0 | 58 | 2.1 | 58 |
| 42110182 {H7} | +1.5 | 262A Ovary T | | | 334A Large Intestin | 422A0622 | 2559 | 1651 | 13.2 | 73 | 3.2 | 73 |
| 42110182 {H7} | -1.4 | 386A Ovary T | | | S40 PBMC (activat | 422J0605 | 534 | 738 | 3.9 | 62 | 2.2 | 62 |
| 42110182 {H7} | -1.3 | 288A Ovary T | | | CT12 Lung N | 422V0625 | 893 | 1120 | 5.3 | 66 | 3.1 | 66 |
| 42110182 {H7} | -1.3 | 335A Ovary T | | | S7 Ovary N | 42220626 | 440 | 567 | 3.3 | 60 | 2.2 | 60 |
| 42110182 {H7} | +1.2 | 9485 OT 1-P (SCID | | | 9485 OT 5-P (SCID | 422Y0602 | 4188 | 3529 | 21.6 | 66 | 9.5 | 66 |
| 42110182 {H7} | +1.1 | 428A Ovary T (mets | | | 243A Esophagus N | 42240612 | 725 | 689 | 6.2 | 65 | 2.8 | 65 |
| 42110182 {H7} | -1.0 | 201A Ovary T | | | S6 Stomach N | 422W0620 | 1008 | 1018 | 7.4 | 62 | 3.2 | 62 |

*Fig. 12*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421V0189 {D1} | +33.2 | 426A Ovary T (mets | | | 415A Aorta N | 422X0611 | 8072 | 243 | 55.2 | 67 | 2.4 | 67 |
| 421V0189 {D1} | +13.7 | S23 Ovary T | | | S56 Spinal Cord N | 422G0628 | 7367 | 537 | 42.6 | 69 | 2.5 | 69 |
| 421V0189 {D1} | +12.6 | 429A Ovary T (mets | | | 364A Ovary N | 422I0614 | 2850 | 227 | 21.7 | 64 | 3.5 | 64 |
| 421V0189 {D1} | +8.0 | 385A Ovary T | | | S91 Fetal tissue | 422X0607 | 11711 | 1469 | 54.0 | 58 | 2.2 | 58 |
| 421V0189 {D1} | +7.3 | 263A Ovary T | | | S73 Breast N | 422H0623 | 6949 | 952 | 37.8 | 69 | 2.6 | 69 |
| 421V0189 {D1} | -5.8 | S25 Ovary T | | | CT4 Bone Marrow | 422H0619 | 208 | 1210 | 2.1 | 44 | 2.9 | 44 |
| 421V0189 {D1} | +5.0 | 205A Ovary T | | | 270A Liver N | 422Q0606 | 8676 | 1737 | 52.3 | 57 | 2.6 | 57 |
| 421V0189 {D1} | +4.5 | 383A Ovary T (mets | | | I1 Colon N | 422B0609 | 3149 | 707 | 17.4 | 57 | 2.0 | 57 |
| 421V0189 {D1} | +4.4 | 261A Ovary T | | | S10 Skeletal muscle | 42230621 | 6332 | 1443 | 29.1 | 77 | 2.9 | 77 |
| 421V0189 {D1} | +4.2 | 264A Ovary T | | | S2 Pancreas N | 422N0629 | 7612 | 1809 | 38.1 | 79 | 3.3 | 79 |
| 421V0189 {D1} | -3.2 | 382A Ovary T | | | CT19 Brain N | 422Q0610 | 468 | 1508 | 3.4 | 60 | 2.3 | 60 |
| 421V0189 {D1} | +2.9 | 9334 Ovary T (SCII | | | I2 Skin N | 422R0601 | 2500 | 860 | 12.3 | 51 | 2.1 | 51 |
| 421V0189 {D1} | +2.5 | S115 Ovary T (mets | | | CT10 Small intestin | 422C0604 | 1424 | 569 | 6.7 | 61 | 2.1 | 61 |
| 421V0189 {D1} | +2.4 | 265A Ovary T | | | CT5 Heart N | 422O0624 | 1742 | 723 | 11.8 | 70 | 2.8 | 70 |
| 421V0189 {D1} | +2.3 | 384A Ovary T (mets | | | 272A Dendritic cells | 42240608 | 3083 | 1342 | 17.0 | 62 | 2.0 | 62 |
| 421V0189 {D1} | +1.9 | 266A Ovary T | | | S27 Ovary N | 42250603 | 1370 | 732 | 8.0 | 47 | 2.0 | 47 |
| 421V0189 {D1} | -1.9 | 386A Ovary T | | | S40 PBMC (activat | 422J0605 | 307 | 580 | 2.6 | 41 | 2.0 | 41 |
| 421V0189 {D1} | +1.7 | 262A Ovary T | | | 334A Large Intestir | 422A0622 | 2097 | 1202 | 11.2 | 86 | 2.7 | 86 |
| 421V0189 {D1} | -1.3 | 335A Ovary T | | | S7 Ovary N | 42220626 | 373 | 470 | 2.9 | 47 | 2.0 | 47 |
| 421V0189 {D1} | -1.1 | 288A Ovary T | | | CT12 Lung N | 422V0625 | 969 | 1094 | 5.6 | 72 | 2.9 | 72 |
| 421V0189 {D1} | +1.1 | 201A Ovary T | | | S6 Stomach N | 422W0620 | 750 | 672 | 5.6 | 62 | 2.4 | 62 |
| 421V0189 {D1} | +1.1 | 428A Ovary T (mets | | | 243A Esophagus N | 42240612 | 498 | 446 | 4.2 | 73 | 2.1 | 73 |
| 421V0189 {D1} | -1.0 | 9485 OT 1-P (SCID | | | 9485 OT 5-P (SCID | 422Y0602 | 3117 | 3174 | 16.7 | 91 | 8.2 | 91 |
| 421V0189 {D1} | | S22 Ovary T | | | CT9 Kidney N | 42290627 | 224 | 409 | 2.3 | 48 | 2.3 | 48 |

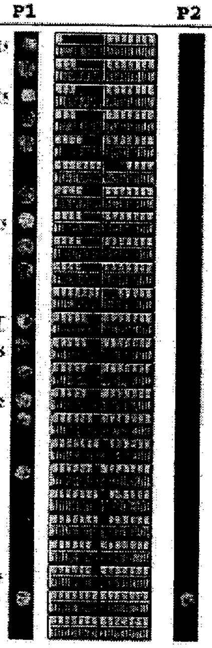

*Fig. 13*

| Gene Name | Bal Exp | Probe 1 Name | P1 | | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|---|
| 421H0187 {E11} | +20.2 | 426A Ovary T (met: |  | 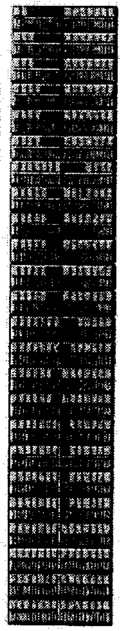 |  | 415A Aorta N | 422X0611 | 5441 | 270 | 36.3 | 50 | 2.3 | 50 |
| 421H0187 {E11} | +10.0 | S23 Ovary T | | | | S56 Spinal Cord N | 422G0628 | 5318 | 533 | 27.1 | 56 | 2.3 | 56 |
| 421H0187 {E11} | +8.3 | 429A Ovary T (met: | | | | 364A Ovary N | 422I0614 | 1252 | 150 | 10.1 | 58 | 2.5 | 58 |
| 421H0187 {E11} | +5.7 | 385A Ovary T | | | | S91 Fetal tissue | 422X0607 | 9507 | 1668 | 35.8 | 45 | 2.1 | 45 |
| 421H0187 {E11} | +4.4 | 205A Ovary T | | | | 270A Liver N | 422Q0606 | 5456 | 1235 | 31.1 | 50 | 2.0 | 50 |
| 421H0187 {E11} | +4.2 | 265A Ovary T | | | | CT5 Heart N | 422O0624 | 1834 | 438 | 11.9 | 48 | 2.0 | 48 |
| 421H0187 {E11} | -4.1 | 382A Ovary T | | | | CT19 Brain N | 422Q0610 | 309 | 1259 | 2.6 | 48 | 2.0 | 48 |
| 421H0187 {E11} | +3.6 | 261A Ovary T | | | | S10 Skeletal muscl | 42230621 | 3733 | 1036 | 17.7 | 55 | 2.3 | 55 |
| 421H0187 {E11} | +3.4 | 263A Ovary T | | | | S73 Breast N | 422H0623 | 4163 | 1239 | 23.0 | 62 | 3.0 | 62 |
| 421H0187 {E11} | +2.5 | S115 Ovary T (mets | | | | CT10 Small intestin | 422C0604 | 1565 | 627 | 8.8 | 47 | 2.1 | 47 |
| 421H0187 {E11} | +2.1 | 264A Ovary T | | | | S2 Pancreas N | 422N0629 | 3455 | 1630 | 14.9 | 60 | 3.0 | 60 |
| 421H0187 {E11} | +2.1 | 384A Ovary T (met: | | | | 272A Dendritic cell | 42240608 | 2667 | 1270 | 13.4 | 44 | 1.9 | 44 |
| 421H0187 {E11} | -2.1 | S22 Ovary T | | | | CT9 Kidney N | 42290627 | 291 | 605 | 2.4 | 51 | 2.5 | 51 |
| 421H0187 {E11} | -1.7 | 386A Ovary T | | | | S40 PBMC (activat | 422J0605 | 410 | 687 | 3.2 | 47 | 2.0 | 47 |
| 421H0187 {E11} | +1.6 | 9334 Ovary T (SCII | | | | I2 Skin N | 422R0601 | 1622 | 984 | 7.9 | 44 | 2.2 | 44 |
| 421H0187 {E11} | +1.5 | 262A Ovary T | | | | 334A Large Intestir | 422A0622 | 1892 | 1245 | 10.1 | 50 | 2.6 | 50 |
| 421H0187 {E11} | -1.5 | 288A Ovary T | | | | CT12 Lung N | 422V0625 | 604 | 908 | 4.1 | 62 | 2.6 | 62 |
| 421H0187 {E11} | -1.4 | 428A Ovary T (met: | | | | 243A Esophagus N | 42240612 | 236 | 325 | 2.7 | 78 | 1.9 | 78 |
| 421H0187 {E11} | -1.3 | 335A Ovary T | | | | S7 Ovary N | 42220626 | 382 | 501 | 2.9 | 58 | 2.0 | 58 |
| 421H0187 {E11} | -1.2 | 201A Ovary T | | | | S6 Stomach N | 422W0620 | 558 | 677 | 4.2 | 58 | 2.3 | 58 |
| 421H0187 {E11} | +1.0 | 9485 OT 1-P (SCID | | | | 9485 OT 5-P (SCID | 422Y0602 | 2582 | 2493 | 15.1 | 57 | 6.3 | 57 |
| 421H0187 {E11} | | 383A Ovary T (met: | | | | I1 Colon N | 422B0609 | 2261 | 562 | 12.5 | 38 | 1.7 | 38 |
| 421H0187 {E11} | | 266A Ovary T | | | | S27 Ovary N | 42250603 | 1739 | 965 | 9.7 | 36 | 2.2 | 36 |
| 421H0187 {E11} | | S25 Ovary T | | | | CT4 Bone Marrow | 422H0619 | 283 | 845 | 2.2 | 44 | 2.2 | 44 |

ACGGTTTCAATGGACACTTTTATTGTTTACTTAATGGATCATCAATTTTGTCTCACTACCTACAAATGGAATTTCA
TCTTGTTTCCATGCTGAGTAGTGAAACAGTGACAAAGCTAATCATAATAACCTACATCAAAAGAGAACTAAGCTAA
CACTGCTCACTTTCTTTTTAACAGGCAAAATATAAATATATGCACTCTAXAATGCACAATGGTTTAGTCACTAAAA
AATTCAAATGGGATCTTGAAGAATGTATGCAAATCCAGGGTGCAGTGAAGATGAGCTGAGATGCTGTGCAACTGTT
TAAGGGTTCCTGGCACTGCATCTCTTGGCCACTAGCTGAATCTTGACATGGAAGGTTTTAGCTAATGCCAAGTGGA
GATGCAGAAAATGCTAAGTTGACTTAGGGGCTGTGCACAGGAACTAAAAGGCAGGAAAGTACTAAATATTGCTGAG
AGCATCCACCCCAGGAAGGACTTTACCTTCCAGGAGCTCCAAACTGGCACCACCCCCAGTGCTCACATGGCTGACT
TTATCCTCCGTGTTCCATTTGGCACAGCAAGTGGCAGTG 11721-2

AAGGCTGGTGGGTTTTTGATCCTGCTGGAGAACCTCCGCTTTCATGTGGAGGAAGAAGGGAAGGGAAAAGATGCTT
CTGGGAACAAGGTTAAAGCCGAGCCAGCCAAAATAGAAGCTTTCCGAGCTTCACTTTCCAAGCTAGGGGATGTCTA
TGTCAATGATGCTTTTGGCACTGCTCACAGAGCCCACAGCTCCATGGTAGGAGTCAATCTGCCACAGAAGGCTGGT
GGGTTTTTGATGAAGAAGGAGCTGAACTACTTTGCAAAGGCCTTGGAGAGCCCAGAGCGACCCTTCCTGGCCATCC
TGGGCGGAGCTAAAGTTGCAGACAAGATCCAGCTCATCAATAATATGCTGGACAAAGTCAATGAGATGATTATTGG
TGGTGGAATGGCTTTTACCTTCCTTAAGGTGCTCAACAACATGGAGATTGGCACTTCTCTGTTTGATGAAGAGGGA
GCCAAGATTGTCAAAGACCTAATGTCCAAAGCTGAGAAGAATGGTGTGAAGATTACCTTGCCTGTTGACTTTGTCA
CTGCTGACAAGTTTGATGA 11724-1

TTTGTTCCTTACATTTTTCTAAAGAGTTACTTAAATCAGTCAACTGGTCTTTGAGACTCTTAAGTTCTGATTCCAA
CTTAGCTAATTCATTCTGAGAACTGTGGTATAGGTGGCGTGTCTCTTCTAGCTGGGACAAAAGTTCTTTGTTTTCC
CCCTGTAGAGTATCACAGACCTTCTGCTGAAGCTGGACCTCTGTCTGGGCCTTGGACTCCCAAATCTGCTTGTCAT
GTTCAAGCCTGGAAATGTTAATCTTTAATTCTTCCATATGGATGGACATCTGTCTAAGTTGATCCTTTAGAACACT
GCAATTATCTTCTTTGAGTCTAATTTCTTCTTCTTTGCTTTGAATCGCATCACTAAACTTCCTCTCCCATTTCTTA
GCTTCATCTATCACCCTGTCACGATCATCCTGGAGGGAAGACATGCTCTTAGTAAAGGCTGCAAGCTGGGTCACAG
TACTGTCCAAGTTTTCCTGAAGTTGCTGAACTTCCTTGTCTTTCTTGTTCAAAGTAACCTGAATCTCTCCAATTGT
CTCTTCCAAGTGGACTTTTTCTCTGCGCAAAGCATCCAG 11724-2

TCATTGCCTGTGATGGCATCTGGAATGTGATGAGCAGCCAGGAAGTTGTAGATTTCATTCAATCAAAGGATTCAGC
ATGTGGTGGAAGCTGTGAGGCAAGAGAAACAAGAACTGTATGGCAAGTTAAGAAGCACAGAGGCAAACAAGAAGGA
GACAGAAAAGCAGTTGCAGGAAGCTGAGCAAGAAATGGAGGAAATGAAAGAAAAGATGAGAAAGTTTGCTAAATCT
AAACAGCAGAAAATCCTAGAGCTGGAAGAAGAGAATGACCGGCTTAGGGCAGAGGTGCACCCTGCAGGAGATACAG
CTAAAGAGTGTATGGAAACACTTCTTTCTTCCAATGCCAGCATGAAGGAAGAACTTGAAAGGGTCAAAATGGAGTA
TGAAACCCTTTCTAAGAAGTTTCAGTCTTTAATGTCTGAGAAAGACTCTCTAAGTGAAGAGGTTCAAGATTTAAAG
CATCAGATAGAAGGTAATGTATCTAAACAAGCTAACCTAGAGGCCACCGAGAAACATGATAACCAAACGAATGTCA
CTGAAGAGGGAACACAGTCTATACCAGGT

AAGCCAATAATCACCATTTATTACTTAATATATGCCAACCACTGTACTTGGCAGTTCACAAATTCTCACCGTTACA
ACAACCCCATGAGGTATTTATTCCCATTCTATAGATAGGGAAACCACAGCTCAAGTAAGTTAGGAAACTGAGCCAA
GTATACACAGAATACGAAGTGGCAAAACTAGAAGGAAAGACTGACACTGCTATCTGCTGGCCTCCAGTGTCCTGGC
TCTTTTCACACGGGtTCAATGTCTCCAGCGCTGCTGCTGCTGCTGCATTACCATGCCCTCATTGTTTTTCTTCCTC
TGGTGTTCAACTGCATCCTTCAAAGAATCTAACTCATTCCAGAGACCACTTATTTCTTTCTCTCTTTCTGAAATTA
CTTTTAATAATTCTTCATGAGGGGGAAAAGAAGATGCCTGTTGGTAGTTTTGTTGTTTAAGCTGCTCAATTTGGGA
CTTAAACAATTTGTTTTCATCTTGTACATCCTGTAACAGCTGTGTTTTGCTAGAAAGATCACTCTCCCTCTCTTTT
AGCATGGCTTCTAACCTCTTCAATTCATTTTCCTTTTCTTTCAACACAATCTCAAGTTCTTCAAACTGTGATGCAG
AAGAGGCCTCTTTCAAGTTATGTTGTGCTACTTCCTGAACATGTGCTTTTAAAGATTCATTTTCTTCTTGAAGATC
CTGTAACCACTTCCCTGTATTGGCTAGGTCTTTCTCTTTCTCTTCCAAAACAGCCTTCATGGTATTCATCTGTTCC
TCTTTTCCTTTTAATAAGTTCAGGAGCTTCAGAAC 11726-1&2

CAAGCTTTTTTTTTTTTTTTAAAAAGTGTTAGCATTAATGTTTTATTGTCACGCAGATGGCAACTGGGTTTATGTC
TTCATATTTTATATTTTTGTAAATTAAAAAAATTACAAGTTTTAAATAGCCAATGGCTGGTTATATTTTCAGAAAA
CATGATTAGACTAATTCATTAATGGTGGCTTCAAGCTTTTCCTTATTGGCTCCAGAAAATTCACCCACCTTTTGTC
CCTTCTTAAAAAACTGGAATGTTGGCATGCATTTGACTTCACACTCTGAAGCAACATCCTGACAGTCATCCACATC
TACTTCAAGGAATATCACGTTGGAATACTTTTCAGAGAGGGAATGAAAGAAAGGCTTGATCATTTTGCAAGGCCCA
CACCACGTGGCTGAGAAGTCAACTACTACAAGTTTATCACCTGCAGCGTCCAAGGCTTCCTGAAAAGCAGTCTTGC
TCTCGATCTGCTTCACCATCTTGGCTGCTGGAGTCTGACGAGCGGCTGTAAGGACCGATGGAAATGGATCCAAAGC
ACCAAACAGAGCTTCAAGACTCGCTGCTTGGCTTGAATTCGGATCCGATATCGCCATGGCCT 11727-1&2

AAGTGTTAGCATTAATGTTTTATTGTCACGCAGATGGCAACTGGGTTTATGTCTTCATATTTTATATTTTTGTAAA
TTAAAAAAATTMCAAGTTTTAAATAGCCAATGGCTGGTTATATTTTCAGAAAACATGATTAGACTAATTCATTAAT
GGTGGCTTCAAGCTTTTCCTTATTGGCTCCAGAAAATTCACCCACCTTTTGTCCCTTCTTAAAAAACTGGAATGTT
GGCATGCATTTGACTTCACACTCTGAAGCAACATCCTGACAGTCATCCACATCTACTTCAAGGAATATCACGTTGG
AATACTTTTCAGAGAGGGAATGAAAGAAAGGCTTGATCATTTTGCAAGGCCCACACCACGTGGCTGAGAAGTCAAC
TACTACAAGTTTATCACCTGCAGCGTCCAAGGCTTCCTGAAAAGCAGTCTTGCTCTCGATCTGCTTCACCATCTTG
GCTGCTGGAGTCTGACGAGCGGCTGTAAGGACCGATGGAAATGGATCCAAAGCACCAAACAGAGCTTCAAGACTCG
CTGCTTGGCATGAATTCGGATCCGA

TACAAACTTTATTGAAACGCACACGCGCACACACACAAACACCCCTGTGGATAGGGAAAAGCACCTGGCCACAGGG
TCCACTGAAACGGGGAGGGGATGGCAGCTTGTAATGTGGCTTTTGCCACAACCCCCTTCTGACAGGGAAGGCCTTA
GATTGAGGCCCCACCTCCCATGGTGATGGGGAGCTCAGAATGGGGTCCAGGGAGAATTTGGTTAGGGGGAGGTGCT
AGGGAGGCATGAGCAGAGGGCACCCTCCGAGTGGGGTCCCGAGGGCTGCAGAGTCTTCAGTACTGTCCCTCACAGC
AGCTGTCTCAAGGCTGGGTCCCTCAAAGGGGCGTCCCAGCGCGGGGCCTCCCTGCGCAAACACTTGGTACCCCTGG
CTGCGCAGCGGAAGCCAGCAGGACAGCAGTGGCGCCGATCAGCACAACAGACGCCCTGGCGGTAGGGACAGCAGGC
CCAGCCCTGTCGGTTGTCTCGGCAGCAGGTCTGGTTATCATGGCAGAAGTGTCCTTCCCACACTTCACGTCCTTCA
CACCCACGTGAXGGCTACXGGCCAGGAAG 11728.2.40.19.19

CCCGTGGGTGCCATCCACGGAGTTGTTACCTGATCTTTGGAAGCAGGATCGCCCGTCTGCACTGCAGTGGAAGCCC
CGTGGGCAGCAGTGATGGCCATCCCCGCATGCCACGGCCTCTGGGAAGGGGCAGCAACTGGAAGTCCCTGAGACGG
TAAAGATGCAGGAGTGGCCGGCAGAGCAGTGGGCATCAACCTGGCAGGGGCCACCCAGATGCCTGCTCAGTGTTGT
GGGCCATTTGTCCAGAAGGGGACGGCAGCAGCTGTAGCTGGCTCCTCCGGGGTCCAGGCAGCAGGCCACAGGGCAG
AACTGACCATCTGGGCACCGCGTTCCAGCCACCAGCCCTGCTGTTAAGGCCACCCAGCTCACCAGGGTCCACATGG
TCTGCCTGCGTCCGACTCCGCGGTCCTTGGGCCCTGATGGTTCTACCTGCTGTGAGCTGCCCAGTGGGAAGTATGG
CTGCTGCCAATGCCCAACGCCACCTGCTGCTCCGATCACCTGCACTGCTGCCCCAAGACACTGTGTGTGACCTGAT
CCAGAGTAAGTGCCTCTCCAAGGAGAACG 11730-1

GAATCACCTTTCTGGTTTAGCTAGTACTTTGTACAGAACAATGAGGTTTCCCACAGCGGAGTCTCCCTGGGCTCTG
TTTGGCTCTCGGTAAGGCAGGCCTACACCTTTTCCTCTCCTCTATGGAGAGGGGAATATGCATTAAGGTGAAAAGT
CACCTTCCAAAAGTGAGAAAGGGATTCGATTGCTGCTTCAGGACTGTGGAATTATTTGGAATGTTTTACAAATGGT
TGCTACAAAACAACAAAAAAGGTAATTACAAAATGTGTACATCACAACATGCTTTTTAAAGACATTATGCATTGTG
CTCACATTCCCTTAAATGTTGTTTCCAAAGGTGCTCAGCCTCTAGCCCAGCTGGATTCTCCGGGAAGAGGCAGAGA
CAGTTTGGCGAAAAAGACACAGGGAAGGAGGGGGTGGTGAAAGGAGAAAGCAGCCTTCCAGTTAAAGATCAGCCCT
CAGTTAAAGGTCAGCTTCCCGCAXGCTGGCCTCAXGCGGAGTCTGGGTCAGAGGGAGGAGCAGCAGCAGGGTGGGA
CTGGGGCGT 11730-2

AACCGGAGCGCGAGCAGTAGCTGGGTGGGCACCATGGCTGGGATCACCACCATCGAGGCGGTGAAGCGCAAGATCC
AGGTTCTGCAGCAGCAGGCAGATGATGCAGAGGAGCGAGCTGAGCGCCTCCAGCGAGAAGTTGAGGGAGAAAGGCG
GGCCCGGGAACAGGCTGAGGCTGAGGTGGCCTCCTTGAACCGTAGGATCCAGCTGGTTGAAGAAGAGCTGGACCGT
GCTCAGGAGCGCCTGGCCACTGCCCTGCAAAAGCTGGAAGAAGCTGAAAAAGCTGCTGATGAGAGTGAGAGAGGTA
TGAAGGTTATTGAAAACCGGGCCTTAAAAGATGAAGAAAAGATGGAACTCCAGGAAATCCAACTCAAAGAAGCTAA
GCACATTGCAGAAGAGGCAGATAGGAAGTATGAAGAGGTGGCTCGTAAGTTGGTGATCATTGAAGGAGACTTGGAA
CGCACAGAGGAACGAGCTGAGCTGGCAGAGTCCCGTTGCCGAGAGATGGATGAGCAGATTAGACTGATGGACCAGA
ACCTGAAGTGTCTGAGTGC

*Fig. 15C*

11732.1contig

GAGAACTTGGCCTTTATTGTGGGCCCAGGAGGGCACAAAGGTCAGGAGGCCCAAGGGAGGGATCTGGTTTTCTGGA
TAGCCAGGTCATAGCATGGGTATCAGTAGGAATCCGCTGTAGCTGCACAGGCCTCACTTGCTGCAGTTCCGGGGAG
AACACCTGCACTGCATGGCGTTGATGACCTCGTGGTACACGACAGAGCCATTGGTGCAGTGCAAGGGCACGCGCAT
GGGCTCCGTCCTCGAGGGCAGGCAGCAGGAGCATTGCTCCTGCACATCCTCGATGTCAATGGAGTACACAGCTTTG
CTGGCACACTTTCCCTGGCAGTAATGAATGTCCACTTCCTCTTGGGACTTACAATCTCCCACTTTGATGTACTGCA
CCTTGGCTGTGATGTCTTTGCAATCAGGCTCCTCACATGTGTCACAGCAGGTGCCTGGAATTTTCACGATTTTGCC
TCCTTCAGCCAGACACTTGTGTTCATCAAATGGTGGGCAGCCCGTGACCCTCTTCTCCCAGATGTACTCTCCTCT 11732.2contig GCCTGGACCTTGCCGGATCAGTGCCACACAGTGACTTGCTTGGCAAATGGCCAGACCTTGCTGCAGAGTCATCGTG
TCAATTGTGACCATGGACCCCGGCCTTCATGTGCCAACAGCCAGTCTCCTGTTCGGGTGGAGGAGACGTGTGGCTG
CCGCTGGACCTGCCCTTGTGTGTGCACGGGCAGTTCCACTCGGCACATCGTCACCTTCGATGGGCAGAATTTCAAG
CTTACTGGTAGCTGCTCCTATGTCATCTTTCAAAACAAGGAGCAGGACCTGGAAGTGCTCCTCCACAATGGGGCCT
GCAGCCCCGGGGCAAAACAAGCCTGCATGAAGTCCATTGAGATTAAGCATGCTGGCGTCTCTGCTGAGCTGCACAG
TAACATGGAGATGGCAGTGGATGGGAGACTGGTCCTTGCCCCGTACGTTGGTGAAAACATGGAAGTCAGCATCTAC
GGCGCTATCATGTATGAAGTCAGGTTTACCCATCTTGGCCACATCCTCACATACACCGCCXCAAAACAACGAGTT 11735-1-2

AGATCAACCTCTGCTGGTCAGGAGGAATGCCTTCCTTGTCTTGGATCTTTGCTTTGACGTTCTCGATAGTRWCAaC
TKKRYTSRAMSKMAAGKGYRATGRWMTTKSYWGWRASYKTMWWMRSGRARAYTTaGaCAYCCCMCCTCWgAGaCGS
AGKACCARGTGCAgAgGTGGACTCTTTCTGGATGTTGTAGTCAGACAGGGTGCGTCCATCTTCCAGCTGTTTCCCA
GCAAAGATCAACCTCTGCTGATCAGGAGGGATGCCTTCCTTATCTTGGATCTTTGCCTTGACATTCTCGATGGTGT
CACTGGGCTCCACCTCGAGGGTGATGGTCTTACCAGTCAGGGTCTTCACGAAGATYTGCATCCCACCTCTGAGACG
GAGCACCAGGTGCAGGGTRGACTCTTTCTGGATGTTGTAGTCAGACAGGGTGCGYCCATCTTCCAGCTGcTTTCCS
aGCAAAGATCAACCTCTGCTGGTCAGGAGGRATGCCTTCCTTGTCYTGGATCTTTGCYTTGACRTTCTCRATGGTG
TCACTCGGCTCCACTTCGAGAGTGATGGTCTTACCAGTCAGGGTCTTCACGAAGATCTGCATCCCACCTCTAA 11740.2.contig AAGTCACAAACAGACAAAGATTATTACCAGCTGCAAGCTATATTAGAAGCTGAACGAAGAGACAGAGGTCATGATT
CTGAGATGATTGGAGACCTTCAAGCTCGAATTACATCTTTACAAGAGGAGGTGAAGCATCTCAAACATAATCTCGA
AAAAGTGGAAGGAGAAAGAAAAGAGGCTCAAGACATGCTTAATCACTCAGAAAAGGAAAAGAATAATTTAGAGATA
GATTTAAACTACAAACTTAAATCATTACAACAACGGTTAGAACAAGAGGTAAATGAACACAAAGTAACCAAAGCTC
GTTTAACTGACAAACATCAATCTATTGAAGAGGCAAAGTCTGTGGCAATGTGTGAGATGGAAAAAAAGCTGAAAGA
AGAAAGAGAAGCTCGAGAGAAGGCTGAAAATCGGGTTGTTCAGATTGAGAAACAGTGTTCCATGCTAGACGTTGAT
CTGAAGCAATCTCAGCAGAAACTAGAACATTTGACTGGAAATAAAGAAAGGATGGAGGATGAAGTTAAGAATCTA

*Fig. 15D*

11765.2&64.2.contig

CGCCTCCACCATGTCCATCAGGGTGACCCAGAAGTCCTACAAGGTGTCCACCTCTGGCCCCCGGGCCTTCAGCAGC
CGCTCCTACACGAGTGGGCCCGGTTCCCGCATCAGCTCCTCGAGCTTCTCCCGAGTGGGCAGCAGCAACTTTCGCG
GTGGCCTGGGCGGCGGCTATGGTGGGGCCAGCGGCATGGGAGGCATCACCGCAGTTACGGTCAACCAGAGCCTGCT
GAGCCCCCTTGTCCTGGAGGTGGACCCCAACATCCAGGCCGTGCGCACCCAGGAGAAGGAGCAGATCAAGACCCTC
AACAACAAGTTTGCCTCCTTCATAGACAAGGTACGGTTCCTGGAGCAGCAGAACAAGATGCTGGAGACCAAGTGGA
GCCTCCTGCAGCAGCAGAAGACGGCTCGAAGCAACATGGACAACATGTTCGAGAGCTACATCAACARCCTTAGGCG
GCAGCTGGAGACTCTGGGCCAGGAGAAGCTGAAGCTGGAGGCGGAGCTTGGCAACATGCAGGGGCTGGTGGAGGAC
TTCAAGAACAAGTATGAGGATGAGATCAATAAGCGTACAGAGATGGAGAACGAATTTGTCCTCATCAAGAAGGATG
TGGATGAAGCTTACATGAACAAGGTAGAGCTGGAGTCTCGCCTGGAAGGGCTGACCGACGAGATCAACTTCCTCAG
GCAGCTGTATGAAGAGGAGATCCGGGAGCTGCAGTCCCAGATCTCGGACACATCTGTGGTGCTGTCCATGGACAAC
AGCCGCTCCCTGGACATGGACAGCATCATTGCTGAGGTCAAGGCACAGTACGAGGATATTGCCAACCGCAGCCGGG
CTGAGGCTGAGAGCATGTACCAGGTCAAGTATGAGGAGCTGCAGAGCCTGGCTGGGAAGCACGGGGATGACCTGCG
GCGCACAAAGACTGAGATCTCTGAGATGAACCCGGAACATCAGCCCGGCTXCAGGCTGAGATTGAGGGCCTCAAAG
GCCAGAXGGCTTXCCTGGAXGXCCGCCAT 11767.2.contig CCCGGAGCCAGCCAACGAGCGGAAAATGGCAGACAATTTTTCGCTCCATGATGCGTTATCTGGGTCTGGAAACCCA
AACCCTCAAGGATGGCCTGGCGCATGGGGGAACCAGCCTGCTGGGGCAGGGGGCTACCCAGGGGCTTCCTATCCTG
GGGCCTACCCCGGGCAGGCACCCCCAGGGGCTTATCCTGGACAGGCACCTCCAGGCGCCTACCCTGGAGCACCTGG
AGCTTATCCCGGAGCACCTGCACCTGGAGTCTACCCAGGGCCACCCAGCGGCCCTGGGGCCTACCCATCTTCTGGA
CAGCCAAGTGCCACCGGAGCCTACCCTGCCACTGGCCCCTATGGCGCCCCTGCTGGGCCACTGATTGTGCCTTATA
ACCTGCCTTTGCCTGGGGGAGTGGTGCCTCGCATGCTGATAACAATTCTGGGCACGGTGAAGCCCAATGCAAACAG
AATTGCTTTAGATTTCCAAAGAGGGAATGATGTTGCCTTCCACTTTAACCCACGCTTCAATGAGAACAACAGGAGA
GTCATTGGTTGCAATACAAAGCTGGATAA 11768-1&2

GGGAATGCAACAACTTTATTGAAAGGAAAGTGCAATGAAATTTGTTGAAACCTTAAAAGGGGAAACTTAGACACCC
CCCCTCRAgCGMAGKACCARGTGCARAgGTGGACTCTTTCTGGATGTTGTAGTCAGACAGGGTRCGWCCATCTTCC
AGCTGTTTYCCRGCAAAGATCAACCTCTGCTGATCAGGAGGRATGCCTTCCTTATCTTGGATCTTTGCCTTGACAT
TCTCGATGGTGTCACTGGGCTCCACCTCGAGGGTGATGGTCTTACCAGTCAGGGTCTTCACGAAGATYTGCATCCC
ACCTCTGAGACGGAGCACCAGGTGCAGGGTRGACTCTTTCTGGATGTTGTAGTCAGACAGGGTGCGYCCATCTTCC
AGCTGcTTTCCSaGCAAAGATCAACCTCTGCTGGTCAGGAGGRATGCCTTCCTTGTCYTGGATCTTTGCYTTGACR
TTCTCAATGGTGTCACTCGGCTCCACTTCGAGAGTGATGGTCTTACCAGTCAGGGTCTTCACGAAGATCTGCATCC
CACCTCTAAGACGGAGCACCAGGTGCAGGGTGGACTCTTTCTGGATGgTTGTAGTCAGACAGGGTGCGTCCATCTT
CCAGCTGTTTCCCAGCAAAGATCAACCT

AGGTTGATCTTTGCTGGGAAACAGCTGGAAGATGGACGCACCCTGTCTGACTACAAcCATCCAGAAAGAGTCCACC
CTGCACCTGGTGCTCCGTCTTAGAGGTGGGATGCAGATCTTCGTGAAGACCCTGACTGGTAAGACCATCACTCTCG
AAGTGGAGCCGAGTGACACCATTGAGAAYGTCAARGCAAAGATCCARGACAAGGAAGGCATYCCTCCTGACCAGCA
GAGGTTGATCTTTGCtSGGAAAgCAGCTGGAAGATGGRCGCACCCTGTCTGACTACAACATCCAGAAAGAGTCYAC
CCTGCACCTGGTGCTCCGTCTCAGAGGTGGGATGCARATCTTCGTGAAGACCCTGACTGGTAAGACCATCACCCTC
GAGGTGGAGCCCAGTGACACCATCGAGAATGTCAAGGCAAAGATCCAAGATAAGGAAGGCATCCCTCCTGATCAGC
AGAGGTTGATCTTTGCTGGGAAACAGCTGGAAGATGGACGCACCCTGTCTGACTACAACATCCAGAAAGAGTCCAC
cTYTGCACYTGGTMCTBCGtCTYaGAGGKGGGRTGcaaaTCTWMGTKWagaCaCtCaCTKKYAAGRYYaTCAMCMW
tgAKKTCgAKYSCASTKWCaCTWTCRAKAAMGTYRWWGCAWagaTCCMAGACAAGGAAGGCATTCCTCCTGACCAG
CAGAGGTTGATCT 11769.1.contig ATGGAGTCTCACTCTGTCGACCAGGCTGGAGCGCTGTGGTGCGATATCGGCTCACTGCAGTCTCCACTTCCTGGGT
TCAAGCGATCCTCCTGCCTCAGCCTCCCGAGTAGCTGGGACTACAGGCAGGCGTCACCATAATTTTTGTATTTTTA
GTAGAGACATGGTTTCGCCATGTTGGCTGGGCTGGTCTCGAACTCCTGACCTCAAGTGATCTGTCCTGGCCTCCCA
AAGTGTTGGGATTACAGGCGAAAGCCAACGCTCCCGGCCAGGGAACAACTTTAGAATGAAGGAAATATGCAAAAGA
ACATCACATCAAGGATCAATTAATTACCATCTATTAATTACTATATGTGGGTAATTATGACTATTTCCCAAGCATT
CTACGTTGACTGCTTGAGAAGATGTTTGTCCTGCATGGTGGAGAGTGGAGAAGGGCCAGGATTCTTAGGTT 11769.2.contig AGCGCGGTCTTCCGGCGCGAGAAAGCTGAAGGTGATGTGGCCGCCCTCAACCGACGCATCCAGCTCGTTGAGGAGG
AGTTGGACAGGGCTCAGGAACGACTGGCCACGGCCCTGCAGAAGCTGGAGGAGGCAGAAAAAGCTGCAGATGAGAG
TGAGAGAGGAATGAAGGTGATAGAAAACCGGGCCATGAAGGATGAGGAGAAGATGGAGATTCAGGAGATGCAGCTC
AAAGAGGCCAAGCACATTGCGGAAGAGGCTGACCGCAAATACGAGGAGGTAGCTCGTAAGCTGGTCATCCTGGAGG
GTGAGCTGGAGAGGGCAGAGGAGCGTGCGGAGGTGTCTGAACTAAAATGTGGTGACCTGGAAGAAGAACTCAAGAA
TGTTACTAACAATCTGAAATCTCTGGAGGCTGCATCTGAAAAGTATTCTGAAAAGGAGGACAAATATGAAGAAGAA
ATTAAACTTCTGTCTGACAAACTGAAAGAGGCTGAGACCCGTGCTGAATTTGCAGAGAGAACGGTTGCAAAACTGG
AAAAGACAATTGATGACCTGGAAGAGAAACTTGCCCAGC 11770.1.contig GTGCACAGGTCCCATTTATTGTAGAAAATAATAATAATTACAGTGATGAATAGCTCTTCTTAAATTACAAAACAGA
AACCACAAAGAAGGAAGAGGAAAAACCCCAGGACTTCCAAGGGTGAAGCTGTCCCCTCCTCCCTGCCACCCTCCCA
GGCTCATTAGTGTCCTTGGAAGGGGCAGAGGACTCAGAGGGGATCAGTCTCCAGGGGCCCTGGGCTGAAGCGGGTG
AGGCAGAGAGTCCTGAGGCCACAGAGCTGGGCAACCTGAGCCGCCTCTCTGGCCCCCTCCCCCACCACTGCCCAAA
CCTGTTTACAGCACCTTCGCCCCTCCCCTCTAAACCCGTCCATCCACTCTGCACTTCCCAGGCAGGTGGGTGGGCC
AGGCCTCAGCCATACTCCTGGGCGCGGGTTTCGGTGAGCAAGGCACAGTCCCAGAGGTGATATCAAGGCCT

*Fig. 15F*

11770.2.contig

GCAAGGAACTGGTCTGCTCACACTTGCTGGCTTGCGCATCAGGACTGGCTTTATCTCCTGACTCACGGTGCAAAGG
TGCACTCTGCGAACGTTAAGTCCGTCCCCAGCGCTTGGAATCCTACGGCCCCCACAGCCGGATCCCCTCAGCCTTC
CAGGTCCTCAACTCCCGTGGACGCTGAACAATGGCCTCCATGGGGCTACAGGTAATGGGCATCGCGCTGGCCGTCC
TGGGCTGGCTGGCCGTCATGCTGTGCTGCGCGCTGCCCATGTGGCGCGTGACGGCCTTCATCGGCAGCAACATTGT
CACCTCGCAGACCATCTGGGAGGGCCTATGGATGAACTGCGTGGTGCAGAGCACCGGCCAGATGCAGTGCAAGGTG
TACGACTCGCTGCTGGCACTGCCGCAGGACCTGCAGGCGGCCCGCGCCCTCGTCATCATCA 11773.1.contig TGCAAAAGGGACACAGGGGTTCAAAAATAAAAATTTCTCTTCCCCCTCCCCAAACCTGTACCCCAGCTCCCCGACC
ACAACCCCCTTCCTCCCCCGGGGAAAGCAAGAAGGAGCAGGTGTGGCATCTGCAGCTGGGAAGAGAGAGGCCGGGG
AGGTGCCGAGCTCGGTGCTGGTCTCTTTCCAAATATAAATACXTGTGTCAGAACTGGAAAATCCTCCAGCACCCAC
CACCCAAGCACTCTCCGTTTTCTGCCGGTGTTTGGAGAGGGGCGGGGGGCAGGGGCGCCAGGCACCGGCTGGCTGC
GGTCTACTGCATCCGCTGGGTGTGCACCCCGCGAGCCTCCTGCTGCTCATTGTAGAAGAGATGACACTCGGGGTCC
CCCCGGATGGTGGGGGCTCCCTGGATCAGCTTCCCGGTGTTGGGGTTCACACACCAGCACTCCCCACGCTGCCCGT
TCAGAGACATCTTGCACTGTTTGAGGTTGTACAGGCCATGCTTGTCACAGTTG 11778.1.contig GGGTTGGAGGGACTGGTTCTTTATTTCAAAAAGACACTTGTCAATATTCAGTATCAAAACAGTTGCACTATTGATT
TCTCTTTCTCCCAATCGGCCCCAAAGAGACCACATAAAAGGAGAGTACATTTTAAGCCAATAAGCTGCAGGATGTA
CACCTAACAGACCTCCTAGAAACCTTACCAGAAAATGGGGACTGGGTAGGGAAGGAAACTTAAAAGATCAACAAAC
TGCCAGCCCACGGACTGCAGAGGCTGTCACAGCCAGATGGGGTGGCCAGGGTGCCACAAACCCAAAGCAAAGTTTC
AAAATAATATAAAATTTAAAAAGTTTTGTACATAAGCTATTCAAGATTTCTCCAGCACTGACTGATACAAAGCACA
ATTGAGATGGCACTTCTAGAGACAGCAGCTTCAAACCCAGAAAAGGGTGATGAGATGAGTTTCACATGGCTAAATC
AGTGGCAAAAACACAGTCTTCTTTCTTTCTTTCTTTCAAGGAGGCAGGAAAGCAATTAAGTGGTCACCTCAACATA
AGGGGGACATGATCCATTCTGTAAGCAGTTGTGAAGGGG 11778-2&30-2

CAGGAACCGGAGCGCGAGCAGTAGCTGGGTGGGCACCATGGCTGGGATCACCACCATCGAGGCGGTGAAGCGCAAG
ATCCAGGTTCTGCAGCAGCAGGCAGATGATGCAGAGGAGCGAGCTGAGCGCCTCCAGCGAGAAGTTGAGGGAGAAA
GGCGGGCCCGGGAACAGGCTGAGGCTGAGGTGGCCTCCTTGAACCGTAGGATCCAGCTGGTTGAAGAAGAGCTGGA
CCGTGCTCAGGAGCGCCTGGCCACTGCCCTGCAAAAGCTGGAAGAAGCTGAAAAAGCTGCTGATGAGAGTGAGAGA
GGTATGAAGGTTATTGAAAACCGGGCCTTAAAAGATGAAGAAAAGATGGAACTCCAGGAAATCCAACTCAAAGAAG
CTAAGCACATTGCAGAAGAGGCAGATAGGAAGTATGAAGAGGTGGCTCGTAAGTTGGTGATCATTGAAGGAGACTT
GGAACGCACAGAGGAACGAGCTGAGCTGGCAGAGTCCCGTTGCCGAGAGATGGATGAGCAGATTAGACTGATGGAC
CAGAACCTGAAGTGTCTGAGTGC

*Fig. 15G*

11782.1.contig

ATCTACGTCATCAATCAGGCTGGAGACACCATGTTCAATCGAGCTAAGCTGCTCAATATTGGCTTTCAAGAGGCCT
TGAAGGACTATGATTACAACTGCTTTGTGTTCAGTGATGTGGACCTCATTCCGATGGACGACCGTAATGCCTACAG
GTGTTTTTCGCAGCCACGGCACATTTCTGTTGCAATGGACAAGTTCGGGTTTAGCCTGCCATATGTTCAGTATTTT
GGAGGTGTCTCTGCTCTCAGTAAACAACAGTTTCTTGCCATCAATGGATTCCCTAATAATTATTGGGGTTGGGGAG
GAGAAGATGACGACATTTTTAACAGATTAGTTCATAAAGGCATGTCTATATCACGTCCAAATGCTGTAGTAGGGAG
GTGTCGAATGATCCGGCATTCAAGAGACAAGAAAAATGAGCCCAATCCTCAGAGGTTTGACCGGATCGCACATACA
AAGGAAACGATGCGCTTCGATGGTTTGAACTCACTTACCTACAAGGTGTTGGATGTCAGAGATACCCGTTATATAC
CCAAATCAC 11782.2.contig CTAGACCTCTAATTAAAAGGCACAATCATGCTGGAGAATGAACAGTCTGACCCCGAGGGCCACAGCGAATTTTAGG
GAAGGAGGCAAAGAGGTGAGAAGGGAAAGGAAAGAAGGAAGGAAGGAGAACAATAAGAACTGGAGACGTTGGGTGG
GTCAGGGAGTGTGGTGGAGGCTCGGAGAGATGGTAAACAAACCTGACTGCTATGAGTTTTCAACCCCATAGTCTAG
GGCCATGAGGGCGTCAGTTCTTGGTGGCTGAGGGTCCTTCCACCCAGCCCACCTGGGGGAGTGGAGTGGGGAGTTC
TGCCAGGTAAGCAGATGTTGTCTCCCAAGTTCCTGACCCAGATGTCTGGCAGGATAACGCTGACCTGTTCCCTCAA
CAAGGGACCTGAAAGTAATTTTGCTCTTTAC 11783-1 & 2

CCGAATTCAAGCGTCAACGATCCYTCCCTTACCATCAAATCAATTGGCCACCAATGGTACTGAACCTACGAGTACA
CCGACTACgGGCGGACTAATCTTCAACTCCTACATACTTCCCCCATTATTCCTAGAACCAGGCGACCTGCGACTCC
TTGACGTTGACAATCGAGTAGTACTCCCGATTGAAGCCCCCATTCGTATAATAATTACATCACAAGACGTCTTGCA
CTCATGAGCTGTCCCCACATTAGGCTTAAAAACAGATGCAATTCCCGGACGTCTAAGCCAAACCACTTTCACCGCT
ACACGACCGGGGGTATACTACGGTCAATGCTCTGAAATCTGTGGAGCAAACCACAGTTTCATGCCCATCGTCCTAG
AATTAATTCCCCTAAAAATCTTTGAAATAGGGCCCGTATTTACCCTATAGCACCCCCTCTACCCCCTCTAG 11786.1.contig GCTCTTCACACTTTTATTGTTAATTCTCTTCACATGGCAGATACAGAGCTGTCGTCTTGAAGACCACCACTGACCA
GGAAATGCCACTTTTACAAAATCATCCCCCCTTTTCATGATTGGAACAGTTTTCCTGACCGTCTGGGAGCGTTGAA
GGGTGACCAGCACATTTGCACATGCAAAAAAGGAGTGACCCCAAGGCCTCAACCACACTTCCCAGAGCTCACCATG
GGCTGCAGGTGACTTGCCAGGTTTGGGGTTCGTGAGCTTTCCTTGCTGCTGCGGTGGGGAGGCCCTCAAGAACTGA
GAGGCCGGGGTATGCTTCATGAGTGTTAACATTTACGGGACAAAAGCGCATCATTAGGATAAGGAACAGCCACAGC
ACTTCATGCTTGTGAGGGTTAGCTGTAGGAGCGGGTGAAAGGATTCCAGTTTATGAAAATTTAAAGCAAACAACGG
TTTTTAGCTGGGTGGGAAACAGGAAAACTGTGATGTCGGCCAATGACCACCATTTTTCTGCCCATGTGAAGGTCCC
CATGAAACC

*Fig. 15H*

11786.2.contig

```
CAAGCGCTTGGCGTTTGGACCCAGTTCAGTGAGGTTCTTGGGTTTTGTGCCTTTGGGGATTTTGGTTTGACCCAGG
GGTCAGCCTTAGGAAGGTCTTCAGGAGGAGGCCGAGTTCCCCTTCAGTACCACCCCTCTCTCCCCACTTTCCCTCT
CCCGGCAACATCTCTGGGAATCAACAGCATATTGACACGTTGGAGCCGAGCCTGAACATGCCCCTCGGCCCCAGCA
CATGGAAAACCCCCTTCCTTGCCTAAGGTGTCTGAGTTTCTGGCTCTTGAGGCATTTCCAGACTTGAAATTCTCAT
CAGTCCATTGCTCTTGAGTCTTTGCAGAGAACCTCAGATCAGGTGCACCTGGGAGAAAGACTTTGTCCCCACTTAC
AGATCTATCTCCTCCCTTGGGAAGGGCAGGGAATGGGGACGGTGTATGGAGGGGAAGGGATCTCCTGCGCCCTTCA
TTGCCACACTTGGTGGGACCATGAACATCTTTAGTGTCTGAGCTTCTCAAATTACTGCAATAGGA
```

13691.1&2

```
AGCGTCAAATCAGAATGGAAAAGACTCAAAACCATCATCAACACCAAGATCAAAAGGACAAGRATCCTTCAAGAAA
CAGGAAAAAACTCCTAAAACACCAAAAGGACCTAGTTCTGTAGAAGACATTAAAGCAAAAATGCAAGCAAGTATAG
AAAAAGGTGGTTCTCTTCCCAAAGTGGAAGCCAAATTCATCAATTATGTGAAGAATTGCTTCCGGATGACTGACCA
AGAGGCTATTCAAGATCTCTGGCAGTGGAGGAAGTCTCTTTAAGAAAATAGTTTAAACAATTTGTTAAAAAATTTT
CCGTCTTATTTCATTTCTGTAACAGTTGATATCTGGCTGTCCTTTTTATAATGCAGAGTGAGAACTTTCCCTACCG
TGTTTGATAAATGTTGTCCAGGTTCTATTGCCAAGAATGTGTTGTCCAAAATGCCTGTTTAGTTTTTAAAGATGGA
ACTCCACCCTTTGCTTGGTTTTAAGTATGTATGGAATGTTATGATAGGACATAGTAGTAGCGGTGGTCAGACATGG
AAATGGTGGGSMGACAAAAATATACATGTGAAATAA
```

13692.1&2

```
TCCGAATTCCAAGCGAATTATGGACAAACGATTCCTTTTAGAGGATTACTTTTTTCAATTTCGGTTTTAGTAATCT
AGGCTTTGCCTGTAAAGAATACAACGATGGATTTTAAATACTGTTTGTGGAATGTGTTTAAAGGATTGATTCTAGA
ACCTTTGTATATTTGATAGTATTTCTAACTTTCATTTCTTTACTGTTTGCAGTTAATGTTCATGTTCTGCTATGCA
ATCGTTTATATGCACGTTTCTTTAATTTTTTTAGATTTTCCTGGATGTATAGTTTAAACAACAAAAAGTCTATTTA
AAACTGTAGCAGTAGTTTACAGTTCTAGCAAAGAGGAAAGTTGTGGGGTTAAACTTTGTATTTTCTTTCTTATAGA
GGCTTCTAAAAAGGTATTTTTATATGTTCTTTTTAACAAATATTGTGTACAACCTTTAAAACATCAATGTTTGGAT
CAAAACAAGACCCAGCTTATTTTCTGC
```

13693.2

```
TGTGGTGGCGCGGGCTGAGGTGGAGGCCCAGGACTCTGACCCTGCCCCTGCCTTCAGCAAGGCCCCCGGCAGCGCC
GGCCACTACGAACTGCCGTGGGTTGAAAAATATAGGCCAGTAAAGCTGAATGAAATTGTCGGGAATGAAGACACCG
TGAGCAGGCTAGAGGTCTTTGCAAGGGAAGGAAATGTGCCCAACATCATCATTGCGGGCCCTCCAGGAACCGGCAA
GACCACAAGCATTCTGTGCTTGGCCCGGGCCCTGCTGGGCCCAGCACTCAAAGATGCCATGTTGGAACTCAATGCT
TCAAATGACAGGGGCATTGACGTTGTGAGGAATAAAATTAAAATGTTTGCTCAACAAAAAGTCACTCTTCCCAAAG
GCCGACATAAGATCATCATTCTGGATGAAGCAGACAGCATGACCGACGGAGCCCAGCAAGCCTTGAGGAGAACCAT
GGAAATCTACTCTAAAACCACTCGTTCGCCCTTGCTTGTAATGCTTCGGATAAGATCATCGAGCC
```

13696.1-13744.1

CTTTGCAAAGCTTTTATTTCATGTCTGCGGCATGGAATCCACCTGCACATGGCATCTTAGCTGTGAAGGAGAAAGC
AGTGCACGAGAAGGAATGAGTGGGCGGAACCAACGGCCTCCACAAGCTGCCTTCCAGCAGCCTGCCAAGGCCATGG
CAGAGAGAGACTGCAAACAAACACAAGCAAACAGAGTCTCTTCACAGCTGGAGTCTGAAAGCTCATAGTGGCATGT
GTGAATCTGACAAAATTAAAAGTGTGCATAGTCCATTACATGCATAAAACACTAATAATAATCCTGTTTACACGTG
ACTGCAGCAGGCAGGTCCAGCTCCACCACTGCCCTCCTGCCACATCACATCAAGTGCCATGGTTTAGAGGGTTTTT
CATATGTAATTCTTTTATTCTGTAAAAGGTAACAAAATATACAGAACAAAACTTTCCCTTTTTAAAACTAATGTTA
CAAATCTGTATTATCACTTGGATATAAATAGTATATAAGCTGATC 13700.1

CAAGGGATATATGTTGAGGGTACRGRGTGACACTGAACAGATCACAAAGCACGAGAAACATTAGTTCTCTCCCTCC
CCAGCGTCTCCTTCGTCTCCCTGGTTTTCCGATGTCCACAGAGTGAGATTGTCCCTAAGTAACTGCATGATCAGAG
TGCTGKCTTTATAAGACTCTTCATTCAGCGTATCCAATTCAGCAATTGCTTCATCAAATGCCGTTTTTGCCAGGCT
ACAGGCCTTTTCAGGAGAGTTTAGAATCTCATAGTAAAAGACTGAGAAATTTAGTGCCAGACCAAGACGAATTGGG
TGTGTAGGCTGCATTNCTTTCTTACTAATTTCAAATGCTTCCTGGTAAGCCTGCTGGGAGTTCGACACAAGTGGTT
TGTTTGTTGCTCCAGATGCCACTTCAGAAAGATACCTAAAATAATCTCCTTTCATTTTCAAAGTAGAACAC 13700.2

TCCGGAGCCGGGGTAGTCGCCGCCGCCGCCGCCGGTGCAGCCACTGCAGGCACCGCTGCCGCCGCCTGAGTAGTGG
GCTTAGGAAGGAAGAGGTCATCTCGCTCGGAGCTTCGCTCGGAAGGGTCTTTGTTCCCTGCAGCCCTCCCACGGGA
ATGACAATGGATAAAAGTGAGCTGGTACAGAAAGCCAAACTCGCTGAGCAGGCTGAGCGATATGATGATATGGCTG
CAGCCATGAAGGCAGTCACAGAACAGGGGCATGAACTCTCCAACGAAGAGAGAAATCTGCTCTCTGTTGCCTACAA
GAATGTGGTAAGGCCGCCCGCCGCTCTTCCTGGCGTGTCATCTCCAGCATTGAGCAGAAAACAGAGAGGAATGAGA
AGAAGCAGCAGATGGGCAAAGAGTACCGTGAGAAGATAGAGGCAGAACTGCAGGACATCTGCAATGATGTTCTGGA
GCTTGTTGGACAAATATCTTATTCCAATGCTACACAACCCAGAAA 13701.1

AAAAAGCAGCARGTTCAACACAAAATAGAAATCTCAAATGTAGGATAGAACAAAACCAAGTGTGTGAGGGGGGAAG
CAACAGCAAAAGGAAGAAATGAGATGTTGCAAAAAAGATGGAGGAGGGTTCCCCTCTCCTCTGGGGACTGACTCAA
ACACTGATGTGGCAGTATACACCATTCCAGAGTCAGGGGTGTTCATTCTTTTTTGGGAGTAAGAAAAGGTGGGGAT
TAAGAAGACGTTTCTGGAGGCTTAGGGACCAAGGCTGGTCTCTTTCCCCCCTCCCAACCCCCTTGATCCCTTTCTC
TGATCAGGGGAAAGGAGCTCGAATGAGGGAGGTAGAGTTGGAAAGGGAAAGGATTCCACTTGACAGAATGGGACAG
ACTCCTTCCCA

TGGCAATAGCACAGCCATCCAGGAGCTCTTCARGCGCATCTCGGAGCAGTTCACTGCCATGTTCCGCCGGAAGGCC
TTCCTCCACTGGTACACAGGCGAGGGCATGGACGAGATGGAGTTCACCGAGGCTGAGAGCAACATGAACGACCTCG
TCTCTGAGTATCAAGCAGTACCAGGATGCCACCGCAGAAGAGGAGGAGGATTTCGGTGAGGAGGCCGAAGAGGAGG
CCTAAGGCAGAGCCCCCATCACCTCAGGCTTCTCAGTTCCCTTAGCCGTCTTACTCAACTGCCCCTTTCCTCTCCC
TCAGAATTTGTGTTTGCTGCCTCTATCTTGTTTTTTGTTTTTTCTTCTGGGGGGGTCTAGAACAGTGCCTGGCACA
TAGTAGGCGCTCAATAAATACTTGGTTGNTGAATGTCTCCT 13702.2

AGCTGGCGCTAGGGCTCGGTTGTGAAATACAGCGTRGTCAGCCCTTGCGCTCAGTGTAGAAACCCACGCCTGTAAG
GTCGGTCTTCGTCCATCTGCTTTTTTCTGAAATACACTAAGAGCAGCCACAAAACTGTAACCTCAAGGAAACCATA
AAGCTTGGAGTGCCTTAATTTTTAACCAGTTTCCAATAAAACGGTTTACTACCT 13704.2-13740.2

GGAGATGAAGATGAGGAAGCTGAGTCAGCTACGGGCARGCGGGCAGCTGAAGATGATGAGGATGACGATGTCGATA
CCAAGAAGCAGAAGACCGACGAGGATGACTAGACAGCAAAAAAGGAAAAGTTAAA 13706.1

GATGAAAATTAAATACTTAAATTAATCAAAAGGCACTACGATACCACCTAAAACCTACTGCCTCAGTGGCAGTAKG
CTAAKGAAGATCAAGCTACAGSACATYATCTAATATGAATGTTAGCAATTACATAKCARGAAGCATGTTTGCTTTC
CAGAAGACTATGGNACAATGGTCATTWGGGCCCAAGAGGATATTTGGCCNGGAAAGGATCAAGATAGATNAANGTA
AAG 13706.2

GAGTAGCAACGCAAAGCGCTTGGTATTGAGTCTGTGGGSGACTTCGGTTCCGGTCTCTGCAGCAGCCGTGATCGCT
TAGTGGAGTGCTTAGGGTAGTTGGCCAGGATGCCGAATATCAAAATCTTCAGCAGGCAGCTCCCACCAGGACTTAT
CTCASAAAATTGCTGACCGCCTGGGCCTGGAGCTAGGCAAGGTGGTGACTAAGAAATTCAGCAACCAGGAGACCTG
TGTGGAAATTGGTGAAAGTGTACCGTGGAGAGGATGTCTACATTGTTCAGAGTGGNTGTGGCGAAATCAATGACAA
TTTAATGGAGCTTTTGATCATGATTAATGCCTGCAAGATTGCTTCAGCCAGCCGGGTTACTGCAGTCATCCCATGC
TTCCCTTATGCCCCGGCAGGATAAGAAAGATNAGAGCCGGGCCGCCAATCTCAGCCAAGCTTGGTGCAAATATGCT
ATCTGTAGCAGTGCAGATCATATTATCACCATGGACCTACATGCTTCTCAAATTCANGGCTTTTT

ATGCAAAAGGGGACACAGGGGGTTCAAAAATAAAAATTTCTCTTCCCCCTCCCCAAACCTGTACCCCAGCTCCCCG
ACCACAACCCCCTTCCTCCCCCGGGGAAAGCAAGAAGGAGCAGGTGTGGCATCTGCAGCTGGGAAGAGAGAGGCCG
GGGAGGTGCCGAGCTCGGTGCTGGTCTCTTTCCAAATATAAATACGTGTGTCAGAACTGGAAAATCCTCCAGCACC
CACCACCCAAGCACTCTCCGTTTTCTGCCGGTGTTTGGAGAGGGGCGGNGGGCAGGGGCGCCAGGCACCGGCTGGC
TGCGGTCTACTGCATCCGCTGGGTGTGCACCCCGCGA 13710.2

AGGTTGGAGAAGGTCATGCAGGTGCAGATTGTCCAGGSKCAGCCACAGGGTCAAGCCCAACAGGCCCAGAGTGGCA
CTGGACAGACCATGCAGGTGATGCAGCAGATCATCACTAACACAGGAGAGATCCAGCAGATCCCGGTGCAGCTGAA
TGCCGGCCAGCTGCAGTATATCCGCTTAGCCCAGCCTGTATCAGGCACTCAAGTTGTGCAGGGACAGATCCAGACA
CTTGCCACCAATGCTCAACAGATTACACAGACAGAGGTCCAGCAAGGACAGCAGCAGTTCAAGCCAGTTCACAAGA
TGGACAGCAGCTCTACCAGATCCAGCAAGTCACCATGCCTGCGGGCCANGACCTCGCCAGCCCATGTTCATCCAGT
CAAGCCAACCAGCCCTTCNACGGGCAGGCCCCCCAGGTGACCGGCGACTGAAGGGCCTGAGCTGGCAAGGCCAANG
ACACCCAACACAATTTTTGCCATACAGCCCCCAGGCAATGGGCACAGCCTTTCTTCCCAGAGGAC 13710-1

TGAGATTTATTGCATTTCATGCAGCTTGAAGTCCATGCAAAGGRGACTAGCACAGTTTTTAATGCATTTAAAAAAT
AAAAGGGAGGTGGGCAGCAAACACACAAAGTCCTAGTTTCCTGGGTCCCTGGGAGAAAAGAGTGTGGCAATGAATC
CACCCACTCTCCACAGGGAATAAATCTGTCTCTTAAATGCAAAGAATGTTTCCATGGCCTCTGGATGCAAATACAC
AGAGCTCTGGGGTCAGAGCAAGGGATGGGGAGAGGACCACGAGTGAAAAAGCAGCTACACACATTCACCTAATTCC
ATCTGAGGGCAAGAACAACGTGGCAAGTCTTGGGGGTAGCAGCTGTT 13711.1

TCCAGACATGCTCCTGTCCTAGGCGGGGAGCAGGAACCAGACCTGCTATGGGAAGCAGAAAGAGTTAAGGGAAGGT
TTCCTTTCATTCCTGTTCCTTCTCTTTTGCTTTTGAACAGTTTTTAAATATACTAATAGCTAAGTCATTTGCCAGC
CAGGTCCCGGTGAACAGTAGAGAACAAGGAGCTTGCTAAGAATTAATTTTGCTGTTTTTCACCCCATTCAAACAGA
GCTGCCCTGTTCCCTGATGGAGTTCCATTCCTGCCAGGGCACGGCTGAGTAACACGAAGCCATTCAAGAAAGGCGG
GTGTGAAATCACTGCCACCCCATGGACAGACCCCTCACTCTTCCTTCTTAGCCGCAGCGCTACTTAATAAATATAT
TTATACTTTGAAATTATGATAACCGATTTTTCCCATGCGGCATCCTAAGGGCACTTGCCAGCTCTTATCCGGACAG
TCAAGCACTGTTGTTGGACAACAGATAAAGGAAAAGAAAAAGAAGAAAACAACCGCAACTTCTGT

TGAGACGGACCACTGGCCTGGTCCCCCCTCATKTGCTGTCGTAGGACCTGACATGAAACGCAGATCTAGTGGCAGA
GAGGAAGATGATGAGGAACTTCTGAGACGTCGGCAGCTTCAAGAAGAGCAATTAATGAAGCTTAACTCAGGCCTGG
GACAGTTGATCTTGAAAGAAGAGATGGAGAAAGAGAGCCGGGAAAGGTCATCTCTGTTAGCCAGTCGCTACGATTC
TCCCATCAACTCAGCTTCACATATTCCATCATCTAAAACTGCATCTCTCCCTGGCTATGGAAGAAATGGGCTTCAC
CGGCCTGTTTCTACCGACTTCGCTCAGTATAACAGCTATGGGGATGTCAGCGGGGGAGTGCGAGATTACCAGACAC
TTCCAGATGGCCACATGCCTGCAATGAGAATGGACCGAGGAGTGTCTATGCCCAACATGTTGGAACCAAAGATATT
TCCATATGAAATGCTCATGGTGACCAACAGAGGGCCGAAACCAAATCTCAGAGAGGTGGACAGAA 13713.1&2

TCACTTTATTTTTCTTGTATAAAAACCCTATGTTGTAGCCACAGCTGGAGCCTGAGTCCGCTGCACGGAGACTCTG
GTGTGGGTCTTGACGAGGTGGTCAGTGAACTCCTGATAGGGAGACTTGGTGAATACAGTCTCCTTCCAGAGGTCGG
GGGTCAGGTAGCTGTAGGTCTTAGAAATGGCATCAAAGGTGGCCTTGGCGAAGTTGCCCAGGGTGGCAGTGCAGCC
CCGGGCTGAGGTGTAGCAGTCATCGATACCAGCCATCATGAG 13715.4

CTGGAATATAGACCCGTGATCGACAAAACTTTGAACGAGGCTGACTGTGCCACCGTCCCGCCAGCCATTCGCTCCT
ACTGATGAGACAAGATGTGGTGATGACAGAATCAGCTTTTGTAATTATGTATAATAGCTCATGCATGTGTCCATGT
CATAACTGTCTTCATACGCTTCTGCACTCTGGGGAAGAAGGAGTACATTGAAGGGAGATTGGCACCTAGTGGCTGG
GAGCTTGCCAGGAACCCAGTGGCCAGGGAGCGTGGCACTTACCTTTGTCCCTTGCTTCATTCTTGTGAGATGATAA
AACTGGGCACAGCTCTTAAATAAAATATAAATGAACA 13717.1&2

TGAATGGGGAGGAGCTGACCCAGGAAATGGAGCTTGNGGAGACCAGGCCTGCAGGGGATGGAACCTTCCAGAAGTG
GGCATCTGTGGTGGTGCCTCTTGGGAAGGAGCAGAAGTACACATGCCATGTGGAACATGAGGGGCTGCCTGAGCCC
CTCACCCTGAGATGGGGCAAGGAGGAGCCTCCTTCATCCACCAAGACTAACACAGTAATCATTGCTGTTCCGGTTG
TCCTTGGAGCTGTGGTCATCCTTGGAGCTGTGATGGCTTTTGTGATGAAGAGGAGGAGAAACACAGGTGGAAAAGG
AGGGGACTATGCTCTGGCTCCAGGCTCCCAGAGCTCTGATATGTCTCTCCCAGATTGTAAAGTGTGAAGACAGCTG
CCTGGTGTGGACTTGGTGACAGACAATGTCTTCACACATCTCCTGTGACATCCAGAGACCTCAGTTCTCTTTAGTC
AAGTGTCTGATGTTCCCTGTGAGTCTGCGGGCTCAAAGTGAAGAACTGTGGAGCCCAGTCCACCCCTGCACACCAG
GACCCTATCCCTGCACTGCCCTGTGTTCCCTTCCACAGCCAACCTTGCTGCTCCAGCCAAACATTGGTGGACATCT
GCAGCCTGTCAGCTCCATGCTACCCTGACCTTCAACTCCTCACTTCCACACTGAGAATAATAATTTGAATGTGGGT
GGCTGGAGAGATGGCTCAGCGCTGACTGCTCTTCCAAAGGTCCTGAGTTCAAATCCCAGCAACCACATGGTGGCTC
ACAACCATCTGTAATGGGATCTAATACCCTCTTCTGCAGTGTCTGAAGACASCTACAGTGTACTTACATATAATAA
TAAATAAG

GGCCGGGCGCGCGCGCCCCCGCCACACGCACGCCGGGCGTGCCAGTTTATAAAGGGAGAGAGCAAGCAGCGAGTCT
TGAAGCTCTGTTTGGTGCTTTGGATCCATTTCCATCGGTCCTTACAGCCGCTCGTCAGACTCCAGCAGCCAAGATG
GTGAAGCAGATCGAGAGCAAGACTGCTTTTCAGGAAGCCTTGGACGCTGCAGGTGATAAACTTGTAGTAGTTGACT
TCTCAGCCACGTGGTGTGGGCCTTGCAAAATGATCAAGCCTTTCTTTCATTCCCTCTCTGAAAAGTATTCCAACGT
GATATTCCTTGAAGTAGATGTGGATGACTGTCAGGATGTTGCTTCAGAGTGTGAAGTCAAATGCATGCCAACATTC
CAGTTTTTTAAGAAGGGACAAAAGGTGGGTGAATTTTCTGGAGCCAATAAGGAAAAGCTTGAAGCCACCATTAATG
AATTAGTCTAATCATGTTTTCTGAAAATATAACCAGCCATTGGCTATTTAAAACTTGTAATTTTTTTAATTTACAA
AAATATAAAATATGAAGACATAAACCCMGTTGCCATCTGCGTGACAATAAAACATTAATGCTAACACTT 13721.1

TCACATAAGAAATTTAAGCAAGTTACRCTATCTTAAAAAACACAACGAATGCATTTTAATAGAGAAACCCTTCCCT
CCCTCCACCTCCCTCCCCCACCCTCCTCATGAATTAAGAATCTAAGAGAAGAAGTAACCATAAAACCAAGTTTTGT
GGAATCCATCATCCAGAGTGCTTACATGGTGATTAGGTTAATATTGCCTTCTTACAAAATTTCTATTTTAAAAAAA
ATTATAACCTTGATTGCTTATTACAAAAAAATTCAGTACAAAAGTTCAATATATTGAAAAATGCTTTTCCCCTCCC
TCACAGCACCGTTTTATATATAGCAGAGAATAATGAAGAGATTGCTAGTCTAGATGGGGCAATCTTCAAATTACAC
CAAGACGCACAGTGGTTTATTTACCCTCCCCTTCTCATAAG 13721.2

GGAAAGGATTCAAGAATTAGAGGACTTGCTTGCTRRAGAAAAAGACAACTCTCGTCGCATGCTGACAGACAAAGAG
AGAGAGATGGCGGAAATAAGGGATCAAATGCAGCAACAGCTGAATGACTATGAACAGCTTCTTGATGTAAAGTTAG
CCCTGGACATGGAAATCAGTGCTTACAGGAAACTCTTAGAAGGCGAAGAAGAGAGGTTGAAGCTGTCTCCAAGCCC
TTCTTCCCGTGTGACAGTATCCCGAGCATCCTCAAGTCGTAGTGTACCGTACAACTAGAGGAAAGCGGAAGAGGGT
TGATGTGGAAGAATCAGAGGCGAAGTAGTAGTGTTAGCATCTCTCATTCCGCCTCAACCACTGGAAATGTTTGCAT
CGAAGAAATTGATGTTGATGGGAAATTTATCCCGCTTGAAGAACACTTCTGAACAGGATCAACCAATGGGAAGGCT
TGGGAGATGATCAGAAAAATTGGAGACACATCAGTCAGTTATAAATATACCTCAA 13723.1

CATGGGTTTCACCAGGTTGGCCAGGCTGCTCTTGAACTSCTGACCTCAGGTGATCCACCCGCCTCGGCCTCCCAAA
GTGCTGGGATTACAGGCGTGAGCCACCACGCCCGGCCCCCAAAGCTGTTTCTTTTGTCTTTAGCGTAAAGCTCTCC
TGCCATGCAGTATCTACATAACTGACGTGACTGCCAGCAAGCTCAGTCACTCCGTGGTCTTTTTCTCTTTCCAGTT
CTTCTCTCTCTCTTCAAGTTCTGCCTCAGTGAAAGCTGCAGGTCCCCAGTTAAGTGATCAGGTGAGGGTTCTTTGA
ACCTGGTTCTATCAGTCGAATTAATCCTTCATGATGG

GATGTGTTGGACCCTCTGTGTCAAAAAAAACCTCACAAAGAATCCCCTGCTCATTACAGAAGAAGATGCATTTAAA
ATATGGGTTATTTTCAACTTTTTATCTGAGGACAAGTATCCATTAATTATTGTGTCAGAAGAGATTGAATACCTGC
TTAAGAAGCTTACAGAAGCTATGGGAGGAGGTTGGCAGCAAGAACAATTTGAACATTATAAAATCAACTTTGATGA
CAGTAAAAATGGCCTTTCTGCATGGGAACTTATTGAGCTTATTGGAAATGGACAGTTTAGCAAAGGCATGGACCGG
CAGACTGTGTCTATGGCAATTAATGAAGTCTTTAATGAACTTATATTAGATGTGTTAAAGCAGGGTTACATGATGA
AAAAGGGCCACAGACGGAAAAACTGGACTGAAAGATGGTTTGTACTAAAACCCAACATAATTTCTTACTATGTGAG
TGAGGATCTGAAGGATAAGAAAGGAGACATTCTCTTGGATGAAAATTGCTGTGTAGAAGTCCTTGCCTGACAAAAG
ATGGAAAGAAATGCCTTTT 13725.1

GACTGGTTCTTTATTTCAAAAAGACACTTGTCAATATTCAGTRTCAAAACAGTTGCACTATTGATTTCTCTTTCTC
CCAATCGGCCCCAAAGAGACCACATAAAAGGAGAGTACATTTTAAGCCAATAAGCTGCAGGATGTACACCTAACAG
ACCTCCTAGAAACCTTACCAGAAAATGGGGACTGGGTAGGGAAGGAAACTTAAAAGATCAACAAACTGCCAGCCCA
CGGACTGCAGAGGCTGTCACAGCCAGATGGGGTGGCCAGGGTGCCACAAACCCAAAGCAAAGTTTCAAAATAATAT
AAAATTTAAAAAGTTTTGTACATAAGCTATTCAAGATTTCTCCAGCACTGACTGATACAAAGCACAATTGAGATGG
CACTTCTAGAGACAGCAGCTTCAAACCCAGAAAAGGGTGATGAGATGAAGTTTCACATGGCTAAATCAGTGGCAAA
AACACAGTCTTCTTTCTTTCTTTCTTTCAAGGANGCAGGAAAGCAATTAAGTGGTCACCTTAACATAAGGGGGAC 13725.2

TGGGTGGGCACCATGGCTGGGATCACCACCATCGAGGCGGTGAAGCGCAAGATCCAGGTTCTGCAGCAGCAGGCAG
ATGATGCAGAGGAGCGAGCTGAGCGCCTCCAGCGAGAAGTTGAGGGAGAAAGGCGGGCCCGGGAACAGGCTGAGGC
TGAGGTGGCCTCCTTGAACCGTAGGATCCAGCTGGTTGAAGAAGAGCTGGACCGTGCTCAGGAGCGCCTGGCCACT
GCCCTGCAAAAGCTGGAAGAAGCTGAAAAAGCTGCTGATGAGAGTGAGAGAGGTATGAAGGTTATTGAAAACCGGG
CCTTAAAAGATGAAGAAAAGATGGAACTCCAGGAAATCCAACTCAAAGAAGCTAAGCACATTGCAGAAGAGGCAGA
TAGGAAGTATGAAGAGGTGGCTCGTAAGTTGGTGATCATTGAAGGAGACTTGGAACCGCACAGAAGGAACGAGCTT
GAGCTTGGCAAAAGTCCCGTTGCCCAGAGATGGGATGAACCAGATTAGACTGATGGACCANAACC 13726.1&2

AGGGGCNGCGGGTGCGTGGGCCACTGGGTGACCGACTTAGCCTGGCCAGACTCTCAGCACCTGGAAGCGCCCCGAG
AGTGACAGCGTGAGGCTGGGAGGGAGGACTTGGCTTGAGCTTGTTAAACTCTGCTCTGAGCCTCCTTGTCGCCTGC
ATTTAGATGGCTCCCGCAAAGAAGGGTGGCGAGAAGAAAAAGGGCCGTTCTGCCATCAACGAAGTGGTAACCCGAG
AATACACCATCAACATTCACAAGCGCATCCATGGAGTGGGCTTCAAGAAGCGTGCACCTCGGGCACTCAAAGAGAT
TCGGAAATTTGCCATGAAGGAGATGGGAACTCCAGATGTGCGCATTGACACCAGGCTCAACAAAGCTGTCTGGGCC
AAAGGAATAAGGAATGTGCCATACCGAATCCGGTGTGCGGCTGTCCAGAAAACGTAATGAGGATGAAGATTCACCA
AATAAGCTATATACTTTGGTTACCTATGTACCTGTTACCACTTTCAAAAATCTACAGACAGTCAATGTGGATGAGA
ACTAATCGCTGATCGTCAGATCAAATAAAGTTATAAAAT

TCGGGAGCCACACTTGGCCCTCTTCCTCTCCAAAGSGCCAGAACCTCCTTCTCTTTGGAGAATGGGGAGGCCTCTT
GGAGACACAGAGGGTTTCACCTTGGATGACCTCTAGAGAAATTGCCCAAGAAGCCCACCTTCTGGTCCCAACCTGC
AGACCCCACAGCAGTCAGTTGGTCAGGCCCTGCTGTAGAAGGTCACTTGGCTCCATTGCCTGCTTCCAACCAATGG
GCAGGAGAGAAGGCCTTTATTTCTCGCCCACCCATTCCTCCTGTACCAGCACCTCCGTTTTCAGTCAGTGTTGTCC
AGCAACGGTACCGTTTACACAGTCACCTCAGACACACCATTTCACCTCCCTTGCCAAGCTGTTAGCCTTAGAGTGA
TTGCAGTGAACACTGTTTACACACCGTGAATCCATTCCCATCAGTCCATTCCAGTTGGCACCAGCCTGAACCATTT
GGTACCTGGTGTTAACTGGAGTCCTGTTTACAAGGTGGAGTCGGGGCTTGCTGACTTCTCTTCATTTGAGGGCAC 13727.2

ACCTAGACAGAAGGTGGGTGAGGGAGGACTGGTAGGAGGCTGAGGCAATTCCTTGGTAGTTTGTCCTGAAACCCTA
CTGGAGAAGTCAGCATGAGGCACCTACTGAGAGAAGTGCCCAGAAACTGCTGACTGCATCTGTTAAGAGTTAACAG
TAAAGAGGTAGAAGTGTGTTTCTGAATCAGAGTGGAAGCGTCTCAAGGGTCCCACAGTGGAGGTCCCTGAGCTACC
TCCCTTCCGTGAGTGGGAAGAGTGAAGCCCATGAAGAACTGAGATGAAGCAAGGATGGGGTTCCTGGGCTCCAGGC
AAGGGCTGTGCTCTCTGCAGCAGGGAGCCCCACGAGTCAGAAGAAAAGAACTAATCATTTGTTGCAAGAAACCTTG
CCCGGATACTAGCGGAAAACTGGAGGCGGNGGTGGGGGCACAGGAAAGTGGAAGTGATTTGATGGAGAGCAGAGAA
GCCTATGCACAGTGGCCGAGTCCACTTGTAAAGTG 13728.1&2

TTCAAGCAATTGTAACAAGTATATGTAGATTAGAGTGAGCAAAATCATATACAATTTTCATTTCCAGTTGCTATTT
TCCAAATTGTTCTGTAATGTCGTTAAAATTACTTAAAAATTAACAAAGCCAAAAATTATATTTATGACAAGAAAGC
CATCCCTACATTAATCTTACTTTTCCACTCACCGGCCCATCTCCTTCCTCTTTTTCCTAACTATGCCATTAAAACT
GTTCTACTGGGCCGGGCGTGTGGCTCATGCCTGTAATCCCAGCATTTTGGGAGGCCAAGGCAGGCGGATCATGAGG
TCAAGAGATTGAGACCATCCTGGCCAACATGGTGAAACCCCGCCTCGACTAAGAATACAAAAATTAGCTGGGCATG
GTGGCGCATGCCTGTAGTCTCAGCTACTCGGGAGGCTGAGGCAGAAGAATCGCTTGAACCCGGGAGGCAGAGGATG
CAGTGAGCCCCGATCGCGCCACTGCACTCTAGCCTGGGCGACAGACTGAGACTCTGCTC 13731.1&2

TGTGCCAGTCTACAGGCCTATCAGCAGCGACTCCTTCAGCAACAGATGGGGTCCCCTGTTCAGCCCAACCCCATGA
GCCCCCAGCAGCATATGCTCCCAAATCAGGCCCAGTCCCCACACCTACAAGGCCAGCAGATCCCTAATTCTCTCTC
CAATCAAGTGCGCTCTCCCCAGCCTGTCCCTTCTCCACGGCCACAGTCCCAGCCCCCCCACTCCAGTCCTTCCCCA
AGGATGCAGCCTCAGCCTTCTCCACACCACGTTTCCCCACAGACAAGTTCCCCACATCCTGGACTGGTAGTTGCCC
AGGCCAACCCCATGGAACAAGGGCATTTTGCCAGCC

TGTAAAAACTTGTTTTTAATTTTGTATAAAATAAAGGTGGTCCATGCCCACGGGGGCTGTAGGAAATCCAAGCAGACCA
GCTGGGGTGGGGGGATGTAGCCTACCTCGGGGGACTGTCTGTCCTCAAAACGGGCTGAGAAGGCCCGTCAGGGGCCCAG
GTCCCACAGAGAGGCCTGGGATACTCCCCCAACCCGAGGGGCAGACTGGGCAGTGGGGAGCCCCCATCGTGCCCCAGAG
GTGGCCACAGGCTGAAGGAGGGGCCTGAGGCACCGCAGCCTGCAACCCCCAGGGCTGCAGTCCACTAACTTTTTACAGA
ATAAAAGGAACATGGGGATGGGGAAAAAAGCACCAGGTCAGGCAGGGCCCGAGGGCCCCAGATCCCAGGAGGGCCAGGA
CTCAGGATGCCAGCACCACCCTAGCAGCTCCCACAGCTCCTGGCACAGGAGGCCGCCACGGATTGGCACAGGCCGCTGC
TGGCCATCACGCCACATTTGGAGAACTTGTCCCGACAGAGGTCAGCTCGGAGGAGCTCCTCGTGGGCACACACTGTACG
AACACAGATCTCCTTGTTAATGACGTACACACGGCGGAGGCTGCGGGGACAGGGCACGGGAGGTCTCAGCCCCACTT 13736.2

ATGGCTGCTGGATTTAGGTGGTAATAGGGGCTGTGGGCCATAAATCTGAAGCCTTGAGAACCTTGGGTCTGGAGAGCCA
TGAAGAGGGAAGGAAAAGAGGGCAAGTCCTGAACCTAACCAATGACCTGATGGATTGCTCGACCAAGACACAGAAGTGA
AGTCTGTGTCTGTGCACTTCCCACAGACTGGAGTTTTTGGTGCTGAATAGAGCCAGTTGCTAAAAAATTGGGGGTTTGG
TGAAGAAATCTGATTGTTGTGTGTATTCAATGTGTGATTTTAAAAATAAACAGCAACAACAATAAAAACCCTGACTGGC
TGTTTTTTCCCTGTATTCTTTACAACTATTTTTTGACCCTCTGAAAATTATTATACTTCACCTAAATGGAAGACTGCTG
TGTTTGTGGAAATTTTGTAATTTTTTAATTTATTTTATTCTCTCTCCTTTTTATTTTGCCTGCAGAATCCGTTGAGAGA
CTAATAAGGCTTAATATTTAATTGATTTGTTTAATATGTATATAAAT 13744.2-13696.2

GGCATGCGAGCGCACTCGGCGGACGCAAGGGCGGCGGGGAGCACACGGAGCACTGCAGGCGCCGGGTTGGGACAGCGTC
TTCGCTGCTGCTGGATAGTCGTGTTTTCGGGGATCGAGGATACTCACCAGAAACCGAAAATGCCGAAACCAATCAATGT
CCGAGTTACCACCATGGATGCAGAGCTGGAGTTTGCAATCCAGCCAAATACAACTGGAAAACAGCTTTTTGATCAGGTG
GTAAAGACTATCGGCCTCCGGGAAGTGTGGTACTTTGGCCTCCACTATGTGGATAATAAAGGATTTCCTACCTGGCTGA
AGCTGGATAAGAAGGTGTCTGCCCAGGAGGTCAGGAAGGAGAATCCCCTCCAGTTCAAGTTCCGGGCCAAaGTTCTACC
CTGAAGATGTGGCTGAGGAGCTCATCCAGGACATCACCCAGAAACTTTTCTTCCTTCAAGTGAAGGAAGGAATCCTTAG
CGATGAGATCTACTGCCCCCCTTGARACTGCCGTGCTCTTGGGGTCCTACGCTTGTGCATGCCAAGTTTGGGGACTACC
ACCAAGAAG 13746.1&2-13720.1&2

GAAGGAGTCGGGATACTCAGCATTGATGCACCCCAATTTCAAAGCGGCATTCTTCGGCAGGTCTCTGGGACAATCTCTA
GGGTCACTACCTGGAAACTCGTTAGGGTACAACTGAATGCTGAAAGGAAAGAACACCTGCAGAACCGGACAGAAATTCA
CCCCGGCGATCAGCTGATTGATCTCGGTCGACCAGAAGTCATGGCTAAAGATGACGAGGACGTTGTCAATTCCCTGGGC
TTTTCGAAGTGAGTCCAGCAGCAGTCTGAGGTATTCGGGCCGGTTATGCACCTGGACCACCAGCACCAGCTCCCGGGGG
GCCCAGGTGCCAGCCTTATCTACATTCCTCAGGGTCTGATCAAAGTTCAGCTGGTACACCAGGGACCGGTACCGCAGCG
TCAGGTTGTCCGCTCGGGCTGGGGGACCGCCGGGACCAGGGAAGCCGCCGACACGTTGGAGACCCTGCGGATGCCCACA
GCCACAGAGGGGTGGTCCCCACCGCGGCCGCCGGCACCCCGCGCGGGTTCGGCGTCCAGCAACGGTGGGGCGAGGGCCT
CGTTCTTCCTTTGTCGCCCATTGCTGCTCCAGAGGACGAAGCCGCAGGCGGCCACCACGAGCGTCAGGATTAGCACCTT
CCGTTTGTAGATGCGGAACCTCATGGTCTCCAGGGCCGGGAGCGCAGCTACAGCTCGAGCGTCGGCGCCGCCGCTAGGA
GCCGCGGCTCGGCTTCGTCTCCGTCCTCTCCATTCAGCACCACGGGTCCCGGAAAAAGCTCAGCCSCGGTCCCAACCGC
ACCCTAGCTTCGTTACCTGCGCCTCGCTTG

CAGATTTTTATTTGCAGTCGTCACTGGGGCCGTTTCTTGCTGCTTATTTGTCTGCTAGCCTGCTCTTCCAGCTGCA
TGGCCAGGCGCAAGGCCTTGATGACATCTCGCAGGGCTGAGAAATGCTTGGCTTGCTGGGCCAGAGCAGATTCCGC
TTTGTTCACAAAGGTCTCCAGGTCATAGTCTGGCTGCTCGGTCATCTCAGAGAGCTCAAGCCAGTCTGGTCCTTGC
TGTATGATCTCCTTGAGCTCTTCCATAGCCTTCTCCTCCAGCTCCCTGATCTGAGTCATGGCTTCGTTAAAGCTGG
ACATCTGGGAAGACAGTTCCTCCTCTTCCTTGGATAAATTGCCTGGAATCAGCGCCCCGTTAGAGCAGGCTTCCAT
CTCTTCTGTTTCCATTTGAATCAACTGCTCTCCACTGGGCCCACTGTGGGGGCTCAGCTCCTTGACCCTGCTGCAT
ATCTTAAGGGTGTTTAAAGGATATTCACAGGAGCTTATGCCTGGT 14347.2

CTCCTCTTGGTACATGAACCCAAGTTGAAAGTGGACTTAACAAAGTATCTGGAGAACCAAGCATTCTGCTTTGACT
TTGCATTTGATGAAACAGCTTCGAATGAAGTTGTCTACAGGTTCACAGCAAGGCCACTGGTACAGACAATCTTTGA
AGGTGGAAAAGCAACTTGTTTTGCATATGGCCAGACAGGAAGTGGCAAGACACATACTATGGGCGGAGACCTCTCT
GGGAAAGCCCAGAATGCATCCAAAGGGATCTATGCCATGGCCTTCCGGGACGTCTTCTTCTGAAGAATCAACCCTG
CTACCGGAAGTTGGGCCTGGAAGTCTATGTGACATTCTTCGAGATCTACAATGGGAAGCTGTTTGACCTGCTCAAC
AAGAAGGCCAAGCTTGCGCGTGCTGGAAGACGGCAAGCAACAGGTGCAAGTGGTGGGGGCTTGCAGGAACATCTGG
NTAACTCTGCTTGATGATGGCANTCAAGATGATCGACATGGGCAGCGCCTGCAGA 14348.2&14350.1&2

TCCCGAATTCAAGCGACAAATTGGAWAGTGAAATGGAAGATGCCTATCATGAACATCAGGCAAATCTTTTGCGCCA
AGATCTGATGAGACGACAGGAAGAATTAAGACGCATGGAAGAACTTCACAATCAAGAAATGCAGAAACGTAAAGAA
ATGCAATTGAGGCAAGAGGAGGAACGACGTAGAAGAGAGGAAGAGATGATGATTCGTCAACGTGAGATGGAAGAAC
AAATGAGGCGCCAAAGAGAGGAAAGTTACAGCCGAATGGGCTACATGGATCCACGGGAAAGAGACATGCGAATGGG
TGGCGGAGGAGCAATGAACATGGGAGATCCCTATGGTTCAGGAGGCCAGAAATTTCCACCTCTAGGAGGTGGTGGT
GGCATAGGTTATGAAGCTAATCCTGGCGTTCCACCAGCAACCATGAGTGGTTCCATGATGGGAAGTGACATGCGTA
CTGAGCGCTTTGGGCAGGGAGGTGCGGGGCCTGTGGGTGGACAGGGTCCTAGAGGAATGGGGCCTGGAACTCCAGC
AGGATATGGTAGAGGGAGAGAAGAGTACGAAGGC 14349.1&2

TTCGTGAAGACCCTGACTGGTAAGACCATCACTCTCGAAGTGGAGCCCGAGTGACACCATTGAGAATGTCAAGGCA
AAGATCCAAGACAAGGAAGGCATCCCTCCTGACCAGCAKAGGTTGATCTTTGCTGGGAAACAGCTGGAAGATGGAC
GCACCCTGTCTGACTACAACATCCAGAAAGAGTCCACCCTGCACCTGGTGCTCCGTCTCAGAGGTGGGATGCAAAT
CTTCGTGAAGACCCTGACTGGTAAGACCATCACCCTCGAGGTGGAGCCCAGTGACACCATCGAGAATGTCAAGGCA
AAGATCCAAGATAAGGAAGGCATCCCTCCTGATCAGCAGAGGTTGATCTTTGCTGGGAAACAGCTGGAAGATGGAC
GCACCCTGTCTGACTACAACATCCAGAAAGAGTCCACTCTGCACTTGGTCCTGCGCTTGAGGGGGGGTGTCTAAGT
TTCCCCTTTTAAGGTTTCAACAAATTTCATTGCACTTTCCTTTCAATAAAGTTGTTGCATTC

GCGCGGGTGCGTGGGCCACTGGGTGACCGACTTAGCCTGGCCAGACTCTCAGCACCTGGAAGCGCCCCGAGAGTGA
CAGCGTGAGGCTGGGAGGGAGGACTTGGCTTGAGCTTGTTAAACTCTGCTCTGAGCCTCCTTGTCGCCTGCATTTA
GATGGCTCCCGCAAAGAAGGGTGGCGAGAAGAAAAAGGGCCCTTCTGCCATCAACGAAGTGGTAACCCGAGAATAC
ACCATCAACATTCACAAGCGCATCCATGGAGTGGGCTTCAAGAAGCGTGCACCTCGGGCACTCAAAGAGATTCGGA
AATTTGCCATGAAGGAGATGGGAACTCCAGATGTGCGCATTGACACCAGGCTCAACAAAGCTGTCTGGGCCAAAGG
AATAAGGAATGTGCCATACCGAATCCGTGTGCGGCTGTCCAGAAAACGTAATGAGGATGAAGATTCACCAAATAAG
CTATATACTTTGGTTACCTATGTACCTGTTACCACTTTCAAAAATCTACAGACAGTCAATGTGGATGAGAACTAAT
CGCTGATCGT 14353.1

AATTCTTTATTTAAATCAACAAACTCATCTTCCTCAAGCCCCAGACCATGGTAGGCAGCCCTCCCTCTCCATCCCC
TCACCCCACCCCTTAGCCACAGTGAAGGGAATGGAAAATGAGAAGCCACGAGGGCCCCTGCCAGGGAAGGCTGCCC
CAGATGTGTGGTGAGCACAGTCAGTGCAGCTGTGGCTGGGGCAGCAGCTGCCACAGGCTCCTCCCTATAAATTAAG
TTCCTGCAGCCACAGCTGTGGGAGAAGCATACTTGTAGAAGCAAGGCCAGTCCAGCATCAGAAGGCAGAGGCAGCA
TCAGTGACTCCCAGCCATGGAATGAACGGAGGACACAGAGCTCAGAGACAGAACAGGCCAGGGGGAAGAAGGAGAG
ACAGAATAGGCCAGGGCATGGCGGTGAGGGA 14353.2

TGATGAATCTGGGTGGGCTGGCAGTAGCCCGAGATGATGGGCTCTTCTCTGGGGATCCCAACTGGTTCCCTAAGAA
ATCCAAGGAGAATCCTCGGAACTTCTCGGATAACCAGCTGCAAGAGGGCAAGAACGTGATCGGGTTACAGATGGGC
ACCAACCGCGGGGCGTCTCANGCAGGCATGACTGGCTACGGGATGCCACGCCAGATCCTCTGATCCCACCCCAGGC
CTTGCCCCTGCCCTCCCACGAATGGTTAATATATATGTAGATATATATTTTAGCAGTGACATTCCCAGAGAGCCCC
AGAGCTCTCAAGCTCCTTTCTGTCAGGGTGGGGGGTTCAAGCCTGTCCTGTCACCTCTGAAGTGCCTGCTGGCATC
CTCTCCCCCATGCTTACTAATACATTCCCTTCCCCATAGCC 17182.1&2

AGCGGAGCTCCCTCCCCTGGTGGCTACAACCCACACACGCCAGGCTCAGGCATCGAGCAGAACTCCAGCGACTGGG
TAACCACTGACATTCAGGTGAAGGTGCGGGACACCTACCTGGATACACAGGTGGTGGGACAGACAGGTGTCATCCG
CAGTGTCACGGGGGGCATGTGCTCTGTGTACCTGAAGGACAGTGAGAAGGTTGTCAGCATTTCCAGTGAGCACCTG
GAGCCTATCACCCCCACCAAGAACAACAAGGTGAAAGTGATCCTGGGCGAGGATCGGGAAGCCACGGGCGTCCTAC
TGAGCATTGATGGTGAGGATGGCATTGTCCGTATGGACCTTGATGAGCAGCTCAAGATCCTCAACCTCCGCTTCCT
GGGGAAGCTCCTGGAAGCCTGAAGCAGGCAGGGCCGGTGGACTTCGTCGGATGAAGAGTGATCCTCCTTCCTTCCC
TGGCCCTTGGCTGTGACACAAGATCCTCCTGCAGGGCTAGGCGGATTGTTCTGGATTTCCTTTTGTTTTTCCTTTT
AGGTTTCCATCTTTTCCCTCCCTGGTGCTCATTGGAATCTGAGTAGAGTCTGGGGGAGGGTCCCCACCTTCCTGTA
CCTCCTCCCCACAGCTTGCTTTTGTTGTACCGTCTTTCAATAAAAAGAAGCTGTTTGGTCTA

GGTTCACAGCACTGCTGCTTGTGTGTTGCCGGCCAGGAATTCCAGGCTCACAAGGCTATCTTAGCAGCTCGTTCTC
CGGTTTTTAGTGCCATGTTTGAACATGAAATGGAGGAGAGCAAAAAGAATCGAGTTGAAATCAATGATGTGGAGCC
TGAAGTTTTTAAGGAAATGATGTGCTTCATTTACACGGGGAAGGCTCCAAACCTCGACAAAATGGCTGATGATTTG
CTGGCAGCTGCTGACAAGTATGCCCTGGAGCGCTTAAAGGTCATGTGTGAGGATGCCCTCTGCAGTAACCTGTCCG
TGGAGAACGCTGCAGAAATTCTCATCCTGGCCGACCTCCACAGTGCAGATCAGTTGAAAACTCAGGCAGTGGATTT
CATCAACTATCATGCTTCGGATGTCTTGGAGACCTCTTGGG 17186.1&2

TCGTAGCCATTTTTCTGCTTCTTTGGAGAATGACGCCACACTGACTGCTCATTGTCGTTGGTTCCATGCCAATTGG
TGAAATAGAACCTCATCCGGTAGTGGAGCCGGAGGGACATCTTGTCATCAACGGTGATGGTGCGATTTGGAGCATA
CCAGAGCTTGGTGTTCTCGCCATACAGGGCAAAGAGGTTGTGACAAAGAGGAGAGATACGGCATGCCTGTGCAGCC
CTGATGCACAGTTCCTCTGCTGTGTACTCTCCACTGCCCAGCCGGAGGGGCTCCCTGTCCGACAGATAGAAGATCA
CTTCCACCCCTGGCTTG 17187.1&2

TGGCACACTGCTCTTAAGAAACTATGAWGATCTGAGATTTTTTTGTGTATGTTTTTGACTCTTTTGAGTGGTAATC
ATATGTGTCTTTATAGATGTACATACCTCCTTGCACAAATGGAGGGGAATTCATTTTCATCACTGGGAGTGTCCTT
AGTGTATAAAAACCATGCTGGTATATGGCTTCAAGTTGTAAAAATGAAAGTGACTTTAAAAGAAAATAGGGGATGG
TCCAGGATCTCCACTGATAAGACTGTTTTTAAGTAACTTAAGGACCTTTGGGTCTACAAGTATATGTGAAAAAAAT
GAGACTTACTGGGTGAGGAAATTCATTGTTTAAAGATGGTCGTGTGTGTGTGTGTGTGTGTGTGTTGTGTTGTG
TTTTGTTTTTTAAGGGAGGGAATTTATTATTTACCGTTGCTTGAAATTACTGKGTAAATATATGTYTGATAATGAT
TTGCTYTTTGVCMACTAAAATTAGGVCTGTATAAGTWCTARATGCMTCCCTGGGKGTTGATYTTCCMAGATATTGA
TGATAMCCCTTAAAATTGTAACCYGCCTTTTTCCCTTTGCTYTCMATTAAAGTCTATTCMAAAG 17191.1&89.1

GGGGGTAGGCTCTTTATTAGACGGTTATTGCTGTACTACAGGGTCAGAGTGCAGTGTAAGCAGTGTCAGAGGCCCG
CGTTCAGCCCAAGAATGTGGATTTTCTCTCCCTATTGATCACAGTGGGTGGGTTTCTTCAGAAAAGCCCCAGAGGC
AGGGACCAGTGAGCTCCAAGGTTAGAAGTGGAACTGGAAGGCTTCAGTCACATGCTGCTTCCACGCTTCCAGGCTG
GGCAGCAAGGAGGAGATGCCCATGACGTGCCAGGTCTCCCCATCTGACACCAGTGAAGTCTGGTAGGACAGCAGCC
GCACGCCTGCCTCTGCCAGGAGGCCAATCATGGTAGGCAGCATTGCAGGGTCAGAGGTCTGAGTCCGGAATAGGAG
CAGGGGCAGGTCCCTGCGGAGAGGCACTTCTGGCCTGAAGACAGCTCCATTGAGCCCCTGCAGTACAGGYGTAGTG
CCTTGGACCAAGCCCACAGCCTGGTAAGGGGCGCCTGCCAGGGCCACGGCCAGGAGGCA

TAATTTCTTAGTCGTTTGGAATCCTTAAGCATGCAAAAGCTTTGAACAGAAGGGTTCACAAAGGAACCAGGGTTGT
CTTATGGCATCCAGTTAAGCCAGAGCTGGGAATGCCTCTGGGTCATCCACATCAGGAGCAGAAGCACTTGACTTGT
CGGTCCTGCTGCCACGGTTTGGGCGCCCACCACGCCCACGTCCACCTCGTCCTCCCCTGCCGCCACGTCCTGGGCG
GCCAAGGTCTCCAAAATTGATCTCCAGCTGAGACGTTATATCATTTGCTGGCTTCCGGAAATGATGGTCCATAACC
GAATCTTCAGCATGAGCCTCTTCACTCTTTGATTTATGAAGAACAAATCCCTTCTTCCACTGCCCATCAGCACCTT
CATTTGGTTTTCGGATATTAAATTCTACTTTTGCCCGGTCCTTATTTTGAATAGCCTTCCACTCATCCAAAGTCAT
CTCTTTTGGACCCTCCTCTTTTACCTCTTCAACTTCATTCTCCTTATTTTCAGTGTCTGCCACTGGATGATGTTCT
TCACCTTCAGGTGTTTCCTCAGTCACATTTGATTGATCCAAGTCAGTTAATTCGTCTTTGACAGTTCCCCAGTTGT
GAGATCCGCTACCTCCACGTTTGTCCTCGTGCTTCAGGCCAGATCTATCACTTCCACTATGCCTATCAAATTCACG
TTTGCCACGAGAATCAAATCCATCTCCTCGGCCCATTCCACGTCCACGGCCCCCTCGACCTCTTCCAAGACCACCA
CGACCTCGAATAGGTCGGTCAATAATCGGTCTATCAACTGAAAATTCGCCTCCTTCACCCTTTTCTTCAAGTGGCT
TTTCGAATCTTCGTTCACGAGGTGGTCGCCTTTCTGGTCTTCTATCAATTATTTTCCCTTCACCCTGAAGTTGTTG
ATCAGGTCTTCTTCCAACTCGTGC

17193

AAGCGGATGGACCTGAGTCAGCCGAATCCTAGCCCCTTCCCTTGGGCCTGCTGTGGTGCTCGACATCAGTGACAGA
CGGAAGCAGCAGACCATCAAGGCTACGGGAGGCCCGGGGCGCTTGCGAAGATGAAGTTTGGCTGCCTCTCCTTCCG
GCAGCCTTATGCTGGCTTTGTCTTAAATGGAATCAAGACTGTGGAGACGCGCTGGCGTCCTCTGCTGAGCAGCCAG
CGGAACTGTACCATCGCCGTCCACATTGCTCACAGGGACTGGGAAGGCGATGCCTGTCGGGAGCTGCTGGTGGAGA
GACTCGGGATGACTCCTGCTCAGATTCAGGCCTTGCTCAGGAAAGGGGAAAAGTTTGGTCGAGGAGTGATAGCGGG
ACTCGTTGACATTGGGGAAACTTTGCAATGCCCCGAAGACTTAACTCCCGATGAGGTTGTGGAACTAGAAAATCAA
GCTGCACTGACCAACCTGAAGCAGAAGTACCTGACTGTGATTTCAAACCCCAGGTGGTTACTGGAGCCCATACCTA
GGAAAGGAGGCAAGGATGTATTCCAGGTAGACATCCCAGAGCACCTGATCCCTTTGGGGCATGAAGTGTGACAAGT
GTGGGCTCCTGAAAGGAATGTTCCRGAGAAACCAGCTAAATCATGGCACCTTCAATTTGCCATCGTGACGCAGACC
TGTATAAATTAGGTTAAAGATGAATTTCCACTGCTTTGGAGAGTCCCACCCACTAAGCACTGTGCATGTAAACAGG
TTCCTTTGCTCAGATGAAGGAAGTAGGGGGTGGGGCTTTCCTTGTGTGATGCCTCCTTAGGCACACAGGCAATGTC
TCAAGTACTTTGACCTTAGGGTAGAAGGCAAAGCTGCCAGTAAATGTCTCAGCATTGCTGCTAATTTTGGTCCTGC
TAGTTTCTGGATTGTACAAATAAATGTGTTGTAGATGA

*Fig. 15U*

16443.1.edit

TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAACCAGTCCTGGTGCANGAC
GGTGAGGACGCTNACCACACGGTACGNGCTGGTGTACTGCTCCTCCCGCGGCTTTGTCTTGGCATTATGCACCTCC
ACGCCGTCCACGTACCAATTGAACTTGACCTCAGGGTCTTCGTGGCTCACGTCCACCACCACGCATGTAACCTCAA
ANCTCGGNCGCGANCACGC 16443.2.edit AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGGTGTACACCCTG
CCCCCATCCCGGGAGGAGATGACCAAGAACCAGGTCAGCCTGACCTGCCTGGTCAAAGGCTTCTATCCCAGCGACA
TCGCCCGTGGAGTGGGAGAGCAATGGGCAGCCGGAGAACAACTACAAGACCACGCCTCCCGTGCTGGACTCCGACA
CCTGCCGGGCGGCCGCTCGA 16444.2.edit AGCGTGGTTNCGGCCGAGGTCCCAACCAAGGCTGCANCCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGNCGCTCGA 16445.1.edit AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGCCGCTCGA

*Fig. 15V*

16445.2.edit

TCGAGCGGTCGCCCGGGCAGGTCCACATCGGCAGGGTCGGAGCCCTGGCCGCCATACTCGAACTGGAATCCATCGG
NCATGCTCTCGCCGAACCAGACATGCCTCTTGNCCTTGGGGTTCTTGCTGATGTACCAGNTCTTCTGGGCCACACT
GGGCTGAGTGGGGTACACGCAGGTCTCACCANTCTCCATGTTGCANAAGACTTTGATGGCATCCAGGTTGCAGCCT
TGGTTGGGGTCAATCCAGTACTCTCCACTCTTCCAGACAGAGTGGCACATCTTGAGGTCACGGCAGGTGCGGGCGG
GGTTCTTGACCTCGGTCGCGACCACGCT

16446.1.edit

TCGAGCGGCCGCCCGGGCAGGTCCTCCTCAGAGCGGTAGCTGTTCTTATTGCCCCGGCAGCCTCCATAGATNAAGT
TATTGCANGAGTTCCTCTCCACGTCAAAGTACCAGCGTGGGAAGGATGCACGGCAAGGCCCAGTGACTGCGTTGGC
GGTGCAGTATTCTTCATAGTTGAACATATCGCTGGAGTGGACTTCAGAATCCTGCCTTCTGGGAGCACTTGGGACA
GAGGAATCCGCTGCATTCCTGCTGGTGGACCTCGGCCGCGACCACGCT

16446.2.edit

AGCGTGGTCGCGGCCGAGGTCCACCAGCAGGAATGCAGCGGATTCCTCTGTCCCAAGTGCTCCCAGAAGGCAGGAT
TCTGAAGACCACTCCAGCGATATGTTCAACTATGAAGAATACTGCACCGCCAACGCAGTCACTGGGCCTTGCCGTG
CATCCTTCCCACGCTGGTACTTTGACGTGGAGAGGAACTCCTGCAATAACTTCATCTATGGAGGCTGCCGGGGCAA
TAAGAACAGCTACCGCTCTGAGGAGGACCTGCCCGGGCGGCCGCTCGA

16447.1.edit

TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGCCAGAATGGCACATCTTGAGGTCACGGCANGTGCGGGCGG
GGTTCTTGACCTCGGCCGCGACCACGCT

*Fig. 15W*

16447.2.edit

AGCGTGGTCGCGGCCGAGGTCAAGAAACCCCGCCCGCACCTGCCGTGACCTCAAGATGTGCCACTCTGGCTGGAAG
AGTGGAGAGTACTGGATTGACCCCAACCAAGGCTGCAACCTGGATGCCATCAAAGTCTTCTGCAACATGGAGACTG
GTGAGACCTGCGTGTACCCCACTCAGCCCAGTGTGGCCCAGAAGAACTGGTACATCAGCAAGAACCCCAAGGACAA
GAGGCATGTCTGGCTCGGCGAGAGCATGACCGATGGATTCCAGTTCGAGTATGGCGGCCAGGGCTCCGACCCTGCC
GATGTGGACCTGCCCGGGCGGCCGCTCGA 16449.1.edit AGCGTGGTCGCGGCCGAGGTCCTGTCAGAGTGGCACTGGTAGAAGNTCCAGGAACCCTGAACTGTAAGGGTTCTTC
ATCAGTGCCAACAGGATGACATGAAATGATGTACTCAGAAGTGTCCTGNAATGGGGCCCATGANATGGTTGNCTGA
GAGAGAGCTTCTTGTCCTACATTCGGCGGGTATGGTCTTGGCCTATGCCTTATGGGGGTGGCCGTTGNGGGCGGTG
NGGTCCGCCTAAAACCATGTTCCTCAAAGATCATTTGTTGCCCAACACTGGGTTGCTGACCANAAGTGCCAGGAAG
CTGAATACCATTTCCAGTGTCATACCCAGGGTGGGTGACGAAAGGGGTCTTTTGAACTGTGGAAGGAACATCCAAG
ATCTCTGNTCCATGAAGATTGGGGTGTGGAAGGGTTACCAGTTGGGGAAGCTCGCTGTCTTTTTCCTTCCAATCAN
GGGCTCGCTCTTCTGAATATTCTTCAGGGCAATGACATAAATTGTATATTCGGTTCCCGGTTCCAGGCCAG 16450.1.edit TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGANGAACATGGNTTT
AGGCGGACCACACCGGCCACAACGGGCACCCCCATAAGGCATAGGCCAAGAACATACCCGNCGAATGTAGGACAAG
AAGCTCTNTCTCANACAANCATCTCATGGGCCCCATTCCANGACACTTCTGAGTACATCANTTCATGGCATCCTGG
TGGCACTGATAAAAACCCTTACAGTTA 16450.2.edit AGCGTGGTCGCGGGCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
NGGGCTCGCTCTTCTGATTATTCTTCAGGGCAATGACATAAATTGTATATTCGGNTCCCGGGTNCAGCCAATAATA
ATAACCCTCTGTGACACCANGGCGGGGCCGAAGGANCACT

*Fig. 15X*

16451.1.edit

AGCGTGGTCGCGGCCGAGGTCCTCACCAGAGGTACCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA 16451.2.edit TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGNTGACAGAGTTGCCCACGGTAACAACCTCTTCCCGAACCTTATGCCTCTGCTGG
TCTTTCAGTGCCTCCACTATGATGTTGTAGGTGGTACCTCTGGTGAGGACCTCGGCCGCGACCACGCT 16452.1.edit AGCGTGGCCGCGGCCGAGGTCCATTGGCTGGAACGGCATCAACTTGGAAGCCAGTGATCGTCTCAGCCTTGGTTCT
CCAGCTAATGGTGATGGNGGTCTCAGTAGCATCTGTCACACGAGCCCTTCTTGGTGGGCTGACATTCTCCAGAGTG
GTGACAACACCCTGAGCTGGTCTGCTTGTCAAAGTGTCCTTAAGAGCATAGACACTCACTTCATATTTGGCGNCCA
CCATAAGTCCTGATACAACCACGGAATGACCTGTCAGGAAC 16452.2.edit TCGAGCGGCCGCCCGGGCAGGTCCTCAGACCGGGTTCTGAGTACACAGTCAGTGTGGTTGCCTTGCACGATGATAT
GGAGAGCCAGCCCCTGATTGGAACCCAGTCCACAGCTATTCCTGCACCAACTGACCTGAAGTTCACTCAGGTCACA
CCCACAAGCCTGAGCGCCCAGTGGACACCACCCAATGTTCAGCTCACTGGATATCGAGTGCGGGTGACCCCCAAGG
AGAAGACCGGACCAATGAAAGAAATCAACCTTGCTCCTGACAGCTCATCCGTGGTTGTATCAGGACTTATGGCGGC
CACCAAATATGAAGTGAGTGTCTATGCTCTTAAGGACACTTTGACAAGCAGACCAGCTCAGGGTGTTGTCACCACT
CTGGAGAATGTCAGCCCACCAAGAAGGGCTCGTGTGACAGATGCTACTGAGACCACCATCACCATTAGCTGGAGAA
CCAAGACTGAGACGATCACTGGCTTCCAAGTTGATGCCGTTCCAGCCAATGGACCTCGGCCGCGACCACGCTT

*Fig. 15Y*

16453.1.edit

AGCGTGGTCGCGGCCGAGGTCTGGCCGAACTGCCAGTGTACAGGGAAGATGTACATGTTATAGNTCTTCTCGAAGT
CCCGGGCCAGCAGCTCCACGGGGTGGTCTCCTGCCTCCAGGCGCTTCTCATTCTCATGGATCTTCTTCACCCGCAG
CTTCTGCTTCTCAGTCAGAAGGTTGTTGTCCTCATCCCTCTCATACAGGGTGACCAGGACGTTCTTGAGCCAGTCC
CGCATGCGCAGGGGGAATTCGGTCAGCTCAGAGTCCAGGCAAGGGGGGATGTATTTGCAAGGCCCGATGTAGTCCA
AGTGGAGCTTGTGGCCCTTCTTGGTGCCCTCCAAGGTGCACTTTGTGGCAAAGAAGTGGCAGGAAGAGTCGAAGGT
CTTGTTGTCATTGCTGCACACCTTCTCAAACTCGCCAATGGGGGCTGGGCAGACCTGCCCGGGCGGCCGCTCGA 16453.2.edit TCGAGCGGCCGCCCGGGCAGGTCTGCCCAGCCCCCATTGGCGAGTTTGAGAAGGNGTGCAGCAATGACAACAAGAC
CTTCGACTCTTCCTGCCACTTCTTTGCCACAAAGTGCACCCTGGAGGGCACCAAGAAGGGCCACAAGCTCCACCTG
GACTACATCGGGCCTTGCAAATACATCCCCCCTTGCCTGGACTCTGAGCTGACCGAATTCCCCCTGCGCATGCGGG
ACTGGCTCAAGAACGTCCTGGTCACCCTGTATGAGAGGGATGAGGACAACAACCTTCTGACTGAGAAGCANAAGCT
GCGGGTGAAGAANATCCATGAGAATGANAAGCGCCTGNAGGCANGAGACCACCCCGTGGAGCTGCTGGCCCGGGAC
TTCGAGAAGAACTATAACATGTACATCTTCCCTGTACACTGGCAGTTCGGCCAGACCTCGGCCGCGACCACGCT 16454.1.edit AGCGTGGNTGCGGACGACGCCCACAAAGCCATTGTATGTAGTTTTANTTCAGCTGCAAANAATACCNCCAGCATCC
ACCTTACTAACCAGCATATGCAGACA 16454.2.edit TCGAGCGGTCGCCCGGGCAGGTCTGGGCGGATAGCACCGGGCATATTTTGGAATGGATGAGGTCTGGCACCCTGAG
CAGCCCAGCGAGGACTTGGTCTTAGTTGAGCAATTTGGCTAGGAGGATAGTATGCAGCACGGTTCTGAGTCTGTGG
GATAGCTGCCATGAAGNAACCTGAAGGAGGCGCTGGCTGGTANGGGTTGATTACAGGGCTGGGAACAGCTCGTACA
CTTGCCATTCTCTGCATATACTGGNTAGTGAGGCGAGCCTGGCGCTCTTCTTTGCGCTGAGCTAAAGCTACATACA
ATGGCTTTGNGGACCTCGGCCGCGACCACGCTT

*Fig. 15Z*

16455.1.edit

TCGAGCGGCCGCCCGGGCAGGTCCATTTTCTCCCTGACGGTCCCACTTCTCTCCAATCTTGTAGTTCACACCATTG
TCATGACACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAAGTTGCCCACGGTAACAACCTCTTCCCGAACCTTATGCCTCTGCTG
GTCTTTCAAGTGCCTCCACTATGATGTTGTAGGTGGCACCTCTGGTGAGGACCTCGGCCGCGACCACGCT 16455.2.edit AGCGTGGTTTGCGGCCGAGGTCCTCACCANAGGTGCCACCTACAACATCATAGTGGAGGCACTGAAAGACCAGCAG
AGGCATAAGGTTCGGGAAGAGGTTGTTACCGTGGGCAACTCTGTCAACGAAGGCTTGAACCAACCTACGGATGACT
CGTGCTTTGACCCCTACACAGNTTCCCATTATGCCGTTGGAGATGAGTGGGAACGAATGTCTGAATCAGGCTTTAA
ACTGTTGTGCCAGTGCTTANGCTTTGGAAGTGGTCATTTCAGATGTGATTCATCTANATGGTGTCATGACAATGGT
GNGAACTACAAGATTGGAGAGAAGTGGNACCGTCAGGGGANAAAATGGACCTGCCCGGGCGGCNCGCTCGA 16456.1.edit AGCGTGGTCGCGGCCGAGGTCTGGCTTNCTGCTCANGTGATTATCCTGAACCATCCAGGCCAAATAAGCGCCGGCT
ATGCCCCTGNATTGGATTGCCACACGGCTCACATTGCATGCAAGTTTGCTGAGCTGAAGGAAAAGATTGATC 16456.2.edit TCGAGCGGCCGCCCGGGCAGGTCCAATTGAAACAAACAGTTCTGAGACCGTTCTTCCACCACTGATTAAGAGTGGG
GNGGCGGGTATTAGGGATAATATTCATTTAGCCTTCTGAGCTTTCTGGGCAGACTTGGTGACCTTGCCAGCTCCAG
CAGCCTTCTGGTCCACTGCTTTGATGACACCCACCGCAACTGTCTGTCTCATATCACGAACAGCAAAGCGACCCAA
AGGTGGATAGTCTGAGAAGCTCTCAACACACATGGGCTTGCCAGGAACCATATCAACAATGGGCAGCATCACCAGA
CTTCAAGAATTTAAGGGCCATCTTCCAGCTTTTTACCAGAACGGCGATCAATCTTTTCCTTCAGCTCAGCAAACTT
GCATGCAATGTGAGCCG

*Fig. 15AA*

16459.1.edit

```
TCGAGCGGCCGCCCGGGCAGGTCCAGAGGGCTGTGCTGAAGTTTGCTGCTGCCACTGGAGCCACTCCAATTGCTGG
CCGCTTCACTCCTGGAACCTTCACTAACCAGATCCAGGCAGCCTTCCGGGAGCCACGGCTTCTTGTGGNTACTGAC
CCCAGGGCTGACCACCAGCCTCTCACGGAGGCATCTTATGTTAACCTACCTACCATTGCGCTGTGTAACACAGATT
CTCCTCTGCGCTATGTGGACATTGCCATCCCATGCAACAACAAGGGAGCTCACTCAGNGGGGTTTGATGTGGTGGA
TGCTGGCTCGGGAAGTTCTGCGCATGCGTGGCACCATTTCCCGTGAACACCCATGGGANGNCATGCCTGATCTGGA
CTTCTACAGAGATCCTGAAGAGATTGAAAAAGAAGAACAGGCTGNTTGCTGANAAAGCAAGTGACCAAGGANGAAA
TTTCANGGGTGAAANGGACTGCTCCCGCTCCTGAATTCACTGCTACTCAACCTGANGNTGCAGACTGGTCTTGAAG
GNGNACANGGGCCCTCTGGGCCTATTTAAGCANCTTCGGTCGCGAACACGNT
```

16459.2.edit

```
AGCGTGNGTCGCGGCCGAGGTGCTGAATAGGCACAGAGGGCACCTGTACACCTTCAGACCAGTCTGCAACCTCAGG
CTGAGTAGCAGTGAACTCAGGAGCGGGAGCAGTCCATTCACCCTGAAATTCCTCCTTGGNCACTGCCTTCTCAGCA
GCAGCCTGCTCTTCTTTTTCAATCTCTTCAGGATCTCTGTAGAAGTACAGATCAGGCATGACCTCCCATGGGTGTT
CACGGGAAATGGTGCCACGCATGCGCAGAACTTCCCGAGCCAGCATCCACCACATCAAACCCACTGAGTGAGCTCC
CTTGTTGTTGCATGGGATGGGCAATGTCCACATAGCGCAGAGGAGAATCTGTGTTACACAGCGCAATGGTAGGTAG
GTTAACATAAGATGCCTCCGCGAGAAGCTGGTGGTCAGCCCTGGGGTCAAGTAACCACAAGAAGCCGTGGCTCCCG
GAAGGCTGCCTGGATCTGGTTAGTGAAGGNTCCAGGAGTGAAGCGGCCAACAATTGGAGTGGCTTCAGTGGCAAGC
AGCAAACTTCAGCACAAGCCCTCTGGACCTGCCCGGCGGCCGCTCGA
```

16460.1.edit

```
TCGAGCGGCCGCCCGGGCAGGTCCATTTTCTCCCTGACGGNCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCNTCCCCGAACCTTATGCCTCTGCTG
GGCTTTCAGNGCCTCCACTATGATGNTGTAGGGGGGCACCTCTGGNGANGACCTCGGCCGCGACCACGCT
```

16460.2.edit

```
AGCGTGGTCGCGGCCGAGGTCCTCACCAGAGGTGCCACCTACAACATCATAGTGGAGGCACTGAAAGACCAGCAGA
GGCATAAGGCTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGGTCATTTCAGATGTGATTCATCTAGATGGTGCCATGACAATGGN
GNGAACTACAAGATTGGAGAGAAGTGGNACCGNCAGGGAGAAAATGGACCTGCCCGGGCGGCCGCTCGA
```

*Fig. 15BB*

16461.1.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGNTGCAACCTTG
GTTGGGGTCAATCCAGTACTCTCCACTCTTCCAGCCAGAGTGGCACATCTTGAGGTCACGGCAGGTGCGGNCGGGG
GNTTTTGCGGCTGCCCTCTGGNCTTCGGNTGTNCTCNATCTGCTGGCTCA 16461.2.edit TCGAGCGGCCGCCCGGGCAGGTCTCGCGGTCGCACTGGTGATGCTGGTCCTGTTGGTCCCCCCGGCCCTCCTGGAC
CTCCTGGCCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGNCGCAAGAACCCCGCCCGCACCTGCCGTG
ACCTCAAGATGTGCCACTCTGACTGGAAGAGTGGAGAGTACTGGATTGACCCCAACCAAGCTGCAACCTGGATGCC
ATCAAAGTCTTCTGCAACATGGAGACTGGTGAGACCTGCGTGTACCCCACTCAGCCCAGTGTGGCCCAAAAGAACT
GGTACATCAGCAAGAACCCCAAGGACAAGAAGCATGTCTGGTTCGGCGAGAACATGACCGATGGATTCCAGTTCGA
GTATGGCGGGCAGGGCTCCGACCCTGCCGATGGGGACCTTGGCCGCGAACACGCT 16463.1.edit AGCGTGGNNGCGGCCGAGGTATAAATATCCAGNCCATATCCTCCCTCCACACGCTGANAGATGAAGCTGTNCAAAG
ATCTCAGGGTGGANAAAACCAT 16463.2.edit TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT

*Fig. 15CC*

16464.1.edit

CGAGCGGGCGACCGGGCAGGTNCAGACTCCAATCCANANAACCATCAAGCCAGATGTCAGAAGCTACACCATCACA
GGTTTACAACCAGGCACTGACTACAAGANCTACCTGCACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGTACATCATCNAGTATGANAAGCCTGGGCCTCCTCCCAGAGAAGNGG
TCCCTCGGCCCCGCCCTGNTGTCCCANAGGNTACTATTACTGNGCCNGCAACCGGCAACCGATATCNATTTTGNCA
TTGGCCTTCAACAATAATTA 16464.2.edit AGCGTGGTTCGCGGCCGANGTCCTGTCAGAGTGGCACTGGTAGAAGTTCCAGGAACCCTGAACTGTAAGGGTTCTT
CATCAGNGCCAACAGGATGACATGAAATGATGTACTCAGAAGTGTCCTGGAATGGGGCCCATGAGATGGTTGTCTG
AGAGAGAGCTTCTTGNCCTGTCTTTTTCCTTCCAATCAGGGGCTCGCTCTTCTGATTATTCTTCAGGGCAATGACA
TAAATTGTATATTCGGGTCCCGGNTCCAGGCCAGTAATAGTANCCTCTGTGACACCAGGGCGGNGCCGAGGGACCA
CTTCTCTGGGAGGAGACCCAGGCTTCTCATACTTGATGATGTAACCGGTAATCCTGGCACGTGGCGGCTGCCATGA
TACCAGCAAGGAATTGGGGTGTGGTGGCCAGGAAACGCAGGTTGGATGGNGCATCAATGGCAGTGGAGGCCGTCGA
TGACCACAGGGGGAGCTCCGACATTGTCATTCAAGGTG 16465.1.edit AGCGTGGNCGCGGCCGAGGTGCAGCGCGGGCTGTGCCACCTTCTGCTCTCTGCCCAACGATAAGGAGGGTNCCTGC
CCCCAGGAGAACATTAACTNTCCCCAGCTCGGCCTCTGCCGG 16465.2.edit TCGAGCGGCCGCCCGGGCAGGTTTTTTTTGCTGAAAGTGGNTACTTTATTGGNTGGGAAAGGGAGAAGCTGTGGTC
AGCCCAAGAGGGAATACAGAGNCCCGAAAAAGGGGAGGGCAGGTGGGCTGGAACCAGACGCAGGGCCAGGCAGAAA
CTTTCTCTCCTCACTGCTCAGCCTGGTGGTGGCTGGAGCTCANAAATTGGGAGTGACACAGGACACCTTCCCACAG
CCATTGCGGCGGCATTTCATCTGGCCAGGACACTGGCTGTCCACCTGGCACTGGTCCCGACAGAAGCCCGAGCTGG
GGAAAGTTAATGTTCACCTGGGGGCAGGAACCCTCCTTATCATTGNGCAGAGAGCAGAAGGTGGCACAGCCCGCGC
TGCACCTCGGCCGCGACCACGCT 16466.2.edit TCGAGCGGCCGCCCGGGCAGGTCCACCATAAGTCCTGATACAACCACGGATGAGCTGTCAGGAGCAAGGTTGATTT
CTTTCATTGGTCCGGNCTTCTCCTTGGGGGNCACCCGCACTCGATATCCAGTGAGCTGAACATTGGGTGGCGTCCA
CTGGGCGCTCAGGCT 16467.2.edit TCGAGCGGTTCGCCCGGGCAGGTCCACCACACCCAATTCCTTGCTGGTATCATGGCAGCCGCCACGTGCCAGGATT
ACCGGCTACATCATCAAGTATGAGAAGCCTGGGTCTCCTCCCAGAGAAGCGGTCCCTCGGCCCCGCCCTGGTGTCA
CAGAGGCTACTATTACTGGCCTGGAACCGGGAACCGAATATACAATTTATGTCATTGNCCTGAAGAATAATCANNA
ANAGCGANCCCCTGATTGGAAGGA

*Fig. 15DD*

01_16469.edit

AGCGTGGTCGCGGCCGAGGTTGTACAAGCTTTTTTTTTTTTTTTTTTTTTTTTTTTTTTTTTTTTTTTTTTTTTTTTTT
TTTTTTTTTTTTTTTT

02_16469.edit

TCGAGCGGNCGCCCGGGCAGGTCTGCCAACACCAAGATTGGCCCCCGCCGCATCCACACAGTCCGTGTGCGGGGAG
GTAACAAGAAATACCGTGCCCTGAGGTTGGACGTGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATCGACAGCACACCGTACCGACAGTGGTACGAGTCCCACTATGCGCTGCCCCTGGGCCGCAAGAAGGGAG
CCAAGCTGACTCCTGAGGAAGAAGAGATTTTAAACAAAAAACGATCTAANAAAAAAAAAAACAAT

03_16470.edit

AGCGTGGTCGCGGCCGAGGTGAAATGGTATTCAGCTTCCTGGCACTTCTGGTCAGCAACCCAGTGTTGGGCAACAA
ATGATCTTTGAGGAACATGGTTTTAGGCGGACCACACCGCCCACAACGGCCACCCCCATAAGGCATAGGCCAAGAC
CATACCCGCCGAATGTAGGACAAGAAGCTCTCTCTCAGACAACCATCTCATGGGCCCCATTCCAGGACACTTCTGA
GTACATCATTTCATGTCATCCTGTTGGCACTGATGAAGAACCCTTACAGTTCAGGGTTCCTGGAACTTCTACCAGT
GCCACTCTGACAGGACCTGCCCGGGCGGCCGCTCGA

04_16470.edit

TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCACCTCGGCCGCGACCACGCTA

05_16471.edit

TCGAGCGGCCGCCCGGGCAGGTCTCCCTTCTTGCGGCCCAGGGGCAGCGCATAGTGGGACTCGTACCACTGTCGGT
ACGGTGTGCTGTCGATGAGCACGATGCAATTCTTCACCAGGGTCTTGGTACGAACCAGCTCGTTATTAGATGCATT
GTAGACAACATCGATGATCCTTGTTTTACGAGTACAACACTCTGAGCCCCAGGAGAAATTCCCCACGTCCAACCTC
AGGGCACGGTATTTCTTGTTACCTCCCCGCACACGGACTGTGTGGATGCGGCGGGGGCCAAGCTGACTCCTGAGGA
AGAAGAGATTTTAAACAAAAAACGATCTAAAAAAATTCAGAAGAAATATGATGAAAGGAAAAAGAATGCCAAAATC
AGCAGTCTCCTGGAGGAGCAGTTCCAGCAGGGCAAGCTTCTTGCGTGCATCGCTTCAAGGCCGGGACAGTGTGACC
GAGCAGATGGCTATGTGCTAGAGGGCAAAGAAGTGGAGTTCTATCTTAAGAAAATCAGGGCCCAGAATGGTGNGTC
TTCAACTAATCCAAAGGGGAGTTTCAGACCAGTGCAATCAGCAAAAACATTGATACTGNTGGCCAAATTTATTGGT
GCAGGGCTTGCACANTANGANNGGCTGGGTCTTGGGGCTTGGATTGGNACAAGCTTTGGCAGCCTTTTCTTTGGTT
TTGCCAAAAACCTTTTGNTGAAGANGANACCTNGGGCGGACCCCTTAACCGATTCCACNCCNGGNGGCGTTCTANG
GNCCCNCTTG

*Fig. 15EE*

06_16471.edit

AGCGTGGTCGCGGCCGAGGTCTGCTGCTTCAGCGAAGGGTTTCTGGCATAACCAATGATAAGGCTGCCAAAGACTG
TTCCAATACCAGCACCAGAACCAGCCACTCCTACTGTTGCAGCACCTGCACCAATAAATTTGGCAGCAGTATCAAT
GTCTCTGCTGATTGCACTGGTCTGAAACTCCCTTTGGATTAGCTGAGACACACCATTCTGGGCCCTGATTTTCCTA
AGATAGAACTCCAACTCTTTGCCCTCTAGCACATAGCCATCTGCTCGGTCACACTGTCCCGGCCTTGAAGCGATGC
ACGCAAGAAGCTTGCCCTGCTGGAACTGCTCCTCCAGGAGACTGCTGATTTTGGCATTCTTTTTCCTTTCATCATA
TTTCTTCTGAATTTTTTTAGATCGTTTTTTGTTTAAAATCTCTTCTTCCTCAGGAGTCAGCTTGGCCCCCGCCGCA
TCCACACAGTCCGTGTGCGGGGAGGTAACAAGAAATACCGTGCCCTGAGGTTGGACGTGGGGAATTTCTCCTGGGG
CTCAGAGTGGTGTACTCGTAAAACAAGGATCATCGATGGTGNCTACAATGCATCTAATAACGAGCTGGGTCGGACC
CAAAGAACCTGGNGAANAAATGGATCGNCTCATCGACAGGACACCGTACCCGACAGGGGNACGANTCCCACTATGC
GCTTGCCCCTGGGCCGCAANAAAGGAAAACTGCCCGGGCGGCCNTCGAAAGCCCAATTNTGGAAAAAAATCCATCAC
ACTGGGNGGCCNGTCGAGCATGCATNTANAGGGGCCCATTCCCCCTNANN

07_16472.edit

TCGAGCGGCCGCCCGGGCAGGTCCCCAACCAAGGCTGCAACCTGGATGCCATCAAAGTCTTCTGCAACATGGAGAC
TGGTGAGACCTGCGTGTACCCCACTCAGCCCAGTGTGGCCCAGAAGAACTGGTACATCAGCAAGAACCCCAAGGAC
AAGAGGCATGTCTGGTTCGGCGAGAGCATGACCGATGGATTCCAGTTCGAGTATGGCGGCCAGGGCTCCGACCCTG
CCGATGTGGACCTCGGCCGCGACCACGCT

08_16472.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGACCTGCCCGGGCGGCCGCTCGA

09_16473.edit

TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGNTTT
AGGCGGACCACACCGCCCACAACGGCCACCCCCATAAGGCATAGGCCAAGACCATACCCGCCGAATGTAGGACAAG
AAGCTNTNTNTCANACACCATNTNATGGGCCCCATTCCAGGACACTTCTGAGTACATCATTTATGNCATCTGTGGC
ACTTGATGAAAACCCTTACAGTTCAGGGTTCTGGAACTTTTACCAGGCCTNTTACAGGACTNGGCCGGACNCCTTA
AGCCNATTNCACCCTGGGGCGTTCTANGGTCCCACTCGNNCACTGGNGAAAATGGCTACTGTN

*Fig. 15FF*

11_16474.edit

AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGNGAAACTCCNAGGACANGAGGGCTAAATTCCATGAAGTTTGTGGATGGCCTGATGATCCACAAT
CGGAGACCCTGTTAACTACTACCGTCTNACCNCCTGCTGTNCNCCCCCNTTTCTGCTNAANACATNGGGNTNNTNC
TTGNCCNTCCTTGGGTNGAANATNNAATNGCCTNCCCNTTCNTANCNCTACTNGNTCCANANTTGGCCTTTAAANA
ATCCNCCTTGCCTTNNNCACTGTTCANNTNTTTNNTCGTAAACCCTATNANTTNNATTANATNNTNNNNNNCTCAC
CCCCCTCNTCATTNANCCNATANGCTNNNAANTCCTTNANNCCTCCCNCCCNNTNCNCTCNTACTNANTNCTTCTN
NCCCATTACNNAGCTCTTTCNTTTAANATAATGNNGCCNNGCTCTNCATNTCTACNATNTGNNNAATNCCCCCNCC
CCCNANCGNNTTTTTGACCTNNNAACCTCCTTTCCTCTTCCCTNCNNAAATTNCNNANTTCCNCNTTCCNNCNTTT
CGGNTNNTCCCATNCTTTCCANNNCTTCANTCTANCNCNCTNCAACTTATTTTCCTNTCATCCCTTNTTCTTTACA
NNCCCCCTNNTCTACTCNNCNNTTNCATTANATTTGAAACTNCCACNNCTANTTNCCTCNCTCTACNNTTTTATTT
TNCGNTCNCTCTACNTAATANTTTAATNANTTNTCN

12_16474.edit

TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAAGCAGTGTCAACGTAGTAAGTTAACAGGGTCTCCGCTGTGGATCA
TCAGGCCATCCACAAACTTCATGGATTTAGCCCTCTGTCCTCGGAGTTTCCCAGACACCACAACCTCGCAGCCTTT
GGCCCCACTCTCCATGATGAACCGCAGCACACCATAGCAGGCCCTCCGCACAAGCAAGCCCTCCTAAGAATTTGTA
ACGCANANACTCTGCTGGCAATGGCACACAAACCTCTAGTGGACCTCGGNCGCGACCACGC

13_16475.edit

TCGAGCGGCCGCCCGGGCAGGTCTGGTCCAGGATAGCCTGCGAGTCCTCCTACTGCTACTCCAGACTTGACATCAT
ATGAATCATACTGGGGAGAATAGTTCTGAGGACCAGTAGGGCATGATTCACAGATTCCAGGGGGGCCAGGAGAACC
AGGGGACCCTGGTTGTCCTGGAATACCAGGGTCACCATTTCTCCCAGGAATACCAGGAGGGCCTGGATCTCCCTTG
GGGCCTTGAGGTCCTTGACCATTAGGAGGGCGAGTAGGAGCAGTTGGAGGCTGTGGGCAAACTGCACAACATTCTC
CAAATGGAATTTCTGGGTTGGGGCAGTCTAATTCTTGATCCGTCACATATTATGTCATCGCAGAGAACGGATCCTG
AGTCACAGACACATATTTGGCATGGTTCTGGCTTCCAGACATCTCTATCCGNCATAGGACTGACCAAGATGGGAAC
ATCCTCCTTCAACAAGCTTNCTGTTGTGCCAAAAATAATAGTGGGATGAAGCAGACCGAGAAGTANCCAGCTCCCC
TTTTTGCACAAAGCNTCATCATGTCTAAATATCAGACATGAGACTTCTTTGGGCAAAAAAGGAGAAAAAGAAAAAG
CAGTTCAAAGTANCCNCCATCAAGTTGGTTCCTTGCCCNTTCAGCACCCGGGCCCCGTTATAAAACACCTNGGGCC
GGACCCCCCTT

*Fig. 15GG*

14_16475.edit

AGCGTGGTCGCGGCCGAGGTGTTTTATGACGGGCCCGGTGCTGAAGGGCAGGGAACAACTTGATGGTGCTACTTTG
AACTGCTTTTCTTTTCTCCTTTTTGCACAAAGAGTCTCATGTCTGATATTTAGACATGATGAGCTTTGTGCAAAAG
GGGAGCTGGCTACTTCTCGCTCTGCTTCATCCCACTATTATTTTGGCACAACAGGAAGCTGTTGAAGGAGGATGTT
CCCATCTTGGTCAGTCCTATGCGGATAGAGATGTCTGGAAGCCAGAACCATGCCAAATATGTGTCTGTGACTCAGG
ATCCGTTCTCTGCGATGACATAATATGTGACGATCAAGAATTAGACTGCCCCAACCCAGAAATTCCATTTGGAGAA
TGTTGTGCAGTTTGCCCACAGCCTCCAACTGCTCCTACTCGCCCTCCTAATGGTCAAGGACCTCAAGGCCCCAAGG
GAGATCCAGGCCCTCCTGGTATTCCTGGGAGAAATGGTGACCCTGGTATTCCAGGACAACCAGGGTCCCCTGGTTC
TCCTGGCCCCCCTGGAATCNGGNGAATCATGCCCTACTGGTCCTCAAACTATTCTCCCANATGATTCATATGATGT
CAAGTCTGGGATAGCNAGTANGGANGGACTCGCAGGCTATTCTGGACCANACCTGCCGGGGGGGCGTTCGAAAGCC
CGAATCTGCANANNTNCNTTCACACTGGCGGCCGTCGAGCTGCTTTAAAAGGGCCATTCCNCCTTTAGNGNGGGGG
ANTACAATTACTNGGCGGCGTTTTANANCGCGNGNCTGGGAAAT

15_16476.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAGGCTCTTGAGGGTGGTGTCCACCTCGA
GGTCACGGTCACGAACCACATTGGCATCATCAGCCCGGTAGTAGCGGCCACCATCGTGAGCCTTCTCTTGANGTGG
CTGGGGCAGGAACTGAAGTCGAAACCAGCGCTGGGAGGACCAGGGGGACCAANAGGTCCAGGAAGGGCCCGGGGGG
GACCAACAGGACCAGCATCACCAAGTGCGACCCGCGAGAACCTGCCCGGCCGNCCGCTCGAA

16_16476.edit

TCGAGCGNNCGCCCGGGCAGGTCTCGCGGTCGCACTGGTGATGCTGGTCCTGTTGGTCCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGCCGCAAGAACCCCGCCCGCACCTGCCGTG
ACCTCAAGATGTGCCACTCTGACTGGAAGAGTGGAGAGTACTGGATTGACCCCAACCAAGGCTGCAACCTGGATGC
CATCAAAGTCTTCTGCAACATGGAGACTGGTGAGACCTGCGTGTACCCCACTCAGCCCAGTGTGGCCCAGAAGAAC
TGGTACATCAGCAAGAACCCCAAGGACAAGAGGCATGTCTGGTTCGGCGAGAGCATGACCGATGGATTCCAGTTCG
AGTATGGCGGCCAGGGCTCCCACCCTGCCGATGTGGACCTCCGGCCGCGACCACCCTT

*Fig. 15HH*

17_16477.edit

TNGAGCGGCCGCCCGGGCAGGNTGNNAACGCTGGTCCTGCTGGTCCTCCTGGCAAGGCTGGTGAAGATGGTCACCC
TGGAAAACCCGGACGACCTGGTGAGAGAGGAGTTGTTGGACCACAGGGTGCTCGTGGTTTCCCTGGAACTCCTGGA
CTTCCTGGCTTCAAAGGCATTAGGGGACACAATGGTCTGGATGGATTGAAGGGACAGCCCGGTGCTCCTGGTGTGA
AGGGTGAACCTGGTGCCCCTGGTGAAAATGGAACTCCAGGTCAAACAGGAGCCCGTGGGCTTCCTGGTGAGAGAGG
ACCGTGTTGGTGCCCCTGGCCCANACCTCGGCCGCGACCACGCTAAGCCCGAATTTCCAGCACACTGGNGGCCGTT
ACTANTGGATCCGAGCTCGGTACCAAGCTTGGCGTAATCATGGTCATAGCTGTTTCCTGNGTGAAATTGTTATCCG
CTCACAATTTCACACANCATACGAAGCCGGAAAGCATAAAGTGTAAAGCCTTGGGGTGCTAATGAGTGAGCTAACT
CNCATTAAATTGCGTTGCGCTCACTGCCCGCTTTTCCANNNGGGAAACCNTGGCNTNGCCNGCTTGCNTTAANTGA
AATCCGCCNACCCCCGGGGAAAAGNCGGTTTGCNGTATTGGGGCNCTTTTTCCCTTTCCTCGGNTTACTTGANTTA
NTGGGCTTTGGNCGNTTCGGGTTGNGGCGANCNGGTTCAACNTCACNCCAAAGGNGGNAANACGGTTTTCCCANAA
TCCGGGGGNTANCCCAANGNAAAACATNNGNCNAANGGGCT

18_16477.edit

AGCGTGGTTNGCGGCCGAGGTCTGGGCCAGGGGCACCAACACGTCCTCTCTCACCAGGAAGCCCACGGGCTCCTGT
TTGACCTGGAGTTCCATTTTCACCAGGGGCACCAGGTTCACCCTTCACACCAGGAGCACCGGGCTGTCCCTTCAAT
CCATNCAGACCATTGTGNCCCCTAATGCCTTTGAAGCCAGGAAGTCCAGGAGTTCCAGGGAAACCACCGAGCACCC
TGTGGTCCAACAACTCCTCTCTCACCAGGTCGTCCGGGTTTTCCAGGGTGACCATCTTCACCAGCCTTGCCAGGAG
GACCAGCAGGACCAGCGTTACCAACCTGCCCGGGCGGCCGCTCGA

21_16479.edit

TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT

22_16479.edit

AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAAGATGTGATTCATCTAGATGGTGCCATGACAATGGT
GTGAACTACAAGATTGGAGAGAAGTGGGACCGTCAGGGAGAAAATGGACCTGCCCGGGCCGGCCGCTCGA

*Fig. 15II*

24_16480.edit

TCGAGCGNNCGCCCGGGCAGGTCCAGTAGTGCCTTCGGGACTGGGTTCACCCCCAGGTCTGCGGCAGTTGTCACAG
CGCCAGCCCCGCTGGCCTCCAAAGCATGTGCAGGAGCAAATGGCACCGAGATATTCCTTCTGCCACTGTTCTCCTA
CGTGGTATGTCTTCCCATCATCGTAACACGTTGCCTCATGAGGGTCACACTTGAATTCTCCTTTTCCGTTCCCAAG
ACATGTGCAGCTCATTTGGCTGGCTCTATAGTTTGGGGAAAGTTTGTTGAAACTGTGCCACTGACCTTTACTTCCT
CCTTCTCTACTGGAGCTTTCGTACCTTCCACTTCTGCTGTTGGTAAAATGGTGGATCTTCTATCAATTTCATTGAC
AGTACCCACTTCTCCCAAACATCCAGGGAAATAGTGATTTCAGAGCGATTAGGAGAACCAAATTATGGGGCAGAAA
TAAGGGGCTTTTCCACAGGTTTTCCTTTGGAGGAAGATTTCAGTGGTGACTTTAAAAGAATACTCAACAGTGTCTT
CATCCCCATAGCAAAAGAAGAAACNGTAAATGATGGAANGCTTCTGGAGATGCCNNCATTTAAGGGACNCCCAGAA
CTTCACCATCTACAGGACCTACTTCAGTTTACANNAAGNCACATANTCTGACTCANAAAGGACCCAAGTAGCNCCA
TGGNCAGCACTTTNAGCCTTTCCCCTGGGGAAAANNTTACNTTCTTAAANCCTNGGCCNNGACCCCCTTAAGNCCA
AATTNTGGAAAANTTCCNTNCNNCTGGGGGGCNGTTCNACATGCNTTTNAAGGGCCCAATTNCCCCNT

25_16481.edit

TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAGCCAGTCCTGGTGCAGGAC
GGTGAGGACGCTGACCACACGGTACGTGCTGTTGTACTGCTCCTCCCGCGGCTTTGTCTTGGCATTATGCACCTCC
ACGCCGTCCACGTACCAGTTGAACTTGACCTCAGGGTCTTCGTGGCTCACGTCCACCACCACGCATGTAACCTCAG
ACCTCGGCCGCGACCACGCT

26_16481.edit

AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAAGCCCCGAGAACCACAGGTGTACACCCT
GCCCCCATCCCGGGAGGAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCCGTGCTGGACTCCGACA
CCTGCCCGGGCGGCCGCTCGA

27_16482.edit

TCGAGCGGCCGCCCGGGCAGGTTGAATGGCTCCTCGCTGACCACCCCGGTGCTGGTGGTGGGTACAGAGCTCCGAT
GGGTGAAACCATTGACATAGAGACTGTCCCTGTCCAGGGTGTAGGGGCCCAGCTCAGTGATGCCGTGGGTCAGCTG
GCTCAGCTTCCAGTACAGCCGCTCTCTGTCCAGTCCAGGGCTTTTGGGGTCAGGACGATGGGTGCAGACAGCATCC
ACTCTGGTGGCTGCCCCATCCTTCTCAGGCCTGAGCAAGGTCAGTCTGCAACCAGAGTACAGAGAGCTGACACTGG
TGTTCTTGAACAAGGGCATAAGCAGACCCTGAAGGACACCTCGGCCGCGACCACGCT

*Fig. 15JJ*

28_16482.edit

AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA

29_16483.edit

AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTCCCGGTTCCAGGCCAGTAATA
GTAGCCTCTGTGACACCAGGGCGGGGCCGAGGGACCCTTCTNTTGGAAGAGACCAGCTTCTCATACTTGATGATGA
GNCCGGTAATCCTGGCACGTGGNGGTTGCATGATNCCACCAAGGAAATNGGNGGGGGNGGACCTGCCCGGCGGCCG
TTCNAAAGCCCAATTCCACACACTTGGNGGCCGTACTATGGATCCCACTCNGTCCAACTTGGNGGAATATGGCATA
ACTTTT

31_16484.edit

TCGAGCGGCCGCCCGGGCAGGTCCTTGACCTTTTCAGCAAGTGGGAAGGTGTAATCCGTCTCCACAGACAAGGCCA
GGACTCGTTTGTACCCGTTGATGATAGAATGGGGTACTGATGCAACAGTTGGGTAGCCAATCTGCAGACAGACACT
GGCAACATTGCGGACACCCTCCAGGAAGCGAGAATGCAGAGTTTCCTCTGTGATATCAAGCACTTCAGGGTTGTAG
ATGCTGCCATTGTCGAACACCTGCTGGATGACCAGCCCAAAGGAGAAGGGGGAGATGTTGAGCATGTTCAGCAGCG
TGGCTTCGCTGGCTCCCACTTTGTCTCCAGTCTTGATCAGACCTCGGCCGCGACCACGCT

37_16487.edit

AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCGCATCCCCCTTCCAAACCTGCCCGGGCGGCCGCTCG

*Fig. 15KK*

38_16487.edit

CGAGCGGCCGCCCGGGCAGGTTTGGAAGGGGGATGCGGGGGAAGAGGAAGACTGACGGTCCCCCCAGGAGTTCAGG
TGCTGGGCACGGTGGGCATGTGTGAGTTTTGTCACAAGATTTGGGCTCAACTCTCTTGTCCACCTTGGTGTTGCTG
GGCTTGTGATCTACGTTGCAGGTGTAGGTCTGGGTGCCGAAGTTGCTGGAGGGCACGGTCACCACGCTGCTGAGGG
AGTAGAGTCCTGAGGACTGTAGGACAGACCTCGGCCGCGACCACGCT

39_16488.edit

NGGNNGGTCCGGNCNGNCAGGACCACTCNTCTTCGAAATA

41_16489.edit

AGCGTGGTCGCGGCCGAGGTCCTCACTTGCCTCCTGCAAAGCACCGATAGCTGCGCTCTGGAAGCGCAGATCTGTT
TTAAAGTCCTGAGCAATTTCTCGCACCAGACGCTGGAAGGGAAGTTTGCGAATCAGAAGTTCAGTGGACTTCTGAT
AACGTCTAATTTCACGGAGCGCCACAGTACCAGGACCTGCCCGGGCGGCCGCTCGA

42_16489.edit

TCGAGCGGCCGCCCGGGCAGGTCCTGGTACTGNGGCGCTCCGTGAAATTAGACGTTATCAGAAGTCCACTGAACTT
CTGATTCGCAAACTTCCCTTCCAGCGTCTGGTGCGAGAAATTGCTCAGGACTTTAAAACAGATCTGCGCTTCCAGA
GCGCAGCTATCGGTGCTTTGCAGGAGGCAAGTGAGGACCTCGGCCGCGACCACGCT

45_16491.edit

TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT

*Fig. 15LL*

46_16491.edit

GTGGGNTTGAACCCNTTTNANCTCCGCTTGGTACCGAGCTCGGATCCACTAGTAACGGCCGCCAGTGTGCTGGAAT
TCGGCTTAGCGTGGTCGCGGCCGAGGTCAAGAACCCCGCCCGCACCTGCCGTGACCTCAAGATGTGCCACTCTGAC
TGGAAGAGTGGAGAGTACTGGATTGACCCCAACCAAGGCTGCAACCTGGATGCCATCAAAGTCTTCTGCAACATGG
AGACTGGTGAGACCTGCGTGTACCCCACTCAGCCCAGTGTGGCCCAGAAGAACTGGTACATCAGCAAGAACCCCAA
GGACAAGAGGCATGTCTGGTTCGGCGAGAGCATGACCGATGGATTCCAGTTCGAGTATGGCGGCCAGGGCTCCGAC
CCTGCCGATGTGGACCTGCCCGGGCGGCCGCTCGA

47_16492.edit

AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAAGTGT
CTATGCTCAGAATCCAAGCGGAGAGAAGTCAGCCTCTGGTTCAGACTGNAAGTAACCAACATTGATCGCCTAAAGG
ACTGGCATTCACTGATGNGGATGCCGATTCCATCAAAATTGNTTGGGAAAACCCACAGGGGCAAGTTTNCANGTCN
AGGNGGACCTACTCGAGCCCTGAGGATGGAATCCTTGACTNTTCCTTNNCCTGATGGGGAAAAAAAACCTTNAAAA
CTTGAAGGACCTGCCCGGGCGGCCGTNCAAAACCCAATTCCACCCCCTTGGGGGCGTTCTATGGGNCCCACTCGGA
CCAAACTTGGGGTAAN

48_16492.edit

TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGGCATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAGTTTTTGTTGGTCCTGGTCCATTTTTGGGAGTGGTGGTTACTCTGT
AACCAGTAACAGGGGAACTTGAAGGCAGCCACTTGACACTAATGCTGTTGTCCTGAACATCGGTCACTTGCATCTG
GGATGGTTTGTCAATTTCTGTTCGGTAATTAATGGAAATTGGCTTGCTGCTTGCGGGGCTTGTCTCCACGGCCAGT
GACAGCATACACAGTGATGGTATAATCAACTCCAGGTTTAAGCCGCTGATGGTAGCTGAAACTTTGCTCCAGGCAC
AAGTGAACTCCTGACAGGGCTATTTCCTNCTGTTCTCCGTAAGTGATCCTGTAATATCTCACTGGGACAGCAGGAN
GCATTCCAAAACTTCGGGCGNGACCCCCTAAGCCGAATTNTGCAATATNCATCACACTGGCGGGCGCTCGANCATT
CATTAAAAGGCCCAATCNCCCCTATAGGGAGTNTANTACAATTNG

*Fig. 15MM*

49_16493.edit

TCGAGCGGCCGCCCGGGCAGGTCACTTTTGGTTTTTGGTCATGTTCGGTTGGTCAAAGATAAAAACTAAGTTTGAG
AGATGAATGCAAAGGAAAAAAATATTTTCCAAAGTCCATGTGAAATTGTCTCCCATTTTTTTGGCTTTTGAGGGGG
TTCAGTTTGGGTTGCTTGTCTGTTTCCGGGTTGGGGGAAAGTTGGTTGGGTGGGAGGGAGCCAGGTTGGGATGGA
GGGAGTTTACAGGAAGCAGACAGGGCCAACGTCG

55_16496.edit

AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA

56_16496.edit

TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT

59_16498.edit

TCGAGCGGCCGCCCGGGCAGGTCCACCATAAGTCCTGATACAACCACGGATGAGCTGTCAGGAGCAAGGTTGATTT
CTTTCATTGGTCCGGTCTTCTCCTTGGGGGTCACCCGCACTCGATATCCAGTGAGCTGAACATTGGGTGGTGTCCA
CTGGGCGCTCAGGCTTGTGGGTGTGACCTGAGTGAACTTCAGGTCAGTTGGTGCAGGAATAGTGGTTACTGCAGTC
TGAACCAGAGGCTGACTCTCTCCGCTTGGATTCTGAGCATAGACACTAACCACATACTCCACTGTGGGCTGCAAGC
CTTCAATAGTCATTTCTGTTTGATCTGGACCTGCAGTTTTAGTTTTTGTTGGTCCTGGTCCATTTTTGGGAGTGGT
GGTTACTCTGTAACCAGTAACAGGGGAACTTGAAGGCAGCCACTTGACACTAATGCTGTTGTCCTGAACATCGGTC
ACTTGCATCTGGGATGGTTTGNCAATTTCTGTTCGGTAATTAATGGAAATTGGCTTGCTGCTTGCGGGGCTGTCTC
CACGGCCAGTGACAGCATACACAGNGATGGNATNATCAACTCCAAGTTTAAGGCCCTGATGGTAACTTTAAACTTG
CTCCCAGCCAGNGAACTTCCGGACAGGGTATTTCTTCTGGTTTTCCGAAAGNGANCCTGGAATNNTCTCCTTGGAN
CAGAAGGANCNTCCAAAACTTGGGCCGGAACCCCTT

*Fig. 15NN*

60_16473.edit

AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTTCCCGGTTCCAGGCCAGTAAT
AGTAGCCTCTTGTGACACCAGGCGGGGCCCANGGACCACTTCTCTGGGANGAGACCCAGCTTCTCATACTTGATGA
TGTAACCCGGTAATCCTGCACGTGGCGGCTGNCATGATACCANCAAGGAATTGGGTGNGGNGGACCTGCCCGGCGG
CCCTCNA

60_16498.edit

AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAGTGTC
TATGCTCAGAATCCAAGCGGAGAGAGTCAGCCTCTGGTTCAGACTGCAGTAACCACTATTCCTGCACCAACTGACC
TGAAGTTCACTCAGGTCACACCCACAAGCCTGAGCCGCCAGTGGACACCACCCAATGTTCACTCACTGGATATCGA
GTGCGGGTGACCCCCAAGGAGAAGACCCGGACCCATGAAAGAAATCAACCTTGCTCCTGACAGCTCATCCGNGGGT
GTATCAGGACTTATGGGGGACTGCCCCGGCNGGCCGNTCGAAANCGAATTNTGAAATTTCCTTCNCACTGGGNGGC
GNTTCGAGCTTNCTTNTANANGGCCCAATTCNCCTNTAGNGGGTCGTN

61_16499.edit

AGCGTGGTCGCGGCCGAGGTCNAGG

62_16483.edit

TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGTTTT
AGGCGGACCACACCGCCCACAACGGGCACCCCCATAAGGNATAGGCCAAGACCATACCCCGCCGAATGTAGGACAA
GAAGCTCTNTCTCAACAACCATCTCATGGGCCCCATTCCAGGACACTTCTGAGTACATCATTTCATGTCATCCTGG
TGGGCACTTGATGAANAACCCTTACAGTTCAGGGTTCCTGGAACTTCTACCAGNGCCACTTCTGACAGGANCTTGG
GCGNGACCACCCT

*Fig. 15OO*

63_16500.edit

AGCGTGGTCGCGGCCGAGGTCCATTTTCTCCCTGACGGTCCCACTTCTCTCCAATCTTGTAGTTCACACCATTGTC
ATGGCACCATCTAGATGAATCACATCTGAAATGACCACTTCCAAAGCCTAAGCACTGGCACAACAGTTTAAAGCCT
GATTCAGACATTCGTTCCCACTCATCTCCAACGGCATAATGGGAAACTGTGTAGGGGTCAAAGCACGAGTCATCCG
TAGGTTGGTTCAAGCCTTCGTTGACAGAGTTGCCCACGGTAACAACCTCTTCCCGAACCTTATGCCTCTGCTGGTC
TTTCAGTGCCTCCACTATGATGTTGTAGGTGGCACCTCTGGTGAGGACCTGCCCGGGCGGCCCGCTCGA

64_16493.edit

AGCGTGGTCGCGGCCGAGGTGTGCCCCAGACCAGGAATTCGGCTTCGACGTTGGCCCTGTCTGCTTCCTGTAAACT
CCCTCCATCCCAACCTGGCTCCCTCCCACCCAACCAACTTTCCCCCCAACCCGGAAACAGACAAGCAACCCAAACT
GAACCCCCTCAAAAGCCAAAAAAATGGGAGACAATTTCACATGGACTTTGGAAAATATTTTTTTCCTTTGCATTCA
TCTCTCAAACTTAGTTTTTATCTTTGACCAACCGAACATGACCAAAAACCAAAAGTGACCTGCCCGGGCGGCCGCT
CGA

64_16500.edit

TCGAGCGGCCGCCCGGGCAGGTCCTCACCAGAGGTGCCACCTACAACATCATAGTGGAGGCACTGAAAGACCAGCA
GAGGCATAAGGTTCGGGAAGAGGTTGTTACCGTGGGCAACTCTGTCAACGAAGGCTTGAACCAACCTACGGATGAC
TCGTGCTTTGACCCCTACACAGTTTCCCATTATGCCGTTGGAGATGAGTGGGAACGAATGTCTGAATCAGGCTTTA
AACTGTTGTGCCAGTGCTTAGGCTTTGGAAGTGGTCATTTCAGATGTGATTCATCTAGATGGTGCCATGACAATGG
TGTGAACTACAAGATTGGAGAGAAGTGGGACCGTCAGGGAGAAAATGGACCTCGGCCGCGACCACGCT

*Fig. 15PP*

16501.edit

TCGAGCGGCCGCCCGGGCAGGTACCGGGGTGGTCAGCGAGGAGCCATTCACACTGAACTTCACCATCAACAACCTG
CGGTATGAGGAGAACATGCAGCACCCTGGCTCCAGGAAGTTCAACACCACGGAGAGGGTCCTTCAGGGCCTGCTCA
GGTCCCTGTTCAAGAGCACCAGTGTTGGCCCTCTGTACTCTGGCTGCAGACTGACTTTGCTCAGACCTGAGAAACA
TGGGGCAGCCACTGGAGTGGACGCCATCTGCACCCTCCGCCTTGATCCCACTGGTNCTGGACTGGACANANAGCGG
CTATACTTGGGAGCTGANCCNAACCTTTGGCGGNGACNCCNCTT 16501.2.edit GAGGACTGGCTCAGCTCCCAGTATAGCCGCTCTCTGTCCAGTCCAGGACCAGTGGGATCAAGGCGGAGGGTGCAGA
TGGCGTCCACTCCAGTGGCTGCCCCATGTTTCTCAAGTCTGAGCAAAGNCAGTCTGCAGCCAGAGTACAGAGGGCC
AACACTGGTGCTCTTGAACAGGGACCTGAGCAGGCCCTGAAGGACCCTCTCCGTGGTGTTGAACTTCCTGGAGCCA
GGGTGCTGCATGTTCTCCTCATACCGCAGGTTGTTGATGGTGAAGTTCAGTGTGAATGGCTCCTCGCTGACCACCC 16502.1.edit AGCGTGGTCGCGGCCGAGGTCCACCACACCCAATTCCTTGCTGGTATCATGGCAGCCGCCACGTGCCAGGATTACC
GGCTACATCATCAAGTATGAGAAGCCTGGGTCTCCTCCCAGAGAAGTGGTCCCTCGGCCCCGCCCTGGTGTCACAG
AGGCTACTATTACTGGCCTGGAACCGGGAACCGAATATACAATTTATGTCATTGCCCTGAAGAATAATCAGAAGAG
CGAGCCCCTGATTGGAAGGAAAAAGACAGACGAGCTTCCCCAACTGGTAACCCTTCCACACCCCAATCTTCATGGA
CCANANANCTTGGATNGTCCTTTCACNGGTTNAAAAAACCCTTTTCGCCCCCCCACCTTGGGGATTAACCTTGGGA
AANGGGGATTTNACCNTTCC 16502.2.edit TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCCAGTGTCATACCCAGGGNGGGTGACCAAAGGGGGTCNTTTNGACCTGGNGAAAGGAACCA
TCCAAAANCTCTGNCCCATG

*Fig. 15QQ*

16503.1.edit

AGCGTGGNCGCGGCCGAGGTCTGAGGATGTAAACTCTTCCCAGGGGAAGGCTGAAGTGCTGACCATGGTGCTACTG
GGTCCTTCTGAGTCAGATATGTGACTGATGNGAACTGAAGTAGGTACTGTAGATGGTGAAGTCTGGGTGTCCCTAA
ATGCTGCATCTCCAGAGCCTTCCATCATTACCGTTTCTTCTTTTGCTATGGGATGAGACACTGTTGAGTATTCTCT
AAAGTCACCACTGAAATCTTCCTCCAAAGGAAAACCTGTGGAAAAGCCCCTTATTTCTGCCCCATAATTTGGTTCT
CCTAATCNCTCTGAAATCACTATTTCCCTGGAANGTTTGGGAAAAANNGGGCNACCTGNCANTGGAAANTGGATAN
AAAGATCCCACCATTTTACCCAACNAGCAGAAAGTGGGAANGGTACCGAAAAGCTCCAAGTAANAAAAAGGAGGGA
AGTAAAGGTCAAGTGGGCACCAGTTTCAAACAAAACTTTCCCCAAACTATANAACCCA 16503.2.edit AAGCGGCCGCCCGGGCAGGNNCAGNAGTGCCTTCGGGACTGGGNTCACCCCCAGGTCTGCGGCAGTTGTCACAGCG
CCAGCCCCGCTGGCCTCCAAAGCATGTGCAGGAGCAAATGGCACCGAGATATTCCTTCTGCCACTGTTCTCCTACG
TGGTATGTCTTCCCATCATCGTAACACGTTGCCTCATGAGGGTCACACTTGAATTCTCCTTTTCCGTTCCCAAGAC
ATGTGCAGCTCATTTGGCTGGCTCTATAGTTTGGGGAAAGTTTGTTGAAACTGTGCCACTGACCTTTACTTCCTCC
TTCTCTACTGGAGCTTTCCGTACCTTCCACTTCTGCTGNTGGNAAAAAGGGNGGAACNTCTTATCAATTTCATTGG
ACAGTANCCCNCTTTCTNCCCAAAACATNCAAGGGAAAATATTGATTNCNAGAGCGGATTAAGGAACAACCCNAAT
TATGGGGGCCAGAAATAAAGGGGGCTTTTCCACAGGTNTTTTCCT 16504.1.edit TCGAGCGGCCGCCCGGGCAGGTCTGCAGGCTATTGTAAGTGTTCTGAGCACATATGAGATAACCTGGGCCAAGCTA
TGATGTTCGATACGTTAGGTGTATTAAATGCACTTTTGACTGCCATCTCAGTGGATGACAGCCTTCTCACTGACAG
CAGAGATCTTCCTCACTGTGCCAGTGGGCAGGAGAAAGAGCATGCTGCGACTGGACCTCGGCCGCGACCACGCT 16504.2.edit AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA

*Fig. 15RR*

16505.1.edit

CGAGCGGCCGCCCGGGCAGGTCCAGACTCCAATCCAGAGAACCACCAAGCCAGATGTCAGAAGCTACACCATCACA
GGTTTACAACCAGGCACTGACTACAAGATCTACCTGTACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGCTACATCATCAAGTATGAGAAGCCTGGGTCTCCTCCCAGAGAAGTG
GTCCCTCGGCCCCGCCCTGGTGNCACAGAAGCTACTATTACTGGCCTGGAACCGGGAACCGAATATACAATTTATG
TCATTGCCCTGAAGAATAATCANAAGAGCGAGCCCCTGATTGGAAGG 16505.2.edit AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTGTCTTTTTCCTTCCAATCAGGGGCTCGCTCTTCTGATTATTCTTCAGGGCAATGACAT
AAATTGTATATTCGGTTCCCGGTTCCAGGCCAGTAATAGTAGCCTCTGTGACACCAGGGCGGGGCCGAGGGACCAC
TTCTCTGGGAGGAGACCCAGGCTTCTCATACTTGATGATGTANCCGGTAATCCTGGCACCGTGGCGGCTGCCATGA
TACCAGCAAGGAATTGGGTGTGGTGGCCAAGAAACGCAGGTTGGATGGTGCATCAATGGCAGTGGAGGCGTCGATN
ACCACAGGGGAGCTCCGANCATTGTCATTCAAGGTGGACAGGTAGAATCTTGTAATCAGGTGCCTGGTTTGTAAAC
CTG 16506.1.edit TCGAGCGGCCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGCCCAGAAGAACTGGTACATCAGCAAGAACC
CCAAGGACAAGAAGCATGTCTGGTTCGGCGAAAGCATGACCGATGGATTCCAGTTCGAGTATGGCGGCCAGGGCTC
CGACCCTGCCGATGTGGACCTCGGCCGCGACCACGCTAAGCCCGAATTCCAGCACACTGGCGGCCGTTACTAGTGG
GATCCGAGCTTCGGTACCAAGCTTGGCGTAATCATGGGNCATAGCTGTTTCCTGNGTGAAAATGGTATTCCGCTTC
ACAATTTCCCAC 16506.2.edit AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAAGCTCTTGAAGGGTGGTGTCCACCTCG
AGGTCACGGTCACGAAACCTGCCCGGGCGGCCGCTCGA

*Fig. 15SS*

16507.1.edit

```
AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGNGCCGGNCCGCTCGAAAAGCCCNAATTTCCAGNCACACTTGGCCGGCCGTTACTACTG
```

16507.2.edit

```
TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT
```

16508.1.edit

```
CGAGCGGCCGCCCGGGCAGGTCCCCCCCCTTTTTTTTTTTTTTTTTTTTTTTTTTTTTTTTTTTTTTTTTTTTTTT
TTTTTTTTTTTTTTTTT
```

16508.2.edit

```
AGCGTGGTCGCGGCCGAGGTCTGGCATTCCTTCGACTTCTCTCCAGCCGAGCTTCCCAGAACATCACATATCACTG
CAAAAATAGCATTGCATACATGGATCAGGCCAGTGGAAATGTAAAGAAGGCCCTGAAGCTGATGGGGTCAAATGAA
GGTGAATTCAAGGCTGAAGGAAATAGCAAATTCACCTACACAGTTCTGGAGGATGGTTGCACGAAACACACTGGGG
AATGGAGCAAAACAGTCTTTGAATATCGAACACGCAAGGCTGTGAGACTACCTATTGTAGATATTGCACCCTATGA
CATTGGTGGTCCTGATCAAGAATTTGGTGTGGACGTTGGCCCTGTTTGCTTTTTATAAACCAAACTCTATCTGAAA
TCCCAACAAAAAAAATTTAACTCCATATGTGNTCCTCTTGTTCTAATCTTGGCAACCAGTGCAAGTGACCGACAAA
ATTCCAGTTATTTATTTCCAAAATGTTTGGAAACAGTATAATTTGACAAAGAAAAAAGGATACTTCTCTTTTTTTG
GCTGGTCCACCAAATACAATTCAAAAGGCTTTTTGGTTTTATTTTTTTANCCAATTCCAATTTCAAAATGTCTCAA
TGGNGCTTATAATAAAATAAACTTTCACCCTTNTTTTNTGAT
```

*Fig. 15TT*

16509.1.edit

AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAAGTAACCACCACTCCCAAAAATGGACCAGGACCAACAAAAA
CTAAAACTGCAGGTCCAGATCAAACAGAAAATGGACTATTGAAGGCTTGCAGCCCACAGTGGAAGTATGTGGNTAG
GNGTCTATGCTCAGAATCCCAAGCCGGAGAAAGTCAGCCTTCTGGTTTAGACTGCAGTAACCAACATTGATCGCCC
TAAAGGACTGGNCATTCACTTGGATGGTGGATGTCCAATTC 16509.2.edit TCGAGCGGCCGCCCGGGCAGGTCCTTGCAGCTCTGCAGNGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGNGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGGTGGTCCTGNCCCATTTTTGGGAAGTGGGGGGTTACTC
TGTAACCAGTAACAGGGGAACTTGAAGGCAGCCACTTGACACTAATGCTGTTGTCCTGAACATCGGTCACTTGCAT
CTGGGGATGGTTTTGACAATTTCTGGTTCGGCAAATTAATGGAAATTGGCTTGCTGCTTGGCGGGGCTGNCTCCAC
GGGCCAGTGACAGCATAC 16510.1.edit TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGTTGGNCCTGNNCCATTTTTGGGGAAGGGGTGGTTACTC
TTGTAACCAGTAACAGGGGAACTTGAAGCAGCCACTTGACACTAATGCTGGTGGCCTGAACATCGGTCACTTGCAT
CTGGGATGGTTTGGTCAATTTCTGTTCGGTAATTAATGGGAAATTGGCTTACTGGCTTGCGGGGGCTGTCTCCACG
GNCAGTGACAAGCATACACAGGNGATGGGTATAATCAACTCCAGGTTTAAGGCCNCTGATGGTA 16510.2.edit AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGTAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGGACCAGGACCAACAAAAA
ACTAAAACTGCANGGTCCAGATCAAACAGAAATGACTATTGAAGGCTTGCAGCCCACAGTGGAGTATGTGGGTTAG
TGTCTATGCTCAGAATNCCAAGCGGAGAGAGTCAGCCTCTGGTTCAGACT

*Fig. 15UU*

16511.1.edit

TCGAGCGGCCGCCCGGGCAGGTCAGCGCTCTCAGGACGTCACCACCATGGCCTGGGCTCTGCTCCTCCTCACCCTC
CTCACTCAGGGCACAGGGTCCTGGGCCCAGTCTGCCCTGACTCAGCCTCCCTCCGCGTCCGGGTCTCCTGGACAGT
CAGTCACCATCTCCTGCACTGGAACCAGCAGTGACGTTGGTGCTTATGAATTTGTCTCCTGGTACCAACAACACCC
AGGCAAGGCCCCCAAACTCATGATTTCTGAGGTCACTAAGCGGCCCTCAGGGGTCCCTGATCGCTTCTCTGGCTCC
AAGTCTGGCAACACGGCCTCCCTGACCGTCTCTGGGCTCCANGCTGAGGATGANGCTGATTATTACTGGAAGCTCA
TATGCAGGCAACAACAATTGGGTGTTCGGCGGAAGGGACCAAGCTGACCGTNCTAAGGTCAAGCCCAAGGCTTGCC
CCCCTCGGTCACTCTGTTCCCACCCTCCTCTGAAGAAGCTTTCAAGCCAACAANGNCACACTGGGTGTGTCTCATA
AGTGGACTTTCTACCC 16511.2.edit AGCGTGGTCGCGGCCGAGGTCTGTAGCTTCTGTGGGACTTCCACTGCTCAGGCGTCAGGCTCAGGTAGCTGCTGGC
CGCGTACTTGTTGTTGCTTTGNTTGGAGGGTGTGGTGGTCTCCACTCCCGCCTTGACGGGGCTGCTATCTGCCTTC
CAGGCCACTGTCACGGCTCCCGGGTAGAAGTCACTTATGAGACACACCAGTGTGGCCTTGTTGGCTTGAAGCTCCT
CAGAGGAGGGTGGGAACAGAGTGACCGAGGGGGCAGCCTTGGGCTGACCTAGGACGGTCAGCTTGGTCCCTCCGCC
GAACACCCAATTGTTGTTGCCTGCATATGAGCTGCAGTAATAATCAGCCTCATCCTCAGCCTGGAGCCCAGAGACN
GTCAAGGGAGGCCCGTGTTTGCCAAGACTTGGAAGCCAGANAAGCGATCAGGGACCCCTGAGGGCCGCTTTACNGA
CCTCAAAAAATCATGAATTTGGGGGGCCTTTGCCTGGGNGTTGGTTGGTNACCAGNAAAACAAAATTTCATAAAGC
ACCAACGTCACTGCTGGTTTCCAGTGCANGAANATGGTGAACTGAANTGTCC 16512.1.edit AGCGTGGTCGCGGCCGAGGTCCAGCATCAGGAGCCCCGCCTTGCCGGCTCTGGTCATCGCCTTTCTTTTTGTGGCC
TGAAACGATGTCATCAATTCGCAGTAGCAGAACTGCCGTCTCCACTGCTGTCTTATAAGTCTGCAGCTTCACAGCC
AATGGCTCCCATATGCCCAGTTCCTTCATGTCCACCAAAGTACCCGTCTCACCATTTACACCCCAGGTCTCACAGT
TCTCCTGGGTGTGCTTGGCCCGAAGGGAGGTAAGTANACGGATGGTGCTGGTCCCACAGTTCTGGATCAGGGTACG
AGGAATGACCTCTAGGGCCTGGGCNACAAGCCCTGTATGGACCTGCCCGGGCGGGCCCGCTCGA 16512.2.edit TCGAGCGGCCGCCCGGGCAGGTCCATACAGGGCTGTTGCCCAGGCCCTAGAGGNCATTCCTTGTACCCTGATCCAG
AACTGTGGGACCAGCACCATCCGTCTACTTACCTCCCTTCGGGCCAAGCACACCCAGGAGAACTGTGAGACCTGGG
GTGTAAATGGNGAGACGGGTACTTTGGTGGACATGAAGGAACTGGGCATATGGGAGCCATTGGCTGNGAAGCTGCA
NACTTATAAGACAGCAGTGGAGACGGCAGTTCTGCTACTGCGAATTGATGACATCGTTTCAGGCCACAAAAAGAAA
GGCGATGACCANAGCCGGCAAGGCGGGGCTTCCTGATGCTGGACCTCGGCCGCCGACCACGCTT

*Fig. 15VV*

16514.1.edit

AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTGCTGTGCGCCACGTGTTGCTCANACAGGGTGTGCTGGGCATCAAGGTG
AAGATCATGCTGCCCTGGGACCCANCTGGCAAAAATGGCCCTTAAAAACCCCTTGCCNTGACCACGTGAACCATTT
GTGNGAACCCCAAGATGAANATACTTGCCCACCACCCCCCATTC 16514.2.edit TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAGTGTCAACGTAGTAGTTAACAGGGTCTCCGCTGTGGATCATC
AGGCCATCCACAAACTTCATGGATTTAGCCCTCTGTCCTCGGAGTTTCCCAAAACACCACAACCTCGCCAGCCTTT
GGGCCCCACTTCTTCATGAATGAAACCGCAGCACACCATTANCAAGGCCCTTCCGCACAGGNAAGCCCTTCCTAAG
GAGTTTTGTAAACGCAAAAAACTCTTGCCTGGGGCAAATGGGCACACAGACCTNTANTNGGACCTTGGNCCGCGAA
CCACCGCTT 16515.1.edit AGCGTGGTCGCGGCCGAGGTCTGGCCCTCCTGGCAAGGCTGGTGAAGATGGTCACCCTGGAAAACCCGGACGACCT
GGTGAGAGAGGAGTTGTTGGACCACAGGGTGCTCGTGGTTTCCCTGGAACTCCTGGACTTCCTGGCTTCAAAGGCA
TTAGGGGACACAATGGTCTGGATGGATTGAAGGGACAGCCCGGTGCTCCTGGTGTGAAGGGTGAACCTGGNGCCCC
TGGTGAAAATGGAACTCCAGGTCAAACAGGAGCCCGNGGGCTTCCTGGNGAGAGAGGACGTGTTGGTGCCCCTGGC
CCANACCTGCCCGGGCGGCCGCTCNAAAAGCCGAAATCCAGNACACTGGCGGCCGNTACTANTGGAATCCGAACTT
CGGTACCAAAGCTTGGCCGTAATCATGGCCATAGCTTGTTCCCTGGGGNGGAAATTGGTATTCCGCTNCCAATTCC
ACACAACATACCGAACCCGGAAAGCATTAAAGTGTAAAAGCCCTGGGGGGGCCTAAATGANGTGAGCNTAACTCNC
ATTTAATTGGCGTTGCGCTTCACTGCCCCGCTTTTCCAGTCCGGGNA 16515.2.edit TCGAGCGGCCGCCCGGGCAGGTCTGGGCCAGGGGCACCAACACGTCCTCTCTCACCAGGAAGCCCACGGGCTCCTG
TTTGACCTGGAGTTCCATTTTCACCAGGGGCACCAGGTTCACCCTTCACACCAGGAGCACCGGGCTGTCCCTTCAA
TCCATCCAGACCATTGTGNCCCCTAATGCCTTTGAAGCCAGGAAGTCCAGGAGTTCCAGGGAAACCACGAGCACCC
TGTGGTCCAACAACTCCTCTCTCACCAGGTCGTCCGGGTTTTCCAGGGTGACCATCTTCACCAGCCTTGCCAGGAG
GGCCAGACCTCGGCCGCGACCACGCT

*Fig. 15WW*

16516.1.edit

ANCGTGGTCGCGGCCGAGGTCCTCACCAGAGGTGNCACCTACAACATCATAGTGGAGGCACTGAAAGACCANCAGA
GGCATAAGGTTCGGGAAGAGG 16516.2.edit TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGTCCACGGTAACAACCTCTTCCCGAACCTTATGCCTCTGCTGG
TCTTTCAGTGCCTCCACTATGATGTTGTAGGTGGCACCTCTGGTGAGGACCTCNGNCCNGAACAACGCTTAAGCCC
GNATTCTGCAGAATAATCCCATCACACTTGGCGGCCGCTTCGANCATGCATCNTAAAAGGGGCCCCAATTTCCCCC
TTATAAGNGAANCCGTATTTNCCAATTTCACTGGNCCCGCCGNTTTTACAAACGNCGGTGAACTGGGGAAAAACCC
TGGCGGTTACCCAACTTTAATCGCCNTTGGCAGCACAATCCCCCCTTTTCGNCCANCNTGGGCGTAAATAACCGAA
AA 16517.1.edit

ANCGNGGTCGCGGCCGANGTNTTTTTTCTTNTTTTTTT 16518.1.edit

AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GGGNGGTCAGCGTCCTCACCGTCCTGCACCAGAATTGGTTGAATGGCAAGGAGTACAAGNGCAAGGTTTCCAACAA
AGCCNTCCCAGCCCCCNTCGAAAAAACCATTTCCAAAGCCAAAGGGCAGCCCCGAGAACCACAGGTGTACACCCTG
CCCCCATCCCGGGAGGAAAAGANCAANAACCNGGTTCAGCCTTAACTTGCTTGGTCNAANGCTTTTTATCCCAACG
NACTTCCCCCNTGGAANTGGGAAAAACCAATGGGCCAANCCGAAAAACAATTACAANAACCCC 16518.2.edit TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGAACACCTGGGGTTCTCGGGGCTTGCCCTTTGGTTTTGAANATGGTTTTC
TCGATGGGGGCTGGAAGGGCTTTGTTGNAAACCTTGCACTTGACTCCTTGCCATTCACCCAGNCCTGGNGCAGGAC
GGNGAGGACNCTNACCACACGGAACCGGGCTGGTGGACTGCTCC

*Fig. 15XX*

16519.1.edit

AGCGTGGTCGCGGACGANGTCCTGTCAGAGTGGNACTGGTAGAAGTTCCANGAACCCTGAACTGTAAGGGTTCTTC
ATCAGTGCCAACAGGATGACATGAAATGATGTACTCAGAAGNGNCCTGGAATGGGGCCCATGANATGGTTGCC 16519.2.edit TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGGCACCCCCCCTGGGTATGAACCTGGGAA
AANGGNANTTAANCTTTCCTGGCA 16520.1.edit AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGGTNCCCTGGTACTGGGTTACAGANTAACCACCACTCCCAAAAATGGACCAGGAACCACAAAAA
CTTAAACTGCAGGGTCCAGATCAAAACAGAAATGACTATTGAANGCTTGCAGCCCACAGTGGGAGTATGNGGGTAG
TGNCTATGCTTCAGAATCCAAGCGGAAAAANGTCAAGCCTTNTGGGTTCAA 16520.2.edit TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGNCTGAACCAGAGG
CTGACTCTCTCCGCTTGGATTCTGAGCATAGACACTAACCACATACTCCACTGTGGGCTGCAANCCTTCAATAANN
CATTTCTGTTTGATCTGGACC 16521.2.edit TCGAGCGGCCGCCCGGGCAGGTCTGGTGGGGTCCTGGCACACGCACATGGGGGNGTTGNTCTNATCCAGCTGCCCA
GCCCCCATTGGCGAGTTTGAGAAGGTGTGCAGCAATGACAACAANACCTTCGACTCTTCCTGCCACTTCTTTGCCA
CAAAGTGCACCCTGGAGGGCACCAAGAAGGGCCACAAGCTCCACCTGGACTACATCGGGCCTTGCAAATACATCCC
CCCTTGCCTGGACTCTGAGCTGACCGAATTCCCCCTTGCGCATGCGGGACTGGCTCAAGAACCGTCCTGGCACCCT
TGTATGANAGGGATGAAGACACNACCC

*Fig. 15YY*

16522.1.edit

AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCGCATCCCCCTTCCAAACCTGCCCGGGCGGCCGCTCGAAAGCCGAATTCCAGCACACTGGCGGCCG
GTACTAGTGGANCCNAACTTGGNANCCAACCTGGNGGAANTAATGGGCATAANCTGTTTCTGGGGGGAAATTGGTA
TCCNGTTTACAATTCCCNCACAACATACGAGCCGGAAGCATAAAAGNGTAAAAGCCTGGGGGNGGCCTANTGAAGT
GAAGCTAAACTCACATTAATTNGCGTTGCCGCTCACTGGCCCGCTTTTCCAGC 16522.2.edit TCGAGCGGCCGCCCGGGCAGGTTTGGAAGGGGGATGCGGGGGAAGAGGAAGACTGACGGTCCCCCCAGGAGTTCAG
GTGCTGGGCACGGTGGGCATGTGTGAGTTTTGTCACAAGATTTGGGCTCAACTCTCTTGTCCACCTTGGTGTTGCT
GGGCTTGTGATCTACGTTGCAGGTGTAGGTCTGGGNGCCGAAGTTGCTGGAGGGCACGGTCACCACGCTGCTGAGG
GAGTAGAGTCCTGAGGACTGTANGACAGACCTCGGCCGNGACCACGCTAAGCCGAATTCTGCAGATATCCATCACA
CTGGCGGCCGCTCCGAGCATGCATTTTAGAGG 16523.1.edit

AGCGTGGNCGCGGACGANGACAACAACCCC 16523.2.edit

TCGAGCGGCCGCCCGGGCAGGNCCACATCGGCAGGGTCGGAGCCCTGGCCGCCATACTCGAACTGGAATCCATCGG
TCATGCTCTTGCCGAACCAGACATGCCTCTTGTCCTTGGGGTTCTTGCTGATGNACCAGTTCTTCTGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCT 16524.1.edit AGCGTGGTCGCGGCCGAGGTCCAGCCTGGAGATAANGGTGAAGGTGGTGCCCCCGGACTTCCAGGTATAGCTGGAC
CTCGTGGTAGCCCTGGTGAGAGAGGTGAAACTGGCCCTCCAGGACCTGCTGGTTTCCCTGGTGCTCCTGGACAGAA
TGGTGAACCTGGNGGTAAAGGAGAAAGAGGGGCTCCGGNTGANAAAGGTGAAGGAGGCCCTCCTGNATTGGCAGGG
GCCCCANGACTTAGAGGTGGAGCTGGCCCCCCTGGCCCCGAAGGAGGAAAGGGTGCTGCTGGTCCTCCTGGGCCAC
CTGG

*Fig. 15ZZ*

16524.2.edit

```
TCGAGCGGCCGCCCGGGCAGGTCTGGGCCAGGAGGACCAATAGGACCAGTAGGACCCCTTGGGCCATCTTTCCCTG
GGACACCATCAGCACCTGGACCGCCTGGTTCACCCTTGTCACCCTTTGGACCAGGACTTCCAAGACCTCCTCTTTC
TCCAGGCATTCCTTGCAGACCAGGAGTACCANCAGCACCAGGTGGCCCAGGAGGACCAGCAGCACCCTTTCCTCCT
TCGGGACCAGGGGGACCAGCTCCACCTCTAAGTCCTGGGGCCCCTGCCAATCCAGGAGGGCCTCCTTCACCTTTCT
CACCCGGAGCCCCTCTTTCT
```

16526.1.edit

```
TCGAGCGGCCGCCCGGGCAGGTCCACCGGGATATTCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGACAACCGGAG
GCTGGAGAGCAAAATCCGGGAGCACTTGGAGAAGAAGGGACCCCAGGTCAGAGACTGGAGCCATTACTTCAAGATC
ATCGAGGACCTGAGGGCTCANATCTTCGCAAATACTGCNGACAATGCCCG
```

16526.2.edit

```
ATGCGNGGTCGCGGCCGANGACCANCTCTGGCTCATACTTGACTCTAAAGNCNTCACCAGNANTTACGGNCATTGC
CAATCTGCAGAACGATGCGGGCATTGTCCGCANTATTTGCGAAGATCTGAGCCCTCAGGNCCTCGATGATCTTGAA
GTAANGGCTCCAGTCTCTGACCTGGGGTCCCTTCTTCTCCAAGTGCTCCCGGATTTTGCTCTCCAGCCTCCGGTTC
TCGGTCTCCAAGNCTTCTCACTCTGTCCAGGAAAAGAGGCCAGGCGGNCGATCAGGGCTTTTGCATGGACT
```

16527.1.edit

```
AGCGTGGTCGCGGCCGAGGTTGTACAAGCTTTTTTTTTTTTTTTTTTTTTTTTTTTTTTTTTTTTTTTTTTTTTTT
TTTTTTTTTTTTTTTTTTTTTTTT
```

16527.2.edit

```
TCGAGCGGCCGCCCGGGCAGGTCTGCCAACACCAAGATTGGCCCCCGCCGCATCCACACAGTTNGTGTGCGGGGAG
GTAACAAGAAATACCGTGCCCTGAGGNTGGACGNGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATNGACAGCACACCGTACCGACAGTGGGTACCGAAGTCCCACTATGCNCCT
```

*Fig. 15AAA*

16528.1.edit

TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAG 16528.2.edit AGCGTGNTCNCGGCCGAGGATGGGGAAGCTCGNCTGTCTTTTTCCTTCCAATCAGGGGCTNNNTCTTCTGATTATT
CTTCAGGGCAANGACATAAATTGTATATTCGGNTCCCGGTTCCAGNCCAGTAATAGTAGCCTCTGTGACACCAGGG
CGGGGCCGAGGGACCACTTCTCTGGGAGGAGACCCAGGCTTCTCATACTTGATGATGAAGCCGGTAATCCTGGCAC
GTGGGCGGCTGCCATGATACCACCAANGAATTGGGTGTGGTGGACCTGCCCGGGCGGGCCGCTCGAAAANCCGAAT
TCNTGCAAGAATATCCATCACACTTGGGCGGGCCGNTCGAACCATGCATCNTAAAAGGGCCCCAATTTCCCCCCTA
TTAGGNGAAGCCNCATTTAACAAATTCCACTTGG 16529.1.edit TCGAGCGGCCGCCCGGGCAGGTCTCGCGGTCGCACTGGTGATGCTGGTCCTGTTGGTCCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTTGAGCCAGCAGAATCGAAAACATTCGGAACCCAAGAAGGGCAAGCCCGCAAAGAAACCCCGCCCGCAC
CTGGCCGNGAACCTCCAAGAANGTGCCCACNTCTTGACTGGGAAAAAAAGGGAAAANTACTTGGAATTGGAC 16529.2.edit AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAAGTGGCACATCTTGAGGTCACGGCAGGGTGCGGGCGG
GGTTCTTGCGGGCTGCCCTTCTGGGCTCCCGGAATGTTCTNNGAACTTGCTGG

*Fig. 15BBB*

16530.1.edit

```
AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTTGCTTGTGCGCCACGTGTTGCTCANACANGGGTGGGCTGGGCATCAAG
GNG
```

16530.2.edit

```
TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAAGTGTCAACGTAAGTAAGTTAACAGGGTCTCCGCTGTGGATC
ATCAGGCCATCCACAAACTTCATGGATTTAACCCTCTGTCCTCGGAG
```

16531.1.edit

```
TCGAGCGGCCGCCCGGGCAGGTGTTTCAGAGGTTCCAAGGTCCACTGTGGAGGTCCCAGGAGTGCTGGTGGTGGGC
ACAGAGGTCCGATGGGTGAAACCATTGACATAGAGACTGTTCCTGTCCAGGGTGTAGGGGCCCAGCTCTTTGATGC
CATTGGCCAGTTGGCTCAGCTCCCAGTACAGCCGCTCTCTGTTGAGTCCAGGGCTTTTGGGGTCAAGATGATGGAT
GCAGATGGCATCCACTCCAGTGGCTGCTCCATCCTTCTCGGACCTGAGAGAGGTCAGTCTGCAGCCAGAGTACAGA
GGGCCAACACTGGTGTTCTTTGAATA
```

16531.2.edit

```
AGCGTGGTCGCGGCCGAGGTCTGTACTGGGAGCTAAGCAAACTGACCAATGACATTGAAGAGCTGGGCCCCTACAC
CCTGGACAGGAACAGTCTCTATGTCAATGGTTTCACCCATCAGAGCTCTGTGNCCACCACCAGCACTCCTGGGACC
TCCACAGTGGATTTCAGAACCTCAGGGACTCCATCCTCCCTCTCCAGCCCCACAATTATGGCTGCTGGCCCTCTCC
TGGTACCATTCACCCTCAACTTCACCATCACCAACCTGCAGTATGGGGAGGACATGGGTCACCCTGNCTCCAGGAA
GTTCAACACCACA
```

16532.1.edit

```
TCGAGCGGCCGCCCGGACAGGTCTGGGCGGATAGCACCGGGCATATTTTGGAATGGATGAGGTCTGGCACCCTGAG
CAGTCCAGCGAGGACTTGGTCTTAGTTGAGCAATTTGGCTAGGAGGATAGTATGCAGCACGGNTCTGAGNCTGTGG
GATAGCTGCCATGAAGTAACCTGAAGGAGGTGCTGGCTGGTANGGGTTGATTACAGGGTTGGGAACAGCTCGTACA
CTTGCCATTCTCTGCATATACTGGTTAGTGAGGTGAGCCTGGCCCTCTTCTTTTG
```

*Fig. 15CCC*

01_16558.3.edit

AGCGTGGTCGCGGCCGAGGTGAGCCACAGGTGACCGGGGCTGAAGCTGGGGCTGCTGGNCCTGCTGGTCCTG

02_16558.4.edit

CAGCNGCTCCNACGGGGCCTGNGGGACCAACAACACCGTTTTCACCCTTAGGCCCTTTGGCTCCTCTTTCTCCTTT
AGCACCAGGTTGACCAGCAGCNCCANCAGGACCAGCAAATCCATTGGGGCCAGCAGGACCGACCTCACCACGTTCA
CCAGGGCTTCCCCGAGGACCAGCAGGACCAGCAGGACCAGCAGCCCCAGCTTCGCCCCGGTCACCTGTGGCTCACC
TCGGCCGCGACCACGCT

03_16535.1.edit

TCGAGCGGTCGCCCGGGCAGGTCCACCGGGATAGCCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGANAACCGGAG
GCTGGANAGCAAAATCCGGGAGCACTTGGAGAAGAAGGGACCCCAGGTCAAGAGACTGGAGCCATTACTTCAAGAT
CATCGAGGGACCTGGAGG

04_16535.2.edit

AGCGNGGTCGCGGCCGAGGTCCAGCTCTGTCTCATACTTGACTCTAAAGTCATCAGCAGCAAGACGGGCATTGTCA
ATCTGCAGAACGATGCGGGCATTGTCCGCAGTATTTGCGAAGATCTGAGCCCTCAGGTCCTCGATGATCTTGAAGT
AATGGCTCCAGTCTCTGACCTGGGGTCCCTTCTTCTCCAAGTGCTCCCGGATTTTGCTCTCCAGCCTCCGGTTCTC
GGTCTCCAGGCTCCTCACTCTGTCCAGGTAAGAAGGCCCAGGCGGTCGTTCAGGCTTTGCATGGTCTCCTTCTCGT
TCTGGATGCCTCCCATTCCTGCCAGACCC

05_16536.1.edit

TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG

*Fig. 15DDD*

07_16537.1.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACCGCAGGTCTCACCAGTCTCCATGTTGCAGAAGACTTTGATGGCATCCAGGTTGCAGCCTT
GGTTGGGGTCAATCCAGTACTCTCCACTCTTCCAGTCAGAAGTGGGCACATCTTGAGGTCACCGGCAGGTGCCGGG
CCGGGGGTTCTTGCGGCTTGCCCTCTGGGCTCCGGATGTTCTCGATCTGCTTGGCTCAGGCTCTTGAGGGTGGGTG
TCCACCTCGAGGTCACGGTCACCGAAACCTGCCCGGGCGGCCCGCTCGA

08_16537.2.edit

TCGAGCGGTCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGGCCCAGAAGAAACTGGTACATCAGCAAGGA
ACCCCAAGGACAAGAGGCATTGTCTTGGTTCGGCGAGNAGCATGACCCGATGGATTCCAGTTTCGAGTATTGGCGG
CCAGGGCTTCCCGACCCTTGCCGATGTGGACCTCGGCCGCGACCACCGCT

*Fig. 15EEE*

SEQUENCE LISTING

```
<160> NUMBER OF SEQ ID NOS:  310

<210> SEQ ID NO 1
<211> LENGTH: 461
<212> TYPE: DNA
<213> ORGANISM: Homo sapiens

<400> SEQUENCE: 1

ttagagaggc acagaaggaa gaagagttaa aagcagcaaa gccgggtttt tttgttttgt      60

tttgttttgt tttgttttga gatggagtct cactctgttg cccaagctgg agtacaacgg     120

catgatctca gctcgctgca acctccgcct cccacgttca agtgattctc ctgcctcagc     180
```

-continued

```
ctcccaagta gctgggatta caggcgcccg ccaccacgct cagctaattt tttttgtatt    240

tttagtagag acagggtttc accaggttgg ccaggctgct cttgaactcc tgacctcagg    300

tgatccaccc gcctcggcct cccaaagtgc tgggattaca ggcgtgagcc accacgcccg    360

gcccccaaag ctgtttcttt tgtctttagc gtaaagctct cctgccatgc agtatctaca    420

taactgacgt gactgccagc aagctcagtc actccgtggt c                        461


<210> SEQ ID NO 2
<211> LENGTH: 540
<212> TYPE: DNA
<213> ORGANISM: Homo sapiens

<400> SEQUENCE: 2

taggatgtgt tggaccctct gtgtcaaaaa aaacctcaca aagaatcccc tgctcattac     60

agaagaagat gcatttaaaa tatgggttat tttcaacttt ttatctgagg acaagtatcc    120

attaattatt gtgtcagaag agattgaata cctgcttaag aagcttacag aagctatggg    180

aggaggttgg cagcaagaac aatttgaaca ttataaaatc aactttgatg acagtaaaaa    240

tggcctttct gcatgggaac ttattgagct tattggaaat ggacagttta gcaaaggcat    300

ggaccggcag actgtgtcta tggcaattaa tgaagtcttt aatgaactta tattagatgt    360

gttaaagcag ggttacatga tgaaaaaggg ccacagacgg aaaaactgga ctgaaagatg    420

gtttgtacta aaacccaaca taatttctta ctatgtgagt gaggatctga aggataagaa    480

aggagacatt ctcttggatg aaaattgctg tgtagagtcc ttgcctgaca aagatggaaa    540


<210> SEQ ID NO 3
<211> LENGTH: 461
<212> TYPE: DNA
<213> ORGANISM: Homo sapiens

<400> SEQUENCE: 3

ttagagaggc acagaaggaa gaagagttaa aagcagcaaa gccgggtttt tttgttttgt     60

tttgttttgt tttgttttga gatggagtct cactctgttg cccaagctgg agtacaacgg    120

catgatctca gctcgctgca acctccgcct cccacgttca agtgattctc ctgcctcagc    180

ctcccaagta gctgggatta caggcgcccg ccaccacgct cagctaattt tttttgtatt    240

tttagtagag acagggtttc accaggttgg ccaggctgct cttgaactcc tgacctcagg    300

tgatccaccc gcctcggcct cccaaagtgc tgggattaca ggcgtgagcc accacgcccg    360

gcccccaaag ctgtttcttt tgtctttagc gtaaagctct cctgccatgc agtatctaca    420

taactgacgt gactgccagc aagctcagtc actccgtggt c                        461


<210> SEQ ID NO 4
<211> LENGTH: 531
<212> TYPE: DNA
<213> ORGANISM: Homo sapiens
<220> FEATURE:
<221> NAME/KEY: modified_base
<222> LOCATION: (454)
<223> OTHER INFORMATION: Where n is a, c, g or t
<221> NAME/KEY: modified_base
<222> LOCATION: (492)
<223> OTHER INFORMATION: Where n is a, c, g or t
<221> NAME/KEY: modified_base
<222> LOCATION: (526)
<223> OTHER INFORMATION: Where n is a, c, g or t

<400> SEQUENCE: 4
```

-continued

```
tctttttctt tcgatttcct tcaatttgtc acgtttgatt ttatgaagtt gttcaagggc     60

taactgctgt gtattatagc tttctctgag ttccttcagc tgattgttaa atgaatccat    120

ttctgagagc ttagatgcag tttctttttc aagagcatct aattgttctt taagtctttg    180

gcataattct tccttttctg atgacttttt atgaagtaaa ctgatccctg aatcaggtgt    240

gttactgagc tgcatgtttt taattctttc gtttaatagc tgcttctcag ggaccagata    300

gataagctta ttttgatatt ccttaagctc ttgttgaagt tgtttgattt ccataatttc    360

caggtcacac tgtttatcca aaacttctag ctcagtcttt tgtgtttgct ttctgatttg    420

gacatcttgt agtctgcctg agatctgctg atgntttcca ttcactgctt ccagttccag    480

gtggagactt tnctttctgg agctcagcct gacaatgcct tcttgntccc t             531


<210> SEQ ID NO 5
<211> LENGTH: 531
<212> TYPE: DNA
<213> ORGANISM: Homo sapiens

<400> SEQUENCE: 5

agccagatgg ctgagagctg caagaagaag tcaggatcat gatggctcag tttcccacag     60

cgatgaatgg agggccaaat atgtgggcta ttacatctga agaacgtact aagcatgata    120

aacagtttga taacctcaaa ccttcaggag gttacataac aggtgatcaa gcccgtactt    180

ttttcctaca gtcaggtctg ccggccccgg ttttagctga aatatgggcc ttatcagatc    240

tgaacaagga tgggaagatg gaccagcaag agttctctat agctatgaaa ctcatcaagt    300

taaagttgca gggccaacag ctgcctgtag tcctccctcc tatcatgaaa caacccccta    360

tgttctctcc actaatctct gctcgttttg ggatgggaag catgcccaat ctgtccattc    420

atcagccatt gcctccagtt gcacctatag caacaccctt gtcttctgct acttcaggga    480

ccagtattcc tcccctaatg atgcctgctc ccctagtgcc ttctgttagt a             531


<210> SEQ ID NO 6
<211> LENGTH: 531
<212> TYPE: DNA
<213> ORGANISM: Homo sapiens

<400> SEQUENCE: 6

aatagattta atgcagagtg tcaacttcaa ttgattgata gtggctgcct agagtgctgt     60

gttgagtagg tttctgagga tgcaccctgg cttgaagaga aagactggca ggattaacaa    120

tatctaaaat ctcacttgta ggagaaacca caggcaccag agctgccact ggtgctggca    180

ccagctccac caaggccagc gaagagccca aatgtgagag tggcggtcag gctggcacca    240

gcactgaagc caccactggt gctggcactg gcactggcac tgttattggt actggtactg    300

gcaccagtgc tggcactgcc actctcttgg gctttggctt tagcttctgc tcccgcctgg    360

atccgggctt tggcccaggg tccgatatca gcttcgtccc agttgcaggg cccggcagca    420

ttctccgagc cgagcccaat gcccattcga gctctaatct cggccctagc cttggcttca    480

gctgcagcct cagctgcagc cttcaaatcc gcttccatcg cctctcggta c             531


<210> SEQ ID NO 7
<211> LENGTH: 531
<212> TYPE: DNA
<213> ORGANISM: Homo sapiens

<400> SEQUENCE: 7

gccaagaaag cccgaaaggt gaagcatctg gatggggaag aggatggcag cagtgatcag     60
```

-continued

```
agtcaggctt ctggaaccac aggtggccga agggtctcaa aggccctaat ggcctcaatg    120

gcccgcaggg cttcaagggg tcccatagcc ttttgggccc gcagggcatc aaggactcgg    180

ttggctgctt gggcccggag agccttgctc tccctgagat cacctaaagc ccgtaggggc    240

aaggctcgcc gtagagctgc caagctccag tcatcccaag agcctgaagc accaccacct    300

cgggatgtgg cccttttgca agggagggca aatgatttgg tgaagtacct tttggctaaa    360

gaccagacga agattcccat caagcgctcg gacatgctga aggacatcat caaagaatac    420

actgatgtgt accccgaaat cattgaacga gcaggctatt ccttggagaa ggtatttggg    480

attcaattga aggaaattga taagaatgac cacttgtaca ttcttctcag c             531
```

```
<210> SEQ ID NO 8
<211> LENGTH: 531
<212> TYPE: DNA
<213> ORGANISM: Homo sapiens
<220> FEATURE:
<221> NAME/KEY: modified_base
<222> LOCATION: (481)
<223> OTHER INFORMATION: Where n is a, c, g or t

<400> SEQUENCE: 8

gaggtctcac tatgttgccc aggctgttct tgaactcctg ggatcaagca atccacccat     60

gttggtctcc aaaagtgctg ggatcatagg cgtgagccac ctcacccagc caccaatttt    120

caatcaggaa gactttttcc ttcttcaaga agtgaagggt ttccagagta tagctacact    180

attgcttgcc tgagggtgac tacaaaattg cttgctaaaa ggttaggatg ggtaaagaat    240

tagattttct gaatgcaaaa ataaaatgtg aactaatgaa ctttaggtaa tacatattca    300

taaaataatt attcacatat ttcctgattt atcacagaaa taatgtatga aatgctttga    360

gtttcttgga gtaaactcca ttactcatcc caagaaacca tattataagt atcactgata    420

ataagaacaa caggaccttg tcataaattc tggataagag aaatagtctc tgggtgtttg    480

ntcttaattg ataaaattta cttgtccatc ttttagttca gaatcacaaa a             531
```

```
<210> SEQ ID NO 9
<211> LENGTH: 531
<212> TYPE: DNA
<213> ORGANISM: Homo sapiens
<220> FEATURE:
<221> NAME/KEY: modified_base
<222> LOCATION: (528)
<223> OTHER INFORMATION: Where n is a, c, g or t

<400> SEQUENCE: 9

aagcggaaat gagaaaggag ggaaaatcat gtggtattga gcggaaaact gctggatgac     60

agggctcagt cctgttggag aactctgggt ggtgctgtag aacagggcca ctcacagtgg    120

ggtgcacaga ccagcacggc tctgtgacct gtttgttaca ggtccatgat gaggtaaaca    180

atacactgag tataagggtt ggtttagaaa ctcttacagc aatttgacaa agtaatcttc    240

tgtgcagtga atctaagaaa aaaattgggg ctgtatttgt atgttccttt ttttcatttc    300

atgttctgag ttacctattt ttattgcatt ttacaaaagc atccttccat gaaggaccgg    360

aagttaaaaa caaagcaggt cctttatcac agcactgtcg tagaacacag ttcagagtta    420

tccacccaag gagccaggga gctgggctaa accaaagaat tttgcttttg gttaatcatc    480

aggtacttga gttggaattg ttttaatccc atcattacca ggctggangt g             531
```

```
<210> SEQ ID NO 10
```

-continued

<211> LENGTH: 861
<212> TYPE: DNA
<213> ORGANISM: Homo sapiens

<400> SEQUENCE: 10
ccgcggctcc tgtccagacc ctgaccctcc ctcccaaggc tcaaccgtcc cccaacaacc 60
gccagccttg tactgatgtc ggctgcgaga gcctgtgctt aagtaagaat caggccttat 120
tggagacatt caagcaaagg ttggacaact acttttccag aacagaaagg aaactcatgc 180
atcagaaaag gtgactaata aaggtaccag aagaatatgg ctgcacaaat accagaatct 240
gatcagataa aacagtttaa ggaatttctg gggacctaca ataaacttac agagacctgc 300
tttttggact gtgttagaga cttcacaaca agagaagtaa aacctgaaga gaccacctgt 360
tcagaacatt gcttacagaa atatttaaaa atgacacaaa gaatatccat gagatttcag 420
gaatatcata ttcagcagaa tgaagccctg gcagccaaag caggactcct tggccaacca 480
cgatagagaa gtcctgatgg atgaactttt gatgaaagat tgccaacagc tgctttattg 540
gaaatgagga ctcatctgat agaatcccct gaaagcagta gccaccatgt tcaaccatct 600
gtcatgactg tttggcaaat ggaaaccgct ggagaaacaa aattgctatt taccaggaat 660
aatcacaata gaaggtctta ttgttcagtg aaataataag atgcaacatt tgttgaggcc 720
ttatgattca gcagcttggt cacttgatta gaaaaataaa ccattgtttc ttcaattgtg 780
actgttaatt ttaaagcaac ttatgtgttc gatcatgtat gagatagaaa aatttttatt 840
actcaaagta aaataaatgg a 861

<210> SEQ ID NO 11
<211> LENGTH: 541
<212> TYPE: DNA
<213> ORGANISM: Homo sapiens

<400> SEQUENCE: 11
gaaaaaaaat ataaaacaca cttttgcgaa aacggtggcc ctaaaagagg aaaagaattt 60
caccaatata aatccaattt tatgaaaact gacaatttaa tccaagaatc acttttgtaa 120
atgaagctag caagtgatga tatgataaaa taaacgtgga ggaaataaaa acacaagact 180
tggcataaga tatatccact tttgatatta aacttgtgaa gcatattctt cgacaaattg 240
tgaaagcgtt cctgatcttg cttgttctcc atttcaaata aggaggcata tcacatccca 300
agagtaacag aaaaagaaaa aagacatttt tgcattttga gatgaaccaa agacacaaaa 360
caaaacgaac aaagtgtcat gtctaattct agcctctgaa ataaaccttg aacatctcct 420
acaaggcacc gtgatttttg taattctaac ctgaagaaat gtgatgactt ttgtggacat 480
gaaaatcaga tgagaaaact gtggtctttc caaagcctga actcccctga aaacctttgc 540
a 541

<210> SEQ ID NO 12
<211> LENGTH: 541
<212> TYPE: DNA
<213> ORGANISM: Homo sapiens

<400> SEQUENCE: 12
ctgggatcat ttctcttgat gtcataaaag actcttcttc ttcctcttca tcctcttctt 60
catcctcttc tgtacagtgc tgccgggtac aacggctatc tttgtcttta tcctgagatg 120
aagatgatgc ttctgtttct cctaccataa ctgaagaaat ttcgctggaa gtcgtttgac 180
tggctgtttc tctgacttca ccttctttgt caaacctgag tctttttacc tcatgcccct 240

-continued

```
cagcttccac agcatcttca tctggatgtt tatttttcaa agggctcact gaggaaactt    300

ctgattcaga ggtcgaagag tcactgtgat ttttctcctc attttgctgc aaatttgcct    360

ctttgctgtc tgtgctctca ggcaacccat ttgttgtcat gggggctgac aaagaaacct    420

ttggtcgatt aagtggcctg ggtgtcccag gcccatttat attagacctc tcagtatagc    480

ttggtgaatt tccaggaaac ataacaccat tcattcgatt taaactattg gaattggttt    540

t                                                                    541


<210> SEQ ID NO 13
<211> LENGTH: 441
<212> TYPE: DNA
<213> ORGANISM: Homo sapiens

<400> SEQUENCE: 13

gagggttggt ggtagcggct tggggaggtg ctcgctctgt cggtcttgct ctctcgcacg     60

cttcccccgg ctcccttcgt ttcccccccc cggtcgcctg cgtgccggag tgtgtgcgag    120

ggaggggggag ggcgtcgggg gggtgggggg aggcgttccg gtccccaaga gacccgcgga    180

gggaggcgga ggctgtgagg gactccggga agccatggac gtcgagaggc tccaggaggc    240

gctgaaagat tttgagaaga gggggaaaaa ggaagtttgt cctgtcctgg atcagtttct    300

ttgtcatgta gccaagactg gagaaacaat gattcagtgg tcccaattta aaggctattt    360

tattttcaaa ctggagaaag tgatggatga tttcagaact tcagctcctg agccaagagg    420

tcctcccaac cctaatgtcg a                                              441


<210> SEQ ID NO 14
<211> LENGTH: 131
<212> TYPE: DNA
<213> ORGANISM: Homo sapiens
<220> FEATURE:
<221> NAME/KEY: modified_base
<222> LOCATION: (126)
<223> OTHER INFORMATION: Where n is a, c, g or t

<400> SEQUENCE: 14

aagcaggcgg ctcccgcgct cgcagggccg tgccacctgc ccgcccgccc gctcgctcgc     60

tcgcccgccg cgccgcgctg ccgaccgcca gcatgctgcc gagagtgggc tgccccgcgc    120

tgccgntgcc g                                                         131


<210> SEQ ID NO 15
<211> LENGTH: 692
<212> TYPE: DNA
<213> ORGANISM: Homo sapiens

<400> SEQUENCE: 15

atctcttgta tgccaaatat ttaatataaa tctttgaaac aagttcagat gaaataaaaa     60

tcaaagtttg caaaaacgtg aagattaact taattgtcaa atattcctca ttgccccaaa    120

tcagtatttt ttttatttct atgcaaaagt atgccttcaa actgcttaaa tgatatatga    180

tatgatacac aaaccagttt tcaaatagta aagccagtca tcttgcaatt gtaagaaata    240

ggtaaaagat tataagacac cttacacaca cacacacaca cacacacgtg tgcacgccaa    300

tgacaaaaaa caatttggcc tctcctaaaa taagaacatg aagaccctta attgctgcca    360

ggagggaaca ctgtgtcacc cctccctaca atccaggtag tttcctttaa tccaatagca    420

aatctgggca tatttgagag gagtgattct gacagccacg ttgaaatcct gtggggaacc    480
```

-continued

```
attcatgtcc acccactggt gccctgaaaa aatgccaata atttttcgct cccacttctg    540

ctgctgtctc ttccacatcc tcacatagac cccagacccg ctggcccctg gctgggcatc    600

gcattgctgg tagagcaagt cataggtctc gtctttgacg tcacagaagc gatacaccaa    660

attgcctggt cggtcattgt cataaccaga ga                                  692
```

<210> SEQ ID NO 16
<211> LENGTH: 728
<212> TYPE: DNA
<213> ORGANISM: Homo sapiens

<400> SEQUENCE: 16

```
cagacggggt ttcactatgt tggctaggct ggtcttgaac tcctgacttc aggtgatctg     60

cctgccttgg cctcccaaag tgctgggatt acaggcataa gccactgcgc ccggctgatc    120

tgatggtttc ataaggcttt tcccccttt gctcagcact tctccttcct gccgccatgt     180

gaagaaggac atgtttgctt ccccttccac cacgattgta agttgtttcc tgaggcctcc    240

ccggccatgc tgaactgtga gtcaattaaa cctctttcct ttataaatta tccagttttg    300

ggtatgtctt tattagtaga atgagaacag actaatacaa cccttaaagg agactgacgg    360

agaggattct tcctggatcc cagcacttcc tctgaatgct actgacattc ttcttgagga    420

ctttaaactg ggagatagaa aacagattcc atggctcagc agcctgagag cagggaggga    480

gccaagctat agatgacatg ggcagcctcc cctgaggcca ggtgtggccg aacctgggca    540

gtgctgccac ccaccccacc agggccaagt cctgtccttg gagagccaag cctcaatcac    600

tgctagcctc aagtgtcccc aagccacagt ggctaggggg actcagggaa cagttcccag    660

tctgccctac ttctcttacc tttacccctc atacctccaa agtagaccat gttcatgagg    720

tccaaagg                                                             728
```

<210> SEQ ID NO 17
<211> LENGTH: 531
<212> TYPE: DNA
<213> ORGANISM: Homo sapiens
<220> FEATURE:
<221> NAME/KEY: modified_base
<222> LOCATION: (518)
<223> OTHER INFORMATION: Where n is a, c, g or t
<221> NAME/KEY: modified_base
<222> LOCATION: (528)
<223> OTHER INFORMATION: Where n is a, c, g or t

<400> SEQUENCE: 17

```
aagcgaggaa gccactgcgg ctcctggctg aaaagcggcg ccaggctcgg gaacagaggg     60

aacgcgaaga acaggagcgg aagctgcagg ctgaaaggga caagcgaatg cgagaggagc    120

agctggcccg ggaggctgaa gcccgggctg aacgtgaggc cgaggcgcgg agacgggagg    180

agcaggaggc tcgagagaag gcgcaggctg agcaggagga gcaggagcga ctgcagaagc    240

agaaagagga agccgaagcc cggtcccggg aagaagctga gcgccagcgc caggagcggg    300

aaaagcactt tcagaaggag gaacaggaga gacaagagcg aagaaagcgg ctggaggaga    360

taatgaagag gactcggaaa tcagaagccg ccgaaaccaa gaagcaggat gcaaaggaga    420

ccgcagctaa caattccggc ccagaccctt gtgaaagctg tagagactcg gccctctggg    480

cttccagaaa ggattctatt gcagaaagga aggagctngg ccccccangg a             531
```

<210> SEQ ID NO 18
<211> LENGTH: 1041
<212> TYPE: DNA

-continued

<213> ORGANISM: Homo sapiens
<220> FEATURE:
<221> NAME/KEY: modified_base
<222> LOCATION: (544)
<223> OTHER INFORMATION: Where n is a, c, g or t

<400> SEQUENCE: 18
ctctgtggaa aactgatgag gaatgaattt accattaccc atgttctcat ccccaagcaa 60
agtgctgggt ctgattactg caacacagag aacgaagaag aacttttcct catacaggat 120
cagcagggcc tcatcacact gggctggatt catactcacc ccacacagac cgcgtttctc 180
tccagtgtcg acctacacac tcactgctct taccagatga tgttgccaga gtcagtagcc 240
attgtttgct cccccaagtt ccaggaaact ggattcttta aactaactga ccatggacta 300
gaggagattt cttcctgtcg ccagaaagga tttcatccac acagcaagga tccacctctg 360
ttctgtagct gcagccacgt gactgttgtg gacagagcag tgaccatcac agaccttcga 420
tgagcgtttg agtccaacac cttccaagaa caacaaaacc atatcagtgt actgtagccc 480
cttaatttaa gctttctaga aagctttgga agtttttgta gatagtagaa agggggggcat 540 cacntgagaa agagctgatt ttgtatttca ggtttgaaaa gaaataactg aacatatttt 600
ttaggcaagt cagaaagaga acatggtcac ccaaaagcaa ctgtaactca gaaattaagt 660
tactcagaaa ttaagtagct cagaaattaa gaaagaatgg tataatgaac ccccatatac 720
ccttccttct ggattcacca attgttaaca tttttttcct ctcagctatc cttctaattt 780
ctctctaatt tcaatttgtt tatatttacc tctgggctca ataagggcat ctgtgcagaa 840
atttggaagc catttagaaa atcttttgga ttttcctgtg gtttatggca atatgaatgg 900
agcttattac tggggtgagg gacagcttac tccatttgac cagattgttt ggctaacaca 960
tcccgaagaa tgattttgtc aggaattatt gttatttaat aaatatttca ggatattttt 1020
cctctacaat aaagtaacaa t 1041

<210> SEQ ID NO 19
<211> LENGTH: 1043
<212> TYPE: DNA
<213> ORGANISM: Homo sapiens

<400> SEQUENCE: 19
ctctgtggaa aactgatgag gaatgaattt accattaccc atgttctcat ccccaagcaa 60
agtgctgggt ctgattactg caacacagag aacgaagaag aacttttcct catacaggat 120
cagcagggcc tcatcacact gggctggatt catactcacc ccacacagac cgcgtttctc 180
tccagtgtcg acctacacac tcactgctct taccagatga tgttgccaga gtcagtagcc 240
attgtttgct cccccaagtt ccaggaaact ggattcttta aactaactga ccatggacta 300
gaggagattt cttcctgtcg ccagaaagga tttcatccac acagcaagga tccacctctg 360
ttctgtagct gcagccacgt gactgttgtg gacagagcag tgaccatcac agaccttcga 420
tgagcgtttg agtccaacac cttccaagaa caacaaaacc atatcagtgt actgtagccc 480
cttaatttaa gctttctaga aagctttgga agtttttgta gatagtagaa agggggggcat 540 cacctgagaa agagctgatt ttgtatttca ggtttgaaaa gaaataactg aacatatttt 600
ttaggcaagt cagaaagaga acatggtcac ccaaaagcaa ctgtaactca gaaattaagt 660
tactcagaaa ttaagtagct cagaaattaa gaaagaatgg tataatgaac ccccatatac 720
ccttccttct ggattcacca attgttaaca tttttttcct ctcagctatc cttctaattt 780
ctctctaatt tcaatttgtt tatatttacc tctgggctca ataagggcat ctgtgcagaa 840

-continued atttggaagc catttagaaa atcttttgga ttttcctgtg gtttatggca atatgaatgg 900
agcttattac tggggtgagg gacagcttac tccatttgac cagattgttt ggctaacaca 960
tcccgaagaa tgattttgtc aggaattatt gttatttaat aaatatttca ggatattttt 1020
cctctacaat aaagtaacaa tta 1043

<210> SEQ ID NO 20
<211> LENGTH: 448
<212> TYPE: DNA
<213> ORGANISM: Homo sapiens

<400> SEQUENCE: 20
ggacgacaag gccatggcga tatcggatcc gaattcaagc ctttggaatt aaataaacct 60
ggaacaggga aggtgaaagt tggagtgaga tgtcttccat atctatacct ttgtgcacag 120
ttgaatggga actgtttggg tttagggcat cttagagttg attgatggaa aaagcagaca 180
ggaactggtg ggaggtcaag tggggaagtt ggtgaatgtg gaataactta cctttgtgct 240
ccacttaaac cagatgtgtt gcagctttcc tgacatgcaa ggatctactt taattccaca 300
ctctcattaa taaattgaat aaaagggaat gttttggcac ctgatataat ctgccaggct 360
atgtgacagt aggaaggaat ggtttcccct aacaagccca atgcactggt ctgactttat 420
aaattattta ataaaatgaa ctattatc 448

<210> SEQ ID NO 21
<211> LENGTH: 411
<212> TYPE: DNA
<213> ORGANISM: Homo sapiens

<400> SEQUENCE: 21
ggcagtgaca ttcaccatca tgggaaccac cttccctttt cttcaggatt ctctgtagtg 60
gaagagagca cccagtgttg ggctgaaaac atctgaaagt agggagaaga acctaaaata 120
atcagtatct cagagggctc taaggtgcca agaagtctca ctggacattt aagtgccaac 180
aaaggcatac tttcggaatc gccaagtcaa aactttctaa cttctgtctc tctcagagac 240
aagtgagact caagagtcta ctgctttagt ggcaactaca gaaaactggt gttacccaga 300
aaaacaggag caattagaaa tggttccaat atttcaaagc tccgcaaaca ggatgtgctt 360
tcctttgccc atttagggtt tcttctcttt cctttctctt tattaaccac t 411

<210> SEQ ID NO 22
<211> LENGTH: 896
<212> TYPE: DNA
<213> ORGANISM: Homo sapiens
<220> FEATURE:
<221> NAME/KEY: modified_base
<222> LOCATION: (230)
<223> OTHER INFORMATION: Where n is a, c, g or t
<221> NAME/KEY: modified_base
<222> LOCATION: (320)
<223> OTHER INFORMATION: Where n is a, c, g or t

<400> SEQUENCE: 22
tgcgctgaaa acaacggcct cctttactgt taaaatgcag ccacaggtgc ttagccgtgg 60
gcatctcaac caccagcctc tgtgggggc aggtgggcgt ccctgtgggc ctctgggccc 120
acgtccagcc tctgtcctct gccttccgtt cttcgacagt gttcccggca tccctggtca 180
cttggtactt ggcgtgggcc tcctgtgctg ctccagcagc tcctccaggn ggtcggcccg 240
cttcaccgca gcctcatgtt gtgtccggag gctgctcacg gcctcctcct tcctcgcgag 300

-continued

```
ggctgtcttc accctccggn gcacctcctc cagctccagc tgctggcggg cctgcagcgt    360

ggccagctcg gccttggcct gccgcgtctc ctcctcarag gctgccagcc ggtcctcgaa    420

ctcctggcgg atcacctggg ccaggttgct gcgctcgcta gaaagctgct cgttcaccgc    480

ctgcgcatcc tccagcgccc gctccttctg ccgcacaagg ccctgcagac gcagattctc    540

gccctcggcc tccccaagct ggcccttcag ctccgagcac cgctcctgaa gcttccgctc    600

cgactgctcc agctcggaga gctcggcctc gtacttgtcc cgtaagcgct tgatgcggct    660

ctcggcagcc ttctcactct cctccttggc cagcgccatg tcggcctcca gccggtgaat    720

gaccagctca atctccttgt cccggccttt ccggatttct tccctcagct cctgttcccg    780

gttcagcagc cacgcctcct ccttcctggt gcggccggcc tcccacgcct gcctctccag    840

ctccagctgc tgcttcaggg tattcagctc catctggcgg gcctgcagcg tggcca        896


<210> SEQ ID NO 23
<211> LENGTH: 111
<212> TYPE: DNA
<213> ORGANISM: Homo sapiens

<400> SEQUENCE: 23

caacttatta cttgaaatta taatatagcc tgtccgtttg ctgtttccag gctgtgatat     60

attttcctag tggtttgact ttaaaaataa ataaggttta attttctccc c             111


<210> SEQ ID NO 24
<211> LENGTH: 531
<212> TYPE: DNA
<213> ORGANISM: Homo sapiens
<220> FEATURE:
<221> NAME/KEY: modified_base
<222> LOCATION: (472)
<223> OTHER INFORMATION: Where n is a, c, g or t
<221> NAME/KEY: modified_base
<222> LOCATION: (494)
<223> OTHER INFORMATION: Where n is a, c, g or t

<400> SEQUENCE: 24

tgcaagtcac gggagtttat ttatttaatt tttttcccca gatggagact ctgtcgccca     60

ggctggagtg caatggtgtg atcttggctc actgcaacct ccacctcctg ggttcaagcg    120

attctcctgc cacagcctcc cgagtagctg ggattacagg tgcccgccac cacacccagc    180

taatttttat atttttagta aagacagggt ttccccatgt tggccaggct ggtcttgaac    240

ttctgacctc aggtgatcca cctgcctcgg cctcccaaag tgttgggatt acaggcgtga    300

gctacccgtg cctggccagc cactggagtt taaaggacag tcatgttggc tccagcctaa    360

ggcggcattt tcccccatca gaaagcccgc ggctcctgta cctcaaaata gggcacctgt    420

aaagtcagtc agtgaagtct ctgctctaac tggccacccg gggccattgg cntctgacac    480

agccttgcca ggangcctgc atctgcaaaa gaaaagttca cttcctttcc g             531


<210> SEQ ID NO 25
<211> LENGTH: 471
<212> TYPE: DNA
<213> ORGANISM: Homo sapiens
<220> FEATURE:
<221> NAME/KEY: modified_base
<222> LOCATION: (377)
<223> OTHER INFORMATION: Where n is a, c, g or t

<400> SEQUENCE: 25

cagagaatct kagaaagatg tcgcgttttc ttttaatgaa tgagagaagc ccatttgtat     60
```

-continued

```
ccctgaatca ttgagaaaag gcggcggtgg cgacagcggc gacctaggga tcgatctgga    120

gggacttggg gagcgtgcag agacctctag ctcgagcgcg agggacctcc cgccgggatg    180

cctggggagc agatggaccc tactggaagt cagttggatt cagatttctc tcagcaagat    240

actccttgcc tgataattga agattctcag cctgaaagcc aggttctaga ggatgattct    300

ggttctcact tcagtatgct atctcgacac cttcctaatc tccagacgca caaagaaaat    360

cctgtgttgg atgttgngtc caatccttga acaaacagct ggagaagaac gaggagaccg    420

gtaatagtgg gttcaatgaa catttgaaag aaaaccaggt tgcagaccct g             471


<210> SEQ ID NO 26
<211> LENGTH: 541
<212> TYPE: DNA
<213> ORGANISM: Homo sapiens

<400> SEQUENCE: 26

gactgtcctg aacaagggac ctctgaccag agagctgcag gagatgcaga gtggtggcag     60

gagtggaagc caaagaacac ccaccttcct cccttgaagg agtagagcaa ccatcagaag    120

atactgtttt attgctctgg tcaaacaagt cttcctgagt tgacaaaacc tcaggctctg    180

gtgacttctg aatctgcagt ccactttcca taagttcttg tgcagacaac tgttcttttg    240

cttccatagc agcaacagat gctttggggc taaaaggcat gtcctctgac cttgcaggtg    300

gtggattttg ctcttttaca acatgtacat ccttactggg ctgtgctgtc acagggatgt    360

ccttgctgga ctgttctgct atggggatat cttcgttgga ctgttcttca tgcttaattg    420

cagtattagc atccacatca gacagcctgg tataaccaga gttggtggtt actgattgta    480

gctgctcttt gtccacttca tatggcacaa gtattttcct caacatcctg gctctgggaa    540

g                                                                    541


<210> SEQ ID NO 27
<211> LENGTH: 461
<212> TYPE: DNA
<213> ORGANISM: Homo sapiens
<220> FEATURE:
<221> NAME/KEY: modified_base
<222> LOCATION: (367)
<223> OTHER INFORMATION: Where n is a, c, g or t

<400> SEQUENCE: 27

gaaatgtata tttaatcatt ctcttgaacg atcagaactc traaatcagt tttctataac     60

arcatgtaat acagtcaccg tggctccaag gtccaggaag gcagtggtta acacatgaag    120

agtgtgggaa gggggctgga aacaaagtat tcttttcctt caaagcttca ttcctcaagg    180

cctcaattca agcagtcatt gtccttgctt tcaaaagtct gtgtgtgctt catggaaggt    240

atatgtttgt tgccttaatt tgaattgtgg ccaggaaggg tctggagatc taaattcaga    300

gtaagaaaac ctgagctaga actcaggcat ttctcttaca gaacttggct tgcagggtag    360

aatgaangga aagaaactta gaagctcaac aagctgaaga taatcccatc aggcatttcc    420

cataggcctt gcaactctgt tcactgagag atgttatcct g                        461


<210> SEQ ID NO 28
<211> LENGTH: 541
<212> TYPE: DNA
<213> ORGANISM: Homo sapiens

<400> SEQUENCE: 28
```

-continued agtctggagt gagcaaacaa gagcaagaaa caarragaag ccaaaagcag aaggctccaa 60
tatgaacaag ataaatctat cttcaaagac atattagaag ttgggaaaat aattcatgtg 120
aactagacaa gtgtgttaag agtgataagt aaaatgcacg tggagacaag tgcatcccca 180
gatctcaggg acctccccct gcctgtcacc tggggagtga gaggacagga tagtgcatgt 240
tctttgtctc tgaattttta gttatatgtg ctgtaatgtt gctctgagga agcccctgga 300
aagtctatcc caacatatcc acatcttata ttccacaaat taagctgtag tatgtaccct 360
aagacgctgc taattgactg ccacttcgca actcaggggc ggctgcattt tagtaatggg 420
tcaaatgatt cactttttat gatgcttccc aaggtgcctt ggcttctctt cccaactgac 480
aaatgcccaa gttgagaaaa atgatcataa ttttagcata aaccgagcaa tcggcgaccc 540
c 541

<210> SEQ ID NO 29
<211> LENGTH: 411
<212> TYPE: DNA
<213> ORGANISM: Homo sapiens

<400> SEQUENCE: 29
tagctgtctt cctcactctt atggcaatga ccccatatct taatggatta agataatgaa 60
agtgtatttc ttacactctg tatctatcac cagaagctga ggtgatagcc cgcttgtcat 120
tgtcatccat attctgggac tcaggcggga actttctgga atattgccag ggagcatggc 180
agaggggcac agtgcattct gggggaatgc acattggctc agcctgggta atgagtgata 240
tacattacct ctgttcacaa ctcattgccc agcaccagtc acaaggcccc accaaatacc 300
agagcccaag aaatgtagtc ctgttgatat ggttttgctg tgtcccaacc caaatctcat 360
cttgaattgt aagctcccat aattcccatg tgttgtggga gggacctggt g 411

<210> SEQ ID NO 30
<211> LENGTH: 511
<212> TYPE: DNA
<213> ORGANISM: Homo sapiens

<400> SEQUENCE: 30
atcatgagga tgttaccaaa gggatggtac taaaccattt gtattcgtct gttttcacac 60
tgctttgaag atactacctg agactgggta atttataaac aaaagagatt taattgactc 120
acagttctgc atggctgaag aggcctcagg aaacttacag tcatggtgga aggcaaagga 180
ggagcaaggc atgtcttaca tgtcagtagg agagagagcg agagcaggag aacctgccac 240
ttataaacca ttcagatctc ataactccct atcatgagaa aaacatggag gaaaccaccc 300
tcatgatcca atcacctccc gccaggtccc tccctcgaca cgtggggatt ataattcagg 360
attagaggga cacagagaca aaccatatca tcattcatga gaaatccacc ctcatagtcc 420
aatcagctcc taccaggccc cacctccaac actggggatt gcaattcaac atgagatttg 480
gatggggaca cagattcaaa ccatatcata c 511

<210> SEQ ID NO 31
<211> LENGTH: 827
<212> TYPE: DNA
<213> ORGANISM: Homo sapiens

<400> SEQUENCE: 31
catggccttt ctccttagag gccagaggtg ctgccctggc tgggagtgaa gctccaggca 60
ctaccagctt tcctgatttt cccgtttggt ccatgtgaag agctaccacg agccccagcc 120

-continued

```
tcacagtgtc cactcaaggg cagcttggtc ctcttgtcct gcagaggcag gctggtgtga    180
ccctgggaac ttgacccggg aacaacaggt ggcccagagt gagtgtggcc tggcccctca    240
acctagtgtc cgtcctcctc tctcctggag ccagtcttga gtttaaaggc attaagtgtt    300
agatacaagc tccttgtggc tggaaaaaca cccctctgct gataaagctc agggggcact    360
gaggaagcag aggccccttg ggggtgccct cctgaagaga gcgtcaggcc atcagctctg    420
tccctctggt gctcccacgt ctgttcctca ccctccatct ctgggagcag ctgcacctga    480
ctggccacgc gggggcagtg gaggcacagg ctcagggtgg ccgggctacc tggcacccta    540
tggcttacaa agtagagttg gcccagtttc cttccacctg aggggagcac tctgactcct    600
aacagtcttc cttgccctgc catcatctgg ggtggctggc tgtcaagaaa ggccgggcat    660
gctttctaaa cacagccaca ggaggcttgt agggcatctt ccaggtgggg aaacagtctt    720
agataagtaa ggtgacttgc ctaaggcctc ccagcaccct tgatcttgga gtctcacagc    780
agactgcatg tsaacaactg gaaccgaaaa catgcctcag tataaaa                 827
```

```
<210> SEQ ID NO 32
<211> LENGTH: 291
<212> TYPE: DNA
<213> ORGANISM: Homo sapiens

<400> SEQUENCE: 32

ccagaacctc cttctctttg gagaatgggg aggcctcttg gagacacaga gggtttcacc     60
ttggatgacc tctagagaaa ttgcccaaga agcccacctt ctggtcccaa cctgcagacc    120
ccacagcagt cagttggtca ggccctgctg tagaaggtca cttggctcca ttgcctgctt    180
ccaaccaatg ggcaggagag aaggccttta tttctcgccc acccattctc ctgtaccagc    240
acctccgttt tcagtcagyg ttgtccagca acggtaccgt ttacacagtc a             291
```

```
<210> SEQ ID NO 33
<211> LENGTH: 491
<212> TYPE: DNA
<213> ORGANISM: Homo sapiens

<400> SEQUENCE: 33

tgcatgtagt tttatttatg tgttttsgtc tggaaaacca agtgtcccag cagcatgact     60
gaacatcact cacttcccct acttgatcta caaggccaac gccgagagcc cagaccagga    120
ttccaaacac actgcacgag aatattgtgg atccgctgtc aggtaagtgt ccgtcactga    180
cccaracgct gttacgtggc acatgactgt acagtgccac gtaacagcac tgtacttttc    240
tcccatgaac agttacctgc catgtatcta catgattcag aacattttga acagttaatt    300
ctgacacttg aataatccca tcaaaaaccg taaaatcact ttgatgtttg taacgacaac    360
atagcatcac tttacgacag aatcatctgg aaaaacagaa caacgaatac atacatctta    420
aaaaatgctg ggtgggccca ggcacagctt cacgcctgta atcccagcac tttgggaggc    480
ttaagcgggt g                                                         491
```

```
<210> SEQ ID NO 34
<211> LENGTH: 521
<212> TYPE: DNA
<213> ORGANISM: Homo sapiens
<220> FEATURE:
<221> NAME/KEY: modified_base
<222> LOCATION: (453)
<223> OTHER INFORMATION: Where n is a, c, g or t
<221> NAME/KEY: modified_base
```

-continued

<222> LOCATION: (476)
<223> OTHER INFORMATION: Where n is a, c, g or t
<221> NAME/KEY: modified_base
<222> LOCATION: (487)
<223> OTHER INFORMATION: Where n is a, c, g or t

<400> SEQUENCE: 34
tggggcggaa agaagccaag gccaaggagc tggtgcggca gctgcagctg gaggccgagg 60
agcagaggaa gcagaagaag cggcagagtg tgtcgggcct gcacagatac cttcacttgc 120
tggatggaaa tgaaaattac ccgtgtcttg tggatgcaga cggtgatgtg atttccttcc 180
caccaataac caacagtgag aagacaaagg ttaagaaaac gacttctgat ttgtttttgg 240
aagtaacaag tgccaccagt ctgcagattt gcaaggatgt catggatgcc ctcattctga 300
aaatggcaag aaatgaaaaa gtacacttta gaaaataaag aggaaggatc actctcagat 360
actgaagccg atgcagtctc tggacaactt ccagatccca caacgaatcc cagtgctgga 420
aaggacgggc ccttccttct ggtggtggaa cangtcccgg tggtggatct tggaanggaa 480
cctgaangtg gtgtaccccg tccaaggccg accttggcca c 521

<210> SEQ ID NO 35
<211> LENGTH: 161
<212> TYPE: DNA
<213> ORGANISM: Homo sapiens
<220> FEATURE:
<221> NAME/KEY: modified_base
<222> LOCATION: (18)
<223> OTHER INFORMATION: Where n is a, c, g or t

<400> SEQUENCE: 35
tcccgcgctc gcagggcncg tgccacctgc cygtccgccc gctcgctcgc tcgcccgccg 60
cgccgcgctg ccgaccgyca gcatgctgcc gagagtgggc tgccccgcgc tgccgctgcc 120
gccgccgccg ctgctgccgc tgctgccgct gctgctgctg c 161

<210> SEQ ID NO 36
<211> LENGTH: 341
<212> TYPE: DNA
<213> ORGANISM: Homo sapiens

<400> SEQUENCE: 36
ggcgggtagg catggaactg agaagaacga agaagctttc agactacgtg gggaagaatg 60
aaaaaaccaa aattatcgcc aagattcagc aaaggggaca gggagctcca gcccgagagc 120
ctattattag cagtgaggag cagaagcagc tgatgctgta ctatcacaga agacaagagg 180
agctcaagag attggaagaa aatgatgatg atgcctattt aaactcacca tgggcggata 240
acactgcttt gaaaagacat tttcatggag tgaaagacat aaagtggaga ccaagatgaa 300
gttcaccagc tgatgacact tccaaagaga ttagctcacc t 341

<210> SEQ ID NO 37
<211> LENGTH: 521
<212> TYPE: DNA
<213> ORGANISM: Homo sapiens
<220> FEATURE:
<221> NAME/KEY: modified_base
<222> LOCATION: (516)
<223> OTHER INFORMATION: Where n is a, c, g or t

<400> SEQUENCE: 37
tctgaaggtt aaatgtttca tctaaatagg gataatgrta aacacctata gcatagagtt 60
gtttgagatt aaatgagata atacatgtaa aattatgtgc ctggcataca gcaagattgt 120

-continued

```
tgttgttgtt gatgatgatg atgatgatga taatattttt ctatccccag tgcacaactg    180

cttgaaccta ttagataatc aatacatgtt tcttgaactg agatcaattt ccccatgttg    240

tctgactgat gaagccctac attttcttct agaggagatg acatttgagc aagatcttaa    300

agaaaatcag atgccttcac ctgaccactg cttggtgatc ccatggcact ttgtacatct    360

ctccattagc tctcatctca ccagcccatc attattgtat gtgctgcctt ctgaagcttg    420

cagctggcta ccatcmggta gaataaaaat catcctttca taaaatagtg accctccttt    480

tttatttgca tttcccaaag ccaagcaccg tggganggta g                        521
```

```
<210> SEQ ID NO 38
<211> LENGTH: 461
<212> TYPE: DNA
<213> ORGANISM: Homo sapiens

<400> SEQUENCE: 38

tatgaagaag ggaaaagaag ataatttgtg aaagaaatgg gtccagttac tagtctttga     60

aaagggtcag tctgtagctc ttcttaatga gaataggcag ctttcagttg ctcagggtca    120

gatttcctta gtggtgtatc taatcacagg aaacatctgt ggttccctcc agtctctttc    180

tgggggactt gggcccactt ctcatttcat ttaattagag gaaatagaac tcaaagtaca    240

atttactgtt gtttaacaat gccacaaaga catggttggg agctatttct tgatttgtgt    300

aaaatgctgt ttttgtgtgc tcataatggt tccaaaaatt gggtgctggc caaagagaga    360

tactgttaca gaagccagca agaagacctc tgttcattca cacccccggg gatatcagga    420

attgactcca gtgtgtgcaa atccagtttg gcctatcttc t                        461
```

```
<210> SEQ ID NO 39
<211> LENGTH: 769
<212> TYPE: DNA
<213> ORGANISM: Homo sapiens

<400> SEQUENCE: 39

tgagggactg attggtttgc tctctgctat tcaattcccc aagcccactt gttcctgcag     60

cgtcctcctt ctcattccct ttagttgtac cctctctttc atctgagacc tttccttctt    120

gatgtcgcct tttcttcttc ttgctttttc tgatgttctg ctcagcatgt tctgggtgct    180

tctcatctgc atcattcctt tcagatgctg tagcttcttc ctcctctttc tgcctccttt    240

tctttttctt ttttttgggg ggcttgctct ctgactgcag ttgaggggcc ccagggtcct    300

ggcctttgag acgagccagg aaggcctgct cctgggcctc taggcgagca agcttggcct    360

tcattgtgat cccaagacgg gcagccttgt gtgctgttcg cccctcacag gcttggagca    420

gcatctcatc agtcagaatc tttggggact tggacccctg gttgtcgtca tcactgcagc    480

tctccaagtc tttgtttggc ttctctccac ctgaagtcaa tgtagccatc ttcacaaact    540

tctgatacag caagttgggc ttgggatgat tataacgggt ggtctcctta gaaaggctcc    600

ttatctgtac tccatcctgc ccagtttcca ctaccaagtt ggccgcagtc ttgttgaaga    660

gctcattcca ccagtggttt gtgaactcct tggcagggtc atgtcctacc ccatgagtgt    720

cttgcttcag ygtcaccctg agagcctgag tgataccatt ctccttccg                769
```

```
<210> SEQ ID NO 40
<211> LENGTH: 292
<212> TYPE: DNA
<213> ORGANISM: Homo sapiens
```

-continued

<400> SEQUENCE: 40
gacaacatga aataaatcct agaggacaaa attaaactca atagagtgta gtctagttaa 60
aaactcgaaa aatgagcaag tctggtggga gtggaggaag ggctatacta taaatccaag 120
tgggcctcct gatcttaaca agccatgctc attatacaca tctctgaact ggacatacca 180
cctttacgca ggaaacaggg cttggaactt ctaagggaaa ttaacatgca ccacccacat 240
ctaacctacc tgccgggtag gtaccatccc tgcttcgctg aaatcagtgc tc 292

<210> SEQ ID NO 41
<211> LENGTH: 406
<212> TYPE: DNA
<213> ORGANISM: Homo sapiens

<400> SEQUENCE: 41
ttggaattaa ataaacctgg aacagggaag gtgaaagttg gagtgagatg tcttccatat 60
ctataccttt gtgcacagtt gaatgggaac tgtttgggtt tagggcatct tagagttgat 120
tgatggaaaa agcagacagg aactggtggg aggtcaagtg gggaagttgg tgaatgtgga 180
ataacttacc tttgtgctcc acttaaacca gatgtgttgc agctttcctg acatgcaagg 240
atctacttta attccacact ctcattaata aattgaataa aagggaatgt tttggcacct 300
gatataatct gccaggctat gtgacagtag gaaggaatgg tttcccctaa caagcccaat 360
gcactggtct gactttataa attatttaat aaaatgaact attatc 406

<210> SEQ ID NO 42
<211> LENGTH: 381
<212> TYPE: DNA
<213> ORGANISM: Homo sapiens

<400> SEQUENCE: 42
aaactggacc tgcaacaggg acatgaattt actgcarggt ctgagcaagc tcagcccctc 60
tacctcaggg ccccacagcc atgactacct cccccaggag cgggagggtg aagggggcct 120
gtctctgcaa gtggagccag agtggaggaa tgagctctga agacacagca cccagccttc 180
tcgcaccagc caagccttaa ctgcctgcct gaccctgaac cagaacccag ctgaactgcc 240
cctccaaggg acaggaaggc tgggggaggg agtttacaac ccaagccatt ccacccccctc 300 ccctgctggg gagaatgaca catcaagctg ctaacaattg gggaagggg aaggaagaaa 360 actctgaaaa caaaatcttg t 381

<210> SEQ ID NO 43
<211> LENGTH: 451
<212> TYPE: DNA
<213> ORGANISM: Homo sapiens

<400> SEQUENCE: 43
catgcgtttc accactgttg gccaggctgg tctcgaactc ctggcctcaa gcaatccacc 60
cgcctcagcc tccaaaagtg ctgggattac agatgtgagc catggcacca tgccaaaagg 120
ctatattcct ggctctgtgt ttccgagact gcttttaatc ccaacttctc tacatttaga 180 ttaaaaaaata ttttattcat ggtcaatctg gaacataatt actgcatctt aagtttccac 240
tgatgtatat agaaggctaa aggcacaatt tttatcaaat ctagtagagt aaccaaacat 300
aaaatcatta attactttca acttaataac taattgacat tcctcaaaag agctgttttc 360
aatcctgata ggttctttat tttttcaaaa tatatttgcc atgggatgct aatttgcaat 420
aaggcgcata atgagaatac cccaaactgg a 451

-continued

<210> SEQ ID NO 44
<211> LENGTH: 521
<212> TYPE: DNA
<213> ORGANISM: Homo sapiens

<400> SEQUENCE: 44
gttggacccc cagggactgg aaagacactt cttgcccgag ctgtggcggg agaagctgat 60
gttccttttt attatgcttc tggatccgaa tttgatgaga tgtttgtggg tgtgggagcc 120
agccgtatca gaaatctttt tagggaagca aaggcgaatg ctccttgtgt tatatttatt 180
gatgaattag attctgttgg tgggaagaga attgaatctc caatgcatcc atattcaagg 240
cagaccataa atcaacttct tgctgaaatg gatggtttta aacccaatga aggagttatc 300
ataataggag ccacaaactt cccagaggca ttagataatg ccttaatacc gtcctggtcg 360
ttttgacatg caagttacag ttccaaggcc agatgtaaaa ggtcgaacag aaattttgaa 420
atggtatctc aataaaataa agtttgatca atcccgttga tccagaaatt atagcctcga 480
ggtactggtg gcttttccgg aagcagagtt gggagaatct t 521

<210> SEQ ID NO 45
<211> LENGTH: 585
<212> TYPE: DNA
<213> ORGANISM: Homo sapiens

<400> SEQUENCE: 45
gcctacaaca tccagaaaga gtctaccctg cacctggtgc tscgtctcag aggtgggatg 60
cagatcttcg tgaagaccct gactggtaag accatcactc tcgaagtgga gccgagtgac 120
accatygaga acgtcaaagc aaagatccar gacaaggaag gcrtycctcc tgaccagcag 180
aggttgatct ttgccggaaa gcagctggaa gatggdcgca ccctgtctga ctacaacatc 240
cagaaagagt cyaccctgca cctggtgctc cgtctcagag gtgggatgca ratcttcgtg 300
aagaccctga ctggtaagac catcaccctc gaggtggagc ccagtgacac catcgagaat 360
gtcaaggcaa agatccaaga taaggaaggc atccctcctg atcagcagag gttgatcttt 420
gctgggaaac agctggaaga tggacgcacc ctgtctgact acaacatcca gaaagagtcc 480
actctgcact tggtcctgcg cttgaggggg ggtgtctaag tttccccttt taaggtttcm 540
acaaatttca ttgcactttc ctttcaataa agttgttgca ttccc 585

<210> SEQ ID NO 46
<211> LENGTH: 481
<212> TYPE: DNA
<213> ORGANISM: Homo sapiens

<400> SEQUENCE: 46
gaactgggcc ctgagcccaa gtcatgcctt gtgtccgcat ctgccgtgtc acctctgtkc 60
ctgcccctca cccctccctc ctggtcttct gagccagcac catctccaaa tagcctattc 120
cttcctgcaa atcacacaca catgcgggcc acacatacct gctgccctgg agatggggaa 180
gtaggagaga tgaatagagg cccatacatt gtacagaagg aggggcaggt gcagataaaa 240
gcagcagacc cagcggcagc tgaggtgcat ggagcacggt tggggccggc attgggctga 300
gcacctgatg ggcctcatct cgtgaatcct cgaggcagcg ccacagcaga ggagttaagt 360
ggcacctggg ccgagcagag caggagactg agggtcagag tggaggctaa gctgccctgg 420
aactcctcaa tcttgcctgc cccctagtat gaagccccct tcctgcccct acaattcctg 480

-continued a 481

<210> SEQ ID NO 47
<211> LENGTH: 461
<212> TYPE: DNA
<213> ORGANISM: Homo sapiens
<220> FEATURE:
<221> NAME/KEY: modified_base
<222> LOCATION: (128)
<223> OTHER INFORMATION: Where n is a, c, g or t

<400> SEQUENCE: 47
atggatctta ctttgccacc caggttggag tgcagtgctg caatcttggc tcactgcagc 60
cttaacctcc caggctcaag ctatcctcct gccaaagcct tccacatagc tgggactaca 120
ggtacacngc caccacaccc agctaaaatt tttgtatttt ttgtagagac gggatctcgc 180
cacgttgccc aggctggtcc catcctgacc tcaagcagat ctgcccacct cagccccccca 240 acgtgctagg attacaggcg tgagccaccg cacccagcct ttgttttgct tttaatggaa 300
tcaccagttc ccctccgtgt ctcagcagca gctgtgagaa atgctttgca tctgtgacct 360
ttatgaaggg gaacttccat gctgaatgag ggtaggatta catgctcctg tttcccgggg 420
gtcaagaaag cctcagactc cagcatgata agcagggtga g 461

<210> SEQ ID NO 48
<211> LENGTH: 571
<212> TYPE: DNA
<213> ORGANISM: Homo sapiens

<400> SEQUENCE: 48
ataggggctt taaggaggga attcaggttc aatgaggtcg taaggccagg gctcttatcc 60
agtaagactg gggtccttag atgagaaaga gacacccgag gtccttctct ctgccgtgtg 120
aggatgcatc aagaaggcgg ccgtctgcaa gcgaaggaga ggccgcacca gaaaccgaca 180
ccttcatctt ggacttgcag cctctagaac tgagaaaata actgtctgtt ggttaagcca 240
cccagtttgt agtattctct tatggcttcc taagcagact aacaaacaaa cacccaaaat 300
taactgatgg cttcgctgtc ttctgtaaaa attgctatga gagaactttt cactcactgt 360
tttgcagttt ctccctcagt ccctggttct ttcttctcac ataatcccaa tttcaattta 420
tagttcatgg cccaggcaga gtcattcatc acggcatctc ctgagctaaa ccagcacctg 480
ctctgctcac ttcttgactg gctgctcatc atcagccctc ttgcagagat ttcatttcct 540
cccgtgccag gtacttcacg caccaagctc a 571

<210> SEQ ID NO 49
<211> LENGTH: 511
<212> TYPE: DNA
<213> ORGANISM: Homo sapiens

<400> SEQUENCE: 49
ggataatgaa gttgttttat ttagcttgga caaaaaggca tattcctcta ttttcttata 60
caacaaatat ccccaaaata aagcaagcat atatatcttg aatgtgtaat aatccagtga 120
taaacaagag cagtacttta aaagaaaaaa aaatatgtat ttctgtcagg ttaaaatgag 180
aatcaaaacc atttactctg ctaactcatt attttttgct ttctttttgg ttaagagagg 240
caatgcaata cactgaaaaa ggtttttatc ttatctggca ttggaattag acatattcaa 300
accccagccc ccatttccaa actttaagac cacaaacaag taatttactt ttctgaacat 360 tggtttttttc tggaaaatgg gaattataaa atagactttg cagactctta tgagattaaa 420

-continued taagataatg tatgaaattc tttcttcttt tttacttctt tttccttttt gagatggagt 480
ctcaccccgt cacccaggct ggagtacagt g 511

<210> SEQ ID NO 50
<211> LENGTH: 561
<212> TYPE: DNA
<213> ORGANISM: Homo sapiens

<400> SEQUENCE: 50
ccactgcact ccagcctggg tgacggagtg agactctgtc tcaaaaaaac aaacaaacaa 60
acaaacaaaa aactgaaaag gaaatagagt tcctctttcc tcatatatga atatattatt 120
tcaacagatt gttgatcacc taccatatgc ttggtattgt tctaattgct ggggatacag 180
caagaggttc tgcagaactt catggagcat gaaagtaaat aaacaaagtt aatttcaagg 240
ccaggcatgg ttgctcacac ctttagtccc agcactttgg gaggctgagg caggtggatc 300
acttgggccc aggagttcaa ggctgcagtg agccaagatt gtgccactac tctccaggct 360
gggcaacaga gcaagaccct gtctcagggg gaacaaaaag ttaatttcag attttgttaa 420
gtgctgtaaa ggaagtaaat aggttgatat tcaagagagc acctgaaggc caggcgtggt 480
ggctcacgcc tgtggtctaa cgctttggga agcccgagcg ggcggatcac aaggtcagga 540
gaattttggc caggcatggt g 561

<210> SEQ ID NO 51
<211> LENGTH: 451
<212> TYPE: DNA
<213> ORGANISM: Homo sapiens

<400> SEQUENCE: 51
agaatccatt tattgggttt taaactagtt acacaactga aatcagtttg gcactacttt 60
atacagggat tacgcctgtg tatgccgaca cttaaatact gtaccaggac cactgctgtg 120
cttaggtctg tattcagtca ttcagcatgt agatactaaa aatatactgt agtgttcctt 180
taaggaagac tgtacagggt gtgttgcaag atgacattca ccaatttgtg aattatttca 240
acccagaaga tacctttcac tctataaact tgtcataggc aaacatgtgg tgttagcatt 300
gagagatgca cacaaaaatg ttacataaaa gttcagacat tctaatgata agtgaactga 360
aaaaaaaaaa aaccccacat ctcaattttt gtaacaagat aaagaaaata atttaaaaac 420
acaaaaaatg gcattcagtg ggtacaaagc c 451

<210> SEQ ID NO 52
<211> LENGTH: 682
<212> TYPE: DNA
<213> ORGANISM: Homo sapiens

<400> SEQUENCE: 52
caaatattta atataaatct ttgaaacaag ttcagakgaa ataaaaatca aagtttgcaa 60
aaacgtgaag attaacttaa ttgtcaaata ttcctcattg ccccaaatca gtattttttt 120
tatttctatg caaaagtatg ccttcaaact gcttaaatga tatatgatat gatacacaaa 180
ccagttttca aatagtaaag ccagtcatct tgcaattgta agaaataggt aaaagattat 240
aagacacctt acacacacac acacacacac acacacacgt gtgcaccgcc aatgacaaaa 300
aacaatttgg cctctcctaa aataagaaca tgaagaccct taattgctgc caggagggaa 360
cactgtgtca cccctcccta caatccaggt agtttccttt aatccaatag caaatctggg 420

-continued

```
catatttgag aggagtgatt ctgacagcca csgttgaaat cctgtgggga accattcatg    480

tccacccact ggtgccctga aaaaatgcca ataatttttc gctcccactt ctgctgctgt    540

ctcttccaca tcctcacata gaccccagac ccgctggccc ctggctgggc atcgcattgc    600

tggtagagca agtcataggt ctcgtctttg acgtcacaga agcgatacac caaattgcct    660

ggtcggtcat tgtcataacc ag                                             682


<210> SEQ ID NO 53
<211> LENGTH: 311
<212> TYPE: DNA
<213> ORGANISM: Homo sapiens
<220> FEATURE:
<221> NAME/KEY: modified_base
<222> LOCATION: (208)
<223> OTHER INFORMATION: Where n is a, c, g or t

<400> SEQUENCE: 53

tttgacttta gtaggggtct gaactattta ttttactttg ccmgtaatat ttaraccyta     60

tatatctttc attatgccat cttatcttct aatgbcaagg gaacagwtgc taamctggct    120

tctgcattwa tcacattaaa aatggctttc ttggaaaatc ttcttgatat gaataaagga    180

tcttttavag ccatcattta aagcmggntt ctctccaaca cgagtctgct sasggggggk    240

gagctgtgaa ctctggctga aggctttccc atacacactg caatgacmtg gtttctgacc    300

agbgtgagtt a                                                         311


<210> SEQ ID NO 54
<211> LENGTH: 561
<212> TYPE: DNA
<213> ORGANISM: Homo sapiens

<400> SEQUENCE: 54

agagaagccc cataaatgca atcagtgtgg gaaggccttc agtcagagct caagcctttt     60

cctccatcat cgggttcata ctggagagaa accctatgta tgtaatgaat gcggcagagc    120

ctttggtttt aactctcatc ttactgaaca cgtaaggatt cacacaggag aaaaacccta    180

tgtttgtaat gagtgcggca aagcctttcg tcggagttcc actcttgttc agcatcgaag    240

agttcacact ggggagaagc cctaccagtg cgttgaatgt gggaaagctt tcagccagag    300

ctcccagctc accctacatc agccgagttc acactggaga gaagccctat gactgtggtg    360

actgtgggaa ggccttcagc cggaggtcaa ccctcattca gcatcagaaa gttcacagcg    420

gagagactcg taagtgcaga aaacatggtc cagcctttgt tcatggctcc agcctcacag    480

cagatggaca gattcccact ggagagaagc acggcagaac ctttaaccat ggtgcaaatc    540

tcattctgcg ctggacagtt c                                              561


<210> SEQ ID NO 55
<211> LENGTH: 811
<212> TYPE: DNA
<213> ORGANISM: Homo sapiens

<400> SEQUENCE: 55

gagacagggt ctcactttgt cacccaggct ggaatgcagt ggtgcgatct tacgtagctc     60

actgcagccc tgacctcctg gactcaaaca attctcctgc ctcagccctg caagtagctg    120

ggactgtggg tgcatgccac catgcctggc taacttttgt agtttttgta aagatggggt    180

tttgccatgt tgcacatgct ggtcttgaac tcctgagctc aaacgatctg cccacctcgg    240

cctcccagaa tgttgggatt acaggggtaa accaccacgc ctggccccat tagggtattc    300
```

-continued

```
ttagcatcca cttgctcact gagattaatc ataagagatg ataagcactg gaagaaaaaa    360

atttttacta ggctttggat atttttttcc tttttcagct ttatacagag gattggatct    420

ttagttttcc tttaactgat aataaaacat tgaaaggaaa taagtttacc tgagattcac    480

agagataacc ggcatcactc ccttgctcaa ttccagtctt taccacatca attattttca    540

gaggtgcagg ataaaggcct ttagtctgct ttcgcacttt ttcttccact tttttgtaaa    600

cctgttgcct gacaaatgga attgacagcg tatgccatga ctattccatt tgtcaggcat    660

acgctgtcaa tttttccacc aatcccttgt ctctctttgg agagatcttc ttatcagcta    720

gtcctttggc aaaagtaatt gcaacttctt ctaggtattc tattgtccgt tccactggtg    780

gaacccctgg gaccaggact aaaacctcca g                                  811
```

```
<210> SEQ ID NO 56
<211> LENGTH: 591
<212> TYPE: DNA
<213> ORGANISM: Homo sapiens
<220> FEATURE:
<221> NAME/KEY: modified_base
<222> LOCATION: (45)
<223> OTHER INFORMATION: Where n is a, c, g or t
<221> NAME/KEY: modified_base
<222> LOCATION: (477)
<223> OTHER INFORMATION: Where n is a, c, g or t
<221> NAME/KEY: modified_base
<222> LOCATION: (490)
<223> OTHER INFORMATION: Where n is a, c, g or t
<221> NAME/KEY: modified_base
<222> LOCATION: (561)
<223> OTHER INFORMATION: Where n is a, c, g or t

<400> SEQUENCE: 56

atctcatata tatatttctt cctgacttta tttgcttgct tctgncacgc atttaaaata     60

tcacagagac caaaatagag cggctttctg gtggaacgca tggcagtcac aggacaaaat    120

acaaaactag gggctctgt cttctcatac atcatacaat tttcaagtat tttttttatg    180

tacaaagagc tactctatct gaaaaaaaat taaaaaataa atgagacaag atagtttatg    240

catcctagga agaaagaatg ggaagaaaga acggggcagt tgggtacaga ttcctgtccc    300

ctgttcccag ggaccactac cttcctgcca ctgagttccc ccacagcctc acccatcatg    360

tcacagggca agtgccaggg taggtgggga ccagtggaga caggaaccag caacatactt    420

tggcctggaa gataaggaga aagtctcaga aacacactgg tgggaagcaa tcccacnggc    480

cgtgccccan gagcttccca cctgctgctg gctccctggg tggctttggg aacagcttgg    540

gcaggccctt ttgggtgggg nccaactggg cctttgggcc cgtgtggaaa g             591
```

```
<210> SEQ ID NO 57
<211> LENGTH: 481
<212> TYPE: DNA
<213> ORGANISM: Homo sapiens

<400> SEQUENCE: 57

aaacattgag atggaatgat agggtttccc agaatcaggt ccatatttta actaaatgaa     60

aattatgatt tatagccttc tcaaatacct gccatacttg atatctcaac cagagctaat    120

tttacctctt tacaaattaa ataagcaagt aactggatcc acaatttata atacctgtca    180

attttttctg tattaaacct ctatcatagt ttaagcctat tagggtactt aatccttaca    240

aataaacagg tttaaaatca cctcaatagg caactgccct tctggttttc ttctttgact    300

aaacaatctg aatgcttaag attttccact ttgggtgcta gcagtacaca gtgttacact    360
```

-continued

```
ctgtattcca gacttcttaa attatagaaa aaggaatgta cactttttgt attctttctg    420

agcagggccg ggaggcaaca tcatctacca tggtagggac ttgtatgcat ggactacttt    480

a                                                                     481
```

<210> SEQ ID NO 58
<211> LENGTH: 141
<212> TYPE: DNA
<213> ORGANISM: Homo sapiens

<400> SEQUENCE: 58

```
actctgtcgc ccaggctgga gcccabtggm gcgatctcga ctccctgcaa gctmcgcctc     60

acaggwtcat gccattctcc tgcctcagca tctggagtag ctgggactac aggcgccagc    120

caccatgccc agctaatttt t                                              141
```

<210> SEQ ID NO 59
<211> LENGTH: 191
<212> TYPE: DNA
<213> ORGANISM: Homo sapiens

<400> SEQUENCE: 59

```
accttaaaga cataggagaa tttatactgg gagagaaagc ttacaaatgt aaggtttctg     60

acaagacttg ggagtgattc acacctggaa caacatactg gacttcacac tggabagaaa    120

ccttacaagt gtaatgagtg tggcaaagcc tttggcaagc agtcaacact tattcaccat    180

caggcaattc a                                                         191
```

<210> SEQ ID NO 60
<211> LENGTH: 480
<212> TYPE: DNA
<213> ORGANISM: Homo sapiens

<400> SEQUENCE: 60

```
agtcaggatc atgatggctc agtttcccac agcgatgaat ggagggccaa atatgtgggc     60

tattacatct gaagaacgta ctaagcatga taaacagttt gataacctca aaccttcagg    120

aggttacata acaggtgatc aagcccgtac ttttttccta cagtcaggtc tgccggcccc    180

ggttttagct gaaatatggg ccttatcaga tctgaacaag gatgggaaga tggaccagca    240

agagttctct atagctatga aactcatcaa gttaaagttg cagggccaac agctgcctgt    300

agtcctccct cctatcatga aacaaccccc tatgttctct ccactaatct ctgctcgttt    360

tgggatggga agcatgccca atctgtccat tcatcagcca ttgcctccag ttgcacctat    420

agcaacaccc ttgtcttctg ctacttcagg gaccagtatt cctccctaat gatgcctgct    480
```

<210> SEQ ID NO 61
<211> LENGTH: 381
<212> TYPE: DNA
<213> ORGANISM: Homo sapiens

<400> SEQUENCE: 61

```
ctttcgattt ccttcaattt gtcacgtttg attttatgaa gttgttcaag ggctaactgc     60

tgtgtattat agctttctct gagttccttc agctgattgt taaatgaatc catttctgag    120

agcttagatg cagtttcttt ttcaagagca tctaattgtt ctttaagtct ttggcataat    180

tcttcctttt ctgatgactt tctatgaagt aaactgatcc ctgaatcagg tgtgttactg    240

agctgcatgt ttttaattct ttcgtttaat agctgcttct cagggaccag atagataagc    300
```

-continued

```
ttattttgat attccttaag ctcttggtga agttgttcga tttccataat ttccaggtca    360

cactggttat cccaaacttc t                                              381


<210> SEQ ID NO 62
<211> LENGTH: 906
<212> TYPE: DNA
<213> ORGANISM: Homo sapiens

<400> SEQUENCE: 62

gtggaggtga aacggaggca agaaaggggg ctacctcagg agcgagggac aaagggggcg     60

tgaggcacct aggccgcggc accccggcga caggaagccg tcctgaaccg ggctaccggg    120

taggggaagg gcccgcgtag tcctcgcagg gccccagagc tggagtcggc tccacagccc    180

cgggccgtcg gcttctcact tcctggacct ccccggcgcc cgggcctgag gactggctcg    240

gcggagggag aagaggaaac agacttgagc agctccccgt tgtctcgcaa ctccactgcc    300

gaggaactct catttcttcc ctcgctcctt caccccccac ctcatgtaga aaggtgctga    360

agcgtccgga gggaagaaga acctgggcta ccgtcctggc cttcccmccc ccttcccggg    420

gcgctttggt gggcgtggag ttggggttgg gggggtgggt gggggttctt ttttggagtg    480

ctggggaact tttttccctt cttcaggtca ggggaaaggg aatgcccaat tcagagagac    540

atgggggcaa gaaggacggg agtggaggag cttctggaac tttgcagccg tcatcgggag    600

gcggcagctc taacagcaga gagcgtcacc gcttggtatc gaagcacaag cggcataagt    660

ccaaacactc caaagacatg ggggttggtga cccccgaagc agcatccctg ggcacagtta    720

tcaaaccttt ggtggagtat gatgatatca gctctgattc cgacaccttc tccgatgaca    780

tggccttcaa actagaccga agggagaacg acgaacgtcg tggatcagat cggagcgacc    840

gcctgcacaa acatcgtcac caccagcaca ggcgttcccg ggacttacta aaagctaaac    900

agaccg                                                               906


<210> SEQ ID NO 63
<211> LENGTH: 491
<212> TYPE: DNA
<213> ORGANISM: Homo sapiens

<400> SEQUENCE: 63

gacatgtttg cctgcagggg accagagaca atgggattag ccagtgctca ctgttcttta     60

tgcttccaga gaggatgggg acagctctca ggtcagaatc caggctgaga aggccatgct    120

ggttgggggc ccccggaagc acggtccgga tcctccctgg catcagcgta gacccgctgc    180

tcaggcttgg ggtaccaaac tcatgctctg tactgttttg gccccatgcg gtgagaggaa    240

aacctagaaa aagattggtc gtgctaagga atcagctgcc ccctcatcct ccgcatccaa    300

tgctggtgac aacatattcc ctctcccagg acacagactc ggtgactcca cactgggctg    360

agtggcctct ggaggctcgt ggcctaaggc agggctccgt aaggctgatc ggctgaactg    420

ggtggggtga gggtttctga cccttcgctt cccatcccat aaccgctgtc aatgagctca    480

cactgtggtc a                                                         491


<210> SEQ ID NO 64
<211> LENGTH: 511
<212> TYPE: DNA
<213> ORGANISM: Homo sapiens

<400> SEQUENCE: 64

gatggcatgg tcgttgctaa tgtgcctgct gggatggagc acttcctcct gtgagcccag     60
```

-continued gggacccgcc tgtccctgga gcttggggca aggagggaag agtgatacca ggaaggtggg 120
gctgcagcca ggggccagag tcagttcagg gagtggtcct cggccctcaa agctcctccg 180
gggactgctc aggagtgatg gtgccctgga gtttgcccca acttccctgg ccaccctgga 240
aggtgcctgg ctgctccagg cctctaggct gggctgatgg gtttctccag gacacaagta 300
tcattaaagc caccctctcc tcagcttgtc aggccgcaca tgtgggacag gctgtgctca 360
caaccccctc gcctgccctg ccctccatca ggaggagcca gtggaacctt cggaaagctc 420
ccagcatctc agcagccctc aaaagtcgtc ctggggcaag ctctggttct cctgactgga 480
ggtcatctgg gcttggcctg ctctctctcg c 511

<210> SEQ ID NO 65
<211> LENGTH: 394
<212> TYPE: DNA
<213> ORGANISM: Homo sapiens

<400> SEQUENCE: 65
taaaaaagtg taacaaaggt ttatttagac tttcttcatg cccccagatc caggatgtct 60
atgtaaaccg ttatcttaca aagaaagcac aatatttggt ataaactaag tcagtgactt 120
gcttaactga aatagcgtcc atccaaaagt gggtttaagg taaaactacc tgacgatatt 180
ggcggggatc ctgcagtttg gactgcttgc cgggtttgtc cagggttccg ggtctgttct 240
tggcactcat ggggacaggc atcctgctcg tctgtggggc cccgctggag cccttacgtg 300
aagctgaagg tatcgaccst aggggggctct agggcagtgg gaccttcatc cggaactaac 360
aagggtcggg gagaggcctc ttgggctatg tggg 394

<210> SEQ ID NO 66
<211> LENGTH: 359
<212> TYPE: DNA
<213> ORGANISM: Homo sapiens

<400> SEQUENCE: 66
caagcgttcc tttatggatg taaattcaaa cagtcatgct gagccatccc gggctgacag 60
tcacgttwaa gacactaggt cgggcgccac agtgccaccc aaggagaaga agaatttgga 120
atttttccat gaagatgtac ggaaatctga tgttgaatat gaaaatggcc cccaaatgga 180
attccaaaag gttaccacag gggctgtaag acctagtgac cctcctaagt gggaaagagg 240
aatggagaat agtatttctg atgcatcaag aacatcagaa tataaaactg agatcataat 300
gaaggaaaat tccatatcca atatgagttt actcagagac agtagaaact attcccagg 359

<210> SEQ ID NO 67
<211> LENGTH: 450
<212> TYPE: DNA
<213> ORGANISM: Homo sapiens
<220> FEATURE:
<221> NAME/KEY: modified_base
<222> LOCATION: (425)
<223> OTHER INFORMATION: Where n is a, c, g or t

<400> SEQUENCE: 67
taggaataac aaatgtttat tcagaaatgg ataagtaata cataatcacc cttcatctct 60
taatgcccct tcctctcctt ctgcacagga gacacagatg ggtaacatag aggcatggga 120
agtggaggag gacacaggac tagcccacca ccttctcttc ccggtctccc aagatgactg 180
cttatagagt ggaggaggca aacaggtccc ctcaatgtac cagatggtca cctatagcac 240

-continued

```
cagctccaga tggccacgtg gttgcagctg gactcaatga aactctgtga caaccagaag    300

atacctgctt tgggatgaga gggaggataa agccatgcag ggaggatatt taccatccct    360

accctaagca cagtgcaagc agtgagcccc cggctcccag tacctgaaaa accaaggcct    420

actgnctttt ggatgctctc ttgggccacg                                     450
```

```
<210> SEQ ID NO 68
<211> LENGTH: 511
<212> TYPE: DNA
<213> ORGANISM: Homo sapiens

<400> SEQUENCE: 68

aagcctcctg ccctggaaat ctggagcccc ttggagctga gctggacggg gcagggaggg     60

gctgagaggc aagaccgtct ccctcctgct gcagctgctt ccccagcagc cactgctggg    120

cacagcagaa acgccagcag agaaaatggg agccgagagt ccttagccct ggagctgagg    180

ctgcctctgg gctgacccgc tggctgtacg tggccagaac tggggttggc atctggcatc    240

catttgaggc cagggtggag gaaagggagg ccaacagagg aaaacctatt cctgctgtga    300

caacacagcc cttgtcccac gcagcctaag tgcagggagc gtgatgaagt caggcagcca    360

gtcggggagg acgaggtaac tcagcagcaa tgtcaccttg tagcctatgc gctcaatggc    420

ccggaggggc agcaaccccc cgcacacgtc agccaacagc agtgcctctg caggcaccaa    480

gagagcgatg atggacttga gcgccgtgtt c                                   511
```

```
<210> SEQ ID NO 69
<211> LENGTH: 511
<212> TYPE: DNA
<213> ORGANISM: Homo sapiens

<400> SEQUENCE: 69

gtttggcaga agacatgttt aataacattt tcatatttaa aaaatacagc aacaattctc     60

tatctgtcca ccatcttgcc ttgcccttcc tggggctgag gcagacaaag gaaaggtaat    120

gaggttaggg cccccaggcg ggctaagtgc tattggcctg ctcctgctca aagagagcca    180

tagccagctg ggcacggccc cctagcccct ccaggttgct gaggcggcag cggtggtaga    240

gttcttcact gagccgtggg ctgcagtctc gcagggagaa cttctgcacc agccctggct    300

ctacggcccg aaagaggtgg agccctgaga accggaggaa aacatccatc acctccagcc    360

cctccagggc ttcctcctct tcctggcctg ccagttcacc tgccagccgg gctcgggccg    420

ccaggtagtc agcgttgtag aagcagccct ccgcagaagc ctgccggtca aatctccccg    480

ctataggagc cccccgggag gggtcagcac c                                   511
```

```
<210> SEQ ID NO 70
<211> LENGTH: 511
<212> TYPE: DNA
<213> ORGANISM: Homo sapiens

<400> SEQUENCE: 70

caagttgaac gtcaggcttg gcagaggtgg agtgtagatg aaaacaaagg tgtgattatg     60

aagaggatgt gagtcctttg ggtgtaggag agaaaggctg ttgagcttct atttcaagat    120

acttttacct gtgcaaaaag cacattttcc acctccttct catggcattt gtgtaaggtg    180

agtatgattc ctattccatc tgcattttag aggtgaagaa taacgtacaa gggattcagt    240

gattagcaag ggacccctca ctaagtgttg atggagttag gacagagctc agctgtttga    300

atctcagagc ccaggcagct ggagctgggt aggatcctgg agctggcact aatgtgaggt    360
```

-continued gcattccctc caacccaggc tcagatccgg aacctgaccg tgctgacccc cgaaggggag 420
gcagggctga gctggcccgt tgggctccct gctcctttca caccacactc tcgctttgag 480
gtgctgggct gggactactt cacagagcag c 511

<210> SEQ ID NO 71
<211> LENGTH: 511
<212> TYPE: DNA
<213> ORGANISM: Homo sapiens

<400> SEQUENCE: 71
tggcctgggc aggattggga gagaggtagc tacccggatg cagtcctttg ggatgaagac 60
tatagggtat gaccccatca tttccccaga ggtctcggcc tcctttggtg ttcagcagct 120
gcccctggag gagatctggc ctctctgtga tttcatcact gtgcacactc ctctcctgcc 180
ctccacgaca ggcttgctga atgacaacac ctttgcccag tgcaagaagg gggtgcgtgt 240
ggtgaactgt gcccgtggag ggatcgtgga cgaaggcgcc ctgctccggg ccctgcagtc 300
tggccagtgt gccggggctg cactggacgt gtttacggaa gagccgccac gggaccgggc 360
cttggtggac catgagaatg tcatcagctg tccccacctg ggtgccagca ccaaggaggc 420
tcagagccgc tgtggggagg aaattgctgt tcagttcgtg gacatggtga aggggaaatc 480
tctcacgggg gttgtgaatg cccaggccct t 511

<210> SEQ ID NO 72
<211> LENGTH: 2017
<212> TYPE: DNA
<213> ORGANISM: Homo sapiens

<400> SEQUENCE: 72
agccagatgg ctgagagctg caagaagaag tcaggatcat gatggctcag tttcccacag 60
cgatgaatgg agggccaaat atgtgggcta ttacatctga agaacgtact aagcatgata 120
aacagtttga taacctcaaa ccttcaggag gttacataac aggtgatcaa gcccgtactt 180
ttttcctaca gtcaggtctg ccggccccgg ttttagctga aatatgggcc ttatcagatc 240
tgaacaagga tgggaagatg gaccagcaag agttctctat agctatgaaa ctcatcaagt 300
taaagttgca gggccaacag ctgcctgtag tcctccctcc tatcatgaaa caacccccta 360
tgttctctcc actaatctct gctcgttttg ggatgggaag catgcccaat ctgtccattc 420
atcagccatt gcctccagtt gcacctatag caacaccctt gtcttctgct acttcaggga 480
ccagtattcc tcccctaatg atgcctgctc ccctagtgcc ttctgttagt acatcctcat 540
taccaaatgg aactgccagt ctcattcagc ctttatccat tccttattct tcttcaacat 600
tgcctcatgc atcatcttac agcctgatga tgggaggatt tggtggtgct agtatccaga 660
aggcccagtc tctgattgat ttaggatcta gtagctcaac ttcctcaact gcttccctct 720
cagggaactc acctaagaca gggacctcag agtgggcagt tcctcagcct tcaagattaa 780
agtatcggca aaaatttaat agtctagaca aaggcatgag cggatacctc tcaggttttc 840
aagctagaaa tgcccttctt cagtcaaatc tctctcaaac tcagctagct actatttgga 900
ctctggctga catcgatggt gacggacagt tgaaagctga agaatttatt ctggcgatgc 960
acctcactga catggccaaa gctggacagc cactaccact gacgttgcct cccgagcttg 1020
tccctccatc tttcagaggg ggaaagcaag ttgattctgt taatggaact ctgccttcat 1080
atcagaaaac acaagaagaa gagcctcaga agaaactgcc agttactttt gaggacaaac 1140

-continued

```
ggaaagccaa ctatgaacga ggaaacatgg agctggagaa gcgacgccaa gtgttgatgg   1200

agcagcagca gagggaggct gaacgcaaag cccagaaaga gaaggaagag tgggagcgga   1260

aacagagaga actgcaagag caagaatgga agaagcagct ggagttggag aaacgcttgg   1320

agaaacagag agagctggag agacagcggg aggaagagag gagaaaggag atagaaagac   1380

gagaggcagc aaaacaggag cttgagagac aacgccgttt agaatgggaa agactccgtc   1440

ggcaggagct gctcagtcag aagaccaggg aacaagaaga cattgtcagg ctgagctcca   1500

gaaagaaaag tctccacctg gaactggaag cagtgaatgg aaaacatcag cagatctcag   1560

gcagactaca agatgtccaa atcagaaagc aaacacaaaa gactgagcta gaagttttgg   1620

ataaacagtg tgacctggaa attatggaaa tcaaacaact tcaacaagag cttaaggaat   1680

atcaaaataa gcttatctat ctggtccctg agaagcagct attaaacgaa agaattaaaa   1740

acatgcagct cagtaacaca cctgattcag ggatcagttt acttcataaa aagtcatcag   1800

aaaaggaaga attatgccaa agacttaaag aacaattaga tgctcttgaa aaagaaactg   1860

catctaagct ctcagaaatg gattcattta acaatcagct gaaggaactc agagaaagct   1920

ataatacaca gcagttagcc cttgaacaac ttcataaaat caaacgtgac aaattgaagg   1980

aaatcgaaag aaaaagatta gagcaaaaaa aaaaaaa                           2017
```

<210> SEQ ID NO 73
<211> LENGTH: 414
<212> TYPE: DNA
<213> ORGANISM: Homo sapiens

<400> SEQUENCE: 73

```
atggcagtga cattcaccat catgggaacc accttccctt ttcttcagga ttctctgtag     60

tggaagagag cacccagtgt tgggctgaaa acatctgaaa gtagggagaa gaacctaaaa    120

taatcagtat ctcagagggc tctaaggtgc caagaagtct cactggacat ttaagtgcca    180

acaaaggcat actttcggaa tcgccaagtc aaaactttct aacttctgtc tctctcagag    240

acaagtgaga ctcaagagtc tactgcttta gtggcaacta cagaaaactg gtgttaccca    300

gaaaaacagg agcaattaga aatggttcca atatttcaaa gctccgcaaa caggatgtgc    360

tttcctttgc ccatttaggg tttcttctct ttcctttctc tttattaacc acta          414
```

<210> SEQ ID NO 74
<211> LENGTH: 1567
<212> TYPE: DNA
<213> ORGANISM: Homo sapiens

<400> SEQUENCE: 74

```
atatctagaa gtctggagtg agcaaacaag agcaagaaac aaaaagaagc caaaagcaga     60

aggctccaat atgaacaaga taaatctatc ttcaaagaca tattagaagt tgggaaaata    120

attcatgtga actagacaag tgtgttaaga gtgataagta aaatgcacgt ggagacaagt    180

gcatccccag atctcaggga cctccccctg cctgtcacct ggggagtgag aggacaggat    240

agtgcatgtt ctttgtctct gaatttttag ttatatgtgc tgtaatgttg ctctgaggaa    300

gcccctggaa agtctatccc aacatatcca catcttatat tccacaaatt aagctgtagt    360

atgtacccta agacgctgct aattgactgc cacttcgcaa ctcaggggcg gctgcatttt    420

agtaatgggt caaatgattc actttttatg atgcttccaa aggtgccttg gcttctcttc    480

ccaactgaca aatgccaaag ttgagaaaaa tgatcataat tttagcataa acagagcagt    540

cggcgacacc gattttataa ataaactgag caccttcttt ttaaacaaac aaatgcgggt    600
```

-continued ttatttctca gatgatgttc atccgtgaat ggtccaggga aggacctttc accttgacta 660
tatggcatta tgtcatcaca agctctgagg cttctccttt ccatcctgcg tggacagcta 720
agacctcagt tttcaatagc atctagagca gtgggactca gctggggtga tttcgccccc 780
catctccggg ggaatgtctg aagacaattt tgttacctca atgagggagt ggaggaggat 840
acagtgctac taccaactag tggataaagg ccagggatgc tgctcaacct cctaccatgt 900
acaggacgtc tccccattac aactacccaa tccgaagtgt caactgtgtc aggactaaga 960
aaccctggtt ttgagtagaa aagggcctgg aaagagggga gccaacaaat ctgtctgctt 1020
cctcacatta gtcattggca aataagcatt ctgtctcttt ggctgctgcc tcagcacaga 1080
gagccagaac tctatcgggc accaggataa catctctcag tgaacagagt tgacaaggcc 1140
tatgggaaat gcctgatggg attatcttca gcttgttgag cttctaagtt tctttccctt 1200
cattctaccc tgcaagccaa gttctgtaag agaaatgcct gagttctagc tcaggttttc 1260
ttactctgaa tttagatctc cagacccttc ctggccacaa ttcaaattaa ggcaacaaac 1320
atataccttc catgaagcac acacagactt ttgaaagcaa ggacaatgac tgcttgaatt 1380
gaggccttga ggaatgaagc tttgaaggaa aagaatactt tgtttccagc ccccttccca 1440
cactcttcat gtgttaacca ctgccttcct ggaccttgga gccacggtga ctgtattaca 1500
tgttgttata gaaaactgat tttagagttc tgatcgttca agagaatgat taaatataca 1560
tttccta 1567

<210> SEQ ID NO 75
<211> LENGTH: 240
<212> TYPE: DNA
<213> ORGANISM: Homo sapiens

<400> SEQUENCE: 75
tcgagcggcc gcccgggcag gtccttcaga cttggactgt gtcacactgc caggcttcca 60
gggctccaac ttgcagacgg cctgttgtgg gacagtctct gtaatcgcga aagcaaccat 120
ggaagacctg ggggaaaaca ccatggtttt atccaccctg agatctttga acaacttcat 180
ctctcagcgt gcggagggag gctctggact ggatatttct acctcggccg cgaccacgct 240

<210> SEQ ID NO 76
<211> LENGTH: 330
<212> TYPE: DNA
<213> ORGANISM: Homo sapiens
<220> FEATURE:
<221> NAME/KEY: modified_base
<222> LOCATION: (288)
<223> OTHER INFORMATION: Where n is a, c, g or t

<400> SEQUENCE: 76
tagcgyggtc gcggccgagg yctgcttytc tgtccagccc agggcctgtg gggtcagggc 60
ggtgggtgca gatggcatcc actccggtgg cttccccatc tttctctggc ctgagcaagg 120
tcagcctgca gccagagtac agagggccaa cactggtgtt cttgaacaag ggccttagca 180
ggccctgaag grccctctct gtagtgttga acttcctgga gccaggccac atgttctcct 240
cataccgcag gytagygatg gtgaagttga gggtgaaata gtattmangr agatggctgg 300
caracctgcc cgggcggccg ctcsaaatcc 330

<210> SEQ ID NO 77
<211> LENGTH: 361
<212> TYPE: DNA

-continued

<213> ORGANISM: Homo sapiens

<400> SEQUENCE: 77

```
agcgtggtcg cggccgaggt gtccttcagg gtctgcttat gcccttgttc aagaacacca     60

gtgtcagctc tctgtactct ggttgcagac tgaccttgct caggcctgag aaggatgggg    120

cagccaccag agtggatgct gtctgcaccc atcgtcctga ccccaaaagc cctggactgg    180

acagagagcg gctgtactgg aagctgagcc agctgaccca cggcatcact gagctgggcc    240

cctacaccct ggacagggac agtctctatg tcaatggttt cacccatcgg agctctgtac    300

ccaccaccag caccggggtg gtcagcgagg agccattcaa cctgcccggg cggccgctcg    360

a                                                                    361
```

<210> SEQ ID NO 78
<211> LENGTH: 356
<212> TYPE: DNA
<213> ORGANISM: Homo sapiens
<220> FEATURE:
<221> NAME/KEY: modified_base
<222> LOCATION: (7)
<223> OTHER INFORMATION: Where n is a, c, g or t
<221> NAME/KEY: modified_base
<222> LOCATION: (346)
<223> OTHER INFORMATION: Where n is a, c, g or t
<221> NAME/KEY: modified_base
<222> LOCATION: (350)
<223> OTHER INFORMATION: Where n is a, c, g or t
<221> NAME/KEY: modified_base
<222> LOCATION: (353)
<223> OTHER INFORMATION: Where n is a, c, g or t

<400> SEQUENCE: 78

```
ttggggnttt mgagcggccg cccgggcagg taccggggtg gtcagcgagg agccattcac     60

actgaacttc accatcaaca acctgcggta tgaggagaac atgcagcacc ctggctccag    120

gaagttcaac accacggaga gggtccttca gggcctgctc aggtccctgt tcaagagcac    180

cagtgttggc cctctgtact ctggctgcag actgactttg ctcagacttg agaaacatgg    240

ggcagccact ggagtggacg ccatctgcac cctccgcctt gatcccactg gtcctggact    300

ggacagagag cggctatact gggagctgag ccagtcctct ggcggngacn ccnctt        356
```

<210> SEQ ID NO 79
<211> LENGTH: 226
<212> TYPE: DNA
<213> ORGANISM: Homo sapiens

<400> SEQUENCE: 79

```
agcgtggtcg cggccgaggt ccagtcgcag catgctcttt ctcctgccca ctggcacagt     60

gaggaagatc tctgctgtca gtgagaaggc tgtcatccac tgagatggca gtcaaaagtg    120

catttaatac acctaacgta tcgaacatca tagcttggcc caggttatct catatgtgct    180

cagaacactt acaatagcct gcagacctgc ccgggcggcc gctcga                   226
```

<210> SEQ ID NO 80
<211> LENGTH: 444
<212> TYPE: DNA
<213> ORGANISM: Homo sapiens
<220> FEATURE:
<221> NAME/KEY: modified_base
<222> LOCATION: (23)
<223> OTHER INFORMATION: Where n is a, c, g or t

<400> SEQUENCE: 80

-continued tgtggtgttg aacttcctgg agncagggtg acccatgtcc tccccatact gcaggttggt 60
gatggtgaag ttgagggtga atggtaccag gagagggcca gcagccataa ttgtsgrgck 120
gsmgmssgag gmwggwgtyy cwgaggttcy rarrtccact gtggaggtcc caggagtgct 180
ggtggtgggc acagagstcy gatgggtgaa accattgaca tagagactgt tcctgtccag 240
ggtgtagggg cccagctctt yratgycatt ggycagttkg ctyagctccc agtacagccr 300
ctctckgyyg mgwccagsgc ttttggggtc aagatgatgg atgcagatgg catccactcc 360
agtggctgct ccatccttct cggacctgag agaggtcagt ctgcagccag agtacagagg 420
gccaacactg gtgttctttg aata 444

<210> SEQ ID NO 81
<211> LENGTH: 310
<212> TYPE: DNA
<213> ORGANISM: Homo sapiens

<400> SEQUENCE: 81
tcgagcggcc gcccgggcag gtcaggaagc acattggtct tagagccact gcctcctgga 60
ttccacctgt gctgcggaca tctccaggga gtgcagaagg gaagcaggtc aaactgctca 120
gatcagtcag actggctgtt ctcagttctc acctgagcaa ggtcagtctg cagccagagt 180
acagagggcc aacactggtg ttcttgaaca agggcttgag cagaccctgc agaaccctct 240
tccgtggtgt tgaacttcct ggaaaccagg gtgttgcatg tttttcctca taatgcaagg 300
ttggtgatgg 310

<210> SEQ ID NO 82
<211> LENGTH: 571
<212> TYPE: DNA
<213> ORGANISM: Homo sapiens
<220> FEATURE:
<221> NAME/KEY: modified_base
<222> LOCATION: (202)
<223> OTHER INFORMATION: Where n is a, c, g or t

<400> SEQUENCE: 82
acggtttcaa tggacacttt tattgtttac ttaatggatc atcaattttg tctcactacc 60
tacaaatgga atttcatctt gtttccatgc tgagtagtga aacagtgaca aagctaatca 120
taataaccta catcaaaaga gaactaagct aacactgctc actttctttt taacaggcaa 180
aatataaata tatgcactct anaatgcaca atggtttagt cactaaaaaa ttcaaatggg 240
atcttgaaga atgtatgcaa atccagggtg cagtgaagat gagctgagat gctgtgcaac 300
tgtttaaggg ttcctggcac tgcatctctt ggccactagc tgaatcttga catggaaggt 360
tttagctaat gccaagtgga gatgcagaaa atgctaagtt gacttagggg ctgtgcacag 420
gaactaaaag gcaggaaagt actaaatatt gctgagagca tccaccccag gaaggacttt 480
accttccagg agctccaaac tggcaccacc cccagtgctc acatggctga ctttatcctc 540
cgtgttccat ttggcacagc aagtggcagt g 571

<210> SEQ ID NO 83
<211> LENGTH: 551
<212> TYPE: DNA
<213> ORGANISM: Homo sapiens

<400> SEQUENCE: 83
aaggctggtg ggtttttgat cctgctggag aacctccgct ttcatgtgga ggaagaaggg 60
aagggaaaag atgcttctgg gaacaaggtt aaagccgagc cagccaaaat agaagctttc 120

-continued cgagcttcac tttccaagct aggggatgtc tatgtcaatg atgcttttgg cactgctcac 180
agagcccaca gctccatggt aggagtcaat ctgccacaga aggctggtgg gtttttgatg 240
aagaaggagc tgaactactt tgcaaaggcc ttggagagcc cagagcgacc cttcctggcc 300
atcctgggcg gagctaaagt tgcagacaag atccagctca tcaataatat gctggacaaa 360
gtcaatgaga tgattattgg tggtggaatg gcttttacct tccttaaggt gctcaacaac 420
atggagattg gcacttctct gtttgatgaa gagggagcca agattgtcaa agacctaatg 480
tccaaagctg agaagaatgg tgtgaagatt accttgcctg ttgactttgt cactgctgac 540
aagtttgatg a 551

<210> SEQ ID NO 84
<211> LENGTH: 571
<212> TYPE: DNA
<213> ORGANISM: Homo sapiens

<400> SEQUENCE: 84
tttgttcctt acatttttct aaagagttac ttaaatcagt caactggtct ttgagactct 60
taagttctga ttccaactta gctaattcat tctgagaact gtggtatagg tggcgtgtct 120
cttctagctg ggacaaaagt tctttgtttt ccccctgtag agtatcacag accttctgct 180
gaagctggac ctctgtctgg gccttggact cccaaatctg cttgtcatgt tcaagcctgg 240
aaatgttaat ctttaattct tccatatgga tggacatctg tctaagttga tcctttagaa 300
cactgcaatt atcttctttg agtctaattt cttcttcttt gctttgaatc gcatcactaa 360
acttcctctc ccatttctta gcttcatcta tcaccctgtc acgatcatcc tggagggaag 420
acatgctctt agtaaaggct gcaagctggg tcacagtact gtccaagttt tcctgaagtt 480
gctgaacttc cttgtctttc ttgttcaaag taacctgaat ctctccaatt gtctcttcca 540
agtggacttt ttctctgcgc aaagcatcca g 571

<210> SEQ ID NO 85
<211> LENGTH: 561
<212> TYPE: DNA
<213> ORGANISM: Homo sapiens

<400> SEQUENCE: 85
tcattgcctg tgatggcatc tggaatgtga tgagcagcca ggaagttgta gatttcattc 60
aatcaaagga ttcagcatgt ggtggaagct gtgaggcaag agaaacaaga actgtatggc 120
aagttaagaa gcacagaggc aaacaagaag gagacagaaa agcagttgca ggaagctgag 180
caagaaatgg aggaaatgaa agaaaagatg agaaagtttg ctaaatctaa acagcagaaa 240
atcctagagc tggaagaaga gaatgaccgg cttagggcag aggtgcaccc tgcaggagat 300
acagctaaag agtgtatgga aacacttctt tcttccaatg ccagcatgaa ggaagaactt 360
gaaagggtca aaatggagta tgaaaccctt tctaagaagt ttcagtcttt aatgtctgag 420
aaagactctc taagtgaaga ggttcaagat ttaaagcatc agatagaagg taatgtatct 480
aaacaagcta acctagaggc caccgagaaa catgataacc aaacgaatgt cactgaagag 540
ggaacacagt ctataccagg t 561

<210> SEQ ID NO 86
<211> LENGTH: 795
<212> TYPE: DNA
<213> ORGANISM: Homo sapiens -continued

<400> SEQUENCE: 86
aagccaataa tcaccattta ttacttaata tatgccaacc actgtacttg gcagttcaca 60
aattctcacc gttacaacaa ccccatgagg tatttattcc cattctatag atagggaaac 120
cacagctcaa gtaagttagg aaactgagcc aagtatacac agaatacgaa gtggcaaaac 180
tagaaggaaa gactgacact gctatctgct ggcctccagt gtcctggctc ttttcacacg 240
ggttcaatgt ctccagcgct gctgctgctg ctgcattacc atgccctcat tgtttttctt 300
cctctggtgt tcaactgcat ccttcaaaga atctaactca ttccagagac cacttatttc 360
tttctctctt tctgaaatta cttttaataa ttcttcatga gggggaaaag aagatgcctg 420
ttggtagttt tgttgtttaa gctgctcaat ttgggactta aacaatttgt tttcatcttg 480
tacatcctgt aacagctgtg ttttgctaga aagatcactc tccctctctt ttagcatggc 540
ttctaacctc ttcaattcat tttccttttc tttcaacaca atctcaagtt cttcaaactg 600
tgatgcagaa gaggcctctt tcaagttatg ttgtgctact tcctgaacat gtgcttttaa 660
agattcattt tcttcttgaa gatcctgtaa ccacttccct gtattggcta ggtctttctc 720
tttctcttcc aaaacagcct tcatggtatt catctgttcc tcttttcctt ttaataagtt 780
caggagcttc agaac 795

<210> SEQ ID NO 87
<211> LENGTH: 594
<212> TYPE: DNA
<213> ORGANISM: Homo sapiens

<400> SEQUENCE: 87
caagcttttt tttttttttt aaaaagtgtt agcattaatg ttttattgtc acgcagatgg 60
caactgggtt tatgtcttca tattttatat ttttgtaaat taaaaaaatt acaagtttta 120
aatagccaat ggctggttat attttcagaa aacatgatta gactaattca ttaatggtgg 180
cttcaagctt ttccttattg gctccagaaa attcacccac cttttgtccc ttcttaaaaa 240
actggaatgt tggcatgcat ttgacttcac actctgaagc aacatcctga cagtcatcca 300
catctacttc aaggaatatc acgttggaat acttttcaga gagggaatga aagaaaggct 360
tgatcatttt gcaaggccca caccacgtgg ctgagaagtc aactactaca agtttatcac 420
ctgcagcgtc caaggcttcc tgaaaagcag tcttgctctc gatctgcttc accatcttgg 480
ctgctggagt ctgacgagcg gctgtaagga ccgatggaaa tggatccaaa gcaccaaaca 540
gagcttcaag actcgctgct tggcttgaat tcggatccga tatcgccatg gcct 594

<210> SEQ ID NO 88
<211> LENGTH: 557
<212> TYPE: DNA
<213> ORGANISM: Homo sapiens

<400> SEQUENCE: 88
aagtgttagc attaatgttt tattgtcacg cagatggcaa ctgggtttat gtcttcatat 60
tttatatttt tgtaaattaa aaaaattmca agttttaaat agccaatggc tggttatatt 120
ttcagaaaac atgattagac taattcatta atggtggctt caagcttttc cttattggct 180
ccagaaaatt cacccacctt ttgtcccttc ttaaaaaact ggaatgttgg catgcatttg 240
acttcacact ctgaagcaac atcctgacag tcatccacat ctacttcaag gaatatcacg 300
ttggaatact tttcagagag ggaatgaaag aaaggcttga tcattttgca aggcccacac 360
cacgtggctg agaagtcaac tactacaagt ttatcacctg cagcgtccaa ggcttcctga 420

-continued

```
aaagcagtct tgctctcgat ctgcttcacc atcttggctg ctggagtctg acgagcggct    480

gtaaggaccg atggaaatgg atccaaagca ccaaacagag cttcaagact cgctgcttgg    540

catgaattcg gatccga                                                   557
```

```
<210> SEQ ID NO 89
<211> LENGTH: 561
<212> TYPE: DNA
<213> ORGANISM: Homo sapiens
<220> FEATURE:
<221> NAME/KEY: modified_base
<222> LOCATION: (544)
<223> OTHER INFORMATION: Where n is a, c, g or t
<221> NAME/KEY: modified_base
<222> LOCATION: (551)
<223> OTHER INFORMATION: Where n is a, c, g or t

<400> SEQUENCE: 89

tacaaacttt attgaaacgc acacgcgcac acacacaaac acccctgtgg atagggaaaa     60

gcacctggcc acagggtcca ctgaaacggg gaggggatgg cagcttgtaa tgtggctttt    120

gccacaaccc ccttctgaca gggaaggcct tagattgagg ccccacctcc catggtgatg    180

gggagctcag aatggggtcc agggagaatt tggttagggg gaggtgctag ggaggcatga    240

gcagagggca ccctccgagt ggggtcccga gggctgcaga gtcttcagta ctgtccctca    300

cagcagctgt ctcaaggctg ggtccctcaa aggggcgtcc cagcgcgggg cctccctgcg    360

caaacacttg gtacccctgg ctgcgcagcg gaagccagca ggacagcagt ggcgccgatc    420

agcacaacag acgccctggc ggtagggaca gcaggcccag ccctgtcggt tgtctcggca    480

gcaggtctgg ttatcatggc agaagtgtcc ttcccacact tcacgtcctt cacacccacg    540

tganggctac nggccaggaa g                                              561
```

```
<210> SEQ ID NO 90
<211> LENGTH: 561
<212> TYPE: DNA
<213> ORGANISM: Homo sapiens

<400> SEQUENCE: 90

cccgtgggtg ccatccacgg agttgttacc tgatctttgg aagcaggatc gcccgtctgc     60

actgcagtgg aagccccgtg ggcagcagtg atggccatcc ccgcatgcca cggcctctgg    120

gaaggggcag caactggaag tccctgagac ggtaaagatg caggagtggc cggcagagca    180

gtgggcatca acctggcagg ggccacccag atgcctgctc agtgttgtgg gccatttgtc    240

cagaagggga cggcagcagc tgtagctggc tcctccgggg tccaggcagc aggccacagg    300

gcagaactga ccatctgggc accgcgttcc agccaccagc cctgctgtta aggccaccca    360

gctcaccagg gtccacatgg tctgcctgcg tccgactccg cggtccttgg gccctgatgg    420

ttctacctgc tgtgagctgc ccagtgggaa gtatggctgc tgccaatgcc caacgccacc    480

tgctgctccg atcacctgca ctgctgcccc aagacactgt gtgtgacctg atccagagta    540

agtgcctctc caaggagaac g                                              561
```

```
<210> SEQ ID NO 91
<211> LENGTH: 541
<212> TYPE: DNA
<213> ORGANISM: Homo sapiens
<220> FEATURE:
<221> NAME/KEY: modified_base
<222> LOCATION: (480)
<223> OTHER INFORMATION: Where n is a, c, g or t
```

-continued

<221> NAME/KEY: modified_base
<222> LOCATION: (491)
<223> OTHER INFORMATION: Where n is a, c, g or t

<400> SEQUENCE: 91
gaatcacctt tctggtttag ctagtacttt gtacagaaca atgaggtttc ccacagcgga 60
gtctccctgg gctctgtttg gctctcggta aggcaggcct acaccttttc ctctcctcta 120
tggagagggg aatatgcatt aaggtgaaaa gtcaccttcc aaaagtgaga aagggattcg 180
attgctgctt caggactgtg gaattatttg gaatgtttta caaatggttg ctacaaaaca 240
acaaaaaagg taattacaaa atgtgtacat cacaacatgc tttttaaaga cattatgcat 300
tgtgctcaca ttcccttaaa tgttgtttcc aaaggtgctc agcctctagc ccagctggat 360
tctccgggaa gaggcagaga cagtttggcg aaaaagacac agggaaggag ggggtggtga 420
aaggagaaag cagccttcca gttaaagatc agccctcagt taaaggtcag cttcccgcan 480
gctggcctca ngcggagtct gggtcagagg gaggagcagc agcagggtgg gactggggcg 540
t 541

<210> SEQ ID NO 92
<211> LENGTH: 551
<212> TYPE: DNA
<213> ORGANISM: Homo sapiens

<400> SEQUENCE: 92
aaccggagcg cgagcagtag ctgggtgggc accatggctg ggatcaccac catcgaggcg 60
gtgaagcgca agatccaggt tctgcagcag caggcagatg atgcagagga gcgagctgag 120
cgcctccagc gagaagttga gggagaaagg cgggcccggg aacaggctga ggctgaggtg 180
gcctccttga accgtaggat ccagctggtt gaagaagagc tggaccgtgc tcaggagcgc 240
ctggccactg ccctgcaaaa gctggaagaa gctgaaaaag ctgctgatga gagtgagaga 300
ggtatgaagg ttattgaaaa ccgggcctta aaagatgaag aaaagatgga actccaggaa 360
atccaactca aagaagctaa gcacattgca gaagaggcag ataggaagta tgaagaggtg 420
gctcgtaagt tggtgatcat tgaaggagac ttggaacgca cagaggaacg agctgagctg 480
gcagagtccc gttgccgaga gatggatgag cagattagac tgatggacca gaacctgaag 540
tgtctgagtg c 551

<210> SEQ ID NO 93
<211> LENGTH: 531
<212> TYPE: DNA
<213> ORGANISM: Homo sapiens

<400> SEQUENCE: 93
gagaacttgg cctttattgt gggcccagga gggcacaaag gtcaggaggc ccaagggagg 60
gatctggttt tctggatagc caggtcatag catgggtatc agtaggaatc cgctgtagct 120
gcacaggcct cacttgctgc agttccgggg agaacacctg cactgcatgg cgttgatgac 180
ctcgtggtac acgacagagc cattggtgca gtgcaagggc acgcgcatgg gctccgtcct 240
cgagggcagg cagcaggagc attgctcctg cacatcctcg atgtcaatgg agtacacagc 300
tttgctggca cactttccct ggcagtaatg aatgtccact tcctcttggg acttacaatc 360
tcccactttg atgtactgca ccttggctgt gatgtctttg caatcaggct cctcacatgt 420
gtcacagcag gtgcctggaa ttttcacgat tttgcctcct tcagccagac acttgtgttc 480
atcaaatggt gggcagcccg tgaccctctt ctcccagatg tactctcctc t 531

-continued

<210> SEQ ID NO 94
<211> LENGTH: 531
<212> TYPE: DNA
<213> ORGANISM: Homo sapiens
<220> FEATURE:
<221> NAME/KEY: modified_base
<222> LOCATION: (517)
<223> OTHER INFORMATION: Where n is a, c, g or t

<400> SEQUENCE: 94
gcctggacct tgccggatca gtgccacaca gtgacttgct tggcaaatgg ccagaccttg 60
ctgcagagtc atcgtgtcaa ttgtgaccat ggaccccggc cttcatgtgc caacagccag 120
tctcctgttc gggtggagga gacgtgtggc tgccgctgga cctgcccttg tgtgtgcacg 180
ggcagttcca ctcggcacat cgtcaccttc gatgggcaga atttcaagct tactggtagc 240
tgctcctatg tcatctttca aaacaaggag caggacctgg aagtgctcct ccacaatggg 300
gcctgcagcc ccggggcaaa acaagcctgc atgaagtcca ttgagattaa gcatgctggc 360
gtctctgctg agctgcacag taacatggag atggcagtgg atgggagact ggtccttgcc 420
ccgtacgttg gtgaaaacat ggaagtcagc atctacggcg ctatcatgta tgaagtcagg 480
tttacccatc ttggccacat cctcacatac accgccncaa aacaacgagt t 531

<210> SEQ ID NO 95
<211> LENGTH: 605
<212> TYPE: DNA
<213> ORGANISM: Homo sapiens

<400> SEQUENCE: 95
agatcaacct ctgctggtca ggaggaatgc cttccttgtc ttggatcttt gctttgacgt 60
tctcgatagt rwcaactkkr ytsramskma agkgyratgr wmttksywgw rasyktmwwm 120
rsgraraytt agacayccm cctcwgagac gsagkaccar gtgcagaggt ggactctttc 180
tggatgttgt agtcagacag ggtgcgtcca tcttccagct gtttcccagc aaagatcaac 240
ctctgctgat caggagggat gccttcctta tcttggatct ttgccttgac attctcgatg 300
gtgtcactgg gctccacctc gagggtgatg gtcttaccag tcagggtctt cacgaagaty 360
tgcatcccac ctctgagacg gagcaccagg tgcagggtrg actctttctg gatgttgtag 420
tcagacaggg tgcgyccatc ttccagctgc tttccsagca aagatcaacc tctgctggtc 480
aggaggratg ccttccttgt cytggatctt tgcyttgacr ttctcratgg tgtcactcgg 540
ctccacttcg agagtgatgg tcttaccagt cagggtcttc acgaagatct gcatcccacc 600
tctaa 605

<210> SEQ ID NO 96
<211> LENGTH: 531
<212> TYPE: DNA
<213> ORGANISM: Homo sapiens

<400> SEQUENCE: 96
aagtcacaaa cagacaaaga ttattaccag ctgcaagcta tattagaagc tgaacgaaga 60
gacagaggtc atgattctga gatgattgga gaccttcaag ctcgaattac atctttacaa 120
gaggaggtga agcatctcaa acataatctc gaaaaagtgg aaggagaaag aaaagaggct 180
caagacatgc ttaatcactc agaaaaggaa aagaataatt tagagataga tttaaactac 240
aaacttaaat cattacaaca acggttagaa caagaggtaa atgaacacaa agtaaccaaa 300

-continued

```
gctcgtttaa ctgacaaaca tcaatctatt gaagaggcaa agtctgtggc aatgtgtgag    360

atggaaaaaa agctgaaaga agaaagagaa gctcgagaga aggctgaaaa tcgggttgtt    420

cagattgaga aacagtgttc catgctagac gttgatctga agcaatctca gcagaaacta    480

gaacatttga ctggaaataa agaaaggatg gaggatgaag ttaagaatct a             531
```

<210> SEQ ID NO 97
<211> LENGTH: 1017
<212> TYPE: DNA
<213> ORGANISM: Homo sapiens
<220> FEATURE:
<221> NAME/KEY: modified_base
<222> LOCATION: (963)
<223> OTHER INFORMATION: Where n is a, c, g or t
<221> NAME/KEY: modified_base
<222> LOCATION: (995)
<223> OTHER INFORMATION: Where n is a, c, g or t
<221> NAME/KEY: modified_base
<222> LOCATION: (1001)
<223> OTHER INFORMATION: Where n is a, c, g or t
<221> NAME/KEY: modified_base
<222> LOCATION: (1008)
<223> OTHER INFORMATION: Where n is a, c, g or t
<221> NAME/KEY: modified_base
<222> LOCATION: (1010)
<223> OTHER INFORMATION: Where n is a, c, g or t

<400> SEQUENCE: 97

```
cgcctccacc atgtccatca gggtgaccca gaagtcctac aaggtgtcca cctctggccc     60

ccgggccttc agcagccgct cctacacgag tgggcccggt tcccgcatca gctcctcgag    120

cttctcccga gtgggcagca gcaactttcg cggtggcctg ggcggcggct atggtggggc    180

cagcggcatg ggaggcatca ccgcagttac ggtcaaccag agcctgctga gccccttgt    240

cctggaggtg gaccccaaca tccaggccgt gcgcacccag gagaaggagc agatcaagac    300

cctcaacaac aagtttgcct ccttcataga caaggtacgg ttcctggagc agcagaacaa    360

gatgctggag accaagtgga gcctcctgca gcagcagaag acggctcgaa gcaacatgga    420

caacatgttc gagagctaca tcaacarcct taggcggcag ctggagactc tgggccagga    480

gaagctgaag ctggaggcgg agcttggcaa catgcagggg ctggtggagg acttcaagaa    540

caagtatgag gatgagatca ataagcgtac agagatggag aacgaatttg tcctcatcaa    600

gaaggatgtg gatgaagctt acatgaacaa ggtagagctg gagtctcgcc tggaagggct    660

gaccgacgag atcaacttcc tcaggcagct gtatgaagag gagatccggg agctgcagtc    720

ccagatctcg gacacatctg tggtgctgtc catggacaac agccgctccc tggacatgga    780

cagcatcatt gctgaggtca aggcacagta cgaggatatt gccaaccgca gccgggctga    840

ggctgagagc atgtaccagg tcaagtatga ggagctgcag agcctggctg ggaagcacgg    900

ggatgacctg cggcgcacaa agactgagat ctctgagatg aacccggaac atcagcccgg    960

ctncaggctg agattgaggg cctcaaaggc caganggctt ncctggangn ccgccat      1017
```

<210> SEQ ID NO 98
<211> LENGTH: 561
<212> TYPE: DNA
<213> ORGANISM: Homo sapiens

<400> SEQUENCE: 98

```
cccggagcca gccaacgagc ggaaaatggc agacaatttt tcgctccatg atgcgttatc     60

tgggtctgga aacccaaacc ctcaaggatg gcctggcgca tgggggaacc agcctgctgg    120

ggcagggggc tacccagggg cttcctatcc tggggcctac cccgggcagg cacccccagg    180
```

-continued

```
ggcttatcct ggacaggcac ctccaggcgc ctaccctgga gcacctggag cttatcccgg    240

agcacctgca cctggagtct acccagggcc acccagcggc cctggggcct acccatcttc    300

tggacagcca agtgccaccg gagcctaccc tgccactggc ccctatggcg cccctgctgg    360

gccactgatt gtgccttata acctgccttt gcctggggga gtggtgcctc gcatgctgat    420

aacaattctg ggcacggtga agcccaatgc aaacagaatt gctttagatt tccaaagagg    480

gaatgatgtt gccttccact ttaacccacg cttcaatgag aacaacagga gagtcattgg    540

ttgcaataca aagctggata a                                              561
```

```
<210> SEQ ID NO 99
<211> LENGTH: 636
<212> TYPE: DNA
<213> ORGANISM: Homo sapiens

<400> SEQUENCE: 99

gggaatgcaa caactttatt gaaaggaaag tgcaatgaaa tttgttgaaa ccttaaaagg     60

ggaaacttag acaccccccc tcragcgmag kaccargtgc araggtggac tctttctgga    120

tgttgtagtc agacagggtr cgwccatctt ccagctgttt yccrgcaaag atcaacctct    180

gctgatcagg aggratgcct tccttatctt ggatctttgc cttgacattc tcgatggtgt    240

cactgggctc cacctcgagg gtgatggtct taccagtcag ggtcttcacg aagatytgca    300

tcccacctct gagacggagc accaggtgca gggtrgactc tttctggatg ttgtagtcag    360

acagggtgcg yccatcttcc agctgctttc csagcaaaga tcaacctctg ctggtcagga    420

ggratgcctt ccttgtcytg gatctttgcy ttgacrttct caatggtgtc actcggctcc    480

acttcgagag tgatggtctt accagtcagg gtcttcacga agatctgcat cccacctcta    540

agacggagca ccaggtgcag ggtggactct ttctggatgg ttgtagtcag acagggtgcg    600

tccatcttcc agctgtttcc cagcaaagat caacct                              636
```

```
<210> SEQ ID NO 100
<211> LENGTH: 697
<212> TYPE: DNA
<213> ORGANISM: Homo sapiens

<400> SEQUENCE: 100

aggttgatct ttgctgggaa acagctggaa gatggacgca ccctgtctga ctacaaccat     60

ccagaaagag tccaccctgc acctggtgct ccgtcttaga ggtgggatgc agatcttcgt    120

gaagaccctg actggtaaga ccatcactct cgaagtggag ccgagtgaca ccattgagaa    180

ygtcaargca aagatccarg acaaggaagg catycctcct gaccagcaga ggttgatctt    240

tgctsggaaa gcagctggaa gatggrcgca ccctgtctga ctacaacatc cagaaagagt    300

cyaccctgca cctggtgctc cgtctcagag gtgggatgca ratcttcgtg aagaccctga    360

ctggtaagac catcaccctc gaggtggagc ccagtgacac catcgagaat gtcaaggcaa    420

agatccaaga taaggaaggc atccctcctg atcagcagag gttgatcttt gctgggaaac    480

agctggaaga tggacgcacc ctgtctgact acaacatcca gaaagagtcc acctytgcac    540

ytggtmctbc gtctyagagg kgggrtgcaa atctwmgtkw agacactcac tkkyaagryy    600

atcamcmwtg akktcgakys castkwcact wtcrakaamg tyrwwgcawa gatccmagac    660

aaggaaggca ttcctcctga ccagcagagg ttgatct                             697
```

```
<210> SEQ ID NO 101
```

-continued

<211> LENGTH: 451
<212> TYPE: DNA
<213> ORGANISM: Homo sapiens

<400> SEQUENCE: 101
atggagtctc actctgtcga ccaggctgga gcgctgtggt gcgatatcgg ctcactgcag 60
tctccacttc ctgggttcaa gcgatcctcc tgcctcagcc tcccgagtag ctgggactac 120
aggcaggcgt caccataatt tttgtatttt tagtagagac atggtttcgc catgttggct 180
gggctggtct cgaactcctg acctcaagtg atctgtcctg gcctcccaaa gtgttgggat 240
tacaggcgaa agccaacgct cccggccagg gaacaacttt agaatgaagg aaatatgcaa 300
aagaacatca catcaaggat caattaatta ccatctatta attactatat gtgggtaatt 360
atgactattt cccaagcatt ctacgttgac tgcttgagaa gatgtttgtc ctgcatggtg 420
gagagtggag aagggccagg attcttaggt t 451

<210> SEQ ID NO 102
<211> LENGTH: 571
<212> TYPE: DNA
<213> ORGANISM: Homo sapiens

<400> SEQUENCE: 102
agcgcggtct tccggcgcga gaaagctgaa ggtgatgtgg ccgccctcaa ccgacgcatc 60
cagctcgttg aggaggagtt ggacagggct caggaacgac tggccacggc cctgcagaag 120
ctggaggagg cagaaaaagc tgcagatgag agtgagagag gaatgaaggt gatagaaaac 180
cgggccatga aggatgagga gaagatggag attcaggaga tgcagctcaa agaggccaag 240
cacattgcgg aagaggctga ccgcaaatac gaggaggtag ctcgtaagct ggtcatcctg 300
gagggtgagc tggagagggc agaggagcgt gcggaggtgt ctgaactaaa atgtggtgac 360
ctggaagaag aactcaagaa tgttactaac aatctgaaat ctctggaggc tgcatctgaa 420
aagtattctg aaaaggagga caaatatgaa gaagaaatta aacttctgtc tgacaaactg 480
aaagaggctg agacccgtgc tgaatttgca gagagaacgg ttgcaaaact ggaaaagaca 540
attgatgacc tggaagagaa acttgcccag c 571

<210> SEQ ID NO 103
<211> LENGTH: 451
<212> TYPE: DNA
<213> ORGANISM: Homo sapiens

<400> SEQUENCE: 103
gtgcacaggt cccatttatt gtagaaaata ataataatta cagtgatgaa tagctcttct 60
taaattacaa aacagaaacc acaaagaagg aagaggaaaa accccaggac ttccaagggt 120
gaagctgtcc cctcctccct gccaccctcc caggctcatt agtgtccttg gaaggggcag 180
aggactcaga ggggatcagt ctccaggggc cctgggctga agcgggtgag gcagagagtc 240
ctgaggccac agagctgggc aacctgagcc gcctctctgg ccccctcccc caccactgcc 300
caaacctgtt tacagcacct tcgcccctcc cctctaaacc cgtccatcca ctctgcactt 360
cccaggcagg tgggtgggcc aggcctcagc catactcctg ggcgcgggtt tcggtgagca 420
aggcacagtc ccagaggtga tatcaaggcc t 451

<210> SEQ ID NO 104
<211> LENGTH: 441
<212> TYPE: DNA
<213> ORGANISM: Homo sapiens -continued

<400> SEQUENCE: 104
gcaaggaact ggtctgctca cacttgctgg cttgcgcatc aggactggct ttatctcctg 60
actcacggtg caaaggtgca ctctgcgaac gttaagtccg tccccagcgc ttggaatcct 120
acggccccca cagccggatc ccctcagcct tccaggtcct caactcccgt ggacgctgaa 180
caatggcctc catggggcta caggtaatgg gcatcgcgct ggccgtcctg ggctggctgg 240
ccgtcatgct gtgctgcgcg ctgcccatgt ggcgcgtgac ggccttcatc ggcagcaaca 300
ttgtcacctc gcagaccatc tgggagggcc tatggatgaa ctgcgtggtg cagagcaccg 360
gccagatgca gtgcaaggtg tacgactcgc tgctggcact gccgcaggac ctgcaggcgg 420
cccgcgccct cgtcatcatc a 441

<210> SEQ ID NO 105
<211> LENGTH: 509
<212> TYPE: DNA
<213> ORGANISM: Homo sapiens
<220> FEATURE:
<221> NAME/KEY: modified_base
<222> LOCATION: (195)
<223> OTHER INFORMATION: Where n is a, c, g or t

<400> SEQUENCE: 105
tgcaaaaggg acacaggggt tcaaaaataa aaatttctct tccccctccc caaacctgta 60
ccccagctcc ccgaccacaa ccccccttcct cccccgggga aagcaagaag gagcaggtgt 120
ggcatctgca gctgggaaga gagaggccgg ggaggtgccg agctcggtgc tggtctcttt 180
ccaaatataa atacntgtgt cagaactgga aaatcctcca gcacccacca cccaagcact 240
ctccgttttc tgccggtgtt tggagagggg cgggggggcag gggcgccagg caccggctgg 300
ctgcggtcta ctgcatccgc tgggtgtgca ccccgcgagc ctcctgctgc tcattgtaga 360
agagatgaca ctcggggtcc ccccggatgg tgggggctcc ctggatcagc ttcccggtgt 420
tggggttcac acaccagcac tccccacgct gcccgttcag agacatcttg cactgtttga 480
ggttgtacag gccatgcttg tcacagttg 509

<210> SEQ ID NO 106
<211> LENGTH: 571
<212> TYPE: DNA
<213> ORGANISM: Homo sapiens

<400> SEQUENCE: 106
gggttggagg gactggttct ttatttcaaa aagacacttg tcaatattca gtatcaaaac 60
agttgcacta ttgatttctc tttctcccaa tcggccccaa agagaccaca taaaaggaga 120
gtacatttta agccaataag ctgcaggatg tacacctaac agacctccta gaaaccttac 180
cagaaaatgg ggactgggta gggaaggaaa cttaaaagat caacaaactg ccagcccacg 240
gactgcagag gctgtcacag ccagatgggg tggccagggt gccacaaacc caaagcaaag 300
tttcaaaata atataaaatt taaaaagttt tgtacataag ctattcaaga tttctccagc 360
actgactgat acaaagcaca attgagatgg cacttctaga gacagcagct tcaaacccag 420
aaaagggtga tgagatgagt ttcacatggc taaatcagtg gcaaaaacac agtcttcttt 480
ctttctttct ttcaaggagg caggaaagca attaagtggt cacctcaaca taagggggac 540
atgatccatt ctgtaagcag ttgtgaaggg g 571

<210> SEQ ID NO 107

-continued

<211> LENGTH: 555
<212> TYPE: DNA
<213> ORGANISM: Homo sapiens

<400> SEQUENCE: 107
caggaaccgg agcgcgagca gtagctgggt gggcaccatg gctgggatca ccaccatcga 60
ggcggtgaag cgcaagatcc aggttctgca gcagcaggca gatgatgcag aggagcgagc 120
tgagcgcctc cagcgagaag ttgagggaga aaggcgggcc cgggaacagg ctgaggctga 180
ggtggcctcc ttgaaccgta ggatccagct ggttgaagaa gagctggacc gtgctcagga 240
gcgcctggcc actgccctgc aaaagctgga agaagctgaa aaagctgctg atgagagtga 300
gagaggtatg aaggttattg aaaaccgggc cttaaaagat gaagaaaaga tggaactcca 360
ggaaatccaa ctcaaagaag ctaagcacat tgcagaagag gcagatagga agtatgaaga 420
ggtggctcgt aagttggtga tcattgaagg agacttggaa cgcacagagg aacgagctga 480
gctggcagag tcccgttgcc gagagatgga tgagcagatt agactgatgg accagaacct 540
gaagtgtctg agtgc 555

<210> SEQ ID NO 108
<211> LENGTH: 541
<212> TYPE: DNA
<213> ORGANISM: Homo sapiens

<400> SEQUENCE: 108
atctacgtca tcaatcaggc tggagacacc atgttcaatc gagctaagct gctcaatatt 60
ggctttcaag aggccttgaa ggactatgat tacaactgct ttgtgttcag tgatgtggac 120
ctcattccga tggacgaccg taatgcctac aggtgttttt cgcagccacg gcacatttct 180
gttgcaatgg acaagttcgg gtttagcctg ccatatgttc agtattttgg aggtgtctct 240
gctctcagta aacaacagtt tcttgccatc aatggattcc ctaataatta ttggggttgg 300
ggaggagaag atgacgacat ttttaacaga ttagttcata aaggcatgtc tatatcacgt 360
ccaaatgctg tagtagggag gtgtcgaatg atccggcatt caagagacaa gaaaaatgag 420
cccaatcctc agaggtttga ccggatcgca catacaaagg aaacgatgcg cttcgatggt 480
ttgaactcac ttacctacaa ggtgttggat gtcagagata cccgttatat acccaaatca 540
c 541

<210> SEQ ID NO 109
<211> LENGTH: 411
<212> TYPE: DNA
<213> ORGANISM: Homo sapiens

<400> SEQUENCE: 109
ctagacctct aattaaaagg cacaatcatg ctggagaatg aacagtctga ccccgagggc 60
cacagcgaat tttagggaag gaggcaaaga ggtgagaagg gaaaggaaag aaggaaggaa 120
ggagaacaat aagaactgga gacgttgggt gggtcaggga gtgtggtgga ggctcggaga 180
gatggtaaac aaacctgact gctatgagtt ttcaacccca tagtctaggg ccatgagggc 240
gtcagttctt ggtggctgag ggtccttcca cccagcccac ctgggggagt ggagtgggga 300
gttctgccag gtaagcagat gttgtctccc aagttcctga cccagatgtc tggcaggata 360
acgctgacct gttccctcaa caagggacct gaaagtaatt ttgctcttta c 411

<210> SEQ ID NO 110
<211> LENGTH: 451

-continued

<212> TYPE: DNA
<213> ORGANISM: Homo sapiens

<400> SEQUENCE: 110
ccgaattcaa gcgtcaacga tccytccctt accatcaaat caattggcca ccaatggtac 60
tgaacctacg agtacaccga ctacgggcgg actaatcttc aactcctaca tacttccccc 120
attattccta gaaccaggcg acctgcgact ccttgacgtt gacaatcgag tagtactccc 180
gattgaagcc cccattcgta taataattac atcacaagac gtcttgcact catgagctgt 240
ccccacatta ggcttaaaaa cagatgcaat tcccggacgt ctaagccaaa ccactttcac 300
cgctacacga ccgggggtat actacggtca atgctctgaa atctgtggag caaaccacag 360
tttcatgccc atcgtcctag aattaattcc cctaaaaatc tttgaaatag ggcccgtatt 420
taccctatag cacccccctct accccctcta g 451

<210> SEQ ID NO 111
<211> LENGTH: 541
<212> TYPE: DNA
<213> ORGANISM: Homo sapiens

<400> SEQUENCE: 111
gctcttcaca cttttattgt taattctctt cacatggcag atacagagct gtcgtcttga 60
agaccaccac tgaccaggaa atgccacttt tacaaaatca tcccccccttt tcatgattgg 120 aacagttttc ctgaccgtct gggagcgttg aagggtgacc agcacatttg cacatgcaaa 180
aaaggagtga ccccaaggcc tcaaccacac ttcccagagc tcaccatggg ctgcaggtga 240
cttgccaggt ttggggttcg tgagctttcc ttgctgctgc ggtggggagg ccctcaagaa 300
ctgagaggcc ggggtatgct tcatgagtgt taacatttac gggacaaaag cgcatcatta 360
ggataaggaa cagccacagc acttcatgct tgtgagggtt agctgtagga gcgggtgaaa 420
ggattccagt ttatgaaaat ttaaagcaaa caacggtttt tagctgggtg ggaaacagga 480
aaactgtgat gtcggccaat gaccaccatt tttctgccca tgtgaaggtc cccatgaaac 540
c 541

<210> SEQ ID NO 112
<211> LENGTH: 521
<212> TYPE: DNA
<213> ORGANISM: Homo sapiens

<400> SEQUENCE: 112
caagcgcttg gcgtttggac ccagttcagt gaggttcttg ggttttgtgc ctttggggat 60
tttggtttga cccaggggtc agccttagga aggtcttcag gaggaggccg agttcccctt 120
cagtaccacc cctctctccc cactttccct ctcccggcaa catctctggg aatcaacagc 180
atattgacac gttggagccg agcctgaaca tgcccctcgg ccccagcaca tggaaaaccc 240
ccttccttgc ctaaggtgtc tgagtttctg gctcttgagg catttccaga cttgaaattc 300
tcatcagtcc attgctcttg agtctttgca gagaacctca gatcaggtgc acctgggaga 360
aagactttgt ccccacttac agatctatct cctcccttgg gaagggcagg gaatggggac 420
ggtgtatgga ggggaaggga tctcctgcgc ccttcattgc cacacttggt gggaccatga 480
acatctttag tgtctgagct tctcaaatta ctgcaatagg a 521

<210> SEQ ID NO 113
<211> LENGTH: 568
<212> TYPE: DNA

-continued

<213> ORGANISM: Homo sapiens

<400> SEQUENCE: 113
agcgtcaaat cagaatggaa aagactcaaa accatcatca acaccaagat caaaaggaca 60
agratccttc aagaaacagg aaaaaactcc taaaacacca aaaggaccta gttctgtaga 120
agacattaaa gcaaaaatgc aagcaagtat agaaaaaggt ggttctcttc ccaaagtgga 180
agccaaattc atcaattatg tgaagaattg cttccggatg actgaccaag aggctattca 240
agatctctgg cagtggagga agtctcttta agaaaatagt ttaaacaatt tgttaaaaaa 300
ttttccgtct tatttcattt ctgtaacagt tgatatctgg ctgtcctttt tataatgcag 360
agtgagaact ttccctaccg tgtttgataa atgttgtcca ggttctattg ccaagaatgt 420
gttgtccaaa atgcctgttt agtttttaaa gatggaactc caccctttgc ttggttttaa 480
gtatgtatgg aatgttatga taggacatag tagtagcggt ggtcagacat ggaaatggtg 540
ggsmgacaaa aatatacatg tgaaataa 568

<210> SEQ ID NO 114
<211> LENGTH: 483
<212> TYPE: DNA
<213> ORGANISM: Homo sapiens

<400> SEQUENCE: 114
tccgaattcc aagcgaatta tggacaaacg attcctttta gaggattact tttttcaatt 60
tcggttttag taatctaggc tttgcctgta aagaatacaa cgatggattt taaatactgt 120
ttgtggaatg tgtttaaagg attgattcta gaacctttgt atatttgata gtatttctaa 180
ctttcatttc tttactgttt gcagttaatg ttcatgttct gctatgcaat cgtttatatg 240
cacgtttctt taattttttt agattttcct ggatgtatag tttaaacaac aaaaagtcta 300
tttaaaactg tagcagtagt ttacagttct agcaaagagg aaagttgtgg ggttaaactt 360
tgtattttct ttcttataga ggcttctaaa aaggtatttt tatatgttct ttttaacaaa 420
tattgtgtac aacctttaaa acatcaatgt ttggatcaaa acaagaccca gcttattttc 480
tgc 483

<210> SEQ ID NO 115
<211> LENGTH: 521
<212> TYPE: DNA
<213> ORGANISM: Homo sapiens

<400> SEQUENCE: 115
tgtggtggcg cgggctgagg tggaggccca ggactctgac cctgcccctg ccttcagcaa 60
ggcccccggc agcgccggcc actacgaact gccgtgggtt gaaaaatata ggccagtaaa 120
gctgaatgaa attgtcggga atgaagacac cgtgagcagg ctagaggtct ttgcaaggga 180
aggaaatgtg cccaacatca tcattgcggg ccctccagga accggcaaga ccacaagcat 240
tctgtgcttg gcccgggccc tgctgggccc agcactcaaa gatgccatgt tggaactcaa 300
tgcttcaaat gacaggggca ttgacgttgt gaggaataaa attaaaatgt ttgctcaaca 360
aaaagtcact cttcccaaag gccgacataa gatcatcatt ctggatgaag cagacagcat 420
gaccgacgga gcccagcaag ccttgaggag aaccatggaa atctactcta aaaccactcg 480
ttcgcccttg cttgtaatgc ttcggataag atcatcgagc c 521

<210> SEQ ID NO 116
<211> LENGTH: 501

-continued

<212> TYPE: DNA
<213> ORGANISM: Homo sapiens

<400> SEQUENCE: 116
ctttgcaaag cttttatttc atgtctgcgg catggaatcc acctgcacat ggcatcttag 60
ctgtgaagga gaaagcagtg cacgagaagg aatgagtggg cggaaccaac ggcctccaca 120
agctgccttc cagcagcctg ccaaggccat ggcagagaga gactgcaaac aaacacaagc 180
aaacagagtc tcttcacagc tggagtctga aagctcatag tggcatgtgt gaatctgaca 240
aaattaaaag tgtgcatagt ccattacatg cataaaacac taataataat cctgtttaca 300
cgtgactgca gcaggcaggt ccagctccac cactgccctc ctgccacatc acatcaagtg 360
ccatggttta gagggttttt catatgtaat tcttttattc tgtaaaaggt aacaaaatat 420
acagaacaaa actttccctt tttaaaacta atgttacaaa tctgtattat cacttggata 480
taaatagtat ataagctgat c 501

<210> SEQ ID NO 117
<211> LENGTH: 451
<212> TYPE: DNA
<213> ORGANISM: Homo sapiens
<220> FEATURE:
<221> NAME/KEY: modified_base
<222> LOCATION: (320)
<223> OTHER INFORMATION: Where n is a, c, g or t

<400> SEQUENCE: 117
caagggatat atgttgaggg tacrgrgtga cactgaacag atcacaaagc acgagaaaca 60
ttagttctct ccctccccag cgtctccttc gtctccctgg ttttccgatg tccacagagt 120
gagattgtcc ctaagtaact gcatgatcag agtgctgkct ttataagact cttcattcag 180
cgtatccaat tcagcaattg cttcatcaaa tgccgttttt gccaggctac aggccttttc 240
aggagagttt agaatctcat agtaaaagac tgagaaattt agtgccagac caagacgaat 300
tgggtgtgta ggctgcattn ctttcttact aatttcaaat gcttcctggt aagcctgctg 360
ggagttcgac acaagtggtt tgtttgttgc tccagatgcc acttcagaaa gatacctaaa 420
ataatctcct ttcattttca aagtagaaca c 451

<210> SEQ ID NO 118
<211> LENGTH: 501
<212> TYPE: DNA
<213> ORGANISM: Homo sapiens

<400> SEQUENCE: 118
tccggagccg gggtagtcgc cgccgccgcc gccggtgcag ccactgcagg caccgctgcc 60
gccgcctgag tagtgggctt aggaaggaag aggtcatctc gctcggagct tcgctcggaa 120
gggtctttgt tccctgcagc cctcccacgg gaatgacaat ggataaaagt gagctggtac 180
agaaagccaa actcgctgag caggctgagc gatatgatga tatggctgca gccatgaagg 240
cagtcacaga acaggggcat gaactctcca acgaagagag aaatctgctc tctgttgcct 300
acaagaatgt ggtaaggccg cccgccgctc ttcctggcgt gtcatctcca gcattgagca 360
gaaaacagag aggaatgaga agaagcagca gatgggcaaa gagtaccgtg agaagataga 420
ggcagaactg caggacatct gcaatgatgt tctggagctt gttggacaaa tatcttattc 480
caatgctaca caacccagaa a 501

<210> SEQ ID NO 119

-continued

<211> LENGTH: 391
<212> TYPE: DNA
<213> ORGANISM: Homo sapiens

<400> SEQUENCE: 119
aaaaagcagc argttcaaca caaaatagaa atctcaaatg taggatagaa caaaaccaag 60
tgtgtgaggg gggaagcaac agcaaaagga agaaatgaga tgttgcaaaa aagatggagg 120
agggttcccc tctcctctgg ggactgactc aaacactgat gtggcagtat acaccattcc 180
agagtcaggg gtgttcattc ttttttggga gtaagaaaag gtggggatta agaagacgtt 240
tctggaggct tagggaccaa ggctggtctc tttcccccct cccaacccccc ttgatccctt 300 tctctgatca ggggaaagga gctcgaatga gggaggtaga gttggaaagg gaaaggattc 360
cacttgacag aatgggacag actccttccc a 391

<210> SEQ ID NO 120
<211> LENGTH: 421
<212> TYPE: DNA
<213> ORGANISM: Homo sapiens
<220> FEATURE:
<221> NAME/KEY: modified_base
<222> LOCATION: (409)
<223> OTHER INFORMATION: Where n is a, c, g or t

<400> SEQUENCE: 120
tggcaatagc acagccatcc aggagctctt cargcgcatc tcggagcagt tcactgccat 60
gttccgccgg aaggccttcc tccactggta cacaggcgag ggcatggacg agatggagtt 120
caccgaggct gagagcaaca tgaacgacct cgtctctgag tatcaagcag taccaggatg 180
ccaccgcaga agaggaggag gatttcggtg aggaggccga agaggaggcc taaggcagag 240
cccccatcac ctcaggcttc tcagttccct tagccgtctt actcaactgc ccctttcctc 300
tccctcagaa tttgtgtttg ctgcctctat cttgtttttt gttttttctt ctgggggggt 360
ctagaacagt gcctggcaca tagtaggcgc tcaataaata cttggttgnt gaatgtctcc 420
t 421

<210> SEQ ID NO 121
<211> LENGTH: 206
<212> TYPE: DNA
<213> ORGANISM: Homo sapiens

<400> SEQUENCE: 121
agctggcgct agggctcggt tgtgaaatac agcgtrgtca gcccttgcgc tcagtgtaga 60
aacccacgcc tgtaaggtcg gtcttcgtcc atctgctttt ttctgaaata cactaagagc 120
agccacaaaa ctgtaacctc aaggaaacca taaagcttgg agtgccttaa tttttaacca 180
gtttccaata aaacggttta ctacct 206

<210> SEQ ID NO 122
<211> LENGTH: 131
<212> TYPE: DNA
<213> ORGANISM: Homo sapiens

<400> SEQUENCE: 122
ggagatgaag atgaggaagc tgagtcagct acgggcargc gggcagctga agatgatgag 60
gatgacgatg tcgataccaa gaagcagaag accgacgagg atgactagac agcaaaaaag 120
gaaaagttaa a 131

-continued

<210> SEQ ID NO 123
<211> LENGTH: 231
<212> TYPE: DNA
<213> ORGANISM: Homo sapiens
<220> FEATURE:
<221> NAME/KEY: modified_base
<222> LOCATION: (166)
<223> OTHER INFORMATION: Where n is a, c, g or t
<221> NAME/KEY: modified_base
<222> LOCATION: (202)
<223> OTHER INFORMATION: Where n is a, c, g or t
<221> NAME/KEY: modified_base
<222> LOCATION: (222)
<223> OTHER INFORMATION: Where n is a, c, g or t
<221> NAME/KEY: modified_base
<222> LOCATION: (225)
<223> OTHER INFORMATION: Where n is a, c, g or t

<400> SEQUENCE: 123
gatgaaaatt aaatacttaa attaatcaaa aggcactacg ataccaccta aaacctactg 60
cctcagtggc agtakgctaa kgaagatcaa gctacagsac atyatctaat atgaatgtta 120
gcaattacat akcargaagc atgtttgctt tccagaagac tatggnacaa tggtcattwg 180
ggcccaagag gatatttggc cnggaaagga tcaagataga tnaangtaaa g 231

<210> SEQ ID NO 124
<211> LENGTH: 521
<212> TYPE: DNA
<213> ORGANISM: Homo sapiens
<220> FEATURE:
<221> NAME/KEY: modified_base
<222> LOCATION: (284)
<223> OTHER INFORMATION: Where n is a, c, g or t
<221> NAME/KEY: modified_base
<222> LOCATION: (412)
<223> OTHER INFORMATION: Where n is a, c, g or t
<221> NAME/KEY: modified_base
<222> LOCATION: (513)
<223> OTHER INFORMATION: Where n is a, c, g or t

<400> SEQUENCE: 124
gagtagcaac gcaaagcgct tggtattgag tctgtgggsg acttcggttc cggtctctgc 60
agcagccgtg atcgcttagt ggagtgctta gggtagttgg ccaggatgcc gaatatcaaa 120
atcttcagca ggcagctccc accaggactt atctcasaaa attgctgacc gcctgggcct 180
ggagctaggc aaggtggtga ctaagaaatt cagcaaccag gagacctgtg tggaaattgg 240
tgaaagtgta ccgtggagag gatgtctaca ttgttcagag tggntgtggc gaaatcaatg 300
acaatttaat ggagcttttg atcatgatta atgcctgcaa gattgcttca gccagccggg 360
ttactgcagt catcccatgc ttcccttatg ccccggcagg ataagaaaga tnagagccgg 420
gccgccaatc tcagccaagc ttggtgcaaa tatgctatct gtagcagtgc agatcatatt 480
atcaccatgg acctacatgc ttctcaaatt canggctttt t 521

<210> SEQ ID NO 125
<211> LENGTH: 341
<212> TYPE: DNA
<213> ORGANISM: Homo sapiens
<220> FEATURE:
<221> NAME/KEY: modified_base
<222> LOCATION: (277)
<223> OTHER INFORMATION: Where n is a, c, g or t

<400> SEQUENCE: 125
atgcaaaagg ggacacaggg ggttcaaaaa taaaaatttc tcttccccct ccccaaacct 60
gtaccccagc tccccgacca caaccccctt cctcccccgg ggaaagcaag aaggagcagg 120

-continued

```
tgtggcatct gcagctggga agagagaggc cggggaggtg ccgagctcgg tgctggtctc    180

tttccaaata taaatacgtg tgtcagaact ggaaaatcct ccagcaccca ccacccaagc    240

actctccgtt ttctgccggt gtttggagag gggcggnggg caggggcgcc aggcaccggc    300

tggctgcggt ctactgcatc cgctgggtgt gcaccccgcg a                        341


<210> SEQ ID NO 126
<211> LENGTH: 521
<212> TYPE: DNA
<213> ORGANISM: Homo sapiens
<220> FEATURE:
<221> NAME/KEY: modified_base
<222> LOCATION: (353)
<223> OTHER INFORMATION: Where n is a, c, g or t
<221> NAME/KEY: modified_base
<222> LOCATION: (399)
<223> OTHER INFORMATION: Where n is a, c, g or t
<221> NAME/KEY: modified_base
<222> LOCATION: (455)
<223> OTHER INFORMATION: Where n is a, c, g or t

<400> SEQUENCE: 126

aggttggaga aggtcatgca ggtgcagatt gtccaggskc agccacaggg tcaagcccaa     60

caggcccaga gtggcactgg acagaccatg caggtgatgc agcagatcat cactaacaca    120

ggagagatcc agcagatccc ggtgcagctg aatgccggcc agctgcagta tatccgctta    180

gcccagcctg tatcaggcac tcaagttgtg cagggacaga tccagacact tgccaccaat    240

gctcaacaga ttacacagac agaggtccag caaggacagc agcagttcaa gccagttcac    300

aagatggaca gcagctctac cagatccagc aagtcaccat gcctgcgggc cangacctcg    360

ccagcccatg ttcatccagt caagccaacc agcccttcna cgggcaggcc ccccaggtga    420

ccggcgactg aagggcctga gctggcaagg ccaangacac ccaacacaat ttttgccata    480

cagcccccag gcaatgggca cagcctttct tcccagagga c                        521


<210> SEQ ID NO 127
<211> LENGTH: 351
<212> TYPE: DNA
<213> ORGANISM: Homo sapiens

<400> SEQUENCE: 127

tgagatttat tgcatttcat gcagcttgaa gtccatgcaa aggrgactag cacagttttt     60

aatgcattta aaaaataaaa gggaggtggg cagcaaacac acaaagtcct agtttcctgg    120

gtccctggga gaaaagagtg tggcaatgaa tccacccact ctccacaggg aataaatctg    180

tctcttaaat gcaaagaatg tttccatggc ctctggatgc aaatacacag agctctgggg    240

tcagagcaag ggatggggag aggaccacga gtgaaaaagc agctacacac attcacctaa    300

ttccatctga gggcaagaac aacgtggcaa gtcttggggg tagcagctgt t             351


<210> SEQ ID NO 128
<211> LENGTH: 521
<212> TYPE: DNA
<213> ORGANISM: Homo sapiens

<400> SEQUENCE: 128

tccagacatg ctcctgtcct aggcggggag caggaaccag acctgctatg ggaagcagaa     60

agagttaagg gaaggtttcc tttcattcct gttccttctc ttttgctttt gaacagtttt    120

taaatatact aatagctaag tcatttgcca gccaggtccc ggtgaacagt agagaacaag    180
```

-continued

```
gagcttgcta agaattaatt ttgctgtttt tcaccccatt caaacagagc tgccctgttc    240

cctgatggag ttccattcct gccagggcac ggctgagtaa cacgaagcca ttcaagaaag    300

gcgggtgtga aatcactgcc accccatgga cagacccctc actcttcctt cttagccgca    360

gcgctactta ataaatatat ttatactttg aaattatgat aaccgatttt tcccatgcgg    420

catcctaagg gcacttgcca gctcttatcc ggacagtcaa gcactgttgt tggacaacag    480

ataaaggaaa agaaaaagaa gaaaacaacc gcaacttctg t                        521
```

<210> SEQ ID NO 129
<211> LENGTH: 521
<212> TYPE: DNA
<213> ORGANISM: Homo sapiens

<400> SEQUENCE: 129

```
tgagacggac cactggcctg gtccccccctc atktgctgtc gtaggacctg acatgaaacg     60

cagatctagt ggcagagagg aagatgatga ggaacttctg agacgtcggc agcttcaaga    120

agagcaatta atgaagctta actcaggcct gggacagttg atcttgaaag aagagatgga    180

gaaagagagc cgggaaaggt catctctgtt agccagtcgc tacgattctc ccatcaactc    240

agcttcacat attccatcat ctaaaactgc atctctccct ggctatggaa gaaatgggct    300

tcaccggcct gtttctaccg acttcgctca gtataacagc tatggggatg tcagcggggg    360

agtgcgagat taccagacac ttccagatgg ccacatgcct gcaatgagaa tggaccgagg    420

agtgtctatg cccaacatgt tggaaccaaa gatatttcca tatgaaatgc tcatggtgac    480

caacagaggg ccgaaaccaa atctcagaga ggtggacaga a                        521
```

<210> SEQ ID NO 130
<211> LENGTH: 270
<212> TYPE: DNA
<213> ORGANISM: Homo sapiens

<400> SEQUENCE: 130

```
tcactttatt tttcttgtat aaaaacccta tgttgtagcc acagctggag cctgagtccg     60

ctgcacggag actctggtgt gggtcttgac gaggtggtca gtgaactcct gatagggaga    120

cttggtgaat acagtctcct tccagaggtc gggggtcagg tagctgtagg tcttagaaat    180

ggcatcaaag gtggccttgg cgaagttgcc cagggtggca gtgcagcccc gggctgaggt    240

gtagcagtca tcgataccag ccatcatgag                                     270
```

<210> SEQ ID NO 131
<211> LENGTH: 341
<212> TYPE: DNA
<213> ORGANISM: Homo sapiens

<400> SEQUENCE: 131

```
ctggaatata gacccgtgat cgacaaaact ttgaacgagg ctgactgtgc caccgtcccg     60

ccagccattc gctcctactg atgagacaag atgtggtgat gacagaatca gcttttgtaa    120

ttatgtataa tagctcatgc atgtgtccat gtcataactg tcttcatacg cttctgcact    180

ctggggaaga aggagtacat tgaagggaga ttggcaccta gtggctggga gcttgccagg    240

aacccagtgg ccagggagcg tggcacttac ctttgtccct tgcttcattc ttgtgagatg    300

ataaaactgg gcacagctct taaataaaat ataaatgaac a                        341
```

<210> SEQ ID NO 132
<211> LENGTH: 844

-continued

<212> TYPE: DNA
<213> ORGANISM: Homo sapiens
<220> FEATURE:
<221> NAME/KEY: modified_base
<222> LOCATION: (37)
<223> OTHER INFORMATION: Where n is a, c, g or t

<400> SEQUENCE: 132
tgaatgggga ggagctgacc caggaaatgg agcttgngga gaccaggcct gcaggggatg 60
gaaccttcca gaagtgggca tctgtggtgg tgcctcttgg gaaggagcag aagtacacat 120
gccatgtgga acatgagggg ctgcctgagc ccctcaccct gagatggggc aaggaggagc 180
ctccttcatc caccaagact aacacagtaa tcattgctgt tccggttgtc cttggagctg 240
tggtcatcct tggagctgtg atggcttttg tgatgaagag gaggagaaac acaggtggaa 300
aaggagggga ctatgctctg gctccaggct cccagagctc tgatatgtct ctcccagatt 360
gtaaagtgtg aagacagctg cctggtgtgg acttggtgac agacaatgtc ttcacacatc 420
tcctgtgaca tccagagacc tcagttctct ttagtcaagt gtctgatgtt ccctgtgagt 480
ctgcgggctc aaagtgaaga actgtggagc ccagtccacc cctgcacacc aggaccctat 540
ccctgcactg ccctgtgttc ccttccacag ccaaccttgc tgctccagcc aaacattggt 600
ggacatctgc agcctgtcag ctccatgcta ccctgacctt caactcctca cttccacact 660
gagaataata atttgaatgt gggtggctgg agagatggct cagcgctgac tgctcttcca 720
aaggtcctga gttcaaatcc cagcaaccac atggtggctc acaaccatct gtaatgggat 780
ctaataccct cttctgcagt gtctgaagac asctacagtg tacttacata taataataaa 840
taag 844

<210> SEQ ID NO 133
<211> LENGTH: 601
<212> TYPE: DNA
<213> ORGANISM: Homo sapiens

<400> SEQUENCE: 133
ggccgggcgc gcgcgccccc gccacacgca cgccgggcgt gccagtttat aaagggagag 60
agcaagcagc gagtcttgaa gctctgtttg gtgctttgga tccatttcca tcggtcctta 120
cagccgctcg tcagactcca gcagccaaga tggtgaagca gatcgagagc aagactgctt 180
ttcaggaagc cttggacgct gcaggtgata aacttgtagt agttgacttc tcagccacgt 240
ggtgtgggcc ttgcaaaatg atcaagcctt tctttcattc cctctctgaa aagtattcca 300
acgtgatatt ccttgaagta gatgtggatg actgtcagga tgttgcttca gagtgtgaag 360
tcaaatgcat gccaacattc cagtttttta agaagggaca aaaggtgggt gaattttctg 420
gagccaataa ggaaaagctt gaagccacca ttaatgaatt agtctaatca tgttttctga 480
aaatataacc agccattggc tatttaaaac ttgtaatttt tttaatttac aaaaatataa 540
aatatgaaga cataaacccm gttgccatct gcgtgacaat aaaacattaa tgctaacact 600
t 601

<210> SEQ ID NO 134
<211> LENGTH: 421
<212> TYPE: DNA
<213> ORGANISM: Homo sapiens

<400> SEQUENCE: 134
tcacataaga aatttaagca agttacrcta tcttaaaaaa cacaacgaat gcattttaat 60

-continued

```
agagaaaccc ttccctccct ccacctccct cccccaccct cctcatgaat taagaatcta    120

agagaagaag taaccataaa accaagtttt gtggaatcca tcatccagag tgcttacatg    180

gtgattaggt taatattgcc ttcttacaaa atttctattt taaaaaaaat tataaccttg    240

attgcttatt acaaaaaaat tcagtacaaa agttcaatat attgaaaaat gcttttcccc    300

tccctcacag caccgtttta tatatagcag agaataatga agagattgct agtctagatg    360

gggcaatctt caaattacac caagacgcac agtggtttat ttaccctccc cttctcataa    420

g                                                                    421
```

<210> SEQ ID NO 135
<211> LENGTH: 511
<212> TYPE: DNA
<213> ORGANISM: Homo sapiens

<400> SEQUENCE: 135

```
ggaaaggatt caagaattag aggacttgct tgctrragaa aaagacaact ctcgtcgcat     60

gctgacagac aaagagagag agatggcgga aataagggat caaatgcagc aacagctgaa    120

tgactatgaa cagcttcttg atgtaaagtt agccctggac atggaaatca gtgcttacag    180

gaaactctta gaaggcgaag aagagaggtt gaagctgtct ccaagccctt cttcccgtgt    240

gacagtatcc cgagcatcct caagtcgtag tgtaccgtac aactagagga aagcggaaga    300

gggttgatgt ggaagaatca gaggcgaagt agtagtgtta gcatctctca ttccgcctca    360

accactggaa atgtttgcat cgaagaaatt gatgttgatg ggaaatttat cccgcttgaa    420

gaacacttct gaacaggatc aaccaatggg aaggcttggg agatgatcag aaaaattgga    480

gacacatcag tcagttataa atatacctca a                                   511
```

<210> SEQ ID NO 136
<211> LENGTH: 341
<212> TYPE: DNA
<213> ORGANISM: Homo sapiens

<400> SEQUENCE: 136

```
catgggtttc accaggttgg ccaggctgct cttgaactsc tgacctcagg tgatccaccc     60

gcctcggcct cccaaagtgc tgggattaca ggcgtgagcc accacgcccg gcccccaaag    120

ctgtttcttt tgtctttagc gtaaagctct cctgccatgc agtatctaca taactgacgt    180

gactgccagc aagctcagtc actccgtggt ctttttctct ttccagttct tctctctctc    240

ttcaagttct gcctcagtga aagctgcagg tccccagtta agtgatcagg tgagggttct    300

ttgaacctgg ttctatcagt cgaattaatc cttcatgatg g                        341
```

<210> SEQ ID NO 137
<211> LENGTH: 551
<212> TYPE: DNA
<213> ORGANISM: Homo sapiens

<400> SEQUENCE: 137

```
gatgtgttgg accctctgtg tcaaaaaaaa cctcacaaag aatcccctgc tcattacaga     60

agaagatgca tttaaaatat gggttatttt caacttttta tctgaggaca agtatccatt    120

aattattgtg tcagaagaga ttgaatacct gcttaagaag cttacagaag ctatgggagg    180

aggttggcag caagaacaat ttgaacatta taaaatcaac tttgatgaca gtaaaaatgg    240

cctttctgca tgggaactta ttgagcttat tggaaatgga cagtttagca aaggcatgga    300

ccggcagact gtgtctatgg caattaatga agtctttaat gaacttatat tagatgtgtt    360
```

-continued

```
aaagcagggt tacatgatga aaaagggcca cagacggaaa aactggactg aaagatggtt    420

tgtactaaaa cccaacataa tttcttacta tgtgagtgag gatctgaagg ataagaaagg    480

agacattctc ttggatgaaa attgctgtgt agaagtcctt gcctgacaaa agatggaaag    540

aaatgccttt t                                                         551
```

<210> SEQ ID NO 138
<211> LENGTH: 531
<212> TYPE: DNA
<213> ORGANISM: Homo sapiens
<220> FEATURE:
<221> NAME/KEY: modified_base
<222> LOCATION: (490)
<223> OTHER INFORMATION: Where n is a, c, g or t

<400> SEQUENCE: 138

```
gactggttct ttatttcaaa aagacacttg tcaatattca gtrtcaaaac agttgcacta     60

ttgatttctc tttctcccaa tcggccccaa agagaccaca taaaaggaga gtacatttta    120

agccaataag ctgcaggatg tacacctaac agacctccta gaaaccttac cagaaaatgg    180

ggactgggta gggaaggaaa cttaaaagat caacaaactg ccagcccacg gactgcagag    240

gctgtcacag ccagatgggg tggccagggt gccacaaacc caaagcaaag tttcaaaata    300

atataaaatt taaaaagttt tgtacataag ctattcaaga tttctccagc actgactgat    360

acaaagcaca attgagatgg cacttctaga gacagcagct tcaaacccag aaaagggtga    420

tgagatgaag tttcacatgg ctaaatcagt ggcaaaaaca cagtcttctt tctttctttc    480

tttcaaggan gcaggaaagc aattaagtgg tcaccttaac ataaggggga c             531
```

<210> SEQ ID NO 139
<211> LENGTH: 521
<212> TYPE: DNA
<213> ORGANISM: Homo sapiens
<220> FEATURE:
<221> NAME/KEY: modified_base
<222> LOCATION: (517)
<223> OTHER INFORMATION: Where n is a, c, g or t

<400> SEQUENCE: 139

```
tgggtgggca ccatggctgg gatcaccacc atcgaggcgg tgaagcgcaa gatccaggtt     60

ctgcagcagc aggcagatga tgcagaggag cgagctgagc gcctccagcg agaagttgag    120

ggagaaaggc gggcccggga acaggctgag gctgaggtgg cctccttgaa ccgtaggatc    180

cagctggttg aagaagagct ggaccgtgct caggagcgcc tggccactgc cctgcaaaag    240

ctggaagaag ctgaaaaagc tgctgatgag agtgagagag gtatgaaggt tattgaaaac    300

cgggccttaa aagatgaaga aaagatggaa ctccaggaaa tccaactcaa agaagctaag    360

cacattgcag aagaggcaga taggaagtat gaagaggtgg ctcgtaagtt ggtgatcatt    420

gaaggagact tggaaccgca cagaaggaac gagcttgagc ttggcaaaag tcccgttgcc    480

cagagatggg atgaaccaga ttagactgat ggaccanaac c                        521
```

<210> SEQ ID NO 140
<211> LENGTH: 571
<212> TYPE: DNA
<213> ORGANISM: Homo sapiens
<220> FEATURE:
<221> NAME/KEY: modified_base
<222> LOCATION: (7)
<223> OTHER INFORMATION: Where n is a, c, g or t -continued

<400> SEQUENCE: 140
aggggcngcg ggtgcgtggg ccactgggtg accgacttag cctggccaga ctctcagcac 60
ctggaagcgc cccgagagtg acagcgtgag gctgggaggg aggacttggc ttgagcttgt 120
taaactctgc tctgagcctc cttgtcgcct gcatttagat ggctcccgca aagaagggtg 180
gcgagaagaa aaagggccgt tctgccatca acgaagtggt aacccgagaa tacaccatca 240
acattcacaa gcgcatccat ggagtgggct tcaagaagcg tgcacctcgg gcactcaaag 300
agattcggaa atttgccatg aaggagatgg gaactccaga tgtgcgcatt gacaccaggc 360
tcaacaaagc tgtctgggcc aaaggaataa ggaatgtgcc ataccgaatc cggtgtgcgg 420
ctgtccagaa aacgtaatga ggatgaagat tcaccaaata agctatatac tttggttacc 480
tatgtacctg ttaccacttt caaaaatcta cagacagtca atgtggatga gaactaatcg 540
ctgatcgtca gatcaaataa agttataaaa t 571

<210> SEQ ID NO 141
<211> LENGTH: 531
<212> TYPE: DNA
<213> ORGANISM: Homo sapiens

<400> SEQUENCE: 141
tcgggagcca cacttggccc tcttcctctc caaagsgcca gaacctcctt ctctttggag 60
aatggggagg cctcttggag acacagaggg tttcaccttg gatgacctct agagaaattg 120
cccaagaagc ccaccttctg gtcccaacct gcagacccca cagcagtcag ttggtcaggc 180
cctgctgtag aaggtcactt ggctccattg cctgcttcca accaatgggc aggagagaag 240
gcctttattt ctcgcccacc cattcctcct gtaccagcac ctccgttttc agtcagtgtt 300
gtccagcaac ggtaccgttt acacagtcac ctcagacaca ccatttcacc tcccttgcca 360
agctgttagc cttagagtga ttgcagtgaa cactgtttac acaccgtgaa tccattccca 420
tcagtccatt ccagttggca ccagcctgaa ccatttggta cctggtgtta actggagtcc 480
tgtttacaag gtggagtcgg ggcttgctga cttctcttca tttgagggca c 531

<210> SEQ ID NO 142
<211> LENGTH: 491
<212> TYPE: DNA
<213> ORGANISM: Homo sapiens
<220> FEATURE:
<221> NAME/KEY: modified_base
<222> LOCATION: (410)
<223> OTHER INFORMATION: Where n is a, c, g or t

<400> SEQUENCE: 142
acctagacag aaggtgggtg agggaggact ggtaggaggc tgaggcaatt ccttggtagt 60
ttgtcctgaa accctactgg agaagtcagc atgaggcacc tactgagaga agtgcccaga 120
aactgctgac tgcatctgtt aagagttaac agtaaagagg tagaagtgtg tttctgaatc 180
agagtggaag cgtctcaagg gtcccacagt ggaggtccct gagctacctc ccttccgtga 240
gtgggaagag tgaagcccat gaagaactga gatgaagcaa ggatggggtt cctgggctcc 300
aggcaagggc tgtgctctct gcagcaggga gccccacgag tcagaagaaa agaactaatc 360
atttgttgca agaaaccttg cccggatact agcggaaaac tggaggcggn ggtgggggca 420
caggaaagtg gaagtgattt gatggagagc agagaagcct atgcacagtg gccgagtcca 480
cttgtaaagt g 491

-continued

<210> SEQ ID NO 143
<211> LENGTH: 515
<212> TYPE: DNA
<213> ORGANISM: Homo sapiens

<400> SEQUENCE: 143
ttcaagcaat tgtaacaagt atatgtagat tagagtgagc aaaatcatat acaattttca 60
tttccagttg ctattttcca aattgttctg taatgtcgtt aaaattactt aaaaattaac 120
aaagccaaaa attatattta tgacaagaaa gccatcccta cattaatctt acttttccac 180
tcaccggccc atctccttcc tctttttcct aactatgcca ttaaaactgt tctactgggc 240
cgggcgtgtg gctcatgcct gtaatcccag cattttggga ggccaaggca ggcggatcat 300
gaggtcaaga gattgagacc atcctggcca acatggtgaa accccgcctc gactaagaat 360
acaaaaatta gctgggcatg gtggcgcatg cctgtagtct cagctactcg ggaggctgag 420
gcagaagaat cgcttgaacc cgggaggcag aggatgcagt gagccccgat cgcgccactg 480
cactctagcc tgggcgacag actgagactc tgctc 515

<210> SEQ ID NO 144
<211> LENGTH: 340
<212> TYPE: DNA
<213> ORGANISM: Homo sapiens

<400> SEQUENCE: 144
tgtgccagtc tacaggccta tcagcagcga ctccttcagc aacagatggg gtcccctgtt 60
cagcccaacc ccatgagccc ccagcagcat atgctcccaa atcaggccca gtccccacac 120
ctacaaggcc agcagatccc taattctctc tccaatcaag tgcgctctcc ccagcctgtc 180
ccttctccac ggccacagtc ccagcccccc cactccagtc cttccccaag gatgcagcct 240
cagccttctc cacaccacgt ttccccacag acaagttccc cacatcctgg actggtagtt 300
gcccaggcca accccatgga acaagggcat tttgccagcc 340

<210> SEQ ID NO 145
<211> LENGTH: 630
<212> TYPE: DNA
<213> ORGANISM: Homo sapiens

<400> SEQUENCE: 145
tgtaaaaact tgtttttaat tttgtataaa ataaaggtgg tccatgccca cgggggctgt 60
aggaaatcca agcagaccag ctggggtggg gggatgtagc ctacctcggg ggactgtctg 120
tcctcaaaac gggctgagaa ggcccgtcag gggcccaggt cccacagaga ggcctgggat 180
actcccccaa cccgaggggc agactgggca gtggggagcc cccatcgtgc cccagaggtg 240
gccacaggct gaaggagggg cctgaggcac cgcagcctgc aacccccagg gctgcagtcc 300
actaactttt tacagaataa aaggaacatg gggatgggga aaaaagcacc aggtcaggca 360
gggcccgagg gccccagatc ccaggagggc caggactcag gatgccagca ccaccctagc 420
agctcccaca gctcctggca caggaggccg ccacggattg gcacaggccg ctgctggcca 480
tcacgccaca tttggagaac ttgtcccgac agaggtcagc tcggaggagc tcctcgtggg 540
cacacactgt acgaacacag atctccttgt taatgacgta cacacggcgg aggctgcggg 600
gacagggcac gggaggtctc agccccactt 630

<210> SEQ ID NO 146
<211> LENGTH: 521
<212> TYPE: DNA

-continued

<213> ORGANISM: Homo sapiens

<400> SEQUENCE: 146
atggctgctg gatttaggtg gtaatagggg ctgtgggcca taaatctgaa gccttgagaa 60
ccttgggtct ggagagccat gaagagggaa ggaaaagagg gcaagtcctg aacctaacca 120
atgacctgat ggattgctcg accaagacac agaagtgaag tctgtgtctg tgcacttccc 180
acagactgga gtttttggtg ctgaatagag ccagttgcta aaaaattggg ggtttggtga 240
agaaatctga ttgttgtgtg tattcaatgt gtgattttaa aaataaacag caacaacaat 300
aaaaaccctg actggctgtt ttttccctgt attctttaca actatttttt gaccctctga 360
aaattattat acttcaccta aatggaagac tgctgtgttt gtggaaattt tgtaattttt 420
taatttattt tattctctct ccttttttatt ttgcctgcag aatccgttga gagactaata 480
aggcttaata tttaattgat ttgtttaata tgtatataaa t 521

<210> SEQ ID NO 147
<211> LENGTH: 562
<212> TYPE: DNA
<213> ORGANISM: Homo sapiens

<400> SEQUENCE: 147
ggcatgcgag cgcactcggc ggacgcaagg gcggcgggga gcacacggag cactgcaggc 60
gccgggttgg gacagcgtct tcgctgctgc tggatagtcg tgttttcggg gatcgaggat 120
actcaccaga aaccgaaaat gccgaaacca atcaatgtcc gagttaccac catggatgca 180
gagctggagt ttgcaatcca gccaaataca actggaaaac agctttttga tcaggtggta 240
aagactatcg gcctccggga agtgtggtac tttggcctcc actatgtgga taataaagga 300
tttcctacct ggctgaagct ggataagaag gtgtctgccc aggaggtcag gaaggagaat 360
cccctccagt tcaagttccg ggccaaagtt ctaccctgaa gatgtggctg aggagctcat 420
ccaggacatc acccagaaac ttttcttcct tcaagtgaag gaaggaatcc ttagcgatga 480
gatctactgc ccccccttgar actgccgtgc tcttggggtc ctacgcttgt gcatgccaag 540
tttggggact accaccaaga ag 562

<210> SEQ ID NO 148
<211> LENGTH: 820
<212> TYPE: DNA
<213> ORGANISM: Homo sapiens

<400> SEQUENCE: 148
gaaggagtcg ggatactcag cattgatgca ccccaatttc aaagcggcat tcttcggcag 60
gtctctggga caatctctag ggtcactacc tggaaactcg ttagggtaca actgaatgct 120
gaaaggaaag aacacctgca gaaccggaca gaaattcacc ccggcgatca gctgattgat 180
ctcggtcgac cagaagtcat ggctaaagat gacgaggacg ttgtcaattc cctgggcttt 240
tcgaagtgag tccagcagca gtctgaggta ttcgggccgg ttatgcacct ggaccaccag 300
caccagctcc cggggggccc aggtgccagc cttatctaca ttcctcaggg tctgatcaaa 360
gttcagctgg tacaccaggg accggtaccg cagcgtcagg ttgtccgctc gggctggggg 420
accgccggga ccagggaagc cgccgacacg ttggagaccc tgcggatgcc cacagccaca 480
gaggggtggt ccccaccgcg gccgccggca ccccgcgcgg gttcggcgtc cagcaacggt 540
ggggcgaggg cctcgttctt cctttgtcgc ccattgctgc tccagaggac gaagccgcag 600
gcggccacca cgagcgtcag gattagcacc ttccgtttgt agatgcggaa cctcatggtc 660

-continued

```
tccagggccg ggagcgcagc tacagctcga gcgtcggcgc cgccgctagg agccgcggct    720

cggcttcgtc tccgtcctct ccattcagca ccacgggtcc cggaaaaagc tcagccscgg    780

tcccaaccgc accctagctt cgttacctgc gcctcgcttg                          820


<210> SEQ ID NO 149
<211> LENGTH: 501
<212> TYPE: DNA
<213> ORGANISM: Homo sapiens

<400> SEQUENCE: 149

cagattttta tttgcagtcg tcactggggc cgtttcttgc tgcttatttg tctgctagcc     60

tgctcttcca gctgcatggc caggcgcaag gccttgatga catctcgcag ggctgagaaa    120

tgcttggctt gctgggccag agcagattcc gctttgttca caaaggtctc caggtcatag    180

tctggctgct cggtcatctc agagagctca agccagtctg gtccttgctg tatgatctcc    240

ttgagctctt ccatagcctt ctcctccagc tccctgatct gagtcatggc ttcgttaaag    300

ctggacatct gggaagacag ttcctcctct tccttggata aattgcctgg aatcagcgcc    360

ccgttagagc aggcttccat ctcttctgtt tccatttgaa tcaactgctc tccactgggc    420

ccactgtggg ggctcagctc cttgaccctg ctgcatatct taagggtgtt taaaggatat    480

tcacaggagc ttatgcctgg t                                              501


<210> SEQ ID NO 150
<211> LENGTH: 511
<212> TYPE: DNA
<213> ORGANISM: Homo sapiens
<220> FEATURE:
<221> NAME/KEY: modified_base
<222> LOCATION: (457)
<223> OTHER INFORMATION: Where n is a, c, g or t
<221> NAME/KEY: modified_base
<222> LOCATION: (479)
<223> OTHER INFORMATION: Where n is a, c, g or t

<400> SEQUENCE: 150

ctcctcttgg tacatgaacc caagttgaaa gtggacttaa caaagtatct ggagaaccaa     60

gcattctgct ttgactttgc atttgatgaa acagcttcga atgaagttgt ctacaggttc    120

acagcaaggc cactggtaca gacaatcttt gaaggtggaa aagcaacttg ttttgcatat    180

ggccagacag gaagtggcaa gacacatact atgggcggag acctctctgg gaaagcccag    240

aatgcatcca aagggatcta tgccatggcc ttccgggacg tcttcttctg aagaatcaac    300

cctgctaccg gaagttgggc ctggaagtct atgtgacatt cttcgagatc tacaatggga    360

agctgtttga cctgctcaac aagaaggcca agcttgcgcg tgctggaaga cggcaagcaa    420

caggtgcaag tggtgggggc ttgcaggaac atctggntaa ctctgcttga tgatggcant    480

caagatgatc gacatgggca gcgcctgcag a                                   511


<210> SEQ ID NO 151
<211> LENGTH: 566
<212> TYPE: DNA
<213> ORGANISM: Homo sapiens

<400> SEQUENCE: 151

tcccgaattc aagcgacaaa ttggawagtg aaatggaaga tgcctatcat gaacatcagg     60

caaatctttt gcgccaagat ctgatgagac gacaggaaga attaagacgc atggaagaac    120

ttcacaatca agaaatgcag aaacgtaaag aaatgcaatt gaggcaagag gaggaacgac    180
```

-continued

```
gtagaagaga ggaagagatg atgattcgtc aacgtgagat ggaagaacaa atgaggcgcc    240

aaagagagga aagttacagc cgaatgggct acatggatcc acgggaaaga gacatgcgaa    300

tgggtggcgg aggagcaatg aacatgggag atccctatgg ttcaggaggc cagaaatttc    360

cacctctagg aggtggtggt ggcataggtt atgaagctaa tcctggcgtt ccaccagcaa    420

ccatgagtgg ttccatgatg ggaagtgaca tgcgtactga gcgctttggg cagggaggtg    480

cggggcctgt gggtggacag ggtcctagag gaatggggcc tggaactcca gcaggatatg    540

gtagagggag agaagagtac gaaggc                                         566
```

<210> SEQ ID NO 152
<211> LENGTH: 518
<212> TYPE: DNA
<213> ORGANISM: Homo sapiens

<400> SEQUENCE: 152

```
ttcgtgaaga ccctgactgg taagaccatc actctcgaag tggagcccga gtgacaccat     60

tgagaatgtc aaggcaaaga tccaagacaa ggaaggcatc cctcctgacc agcakaggtt    120

gatctttgct gggaaacagc tggaagatgg acgcaccctg tctgactaca acatccagaa    180

agagtccacc ctgcacctgg tgctccgtct cagaggtggg atgcaaatct tcgtgaagac    240

cctgactggt aagaccatca ccctcgaggt ggagcccagt gacaccatcg agaatgtcaa    300

ggcaaagatc caagataagg aaggcatccc tcctgatcag cagaggttga tctttgctgg    360

gaaacagctg gaagatggac gcaccctgtc tgactacaac atccagaaag agtccactct    420

gcacttggtc ctgcgcttga gggggggtgt ctaagtttcc ccttttaagg tttcaacaaa    480

tttcattgca ctttcctttc aataaagttg ttgcattc                            518
```

<210> SEQ ID NO 153
<211> LENGTH: 542
<212> TYPE: DNA
<213> ORGANISM: Homo sapiens

<400> SEQUENCE: 153

```
gcgcgggtgc gtgggccact gggtgaccga cttagcctgg ccagactctc agcacctgga     60

agcgccccga gagtgacagc gtgaggctgg gagggaggac ttggcttgag cttgttaaac    120

tctgctctga gcctccttgt cgcctgcatt tagatggctc ccgcaaagaa gggtggcgag    180

aagaaaaagg gccgttctgc catcaacgaa gtggtaaccc gagaatacac catcaacatt    240

cacaagcgca tccatggagt gggcttcaag aagcgtgcac ctcgggcact caaagagatt    300

cggaaatttg ccatgaagga gatgggaact ccagatgtgc gcattgacac caggctcaac    360

aaagctgtct gggccaaagg aataaggaat gtgccatacc gaatccgtgt gcggctgtcc    420

agaaaacgta atgaggatga agattcacca aataagctat atactttggt tacctatgta    480

cctgttacca ctttcaaaaa tctacagaca gtcaatgtgg atgagaacta atcgctgatc    540

gt                                                                   542
```

<210> SEQ ID NO 154
<211> LENGTH: 411
<212> TYPE: DNA
<213> ORGANISM: Homo sapiens

<400> SEQUENCE: 154

```
aattctttat ttaaatcaac aaactcatct tcctcaagcc ccagaccatg gtaggcagcc     60
```

-continued

```
ctccctctcc atcccctcac cccaccccctt agccacagtg aagggaatgg aaaatgagaa    120

gccacgaggg cccctgccag ggaaggctgc cccagatgtg tggtgagcac agtcagtgca    180

gctgtggctg gggcagcagc tgccacaggc tcctccctat aaattaagtt cctgcagcca    240

cagctgtggg agaagcatac ttgtagaagc aaggccagtc cagcatcaga aggcagaggc    300

agcatcagtg actcccagcc atggaatgaa cggaggacac agagctcaga gacagaacag    360

gccaggggga agaaggagag acagaatagg ccagggcatg gcggtgaggg a              411
```

<210> SEQ ID NO 155
<211> LENGTH: 421
<212> TYPE: DNA
<213> ORGANISM: Homo sapiens
<220> FEATURE:
<221> NAME/KEY: modified_base
<222> LOCATION: (173)
<223> OTHER INFORMATION: Where n is a, c, g or t

<400> SEQUENCE: 155

```
tgatgaatct gggtgggctg gcagtagccc gagatgatgg gctcttctct ggggatccca     60

actggttccc taagaaatcc aaggagaatc ctcggaactt ctcggataac cagctgcaag    120

agggcaagaa cgtgatcggg ttacagatgg gcaccaaccg cggggcgtct cangcaggca    180

tgactggcta cgggatgcca cgccagatcc tctgatccca ccccaggcct tgcccctgcc    240

ctcccacgaa tggttaatat atatgtagat atatatttta gcagtgacat tcccagagag    300

ccccagagct ctcaagctcc tttctgtcag ggtggggggt tcaagcctgt cctgtcacct    360

ctgaagtgcc tgctggcatc ctctccccca tgcttactaa tacattccct tccccatagc    420

c                                                                    421
```

<210> SEQ ID NO 156
<211> LENGTH: 670
<212> TYPE: DNA
<213> ORGANISM: Homo sapiens

<400> SEQUENCE: 156

```
agcggagctc cctcccctgg tggctacaac ccacacacgc caggctcagg catcgagcag     60

aactccagcg actgggtaac cactgacatt caggtgaagg tgcgggacac ctacctggat    120

acacaggtgg tgggacagac aggtgtcatc cgcagtgtca cggggggcat gtgctctgtg    180

tacctgaagg acagtgagaa ggttgtcagc atttccagtg agcacctgga gcctatcacc    240

cccaccaaga acaacaaggt gaaagtgatc ctgggcgagg atcgggaagc cacgggcgtc    300

ctactgagca ttgatggtga ggatggcatt gtccgtatgg accttgatga gcagctcaag    360

atcctcaacc tccgcttcct ggggaagctc ctggaagcct gaagcaggca gggccggtgg    420

acttcgtcgg atgaagagtg atcctccttc cttccctggc ccttggctgt gacacaagat    480

cctcctgcag ggctaggcgg attgttctgg atttcctttt gtttttcctt ttaggtttcc    540

atcttttccc tccctggtgc tcattggaat ctgagtagag tctgggggag ggtccccacc    600

ttcctgtacc tcctccccac agcttgcttt tgttgtaccg tctttcaata aaaagaagct    660

gtttggtcta                                                           670
```

<210> SEQ ID NO 157
<211> LENGTH: 421
<212> TYPE: DNA
<213> ORGANISM: Homo sapiens

<400> SEQUENCE: 157

-continued ggttcacagc actgctgctt gtgtgttgcc ggccaggaat tccaggctca caaggctatc 60
ttagcagctc gttctccggt ttttagtgcc atgtttgaac atgaaatgga ggagagcaaa 120
aagaatcgag ttgaaatcaa tgatgtggag cctgaagttt ttaaggaaat gatgtgcttc 180
atttacacgg ggaaggctcc aaacctcgac aaaatggctg atgatttgct ggcagctgct 240
gacaagtatg ccctggagcg cttaaaggtc atgtgtgagg atgccctctg cagtaacctg 300
tccgtggaga acgctgcaga aattctcatc ctggccgacc tccacagtgc agatcagttg 360
aaaactcagg cagtggattt catcaactat catgcttcgg atgtcttgga gacctcttgg 420
g 421

<210> SEQ ID NO 158
<211> LENGTH: 321
<212> TYPE: DNA
<213> ORGANISM: Homo sapiens

<400> SEQUENCE: 158
tcgtagccat ttttctgctt ctttggagaa tgacgccaca ctgactgctc attgtcgttg 60
gttccatgcc aattggtgaa atagaacctc atccggtagt ggagccggag ggacatcttg 120
tcatcaacgg tgatggtgcg atttggagca taccagagct tggtgttctc gccatacagg 180
gcaaagaggt tgtgacaaag aggagagata cggcatgcct gtgcagccct gatgcacagt 240
tcctctgctg tgtactctcc actgcccagc cggaggggct ccctgtccga cagatagaag 300
atcacttcca cccctggctt g 321

<210> SEQ ID NO 159
<211> LENGTH: 596
<212> TYPE: DNA
<213> ORGANISM: Homo sapiens

<400> SEQUENCE: 159
tggcacactg ctcttaagaa actatgawga tctgagattt ttttgtgtat gtttttgact 60
cttttgagtg gtaatcatat gtgtctttat agatgtacat acctccttgc acaaatggag 120
gggaattcat tttcatcact gggagtgtcc ttagtgtata aaaaccatgc tggtatatgg 180
cttcaagttg taaaaatgaa agtgacttta aaagaaaata ggggatggtc caggatctcc 240
actgataaga ctgtttttaa gtaacttaag gacctttggg tctacaagta tatgtgaaaa 300
aaatgagact tactgggtga ggaaattcat tgtttaaaga tggtcgtgtg tgtgtgtgtg 360
tgtgtgtgtg ttgtgttgtg ttttgttttt taagggaggg aatttattat ttaccgttgc 420
ttgaaattac tgkgtaaata tatgtytgat aatgatttgc tytttgvcma ctaaaattag 480
gvctgtataa gtwctaratg cmtccctggg kgttgatytt ccmagatatt gatgatamcc 540
cttaaaattg taaccygcct ttttcccttt gctytcmatt aaagtctatt cmaaag 596

<210> SEQ ID NO 160
<211> LENGTH: 515
<212> TYPE: DNA
<213> ORGANISM: Homo sapiens

<400> SEQUENCE: 160
gggggtaggc tctttattag acggttattg ctgtactaca gggtcagagt gcagtgtaag 60
cagtgtcaga ggcccgcgtt cagcccaaga atgtggattt tctctcccta ttgatcacag 120
tgggtgggtt tcttcagaaa agccccagag gcagggacca gtgagctcca aggttagaag 180

-continued tggaactgga aggcttcagt cacatgctgc ttccacgctt ccaggctggg cagcaaggag 240
gagatgccca tgacgtgcca ggtctcccca tctgacacca gtgaagtctg gtaggacagc 300
agccgcacgc ctgcctctgc caggaggcca atcatggtag gcagcattgc agggtcagag 360
gtctgagtcc ggaataggag caggggcagg tccctgcgga gaggcacttc tggcctgaag 420
acagctccat tgagcccctg cagtacaggy gtagtgcctt ggaccaagcc cacagcctgg 480
taaggggcgc ctgccagggc cacggccagg aggca 515

<210> SEQ ID NO 161
<211> LENGTH: 936
<212> TYPE: DNA
<213> ORGANISM: Homo sapiens

<400> SEQUENCE: 161
taatttctta gtcgtttgga atccttaagc atgcaaaagc tttgaacaga agggttcaca 60
aaggaaccag ggttgtctta tggcatccag ttaagccaga gctgggaatg cctctgggtc 120
atccacatca ggagcagaag cacttgactt gtcggtcctg ctgccacggt ttgggcgccc 180
accacgccca cgtccacctc gtcctcccct gccgccacgt cctgggcggc caaggtctcc 240
aaaattgatc tccagctgag acgttatatc atttgctggc ttccggaaat gatggtccat 300
aaccgaatct tcagcatgag cctcttcact ctttgattta tgaagaacaa atcccttctt 360
ccactgccca tcagcacctt catttggttt tcggatatta aattctactt ttgcccggtc 420
cttattttga atagccttcc actcatccaa agtcatctct tttggaccct cctcttttac 480
ctcttcaact tcattctcct tattttcagt gtctgccact ggatgatgtt cttcaccttc 540
aggtgtttcc tcagtcacat ttgattgatc caagtcagtt aattcgtctt tgacagttcc 600
ccagttgtga gatccgctac ctccacgttt gtcctcgtgc ttcaggccag atctatcact 660
tccactatgc ctatcaaatt cacgtttgcc acgagaatca aatccatctc ctcggcccat 720
tccacgtcca cggcccctc gacctcttcc aagaccacca cgacctcgaa taggtcggtc 780
aataatcggt ctatcaactg aaaattcgcc tccttcaccc ttttcttcaa gtggcttttc 840
gaatcttcgt tcacgaggtg gtcgcctttc tggtcttcta tcaattattt tcccttcacc 900
ctgaagttgt tgatcaggtc ttcttccaac tcgtgc 936

<210> SEQ ID NO 162
<211> LENGTH: 950
<212> TYPE: DNA
<213> ORGANISM: Homo sapiens

<400> SEQUENCE: 162
aagcggatgg acctgagtca gccgaatcct agccccttcc cttgggcctg ctgtggtgct 60
cgacatcagt gacagacgga agcagcagac catcaaggct acgggaggcc cggggcgctt 120
gcgaagatga agtttggctg cctctccttc cggcagcctt atgctggctt tgtcttaaat 180
ggaatcaaga ctgtggagac gcgctggcgt cctctgctga gcagccagcg gaactgtacc 240
atcgccgtcc acattgctca cagggactgg gaaggcgatg cctgtcggga gctgctggtg 300
gagagactcg ggatgactcc tgctcagatt caggccttgc tcaggaaagg ggaaaagttt 360
ggtcgaggag tgatagcggg actcgttgac attggggaaa ctttgcaatg ccccgaagac 420
ttaactcccg atgaggttgt ggaactagaa aatcaagctg cactgaccaa cctgaagcag 480
aagtacctga ctgtgatttc aaaccccagg tggttactgg agcccatacc taggaaagga 540
ggcaaggatg tattccaggt agacatccca gagcacctga tccctttggg gcatgaagtg 600

-continued

```
tgacaagtgt gggctcctga aaggaatgtt ccrgagaaac cagctaaatc atggcacctt    660

caatttgcca tcgtgacgca gacctgtata aattaggtta aagatgaatt tccactgctt    720

tggagagtcc cacccactaa gcactgtgca tgtaaacagg ttcctttgct cagatgaagg    780

aagtaggggg tggggctttc cttgtgtgat gcctccttag gcacacaggc aatgtctcaa    840

gtactttgac cttagggtag aaggcaaagc tgccagtaaa tgtctcagca ttgctgctaa    900

ttttggtcct gctagtttct ggattgtaca aataaatgtg ttgtagatga               950


<210> SEQ ID NO 163
<211> LENGTH: 475
<212> TYPE: DNA
<213> ORGANISM: Homo sapiens
<220> FEATURE:
<221> NAME/KEY: modified_base
<222> LOCATION: (301)
<223> OTHER INFORMATION: Where n is a, c, g or t
<221> NAME/KEY: modified_base
<222> LOCATION: (317)
<223> OTHER INFORMATION: Where n is a, c, g or t
<221> NAME/KEY: modified_base
<222> LOCATION: (331)
<223> OTHER INFORMATION: Where n is a, c, g or t
<221> NAME/KEY: modified_base
<222> LOCATION: (458)
<223> OTHER INFORMATION: Where n is a, c, g or t
<221> NAME/KEY: modified_base
<222> LOCATION: (464)
<223> OTHER INFORMATION: Where n is a, c, g or t
<221> NAME/KEY: modified_base
<222> LOCATION: (470)
<223> OTHER INFORMATION: Where n is a, c, g or t

<400> SEQUENCE: 163

tcgagcggcc gcccgggcag gtgtcggagt ccagcacggg aggcgtggtc ttgtagttgt     60

tctccggctg cccattgctc tcccactcca cggcgatgtc gctgggatag aagcctttga    120

ccaggcaggt caggctgacc tggttcttgg tcatctcctc ccgggatggg ggcagggtgt    180

acacctgtgg ttctcggggc tgccctttgg ctttggagat ggttttctcg atgggggctg    240

ggagggcttt gttggagacc ttgcacttgt actccttgcc attcaaccag tcctggtgca    300

ngacggtgag gacgctnacc acacggtacg ngctggtgta ctgctcctcc cgcggctttg    360

tcttggcatt atgcacctcc acgccgtcca cgtaccaatt gaacttgacc tcagggtctt    420

cgtggctcac gtccaccacc acgcatgtaa cctcaaanct cggncgcgan cacgc         475


<210> SEQ ID NO 164
<211> LENGTH: 476
<212> TYPE: DNA
<213> ORGANISM: Homo sapiens

<400> SEQUENCE: 164

agcgtggtcg cggccgaggt ctgaggttac atgcgtggtg gtggacgtga gccacgaaga     60

ccctgaggtc aagttcaact ggtacgtgga cggcgtggag gtgcataatg ccaagacaaa    120

gccgcgggag gagcagtaca acagcacgta ccgtgtggtc agcgtcctca ccgtcctgca    180

ccaggactgg ctgaatggca aggagtacaa gtgcaaggtc tccaacaaag ccctcccagc    240

ccccatcgag aaaaccatct ccaaagccaa agggcagccc cgagaaccac aggtgtacac    300

cctgccccca tcccgggagg agatgaccaa gaaccaggtc agcctgacct gcctggtcaa    360

aggcttctat cccagcgaca tcgcccgtgg agtgggagag caatgggcag ccggagaaca    420

actacaagac cacgcctccc gtgctggact ccgacacctg ccgggcggcc gctcga         476
```

-continued

<210> SEQ ID NO 165
<211> LENGTH: 256
<212> TYPE: DNA
<213> ORGANISM: Homo sapiens
<220> FEATURE:
<221> NAME/KEY: modified_base
<222> LOCATION: (10)
<223> OTHER INFORMATION: Where n is a, c, g or t
<221> NAME/KEY: modified_base
<222> LOCATION: (37)
<223> OTHER INFORMATION: Where n is a, c, g or t
<221> NAME/KEY: modified_base
<222> LOCATION: (249)
<223> OTHER INFORMATION: Where n is a, c, g or t

<400> SEQUENCE: 165
agcgtggttn cggccgaggt cccaaccaag gctgcancct ggatgccatc aaagtcttct 60
gcaacatgga gactggtgag acctgcgtgt accccactca gcccagtgtg gcccagaaga 120
actggtacat cagcaagaac cccaaggaca agaggcatgt ctggttcggc gagagcatga 180
ccgatggatt ccagttcgag tatggcggcc agggctccga ccctgccgat gtggacctgc 240
ccgggcggnc gctcga 256

<210> SEQ ID NO 166
<211> LENGTH: 332
<212> TYPE: DNA
<213> ORGANISM: Homo sapiens

<400> SEQUENCE: 166
agcgtggtcg cggccgaggt caagaacccc gcccgcacct gccgtgacct caagatgtgc 60
cactctgact ggaagagtgg agagtactgg attgacccca accaaggctg caacctggat 120
gccatcaaag tcttctgcaa catggagact ggtgagacct gcgtgtaccc cactcagccc 180
agtgtggccc agaagaactg gtacatcagc aagaacccca aggacaagag gcatgtctgg 240
ttcggcgaga gcatgaccga tggattccag ttcgagtatg gcggccaggg ctccgaccct 300
gccgatgtgg acctgcccgg gcggccgctc ga 332

<210> SEQ ID NO 167
<211> LENGTH: 332
<212> TYPE: DNA
<213> ORGANISM: Homo sapiens
<220> FEATURE:
<221> NAME/KEY: modified_base
<222> LOCATION: (77)
<223> OTHER INFORMATION: Where n is a, c, g or t
<221> NAME/KEY: modified_base
<222> LOCATION: (109)
<223> OTHER INFORMATION: Where n is a, c, g or t
<221> NAME/KEY: modified_base
<222> LOCATION: (136)
<223> OTHER INFORMATION: Where n is a, c, g or t
<221> NAME/KEY: modified_base
<222> LOCATION: (184)
<223> OTHER INFORMATION: Where n is a, c, g or t
<221> NAME/KEY: modified_base
<222> LOCATION: (198)
<223> OTHER INFORMATION: Where n is a, c, g or t

<400> SEQUENCE: 167
tcgagcggtc gcccgggcag gtccacatcg gcagggtcgg agccctggcc gccatactcg 60
aactggaatc catcggncat gctctcgccg aaccagacat gcctcttgnc cttggggttc 120
ttgctgatgt accagntctt ctgggccaca ctgggctgag tggggtacac gcaggtctca 180

-continued ccantctcca tgttgcanaa gactttgatg gcatccaggt tgcagccttg gttggggtca 240
atccagtact ctccactctt ccagacagag tggcacatct tgaggtcacg gcaggtgcgg 300
gcggggttct tgacctcggt cgcgaccacg ct 332

<210> SEQ ID NO 168
<211> LENGTH: 276
<212> TYPE: DNA
<213> ORGANISM: Homo sapiens
<220> FEATURE:
<221> NAME/KEY: modified_base
<222> LOCATION: (72)
<223> OTHER INFORMATION: Where n is a, c, g or t
<221> NAME/KEY: modified_base
<222> LOCATION: (84)
<223> OTHER INFORMATION: Where n is a, c, g or t

<400> SEQUENCE: 168
tcgagcggcc gcccgggcag gtcctcctca gagcggtagc tgttcttatt gccccggcag 60
cctccataga tnaagttatt gcangagttc ctctccacgt caaagtacca gcgtgggaag 120
gatgcacggc aaggcccagt gactgcgttg gcggtgcagt attcttcata gttgaacata 180
tcgctggagt ggacttcaga atcctgcctt ctgggagcac ttgggacaga ggaatccgct 240
gcattcctgc tggtggacct cggccgcgac cacgct 276

<210> SEQ ID NO 169
<211> LENGTH: 276
<212> TYPE: DNA
<213> ORGANISM: Homo sapiens

<400> SEQUENCE: 169
agcgtggtcg cggccgaggt ccaccagcag gaatgcagcg gattcctctg tcccaagtgc 60
tcccagaagg caggattctg aagaccactc cagcgatatg ttcaactatg aagaatactg 120
caccgccaac gcagtcactg ggccttgccg tgcatccttc ccacgctggt actttgacgt 180
ggagaggaac tcctgcaata acttcatcta tggaggctgc cggggcaata agaacagcta 240
ccgctctgag gaggacctgc ccgggcggcc gctcga 276

<210> SEQ ID NO 170
<211> LENGTH: 332
<212> TYPE: DNA
<213> ORGANISM: Homo sapiens
<220> FEATURE:
<221> NAME/KEY: modified_base
<222> LOCATION: (294)
<223> OTHER INFORMATION: Where n is a, c, g or t

<400> SEQUENCE: 170
tcgagcggcc gcccgggcag gtccacatcg gcagggtcgg agccctggcc gccatactcg 60
aactggaatc catcggtcat gctctcgccg aaccagacat gcctcttgtc cttggggttc 120
ttgctgatgt accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagccagaa tggcacatct tgaggtcacg gcangtgcgg 300
gcggggttct tgacctcggc cgcgaccacg ct 332

<210> SEQ ID NO 171
<211> LENGTH: 333
<212> TYPE: DNA
<213> ORGANISM: Homo sapiens -continued

<400> SEQUENCE: 171
agcgtggtcg cggccgaggt caagaaaccc cgcccgcacc tgccgtgacc tcaagatgtg 60
ccactctggc tggaagagtg gagagtactg gattgacccc aaccaaggct gcaacctgga 120
tgccatcaaa gtcttctgca acatggagac tggtgagacc tgcgtgtacc ccactcagcc 180
cagtgtggcc cagaagaact ggtacatcag caagaacccc aaggacaaga ggcatgtctg 240
gctcggcgag agcatgaccg atggattcca gttcgagtat ggcggccagg gctccgaccc 300
tgccgatgtg gacctgcccg ggcggccgct cga 333

<210> SEQ ID NO 172
<211> LENGTH: 527
<212> TYPE: DNA
<213> ORGANISM: Homo sapiens
<220> FEATURE:
<221> NAME/KEY: modified_base
<222> LOCATION: (46)
<223> OTHER INFORMATION: Where n is a, c, g or t
<221> NAME/KEY: modified_base
<222> LOCATION: (125)
<223> OTHER INFORMATION: Where n is a, c, g or t
<221> NAME/KEY: modified_base
<222> LOCATION: (140)
<223> OTHER INFORMATION: Where n is a, c, g or t
<221> NAME/KEY: modified_base
<222> LOCATION: (148)
<223> OTHER INFORMATION: Where n is a, c, g or t
<221> NAME/KEY: modified_base
<222> LOCATION: (220)
<223> OTHER INFORMATION: Where n is a, c, g or t
<221> NAME/KEY: modified_base
<222> LOCATION: (229)
<223> OTHER INFORMATION: Where n is a, c, g or t
<221> NAME/KEY: modified_base
<222> LOCATION: (291)
<223> OTHER INFORMATION: Where n is a, c, g or t
<221> NAME/KEY: modified_base
<222> LOCATION: (388)
<223> OTHER INFORMATION: Where n is a, c, g or t
<221> NAME/KEY: modified_base
<222> LOCATION: (456)
<223> OTHER INFORMATION: Where n is a, c, g or t

<400> SEQUENCE: 172
agcgtggtcg cggccgaggt cctgtcagag tggcactggt agaagntcca ggaaccctga 60
actgtaaggg ttcttcatca gtgccaacag gatgacatga aatgatgtac tcagaagtgt 120
cctgnaatgg ggcccatgan atggttgnct gagagagagc ttcttgtcct acattcggcg 180
ggtatggtct tggcctatgc cttatggggg tggccgttgn gggcggtgng gtccgcctaa 240
aaccatgttc ctcaaagatc atttgttgcc caacactggg ttgctgacca naagtgccag 300
gaagctgaat accatttcca gtgtcatacc cagggtgggt gacgaaaggg gtcttttgaa 360
ctgtggaagg aacatccaag atctctgntc catgaagatt ggggtgtgga agggttacca 420
gttggggaag ctcgctgtct ttttccttcc aatcangggc tcgctcttct gaatattctt 480
cagggcaatg acataaattg tatattcggt tcccggttcc aggccag 527

<210> SEQ ID NO 173
<211> LENGTH: 635
<212> TYPE: DNA
<213> ORGANISM: Homo sapiens
<220> FEATURE:
<221> NAME/KEY: modified_base
<222> LOCATION: (444)
<223> OTHER INFORMATION: Where n is a, c, g or t
<221> NAME/KEY: modified_base
<222> LOCATION: (453)

-continued

<223> OTHER INFORMATION: Where n is a, c, g or t
<221> NAME/KEY: modified_base
<222> LOCATION: (517)
<223> OTHER INFORMATION: Where n is a, c, g or t
<221> NAME/KEY: modified_base
<222> LOCATION: (540)
<223> OTHER INFORMATION: Where n is a, c, g or t
<221> NAME/KEY: modified_base
<222> LOCATION: (546)
<223> OTHER INFORMATION: Where n is a, c, g or t
<221> NAME/KEY: modified_base
<222> LOCATION: (551)
<223> OTHER INFORMATION: Where n is a, c, g or t
<221> NAME/KEY: modified_base
<222> LOCATION: (573)
<223> OTHER INFORMATION: Where n is a, c, g or t
<221> NAME/KEY: modified_base
<222> LOCATION: (593)
<223> OTHER INFORMATION: Where n is a, c, g or t

<400> SEQUENCE: 173

```
tcgagcggcc gcccgggcag gtccaccaca cccaattcct tgctggtatc atggcagccg     60

ccacgtgcca ggattaccgg ctacatcatc aagtatgaga agcctgggtc tcctcccaga    120

gaagtggtcc ctcggccccg ccctggtgtc acagaggcta ctattactgg cctggaaccg    180

ggaaccgaat atacaattta tgtcattgcc ctgaagaata atcagaagag cgagcccctg    240

attggaagga aaaagacaga cgagcttccc caactggtaa cccttccaca ccccaatctt    300

catggaccag agatcttgga tgttccttcc acagttcaaa agaccccttt cgtcacccac    360

cctgggtatg acactggaaa tggtattcag cttcctggca cttctggtca gcaacccagt    420

gttgggcaac aaatgatctt tgangaacat ggntttaggc ggaccacacc ggccacaacg    480

ggcacccccca taaggcatag gccaagaaca tacccgncga atgtaggaca agaagctctn    540

tctcanacaa ncatctcatg ggccccattc cangacactt ctgagtacat canttcatgg    600

catcctggtg gcactgataa aaacccttac agtta                               635
```

<210> SEQ ID NO 174
<211> LENGTH: 572
<212> TYPE: DNA
<213> ORGANISM: Homo sapiens
<220> FEATURE:
<221> NAME/KEY: modified_base
<222> LOCATION: (457)
<223> OTHER INFORMATION: Where n is a, c, g or t
<221> NAME/KEY: modified_base
<222> LOCATION: (511)
<223> OTHER INFORMATION: Where n is a, c, g or t
<221> NAME/KEY: modified_base
<222> LOCATION: (520)
<223> OTHER INFORMATION: Where n is a, c, g or t
<221> NAME/KEY: modified_base
<222> LOCATION: (552)
<223> OTHER INFORMATION: Where n is a, c, g or t
<221> NAME/KEY: modified_base
<222> LOCATION: (568)
<223> OTHER INFORMATION: Where n is a, c, g or t

<400> SEQUENCE: 174

```
agcgtggtcg cgggcgaggt cctgtcagag tggcactggt agaagttcca ggaaccctga     60

actgtaaggg ttcttcatca gtgccaacag gatgacatga aatgatgtac tcagaagtgt    120

cctggaatgg ggcccatgag atggttgtct gagagagagc ttcttgtcct acattcggcg    180

ggtatggtct tggcctatgc cttatggggg tggccgttgt gggcggtgtg gtccgcctaa    240

aaccatgttc ctcaaagatc atttgttgcc caacactggg ttgctgacca gaagtgccag    300

gaagctgaat accatttcca gtgtcatacc cagggtgggt gacgaaaggg gtcttttgaa    360
```

-continued ctgtggaagg aacatccaag atctctggtc catgaagatt ggggtgtgga agggttacca 420
gttggggaag ctcgtctgtc tttttccttc caatcanggg ctcgctcttc tgattattct 480
tcagggcaat gacataaatt gtatattcgg ntcccgggtn cagccaataa taataaccct 540
ctgtgacacc anggcggggc cgaagganca ct 572

<210> SEQ ID NO 175
<211> LENGTH: 372
<212> TYPE: DNA
<213> ORGANISM: Homo sapiens
<220> FEATURE:
<221> NAME/KEY: modified_base
<222> LOCATION: (247)
<223> OTHER INFORMATION: Where n is a, c, g or t

<400> SEQUENCE: 175
agcgtggtcg cggccgaggt cctcaccaga ggtaccacct acaacatcat agtggaggca 60
ctgaaagacc agcagaggca taaggttcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttangct ttggaagtgg tcatttcaga tgtgattcat ctagatggtg ccatgacaat 300
ggtgtgaact acaagattgg agagaagtgg gaccgtcagg gagaaaatgg acctgcccgg 360
gcggccgctc ga 372

<210> SEQ ID NO 176
<211> LENGTH: 372
<212> TYPE: DNA
<213> ORGANISM: Homo sapiens
<220> FEATURE:
<221> NAME/KEY: modified_base
<222> LOCATION: (251)
<223> OTHER INFORMATION: Where n is a, c, g or t

<400> SEQUENCE: 176
tcgagcggcc gcccgggcag gtccattttc tccctgacgg tcccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ntgacagagt tgcccacggt aacaacctct tcccgaacct tatgcctctg 300
ctggtctttc agtgcctcca ctatgatgtt gtaggtggta cctctggtga ggacctcggc 360
cgcgaccacg ct 372

<210> SEQ ID NO 177
<211> LENGTH: 269
<212> TYPE: DNA
<213> ORGANISM: Homo sapiens
<220> FEATURE:
<221> NAME/KEY: modified_base
<222> LOCATION: (94)
<223> OTHER INFORMATION: Where n is a, c, g or t
<221> NAME/KEY: modified_base
<222> LOCATION: (225)
<223> OTHER INFORMATION: Where n is a, c, g or t

<400> SEQUENCE: 177
agcgtggccg cggccgaggt ccattggctg gaacggcatc aacttggaag ccagtgatcg 60
tctcagcctt ggttctccag ctaatggtga tggnggtctc agtagcatct gtcacacgag 120

-continued

```
cccttcttgg tgggctgaca ttctccagag tggtgacaac accctgagct ggtctgcttg    180

tcaaagtgtc cttaagagca tagacactca cttcatattt ggcgnccacc ataagtcctg    240

atacaaccac ggaatgacct gtcaggaac                                      269


<210> SEQ ID NO 178
<211> LENGTH: 529
<212> TYPE: DNA
<213> ORGANISM: Homo sapiens

<400> SEQUENCE: 178

tcgagcggcc gcccgggcag gtcctcagac cgggttctga gtacacagtc agtgtggttg     60

ccttgcacga tgatatggag agccagcccc tgattggaac ccagtccaca gctattcctg    120

caccaactga cctgaagttc actcaggtca cacccacaag cctgagcgcc cagtggacac    180

cacccaatgt tcagctcact ggatatcgag tgcgggtgac ccccaaggag aagaccggac    240

caatgaaaga aatcaacctt gctcctgaca gctcatccgt ggttgtatca ggacttatgg    300

cggccaccaa atatgaagtg agtgtctatg ctcttaagga cactttgaca agcagaccag    360

ctcagggtgt tgtcaccact ctggagaatg tcagcccacc aagaagggct cgtgtgacag    420

atgctactga gaccaccatc accattagct ggagaaccaa gactgagacg atcactggct    480

tccaagttga tgccgttcca gccaatggac ctcggccgcg accacgctt                529


<210> SEQ ID NO 179
<211> LENGTH: 454
<212> TYPE: DNA
<213> ORGANISM: Homo sapiens
<220> FEATURE:
<221> NAME/KEY: modified_base
<222> LOCATION: (64)
<223> OTHER INFORMATION: Where n is a, c, g or t

<400> SEQUENCE: 179

agcgtggtcg cggccgaggt ctggccgaac tgccagtgta cagggaagat gtacatgtta     60

tagntcttct cgaagtcccg ggccagcagc tccacggggt ggtctcctgc ctccaggcgc    120

ttctcattct catggatctt cttcacccgc agcttctgct tctcagtcag aaggttgttg    180

tcctcatccc tctcatacag ggtgaccagg acgttcttga gccagtcccg catgcgcagg    240

gggaattcgg tcagctcaga gtccaggcaa ggggggatgt atttgcaagg cccgatgtag    300

tccaagtgga gcttgtggcc cttcttggtg ccctccaagg tgcactttgt ggcaaagaag    360

tggcaggaag agtcgaaggt cttgttgtca ttgctgcaca ccttctcaaa ctcgccaatg    420

ggggctgggc agacctgccc gggcggccgc tcga                                454


<210> SEQ ID NO 180
<211> LENGTH: 454
<212> TYPE: DNA
<213> ORGANISM: Homo sapiens
<220> FEATURE:
<221> NAME/KEY: modified_base
<222> LOCATION: (55)
<223> OTHER INFORMATION: Where n is a, c, g or t
<221> NAME/KEY: modified_base
<222> LOCATION: (299)
<223> OTHER INFORMATION: Where n is a, c, g or t
<221> NAME/KEY: modified_base
<222> LOCATION: (317)
<223> OTHER INFORMATION: Where n is a, c, g or t
<221> NAME/KEY: modified_base
<222> LOCATION: (332)
<223> OTHER INFORMATION: Where n is a, c, g or t
```

-continued

```
<221> NAME/KEY: modified_base
<222> LOCATION: (342)
<223> OTHER INFORMATION: Where n is a, c, g or t
<221> NAME/KEY: modified_base
<222> LOCATION: (348)
<223> OTHER INFORMATION: Where n is a, c, g or t

<400> SEQUENCE: 180

tcgagcggcc gcccgggcag gtctgcccag cccccattgg cgagtttgag aaggngtgca     60

gcaatgacaa caagaccttc gactcttcct gccacttctt tgccacaaag tgcaccctgg    120

agggcaccaa gaagggccac aagctccacc tggactacat cgggccttgc aaatacatcc    180

ccccttgcct ggactctgag ctgaccgaat tccccctgcg catgcgggac tggctcaaga    240

acgtcctggt caccctgtat gagagggatg aggacaacaa ccttctgact gagaagcana    300

agctgcgggt gaagaanatc catgagaatg anaagcgcct gnaggcanga gaccaccccg    360

tggagctgct ggcccgggac ttcgagaaga actataacat gtacatcttc cctgtacact    420

ggcagttcgg ccagacctcg gccgcgacca cgct                                454


<210> SEQ ID NO 181
<211> LENGTH: 102
<212> TYPE: DNA
<213> ORGANISM: Homo sapiens
<220> FEATURE:
<221> NAME/KEY: modified_base
<222> LOCATION: (8)
<223> OTHER INFORMATION: Where n is a, c, g or t
<221> NAME/KEY: modified_base
<222> LOCATION: (47)
<223> OTHER INFORMATION: Where n is a, c, g or t
<221> NAME/KEY: modified_base
<222> LOCATION: (60)
<223> OTHER INFORMATION: Where n is a, c, g or t
<221> NAME/KEY: modified_base
<222> LOCATION: (67)
<223> OTHER INFORMATION: Where n is a, c, g or t

<400> SEQUENCE: 181

agcgtggntg cggacgacgc ccacaaagcc attgtatgta gttttanttc agctgcaaan     60

aataccncca gcatccacct tactaaccag catatgcaga ca                       102


<210> SEQ ID NO 182
<211> LENGTH: 337
<212> TYPE: DNA
<213> ORGANISM: Homo sapiens
<220> FEATURE:
<221> NAME/KEY: modified_base
<222> LOCATION: (169)
<223> OTHER INFORMATION: Where n is a, c, g or t
<221> NAME/KEY: modified_base
<222> LOCATION: (195)
<223> OTHER INFORMATION: Where n is a, c, g or t
<221> NAME/KEY: modified_base
<222> LOCATION: (253)
<223> OTHER INFORMATION: Where n is a, c, g or t
<221> NAME/KEY: modified_base
<222> LOCATION: (314)
<223> OTHER INFORMATION: Where n is a, c, g or t

<400> SEQUENCE: 182

tcgagcggtc gcccgggcag gtctgggcgg atagcaccgg gcatattttg gaatggatga     60

ggtctggcac cctgagcagc ccagcgagga cttggtctta gttgagcaat ttggctagga    120

ggatagtatg cagcacggtt ctgagtctgt gggatagctg ccatgaagna acctgaagga    180

ggcgctggct ggtangggtt gattacaggg ctgggaacag ctcgtacact tgccattctc    240
```

-continued

```
tgcatatact ggntagtgag gcgagcctgg cgctcttctt tgcgctgagc taaagctaca    300

tacaatggct ttgnggacct cggccgcgac cacgctt                             337


<210> SEQ ID NO 183
<211> LENGTH: 374
<212> TYPE: DNA
<213> ORGANISM: Homo sapiens

<400> SEQUENCE: 183

tcgagcggcc gcccgggcag gtccattttc tccctgacgg tcccacttct ctccaatctt     60

gtagttcaca ccattgtcat gacaccatct agatgaatca catctgaaat gaccacttcc    120

aaagcctaag cactggcaca acagtttaaa gcctgattca gacattcgtt cccactcatc    180

tccaacggca taatgggaaa ctgtgtaggg gtcaaagcac gagtcatccg taggttggtt    240

caagccttcg ttgacagaag ttgcccacgg taacaacctc ttcccgaacc ttatgcctct    300

gctggtcttt caagtgcctc cactatgatg ttgtaggtgg cacctctggt gaggacctcg    360

gccgcgacca cgct                                                      374


<210> SEQ ID NO 184
<211> LENGTH: 375
<212> TYPE: DNA
<213> ORGANISM: Homo sapiens
<220> FEATURE:
<221> NAME/KEY: modified_base
<222> LOCATION: (30)
<223> OTHER INFORMATION: Where n is a, c, g or t
<221> NAME/KEY: modified_base
<222> LOCATION: (174)
<223> OTHER INFORMATION: Where n is a, c, g or t
<221> NAME/KEY: modified_base
<222> LOCATION: (248)
<223> OTHER INFORMATION: Where n is a, c, g or t
<221> NAME/KEY: modified_base
<222> LOCATION: (285)
<223> OTHER INFORMATION: Where n is a, c, g or t
<221> NAME/KEY: modified_base
<222> LOCATION: (306)
<223> OTHER INFORMATION: Where n is a, c, g or t
<221> NAME/KEY: modified_base
<222> LOCATION: (332)
<223> OTHER INFORMATION: Where n is a, c, g or t
<221> NAME/KEY: modified_base
<222> LOCATION: (345)
<223> OTHER INFORMATION: Where n is a, c, g or t
<221> NAME/KEY: modified_base
<222> LOCATION: (368)
<223> OTHER INFORMATION: Where n is a, c, g or t

<400> SEQUENCE: 184

agcgtggttt gcggccgagg tcctcaccan aggtgccacc tacaacatca tagtggaggc     60

actgaaagac cagcagaggc ataaggttcg ggaagaggtt gttaccgtgg gcaactctgt    120

caacgaaggc ttgaaccaac ctacggatga ctcgtgcttt gacccctaca cagnttccca    180

ttatgccgtt ggagatgagt gggaacgaat gtctgaatca ggctttaaac tgttgtgcca    240

gtgcttangc tttggaagtg gtcatttcag atgtgattca tctanatggt gtcatgacaa    300

tggtgngaac tacaagattg gagagaagtg gnaccgtcag gggananaaat ggacctgccc    360

gggcggcncg ctcga                                                     375


<210> SEQ ID NO 185
<211> LENGTH: 148
<212> TYPE: DNA
<213> ORGANISM: Homo sapiens
<220> FEATURE:
```

-continued

<221> NAME/KEY: modified_base
<222> LOCATION: (28)
<223> OTHER INFORMATION: Where n is a, c, g or t
<221> NAME/KEY: modified_base
<222> LOCATION: (36)
<223> OTHER INFORMATION: Where n is a, c, g or t
<221> NAME/KEY: modified_base
<222> LOCATION: (86)
<223> OTHER INFORMATION: Where n is a, c, g or t

<400> SEQUENCE: 185
agcgtggtcg cggccgaggt ctggcttnct gctcangtga ttatcctgaa ccatccaggc 60
caaataagcg ccggctatgc ccctgnattg gattgccaca cggctcacat tgcatgcaag 120
tttgctgagc tgaaggaaaa gattgatc 148

<210> SEQ ID NO 186
<211> LENGTH: 397
<212> TYPE: DNA
<213> ORGANISM: Homo sapiens
<220> FEATURE:
<221> NAME/KEY: modified_base
<222> LOCATION: (78)
<223> OTHER INFORMATION: Where n is a, c, g or t

<400> SEQUENCE: 186
tcgagcggcc gcccgggcag gtccaattga aacaaacagt tctgagaccg ttcttccacc 60
actgattaag agtggggngg cgggtattag ggataatatt catttagcct tctgagcttt 120
ctgggcagac ttggtgacct tgccagctcc agcagccttc tggtccactg ctttgatgac 180
acccaccgca actgtctgtc tcatatcacg aacagcaaag cgacccaaag gtggatagtc 240
tgagaagctc tcaacacaca tgggcttgcc aggaaccata tcaacaatgg gcagcatcac 300
cagacttcaa gaatttaagg gccatcttcc agctttttac cagaacggcg atcaatcttt 360
tccttcagct cagcaaactt gcatgcaatg tgagccg 397

<210> SEQ ID NO 187
<211> LENGTH: 584
<212> TYPE: DNA
<213> ORGANISM: Homo sapiens
<220> FEATURE:
<221> NAME/KEY: modified_base
<222> LOCATION: (145)
<223> OTHER INFORMATION: Where n is a, c, g or t
<221> NAME/KEY: modified_base
<222> LOCATION: (286)
<223> OTHER INFORMATION: Where n is a, c, g or t
<221> NAME/KEY: modified_base
<222> LOCATION: (363)
<223> OTHER INFORMATION: Where n is a, c, g or t
<221> NAME/KEY: modified_base
<222> LOCATION: (365)
<223> OTHER INFORMATION: Where n is a, c, g or t
<221> NAME/KEY: modified_base
<222> LOCATION: (425)
<223> OTHER INFORMATION: Where n is a, c, g or t
<221> NAME/KEY: modified_base
<222> LOCATION: (433)
<223> OTHER INFORMATION: Where n is a, c, g or t
<221> NAME/KEY: modified_base
<222> LOCATION: (452)
<223> OTHER INFORMATION: Where n is a, c, g or t
<221> NAME/KEY: modified_base
<222> LOCATION: (462)
<223> OTHER INFORMATION: Where n is a, c, g or t
<221> NAME/KEY: modified_base
<222> LOCATION: (471)
<223> OTHER INFORMATION: Where n is a, c, g or t
<221> NAME/KEY: modified_base
<222> LOCATION: (512)

-continued

<223> OTHER INFORMATION: Where n is a, c, g or t
<221> NAME/KEY: modified_base
<222> LOCATION: (514)
<223> OTHER INFORMATION: Where n is a, c, g or t
<221> NAME/KEY: modified_base
<222> LOCATION: (534)
<223> OTHER INFORMATION: Where n is a, c, g or t
<221> NAME/KEY: modified_base
<222> LOCATION: (536)
<223> OTHER INFORMATION: Where n is a, c, g or t
<221> NAME/KEY: modified_base
<222> LOCATION: (540)
<223> OTHER INFORMATION: Where n is a, c, g or t
<221> NAME/KEY: modified_base
<222> LOCATION: (565)
<223> OTHER INFORMATION: Where n is a, c, g or t
<221> NAME/KEY: modified_base
<222> LOCATION: (583)
<223> OTHER INFORMATION: Where n is a, c, g or t

<400> SEQUENCE: 187
tcgagcggcc gcccgggcag gtccagaggg ctgtgctgaa gtttgctgct gccactggag 60
ccactccaat tgctggccgc ttcactcctg gaaccttcac taaccagatc caggcagcct 120
tccgggagcc acggcttctt gtggntactg accccagggc tgaccaccag cctctcacgg 180
aggcatctta tgttaaccta cctaccattg cgctgtgtaa cacagattct cctctgcgct 240
atgtggacat tgccatccca tgcaacaaca agggagctca ctcagngggg tttgatgtgg 300
tggatgctgg ctcgggaagt tctgcgcatg cgtggcacca tttcccgtga acacccatgg 360
gangncatgc ctgatctgga cttctacaga gatcctgaag agattgaaaa agaagaacag 420
gctgnttgct ganaaagcaa gtgaccaagg angaaatttc angggtgaaa nggactgctc 480
ccgctcctga attcactgct actcaacctg angntgcaga ctggtcttga aggngnacan 540
gggccctctg ggcctattta agcancttcg gtcgcgaaca cgnt 584

<210> SEQ ID NO 188
<211> LENGTH: 579
<212> TYPE: DNA
<213> ORGANISM: Homo sapiens
<220> FEATURE:
<221> NAME/KEY: modified_base
<222> LOCATION: (7)
<223> OTHER INFORMATION: Where n is a, c, g or t
<221> NAME/KEY: modified_base
<222> LOCATION: (136)
<223> OTHER INFORMATION: Where n is a, c, g or t
<221> NAME/KEY: modified_base
<222> LOCATION: (486)
<223> OTHER INFORMATION: Where n is a, c, g or t

<400> SEQUENCE: 188
agcgtgngtc gcggccgagg tgctgaatag gcacagaggg cacctgtaca ccttcagacc 60
agtctgcaac ctcaggctga gtagcagtga actcaggagc gggagcagtc cattcaccct 120
gaaattcctc cttggncact gccttctcag cagcagcctg ctcttctttt tcaatctctt 180
caggatctct gtagaagtac agatcaggca tgacctccca tgggtgttca cgggaaatgg 240
tgccacgcat gcgcagaact tcccgagcca gcatccacca catcaaaccc actgagtgag 300
ctcccttgtt gttgcatggg atgggcaatg tccacatagc gcagaggaga atctgtgtta 360
cacagcgcaa tggtaggtag gttaacataa gatgcctccg cgagaagctg gtggtcagcc 420
ctggggtcaa gtaaccacaa gaagccgtgg ctcccggaag gctgcctgga tctggttagt 480
gaaggntcca ggagtgaagc ggccaacaat tggagtggct tcagtggcaa gcagcaaact 540
tcagcacaag ccctctggac ctgcccggcg gccgctcga 579

<210> SEQ ID NO 189
<211> LENGTH: 374
<212> TYPE: DNA
<213> ORGANISM: Homo sapiens
<220> FEATURE:
<221> NAME/KEY: modified_base
<222> LOCATION: (41)
<223> OTHER INFORMATION: Where n is a, c, g or t
<221> NAME/KEY: modified_base
<222> LOCATION: (280)
<223> OTHER INFORMATION: Where n is a, c, g or t
<221> NAME/KEY: modified_base
<222> LOCATION: (314)
<223> OTHER INFORMATION: Where n is a, c, g or t
<221> NAME/KEY: modified_base
<222> LOCATION: (330)
<223> OTHER INFORMATION: Where n is a, c, g or t
<221> NAME/KEY: modified_base
<222> LOCATION: (350)
<223> OTHER INFORMATION: Where n is a, c, g or t
<221> NAME/KEY: modified_base
<222> LOCATION: (353)
<223> OTHER INFORMATION: Where n is a, c, g or t

<400> SEQUENCE: 189
tcgagcggcc gcccgggcag gtccattttc tccctgacgg ncccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ttgacagagt tgcccacggt aacaacctcn tccccgaacc ttatgcctct 300
gctgggcttt cagngcctcc actatgatgn tgtagggggg cacctctggn gangacctcg 360
gccgcgacca cgct 374

<210> SEQ ID NO 190
<211> LENGTH: 373
<212> TYPE: DNA
<213> ORGANISM: Homo sapiens
<220> FEATURE:
<221> NAME/KEY: modified_base
<222> LOCATION: (247)
<223> OTHER INFORMATION: Where n is a, c, g or t
<221> NAME/KEY: modified_base
<222> LOCATION: (304)
<223> OTHER INFORMATION: Where n is a, c, g or t
<221> NAME/KEY: modified_base
<222> LOCATION: (306)
<223> OTHER INFORMATION: Where n is a, c, g or t
<221> NAME/KEY: modified_base
<222> LOCATION: (332)
<223> OTHER INFORMATION: Where n is a, c, g or t
<221> NAME/KEY: modified_base
<222> LOCATION: (337)
<223> OTHER INFORMATION: Where n is a, c, g or t

<400> SEQUENCE: 190
agcgtggtcg cggccgaggt cctcaccaga ggtgccacct acaacatcat agtggaggca 60
ctgaaagacc agcagaggca taaggctcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttangct ttggaagtgg gtcatttcag atgtgattca tctagatggt gccatgacaa 300
tggngngaac tacaagattg gagagaagtg gnaccgncag ggagaaaatg gacctgcccg 360
ggcggccgct cga 373

-continued

<210> SEQ ID NO 191
<211> LENGTH: 354
<212> TYPE: DNA
<213> ORGANISM: Homo sapiens
<220> FEATURE:
<221> NAME/KEY: modified_base
<222> LOCATION: (218)
<223> OTHER INFORMATION: Where n is a, c, g or t
<221> NAME/KEY: modified_base
<222> LOCATION: (299)
<223> OTHER INFORMATION: Where n is a, c, g or t
<221> NAME/KEY: modified_base
<222> LOCATION: (306)
<223> OTHER INFORMATION: Where n is a, c, g or t
<221> NAME/KEY: modified_base
<222> LOCATION: (326)
<223> OTHER INFORMATION: Where n is a, c, g or t
<221> NAME/KEY: modified_base
<222> LOCATION: (333)
<223> OTHER INFORMATION: Where n is a, c, g or t
<221> NAME/KEY: modified_base
<222> LOCATION: (337)
<223> OTHER INFORMATION: Where n is a, c, g or t
<221> NAME/KEY: modified_base
<222> LOCATION: (341)
<223> OTHER INFORMATION: Where n is a, c, g or t

<400> SEQUENCE: 191
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacacgc aggtctcacc 180
agtctccatg ttgcagaaga ctttgatggc atccaggntg caaccttggt tggggtcaat 240
ccagtactct ccactcttcc agccagagtg gcacatcttg aggtcacggc aggtgcggnc 300
gggggntttt gcggctgccc tctggncttc ggntgtnctc natctgctgg ctca 354

<210> SEQ ID NO 192
<211> LENGTH: 587
<212> TYPE: DNA
<213> ORGANISM: Homo sapiens
<220> FEATURE:
<221> NAME/KEY: modified_base
<222> LOCATION: (276)
<223> OTHER INFORMATION: Where n is a, c, g or t

<400> SEQUENCE: 192
tcgagcggcc gcccgggcag gtctcgcggt cgcactggtg atgctggtcc tgttggtccc 60
cccggccctc ctggacctcc tggccccccct ggtcctccca gcgctggttt cgacttcagc 120
ttcctgcccc agccacctca agagaaggct cacgatggtg gccgctacta ccgggctgat 180
gatgccaatg tggttcgtga ccgtgacctc gaggtggaca ccaccctcaa gagcctgagc 240
cagcagatcg agaacatccg gagcccagag ggcagncgca agaaccccgc ccgcacctgc 300
cgtgacctca agatgtgcca ctctgactgg aagagtggag agtactggat tgaccccaac 360
caagctgcaa cctggatgcc atcaaagtct tctgcaacat ggagactggt gagacctgcg 420
tgtaccccac tcagcccagt gtggcccaaa agaactggta catcagcaag aaccccaagg 480
acaagaagca tgtctggttc ggcgagaaca tgaccgatgg attccagttc gagtatggcg 540
ggcagggctc cgaccctgcc gatggggacc ttggccgcga acacgct 587

<210> SEQ ID NO 193
<211> LENGTH: 98
<212> TYPE: DNA

-continued

<213> ORGANISM: Homo sapiens
<220> FEATURE:
<221> NAME/KEY: modified_base
<222> LOCATION: (8)
<223> OTHER INFORMATION: Where n is a, c, g or t
<221> NAME/KEY: modified_base
<222> LOCATION: (9)
<223> OTHER INFORMATION: Where n is a, c, g or t
<221> NAME/KEY: modified_base
<222> LOCATION: (33)
<223> OTHER INFORMATION: Where n is a, c, g or t
<221> NAME/KEY: modified_base
<222> LOCATION: (58)
<223> OTHER INFORMATION: Where n is a, c, g or t
<221> NAME/KEY: modified_base
<222> LOCATION: (71)
<223> OTHER INFORMATION: Where n is a, c, g or t
<221> NAME/KEY: modified_base
<222> LOCATION: (90)
<223> OTHER INFORMATION: Where n is a, c, g or t

<400> SEQUENCE: 193
agcgtggnng cggccgaggt ataaatatcc agnccatatc ctccctccac acgctganag 60
atgaagctgt ncaaagatct cagggtggan aaaaccat 98

<210> SEQ ID NO 194
<211> LENGTH: 240
<212> TYPE: DNA
<213> ORGANISM: Homo sapiens

<400> SEQUENCE: 194
tcgagcggcc gcccgggcag gtccttcaga cttggactgt gtcacactgc caggcttcca 60
gggctccaac ttgcagacgg cctgttgtgg gacagtctct gtaatcgcga aagcaaccat 120
ggaagacctg ggggaaaaca ccatggtttt atccaccctg agatctttga acaacttcat 180
ctctcagcgt gcggagggag gctctggact ggatatttct acctcggccg cgaccacgct 240

<210> SEQ ID NO 195
<211> LENGTH: 400
<212> TYPE: DNA
<213> ORGANISM: Homo sapiens
<220> FEATURE:
<221> NAME/KEY: modified_base
<222> LOCATION: (22)
<223> OTHER INFORMATION: Where n is a, c, g or t
<221> NAME/KEY: modified_base
<222> LOCATION: (37)
<223> OTHER INFORMATION: Where n is a, c, g or t
<221> NAME/KEY: modified_base
<222> LOCATION: (39)
<223> OTHER INFORMATION: Where n is a, c, g or t
<221> NAME/KEY: modified_base
<222> LOCATION: (105)
<223> OTHER INFORMATION: Where n is a, c, g or t
<221> NAME/KEY: modified_base
<222> LOCATION: (268)
<223> OTHER INFORMATION: Where n is a, c, g or t
<221> NAME/KEY: modified_base
<222> LOCATION: (276)
<223> OTHER INFORMATION: Where n is a, c, g or t
<221> NAME/KEY: modified_base
<222> LOCATION: (302)
<223> OTHER INFORMATION: Where n is a, c, g or t
<221> NAME/KEY: modified_base
<222> LOCATION: (323)
<223> OTHER INFORMATION: Where n is a, c, g or t
<221> NAME/KEY: modified_base
<222> LOCATION: (331)
<223> OTHER INFORMATION: Where n is a, c, g or t
<221> NAME/KEY: modified_base
<222> LOCATION: (335)
<223> OTHER INFORMATION: Where n is a, c, g or t -continued
<221> NAME/KEY: modified_base
<222> LOCATION: (347)
<223> OTHER INFORMATION: Where n is a, c, g or t
<221> NAME/KEY: modified_base
<222> LOCATION: (351)
<223> OTHER INFORMATION: Where n is a, c, g or t
<221> NAME/KEY: modified_base
<222> LOCATION: (371)
<223> OTHER INFORMATION: Where n is a, c, g or t
<221> NAME/KEY: modified_base
<222> LOCATION: (378)
<223> OTHER INFORMATION: Where n is a, c, g or t

<400> SEQUENCE: 195
cgagcgggcg accgggcagg tncagactcc aatccanana accatcaagc cagatgtcag 60
aagctacacc atcacaggtt tacaaccagg cactgactac aaganctacc tgcacacctt 120
gaatgacaat gctcggagct cccctgtggt catcgacgcc tccactgcca ttgatgcacc 180
atccaacctg cgtttcctgg ccaccacacc caattccttg ctggtatcat ggcagccgcc 240
acgtgccagg attaccggta catcatcnag tatganaagc ctgggcctcc tcccagagaa 300
gnggtccctc ggccccgccc tgntgtccca naggntacta ttactgngcc ngcaaccggc 360
aaccgatatc nattttgnca ttggccttca acaataatta 400

<210> SEQ ID NO 196
<211> LENGTH: 494
<212> TYPE: DNA
<213> ORGANISM: Homo sapiens
<220> FEATURE:
<221> NAME/KEY: modified_base
<222> LOCATION: (19)
<223> OTHER INFORMATION: Where n is a, c, g or t
<221> NAME/KEY: modified_base
<222> LOCATION: (83)
<223> OTHER INFORMATION: Where n is a, c, g or t
<221> NAME/KEY: modified_base
<222> LOCATION: (168)
<223> OTHER INFORMATION: Where n is a, c, g or t
<221> NAME/KEY: modified_base
<222> LOCATION: (252)
<223> OTHER INFORMATION: Where n is a, c, g or t
<221> NAME/KEY: modified_base
<222> LOCATION: (271)
<223> OTHER INFORMATION: Where n is a, c, g or t
<221> NAME/KEY: modified_base
<222> LOCATION: (292)
<223> OTHER INFORMATION: Where n is a, c, g or t
<221> NAME/KEY: modified_base
<222> LOCATION: (430)
<223> OTHER INFORMATION: Where n is a, c, g or t

<400> SEQUENCE: 196
agcgtggttc gcggccgang tcctgtcaga gtggcactgg tagaagttcc aggaaccctg 60
aactgtaagg gttcttcatc agngccaaca ggatgacatg aaatgatgta ctcagaagtg 120
tcctggaatg gggcccatga gatggttgtc tgagagagag cttcttgncc tgtctttttc 180
cttccaatca ggggctcgct cttctgatta ttcttcaggg caatgacata aattgtatat 240
tcgggtcccg gntccaggcc agtaatagta ncctctgtga caccagggcg gngccgaggg 300
accacttctc tgggaggaga cccaggcttc tcatacttga tgatgtaacc ggtaatcctg 360
gcacgtggcg gctgccatga taccagcaag gaattggggt gtggtggcca ggaaacgcag 420
gttggatggn gcatcaatgg cagtggaggc cgtcgatgac cacaggggga gctccgacat 480
tgtcattcaa ggtg 494

<210> SEQ ID NO 197

-continued

<211> LENGTH: 118
<212> TYPE: DNA
<213> ORGANISM: Homo sapiens
<220> FEATURE:
<221> NAME/KEY: modified_base
<222> LOCATION: (8)
<223> OTHER INFORMATION: Where n is a, c, g or t
<221> NAME/KEY: modified_base
<222> LOCATION: (71)
<223> OTHER INFORMATION: Where n is a, c, g or t
<221> NAME/KEY: modified_base
<222> LOCATION: (96)
<223> OTHER INFORMATION: Where n is a, c, g or t

<400> SEQUENCE: 197
agcgtggncg cggccgaggt gcagcgcggg ctgtgccacc ttctgctctc tgcccaacga 60
taaggagggt ncctgccccc aggagaacat taactntccc cagctcggcc tctgccgg 118

<210> SEQ ID NO 198
<211> LENGTH: 403
<212> TYPE: DNA
<213> ORGANISM: Homo sapiens
<220> FEATURE:
<221> NAME/KEY: modified_base
<222> LOCATION: (41)
<223> OTHER INFORMATION: Where n is a, c, g or t
<221> NAME/KEY: modified_base
<222> LOCATION: (53)
<223> OTHER INFORMATION: Where n is a, c, g or t
<221> NAME/KEY: modified_base
<222> LOCATION: (98)
<223> OTHER INFORMATION: Where n is a, c, g or t
<221> NAME/KEY: modified_base
<222> LOCATION: (195)
<223> OTHER INFORMATION: Where n is a, c, g or t
<221> NAME/KEY: modified_base
<222> LOCATION: (350)
<223> OTHER INFORMATION: Where n is a, c, g or t

<400> SEQUENCE: 198
tcgagcggcc gcccgggcag gttttttttg ctgaaagtgg ntactttatt ggntgggaaa 60
gggagaagct gtggtcagcc caagagggaa tacagagncc cgaaaaaggg gagggcaggt 120
gggctggaac cagacgcagg gccaggcaga aactttctct cctcactgct cagcctggtg 180
gtggctggag ctcanaaatt gggagtgaca caggacacct tcccacagcc attgcggcgg 240
catttcatct ggccaggaca ctggctgtcc acctggcact ggtcccgaca gaagcccgag 300
ctggggaaag ttaatgttca cctgggggca ggaaccctcc ttatcattgn gcagagagca 360
gaaggtggca cagcccgcgc tgcacctcgg ccgcgaccac gct 403

<210> SEQ ID NO 199
<211> LENGTH: 167
<212> TYPE: DNA
<213> ORGANISM: Homo sapiens
<220> FEATURE:
<221> NAME/KEY: modified_base
<222> LOCATION: (92)
<223> OTHER INFORMATION: Where n is a, c, g or t
<221> NAME/KEY: modified_base
<222> LOCATION: (107)
<223> OTHER INFORMATION: Where n is a, c, g or t

<400> SEQUENCE: 199
tcgagcggcc gcccgggcag gtccaccata agtcctgata caaccacgga tgagctgtca 60
ggagcaaggt tgatttcttt cattggtccg gncttctcct tgggggncac ccgcactcga 120
tatccagtga gctgaacatt gggtggcgtc cactgggcgc tcaggct 167

-continued

<210> SEQ ID NO 200
<211> LENGTH: 252
<212> TYPE: DNA
<213> ORGANISM: Homo sapiens
<220> FEATURE:
<221> NAME/KEY: modified_base
<222> LOCATION: (210)
<223> OTHER INFORMATION: Where n is a, c, g or t
<221> NAME/KEY: modified_base
<222> LOCATION: (226)
<223> OTHER INFORMATION: Where n is a, c, g or t
<221> NAME/KEY: modified_base
<222> LOCATION: (227)
<223> OTHER INFORMATION: Where n is a, c, g or t
<221> NAME/KEY: modified_base
<222> LOCATION: (230)
<223> OTHER INFORMATION: Where n is a, c, g or t
<221> NAME/KEY: modified_base
<222> LOCATION: (236)
<223> OTHER INFORMATION: Where n is a, c, g or t

<400> SEQUENCE: 200
tcgagcggtt cgcccgggca ggtccaccac acccaattcc ttgctggtat catggcagcc 60
gccacgtgcc aggattaccg gctacatcat caagtatgag aagcctgggt ctcctcccag 120
agaagcggtc cctcggcccc gccctggtgt cacagaggct actattactg gcctggaacc 180
gggaaccgaa tatacaattt atgtcattgn cctgaagaat aatcannaan agcgancccc 240
tgattggaag ga 252

<210> SEQ ID NO 201
<211> LENGTH: 91
<212> TYPE: DNA
<213> ORGANISM: Homo sapiens

<400> SEQUENCE: 201
agcgtggtcg cggccgaggt tgtacaagct tttttttttt tttttttttt tttttttttt 60
tttttttttt tttttttttt tttttttttt t 91

<210> SEQ ID NO 202
<211> LENGTH: 368
<212> TYPE: DNA
<213> ORGANISM: Homo sapiens
<220> FEATURE:
<221> NAME/KEY: modified_base
<222> LOCATION: (9)
<223> OTHER INFORMATION: Where n is a, c, g or t
<221> NAME/KEY: modified_base
<222> LOCATION: (354)
<223> OTHER INFORMATION: Where n is a, c, g or t

<400> SEQUENCE: 202
tcgagcggnc gcccgggcag gtctgccaac accaagattg gcccccgccg catccacaca 60
gtccgtgtgc ggggaggtaa caagaaatac cgtgccctga ggttggacgt ggggaatttc 120
tcctggggct cagagtgttg tactcgtaaa acaaggatca tcgatgttgt ctacaatgca 180
tctaataacg agctggttcg taccaagacc ctggtgaaga attgcatcgt gctcatcgac 240
agcacaccgt accgacagtg gtacgagtcc cactatgcgc tgcccctggg ccgcaagaag 300
ggagccaagc tgactcctga ggaagaagag attttaaaca aaaaacgatc taanaaaaaa 360
aaaacaat 368

<210> SEQ ID NO 203
<211> LENGTH: 340
<212> TYPE: DNA

-continued

<213> ORGANISM: Homo sapiens

<400> SEQUENCE: 203
agcgtggtcg cggccgaggt gaaatggtat tcagcttcct ggcacttctg gtcagcaacc 60
cagtgttggg caacaaatga tctttgagga acatggtttt aggcggacca caccgcccac 120
aacggccacc cccataaggc ataggccaag accatacccg ccgaatgtag gacaagaagc 180
tctctctcag acaaccatct catgggcccc attccaggac acttctgagt acatcatttc 240
atgtcatcct gttggcactg atgaagaacc cttacagttc agggttcctg gaacttctac 300
cagtgccact ctgacaggac ctgcccgggc ggccgctcga 340

<210> SEQ ID NO 204
<211> LENGTH: 341
<212> TYPE: DNA
<213> ORGANISM: Homo sapiens

<400> SEQUENCE: 204
tcgagcggcc gcccgggcag gtcctgtcag agtggcactg gtagaagttc caggaaccct 60
gaactgtaag ggttcttcat cagtgccaac aggatgacat gaaatgatgt actcagaagt 120
gtcctggaat ggggcccatg agatggttgt ctgagagaga gcttcttgtc ctacattcgg 180
cgggtatggt cttggcctat gccttatggg ggtggccgtt gtgggcggtg tggtccgcct 240
aaaaccatgt tcctcaaaga tcatttgttg cccaacactg ggttgctgac cagaagtgcc 300
aggaagctga ataccatttc acctcggccg cgaccacgct a 341

<210> SEQ ID NO 205
<211> LENGTH: 770
<212> TYPE: DNA
<213> ORGANISM: Homo sapiens
<220> FEATURE:
<221> NAME/KEY: modified_base
<222> LOCATION: (529)
<223> OTHER INFORMATION: Where n is a, c, g or t
<221> NAME/KEY: modified_base
<222> LOCATION: (591)
<223> OTHER INFORMATION: Where n is a, c, g or t
<221> NAME/KEY: modified_base
<222> LOCATION: (623)
<223> OTHER INFORMATION: Where n is a, c, g or t
<221> NAME/KEY: modified_base
<222> LOCATION: (626)
<223> OTHER INFORMATION: Where n is a, c, g or t
<221> NAME/KEY: modified_base
<222> LOCATION: (629)
<223> OTHER INFORMATION: Where n is a, c, g or t
<221> NAME/KEY: modified_base
<222> LOCATION: (630)
<223> OTHER INFORMATION: Where n is a, c, g or t
<221> NAME/KEY: modified_base
<222> LOCATION: (656)
<223> OTHER INFORMATION: Where n is a, c, g or t
<221> NAME/KEY: modified_base
<222> LOCATION: (702)
<223> OTHER INFORMATION: Where n is a, c, g or t
<221> NAME/KEY: modified_base
<222> LOCATION: (709)
<223> OTHER INFORMATION: Where n is a, c, g or t
<221> NAME/KEY: modified_base
<222> LOCATION: (712)
<223> OTHER INFORMATION: Where n is a, c, g or t
<221> NAME/KEY: modified_base
<222> LOCATION: (717)
<223> OTHER INFORMATION: Where n is a, c, g or t
<221> NAME/KEY: modified_base
<222> LOCATION: (743)
<223> OTHER INFORMATION: Where n is a, c, g or t
<221> NAME/KEY: modified_base -continued
<222> LOCATION: (746)
<223> OTHER INFORMATION: Where n is a, c, g or t
<221> NAME/KEY: modified_base
<222> LOCATION: (749)
<223> OTHER INFORMATION: Where n is a, c, g or t
<221> NAME/KEY: modified_base
<222> LOCATION: (759)
<223> OTHER INFORMATION: Where n is a, c, g or t
<221> NAME/KEY: modified_base
<222> LOCATION: (762)
<223> OTHER INFORMATION: Where n is a, c, g or t
<221> NAME/KEY: modified_base
<222> LOCATION: (766)
<223> OTHER INFORMATION: Where n is a, c, g or t

<400> SEQUENCE: 205
tcgagcggcc gcccgggcag gtctcccttc ttgcggccca ggggcagcgc atagtgggac 60
tcgtaccact gtcggtacgg tgtgctgtcg atgagcacga tgcaattctt caccagggtc 120
ttggtacgaa ccagctcgtt attagatgca ttgtagacaa catcgatgat ccttgtttta 180
cgagtacaac actctgagcc ccaggagaaa ttccccacgt ccaacctcag ggcacggtat 240
ttcttgttac ctccccgcac acggactgtg tggatgcggc gggggccaag ctgactcctg 300
aggaagaaga gattttaaac aaaaaacgat ctaaaaaaat tcagaagaaa tatgatgaaa 360
ggaaaaagaa tgccaaaatc agcagtctcc tggaggagca gttccagcag ggcaagcttc 420
ttgcgtgcat cgcttcaagg ccgggacagt gtgaccgagc agatggctat gtgctagagg 480
gcaaagaagt ggagttctat cttaagaaaa tcagggccca gaatggtgng tcttcaacta 540
atccaaaggg gagtttcaga ccagtgcaat cagcaaaaac attgatactg ntggccaaat 600
ttattggtgc agggcttgca cantangann ggctgggtct tggggcttgg attggnacaa 660
gctttggcag ccttttcttt ggttttgcca aaaacctttt gntgaagang anacctnggg 720
cggacccctt aaccgattcc acnccnggng gcgttctang gncccncttg 770

<210> SEQ ID NO 206
<211> LENGTH: 810
<212> TYPE: DNA
<213> ORGANISM: Homo sapiens
<220> FEATURE:
<221> NAME/KEY: modified_base
<222> LOCATION: (574)
<223> OTHER INFORMATION: Where n is a, c, g or t
<221> NAME/KEY: modified_base
<222> LOCATION: (621)
<223> OTHER INFORMATION: Where n is a, c, g or t
<221> NAME/KEY: modified_base
<222> LOCATION: (625)
<223> OTHER INFORMATION: Where n is a, c, g or t
<221> NAME/KEY: modified_base
<222> LOCATION: (636)
<223> OTHER INFORMATION: Where n is a, c, g or t
<221> NAME/KEY: modified_base
<222> LOCATION: (668)
<223> OTHER INFORMATION: Where n is a, c, g or t
<221> NAME/KEY: modified_base
<222> LOCATION: (673)
<223> OTHER INFORMATION: Where n is a, c, g or t
<221> NAME/KEY: modified_base
<222> LOCATION: (704)
<223> OTHER INFORMATION: Where n is a, c, g or t
<221> NAME/KEY: modified_base
<222> LOCATION: (728)
<223> OTHER INFORMATION: Where n is a, c, g or t
<221> NAME/KEY: modified_base
<222> LOCATION: (743)
<223> OTHER INFORMATION: Where n is a, c, g or t
<221> NAME/KEY: modified_base
<222> LOCATION: (767)
<223> OTHER INFORMATION: Where n is a, c, g or t -continued
<221> NAME/KEY: modified_base
<222> LOCATION: (772)
<223> OTHER INFORMATION: Where n is a, c, g or t
<221> NAME/KEY: modified_base
<222> LOCATION: (786)
<223> OTHER INFORMATION: Where n is a, c, g or t
<221> NAME/KEY: modified_base
<222> LOCATION: (789)
<223> OTHER INFORMATION: Where n is a, c, g or t
<221> NAME/KEY: modified_base
<222> LOCATION: (807)
<223> OTHER INFORMATION: Where n is a, c, g or t
<221> NAME/KEY: modified_base
<222> LOCATION: (809)
<223> OTHER INFORMATION: Where n is a, c, g or t
<221> NAME/KEY: modified_base
<222> LOCATION: (810)
<223> OTHER INFORMATION: Where n is a, c, g or t

<400> SEQUENCE: 206
agcgtggtcg cggccgaggt ctgctgcttc agcgaagggt ttctggcata accaatgata 60
aggctgccaa agactgttcc aataccagca ccagaaccag ccactcctac tgttgcagca 120
cctgcaccaa taaatttggc agcagtatca atgtctctgc tgattgcact ggtctgaaac 180
tccctttgga ttagctgaga cacaccattc tgggccctga ttttcctaag atagaactcc 240
aactctttgc cctctagcac atagccatct gctcggtcac actgtcccgg ccttgaagcg 300
atgcacgcaa gaagcttgcc ctgctggaac tgctcctcca ggagactgct gatttggca 360 ttctttttcc tttcatcata tttcttctga attttttag atcgtttttt gtttaaaatc 420
tcttcttcct caggagtcag cttggccccc gccgcatcca cacagtccgt gtgcggggag 480
gtaacaagaa ataccgtgcc ctgaggttgg acgtggggaa tttctcctgg ggctcagagt 540
ggtgtactcg taaaacaagg atcatcgatg gtgnctacaa tgcatctaat aacgagctgg 600
gtcggaccca aagaacctgg ngaanaaatg gatcgnctca tcgacaggac accgtacccg 660
acaggggnac gantcccact atgcgcttgc ccctgggccg caanaaagga aaactgcccg 720
ggcggccntc gaaagcccaa ttntggaaaa aatccatcac actgggnggc cngtcgagca 780
tgcatntana ggggcccatt ccccctnann 810

<210> SEQ ID NO 207
<211> LENGTH: 257
<212> TYPE: DNA
<213> ORGANISM: Homo sapiens

<400> SEQUENCE: 207
tcgagcggcc gcccgggcag gtccccaacc aaggctgcaa cctggatgcc atcaaagtct 60
tctgcaacat ggagactggt gagacctgcg tgtaccccac tcagcccagt gtggcccaga 120
agaactggta catcagcaag aaccccaagg acaagaggca tgtctggttc ggcgagagca 180
tgaccgatgg attccagttc gagtatggcg gccagggctc cgaccctgcc gatgtggacc 240
tcggccgcga ccacgct 257

<210> SEQ ID NO 208
<211> LENGTH: 257
<212> TYPE: DNA
<213> ORGANISM: Homo sapiens

<400> SEQUENCE: 208
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120

-continued

```
gctgatgtac cagttcttct gggccacact gggctgagtg gggtacacgc aggtctcacc    180

agtctccatg ttgcagaaga ctttgatggc atccaggttg cagccttggt tggggacctg    240

cccgggcggc cgctcga                                                   257
```

<210> SEQ ID NO 209
<211> LENGTH: 747
<212> TYPE: DNA
<213> ORGANISM: Homo sapiens
<220> FEATURE:
<221> NAME/KEY: modified_base
<222> LOCATION: (453)
<223> OTHER INFORMATION: Where n is a, c, g or t
<221> NAME/KEY: modified_base
<222> LOCATION: (538)
<223> OTHER INFORMATION: Where n is a, c, g or t
<221> NAME/KEY: modified_base
<222> LOCATION: (540)
<223> OTHER INFORMATION: Where n is a, c, g or t
<221> NAME/KEY: modified_base
<222> LOCATION: (542)
<223> OTHER INFORMATION: Where n is a, c, g or t
<221> NAME/KEY: modified_base
<222> LOCATION: (546)
<223> OTHER INFORMATION: Where n is a, c, g or t
<221> NAME/KEY: modified_base
<222> LOCATION: (554)
<223> OTHER INFORMATION: Where n is a, c, g or t
<221> NAME/KEY: modified_base
<222> LOCATION: (556)
<223> OTHER INFORMATION: Where n is a, c, g or t
<221> NAME/KEY: modified_base
<222> LOCATION: (598)
<223> OTHER INFORMATION: Where n is a, c, g or t
<221> NAME/KEY: modified_base
<222> LOCATION: (659)
<223> OTHER INFORMATION: Where n is a, c, g or t
<221> NAME/KEY: modified_base
<222> LOCATION: (670)
<223> OTHER INFORMATION: Where n is a, c, g or t
<221> NAME/KEY: modified_base
<222> LOCATION: (679)
<223> OTHER INFORMATION: Where n is a, c, g or t
<221> NAME/KEY: modified_base
<222> LOCATION: (689)
<223> OTHER INFORMATION: Where n is a, c, g or t
<221> NAME/KEY: modified_base
<222> LOCATION: (693)
<223> OTHER INFORMATION: Where n is a, c, g or t
<221> NAME/KEY: modified_base
<222> LOCATION: (711)
<223> OTHER INFORMATION: Where n is a, c, g or t
<221> NAME/KEY: modified_base
<222> LOCATION: (723)
<223> OTHER INFORMATION: Where n is a, c, g or t
<221> NAME/KEY: modified_base
<222> LOCATION: (724)
<223> OTHER INFORMATION: Where n is a, c, g or t
<221> NAME/KEY: modified_base
<222> LOCATION: (731)
<223> OTHER INFORMATION: Where n is a, c, g or t
<221> NAME/KEY: modified_base
<222> LOCATION: (747)
<223> OTHER INFORMATION: Where n is a, c, g or t

<400> SEQUENCE: 209

```
tcgagcggcc gcccgggcag gtccaccaca cccaattcct tgctggtatc atggcagccg     60

ccacgtgcca ggattaccgg ctacatcatc aagtatgaga agcctgggtc tcctcccaga    120

gaagtggtcc ctcggccccg ccctggtgtc acagaggcta ctattactgg cctggaaccg    180

ggaaccgaat atacaattta tgtcattgcc ctgaagaata atcagaagag cgagcccctg    240

attggaagga aaaagacaga cgagcttccc caactggtaa cccttccaca ccccaatctt    300
```

-continued

```
catggaccag agatcttgga tgttccttcc acagttcaaa agaccccttt cgtcacccac    360

cctgggtatg acactggaaa tggtattcag cttcctggca cttctggtca gcaacccagt    420

gttgggcaac aaatgatctt tgaggaacat ggntttaggc ggaccacacc gcccacaacg    480

gccaccccca taaggcatag gccaagacca tacccgccga atgtaggaca agaagctntn    540

tntcanacac catntnatgg gccccattcc aggacacttc tgagtacatc atttatgnca    600

tctgtggcac ttgatgaaaa cccttacagt tcagggttct ggaactttta ccaggcctnt    660

tacaggactn ggccggacnc cttaagccna ttncaccctg ggcgttcta nggtcccact    720

cgnncactgg ngaaaatggc tactgtn                                        747
```

<210> SEQ ID NO 210
<211> LENGTH: 872
<212> TYPE: DNA
<213> ORGANISM: Homo sapiens
<220> FEATURE:
<221> NAME/KEY: modified_base
<222> LOCATION: (165)
<223> OTHER INFORMATION: Where n is a, c, g or t
<221> NAME/KEY: modified_base
<222> LOCATION: (174)
<223> OTHER INFORMATION: Where n is a, c, g or t
<221> NAME/KEY: modified_base
<222> LOCATION: (181)
<223> OTHER INFORMATION: Where n is a, c, g or t
<221> NAME/KEY: modified_base
<222> LOCATION: (256)
<223> OTHER INFORMATION: Where n is a, c, g or t
<221> NAME/KEY: modified_base
<222> LOCATION: (260)
<223> OTHER INFORMATION: Where n is a, c, g or t
<221> NAME/KEY: modified_base
<222> LOCATION: (269)
<223> OTHER INFORMATION: Where n is a, c, g or t
<221> NAME/KEY: modified_base
<222> LOCATION: (271)
<223> OTHER INFORMATION: Where n is a, c, g or t
<221> NAME/KEY: modified_base
<222> LOCATION: (277)
<223> OTHER INFORMATION: Where n is a, c, g or t
<221> NAME/KEY: modified_base
<222> LOCATION: (286)
<223> OTHER INFORMATION: Where n is a, c, g or t
<221> NAME/KEY: modified_base
<222> LOCATION: (289)
<223> OTHER INFORMATION: Where n is a, c, g or t
<221> NAME/KEY: modified_base
<222> LOCATION: (294)
<223> OTHER INFORMATION: Where n is a, c, g or t
<221> NAME/KEY: modified_base
<222> LOCATION: (298)
<223> OTHER INFORMATION: Where n is a, c, g or t
<221> NAME/KEY: modified_base
<222> LOCATION: (300)
<223> OTHER INFORMATION: Where n is a, c, g or t
<221> NAME/KEY: modified_base
<222> LOCATION: (301)
<223> OTHER INFORMATION: Where n is a, c, g or t
<221> NAME/KEY: modified_base
<222> LOCATION: (303)
<223> OTHER INFORMATION: Where n is a, c, g or t
<221> NAME/KEY: modified_base
<222> LOCATION: (308)
<223> OTHER INFORMATION: Where n is a, c, g or t
<221> NAME/KEY: modified_base
<222> LOCATION: (311)
<223> OTHER INFORMATION: Where n is a, c, g or t
<221> NAME/KEY: modified_base
<222> LOCATION: (321)
<223> OTHER INFORMATION: Where n is a, c, g or t
<221> NAME/KEY: modified_base
<222> LOCATION: (325)
<223> OTHER INFORMATION: Where n is a, c, g or t -continued
<221> NAME/KEY: modified_base
<222> LOCATION: (328)
<223> OTHER INFORMATION: Where n is a, c, g or t
<221> NAME/KEY: modified_base
<222> LOCATION: (329)
<223> OTHER INFORMATION: Where n is a, c, g or t
<221> NAME/KEY: modified_base
<222> LOCATION: (333)
<223> OTHER INFORMATION: Where n is a, c, g or t
<221> NAME/KEY: modified_base
<222> LOCATION: (338)
<223> OTHER INFORMATION: Where n is a, c, g or t
<221> NAME/KEY: modified_base
<222> LOCATION: (342)
<223> OTHER INFORMATION: Where n is a, c, g or t
<221> NAME/KEY: modified_base
<222> LOCATION: (346)
<223> OTHER INFORMATION: Where n is a, c, g or t
<221> NAME/KEY: modified_base
<222> LOCATION: (349)
<223> OTHER INFORMATION: Where n is a, c, g or t
<221> NAME/KEY: modified_base
<222> LOCATION: (351)
<223> OTHER INFORMATION: Where n is a, c, g or t
<221> NAME/KEY: modified_base
<222> LOCATION: (357)
<223> OTHER INFORMATION: Where n is a, c, g or t
<221> NAME/KEY: modified_base
<222> LOCATION: (359)
<223> OTHER INFORMATION: Where n is a, c, g or t
<221> NAME/KEY: modified_base
<222> LOCATION: (364)
<223> OTHER INFORMATION: Where n is a, c, g or t
<221> NAME/KEY: modified_base
<222> LOCATION: (366)
<223> OTHER INFORMATION: Where n is a, c, g or t
<221> NAME/KEY: modified_base
<222> LOCATION: (379)
<223> OTHER INFORMATION: Where n is a, c, g or t
<221> NAME/KEY: modified_base
<222> LOCATION: (385)
<223> OTHER INFORMATION: Where n is a, c, g or t
<221> NAME/KEY: modified_base
<222> LOCATION: (395)
<223> OTHER INFORMATION: Where n is a, c, g or t
<221> NAME/KEY: modified_base
<222> LOCATION: (396)
<223> OTHER INFORMATION: Where n is a, c, g or t
<221> NAME/KEY: modified_base
<222> LOCATION: (397)
<223> OTHER INFORMATION: Where n is a, c, g or t
<221> NAME/KEY: modified_base
<222> LOCATION: (407)
<223> OTHER INFORMATION: Where n is a, c, g or t
<221> NAME/KEY: modified_base
<222> LOCATION: (408)
<223> OTHER INFORMATION: Where n is a, c, g or t
<221> NAME/KEY: modified_base
<222> LOCATION: (410)
<223> OTHER INFORMATION: Where n is a, c, g or t
<221> NAME/KEY: modified_base
<222> LOCATION: (414)
<223> OTHER INFORMATION: Where n is a, c, g or t
<221> NAME/KEY: modified_base
<222> LOCATION: (415)
<223> OTHER INFORMATION: Where n is a, c, g or t
<221> NAME/KEY: modified_base
<222> LOCATION: (429)
<223> OTHER INFORMATION: Where n is a, c, g or t
<221> NAME/KEY: modified_base
<222> LOCATION: (431)
<223> OTHER INFORMATION: Where n is a, c, g or t
<221> NAME/KEY: modified_base
<222> LOCATION: (434)
<223> OTHER INFORMATION: Where n is a, c, g or t
<221> NAME/KEY: modified_base
<222> LOCATION: (435)
<223> OTHER INFORMATION: Where n is a, c, g or t
<221> NAME/KEY: modified_base -continued
<222> LOCATION: (440)
<223> OTHER INFORMATION: Where n is a, c, g or t
<221> NAME/KEY: modified_base
<222> LOCATION: (443)
<223> OTHER INFORMATION: Where n is a, c, g or t
<221> NAME/KEY: modified_base
<222> LOCATION: (444)
<223> OTHER INFORMATION: Where n is a, c, g or t
<221> NAME/KEY: modified_base
<222> LOCATION: (446)
<223> OTHER INFORMATION: Where n is a, c, g or t
<221> NAME/KEY: modified_base
<222> LOCATION: (447)
<223> OTHER INFORMATION: Where n is a, c, g or t
<221> NAME/KEY: modified_base
<222> LOCATION: (448)
<223> OTHER INFORMATION: Where n is a, c, g or t
<221> NAME/KEY: modified_base
<222> LOCATION: (449)
<223> OTHER INFORMATION: Where n is a, c, g or t
<221> NAME/KEY: modified_base
<222> LOCATION: (450)
<223> OTHER INFORMATION: Where n is a, c, g or t
<221> NAME/KEY: modified_base
<222> LOCATION: (451)
<223> OTHER INFORMATION: Where n is a, c, g or t
<221> NAME/KEY: modified_base
<222> LOCATION: (464)
<223> OTHER INFORMATION: Where n is a, c, g or t
<221> NAME/KEY: modified_base
<222> LOCATION: (470)
<223> OTHER INFORMATION: Where n is a, c, g or t
<221> NAME/KEY: modified_base
<222> LOCATION: (472)
<223> OTHER INFORMATION: Where n is a, c, g or t
<221> NAME/KEY: modified_base
<222> LOCATION: (475)
<223> OTHER INFORMATION: Where n is a, c, g or t
<221> NAME/KEY: modified_base
<222> LOCATION: (479)
<223> OTHER INFORMATION: Where n is a, c, g or t
<221> NAME/KEY: modified_base
<222> LOCATION: (483)
<223> OTHER INFORMATION: Where n is a, c, g or t
<221> NAME/KEY: modified_base
<222> LOCATION: (484)
<223> OTHER INFORMATION: Where n is a, c, g or t
<221> NAME/KEY: modified_base
<222> LOCATION: (485)
<223> OTHER INFORMATION: Where n is a, c, g or t
<221> NAME/KEY: modified_base
<222> LOCATION: (488)
<223> OTHER INFORMATION: Where n is a, c, g or t
<221> NAME/KEY: modified_base
<222> LOCATION: (494)
<223> OTHER INFORMATION: Where n is a, c, g or t
<221> NAME/KEY: modified_base
<222> LOCATION: (496)
<223> OTHER INFORMATION: Where n is a, c, g or t
<221> NAME/KEY: modified_base
<222> LOCATION: (497)
<223> OTHER INFORMATION: Where n is a, c, g or t
<221> NAME/KEY: modified_base
<222> LOCATION: (504)
<223> OTHER INFORMATION: Where n is a, c, g or t
<221> NAME/KEY: modified_base
<222> LOCATION: (508)
<223> OTHER INFORMATION: Where n is a, c, g or t
<221> NAME/KEY: modified_base
<222> LOCATION: (509)
<223> OTHER INFORMATION: Where n is a, c, g or t
<221> NAME/KEY: modified_base
<222> LOCATION: (511)
<223> OTHER INFORMATION: Where n is a, c, g or t
<221> NAME/KEY: modified_base
<222> LOCATION: (513)
<223> OTHER INFORMATION: Where n is a, c, g or t
<221> NAME/KEY: modified_base
<222> LOCATION: (517)

-continued

<223> OTHER INFORMATION: Where n is a, c, g or t
<221> NAME/KEY: modified_base
<222> LOCATION: (522)
<223> OTHER INFORMATION: Where n is a, c, g or t
<221> NAME/KEY: modified_base
<222> LOCATION: (524)
<223> OTHER INFORMATION: Where n is a, c, g or t
<221> NAME/KEY: modified_base
<222> LOCATION: (526)
<223> OTHER INFORMATION: Where n is a, c, g or t
<221> NAME/KEY: modified_base
<222> LOCATION: (532)
<223> OTHER INFORMATION: Where n is a, c, g or t
<221> NAME/KEY: modified_base
<222> LOCATION: (533)
<223> OTHER INFORMATION: Where n is a, c, g or t
<221> NAME/KEY: modified_base
<222> LOCATION: (542)
<223> OTHER INFORMATION: Where n is a, c, g or t
<221> NAME/KEY: modified_base
<222> LOCATION: (543)
<223> OTHER INFORMATION: Where n is a, c, g or t
<221> NAME/KEY: modified_base
<222> LOCATION: (553)
<223> OTHER INFORMATION: Where n is a, c, g or t
<221> NAME/KEY: modified_base
<222> LOCATION: (559)
<223> OTHER INFORMATION: Where n is a, c, g or t
<221> NAME/KEY: modified_base
<222> LOCATION: (566)
<223> OTHER INFORMATION: Where n is a, c, g or t
<221> NAME/KEY: modified_base
<222> LOCATION: (567)
<223> OTHER INFORMATION: Where n is a, c, g or t
<221> NAME/KEY: modified_base
<222> LOCATION: (571)
<223> OTHER INFORMATION: Where n is a, c, g or t
<221> NAME/KEY: modified_base
<222> LOCATION: (572)
<223> OTHER INFORMATION: Where n is a, c, g or t
<221> NAME/KEY: modified_base
<222> LOCATION: (578)
<223> OTHER INFORMATION: Where n is a, c, g or t
<221> NAME/KEY: modified_base
<222> LOCATION: (582)
<223> OTHER INFORMATION: Where n is a, c, g or t
<221> NAME/KEY: modified_base
<222> LOCATION: (588)
<223> OTHER INFORMATION: Where n is a, c, g or t
<221> NAME/KEY: modified_base
<222> LOCATION: (591)
<223> OTHER INFORMATION: Where n is a, c, g or t
<221> NAME/KEY: modified_base
<222> LOCATION: (594)
<223> OTHER INFORMATION: Where n is a, c, g or t
<221> NAME/KEY: modified_base
<222> LOCATION: (595)
<223> OTHER INFORMATION: Where n is a, c, g or t
<221> NAME/KEY: modified_base
<222> LOCATION: (596)
<223> OTHER INFORMATION: Where n is a, c, g or t
<221> NAME/KEY: modified_base
<222> LOCATION: (600)
<223> OTHER INFORMATION: Where n is a, c, g or t
<221> NAME/KEY: modified_base
<222> LOCATION: (606)
<223> OTHER INFORMATION: Where n is a, c, g or t
<221> NAME/KEY: modified_base
<222> LOCATION: (612)
<223> OTHER INFORMATION: Where n is a, c, g or t
<221> NAME/KEY: modified_base
<222> LOCATION: (614)
<223> OTHER INFORMATION: Where n is a, c, g or t
<221> NAME/KEY: modified_base
<222> LOCATION: (617)
<223> OTHER INFORMATION: Where n is a, c, g or t
<221> NAME/KEY: modified_base
<222> LOCATION: (618)
<223> OTHER INFORMATION: Where n is a, c, g or t -continued
<221> NAME/KEY: modified_base
<222> LOCATION: (629)
<223> OTHER INFORMATION: Where n is a, c, g or t
<221> NAME/KEY: modified_base
<222> LOCATION: (630)
<223> OTHER INFORMATION: Where n is a, c, g or t
<221> NAME/KEY: modified_base
<222> LOCATION: (631)
<223> OTHER INFORMATION: Where n is a, c, g or t
<221> NAME/KEY: modified_base
<222> LOCATION: (652)
<223> OTHER INFORMATION: Where n is a, c, g or t
<221> NAME/KEY: modified_base
<222> LOCATION: (654)
<223> OTHER INFORMATION: Where n is a, c, g or t
<221> NAME/KEY: modified_base
<222> LOCATION: (655)
<223> OTHER INFORMATION: Where n is a, c, g or t
<221> NAME/KEY: modified_base
<222> LOCATION: (661)
<223> OTHER INFORMATION: Where n is a, c, g or t
<221> NAME/KEY: modified_base
<222> LOCATION: (663)
<223> OTHER INFORMATION: Where n is a, c, g or t
<221> NAME/KEY: modified_base
<222> LOCATION: (664)
<223> OTHER INFORMATION: Where n is a, c, g or t
<221> NAME/KEY: modified_base
<222> LOCATION: (666)
<223> OTHER INFORMATION: Where n is a, c, g or t
<221> NAME/KEY: modified_base
<222> LOCATION: (671)
<223> OTHER INFORMATION: Where n is a, c, g or t
<221> NAME/KEY: modified_base
<222> LOCATION: (673)
<223> OTHER INFORMATION: Where n is a, c, g or t
<221> NAME/KEY: modified_base
<222> LOCATION: (678)
<223> OTHER INFORMATION: Where n is a, c, g or t
<221> NAME/KEY: modified_base
<222> LOCATION: (679)
<223> OTHER INFORMATION: Where n is a, c, g or t
<221> NAME/KEY: modified_base
<222> LOCATION: (681)
<223> OTHER INFORMATION: Where n is a, c, g or t
<221> NAME/KEY: modified_base
<222> LOCATION: (688)
<223> OTHER INFORMATION: Where n is a, c, g or t
<221> NAME/KEY: modified_base
<222> LOCATION: (690)
<223> OTHER INFORMATION: Where n is a, c, g or t
<221> NAME/KEY: modified_base
<222> LOCATION: (691)
<223> OTHER INFORMATION: Where n is a, c, g or t
<221> NAME/KEY: modified_base
<222> LOCATION: (698)
<223> OTHER INFORMATION: Where n is a, c, g or t
<221> NAME/KEY: modified_base
<222> LOCATION: (706)
<223> OTHER INFORMATION: Where n is a, c, g or t
<221> NAME/KEY: modified_base
<222> LOCATION: (707)
<223> OTHER INFORMATION: Where n is a, c, g or t
<221> NAME/KEY: modified_base
<222> LOCATION: (708)
<223> OTHER INFORMATION: Where n is a, c, g or t
<221> NAME/KEY: modified_base
<222> LOCATION: (714)
<223> OTHER INFORMATION: Where n is a, c, g or t
<221> NAME/KEY: modified_base
<222> LOCATION: (719)
<223> OTHER INFORMATION: Where n is a, c, g or t
<221> NAME/KEY: modified_base
<222> LOCATION: (721)
<223> OTHER INFORMATION: Where n is a, c, g or t
<221> NAME/KEY: modified_base
<222> LOCATION: (723)
<223> OTHER INFORMATION: Where n is a, c, g or t
<221> NAME/KEY: modified_base -continued
<222> LOCATION: (726)
<223> OTHER INFORMATION: Where n is a, c, g or t
<221> NAME/KEY: modified_base
<222> LOCATION: (741)
<223> OTHER INFORMATION: Where n is a, c, g or t
<221> NAME/KEY: modified_base
<222> LOCATION: (751)
<223> OTHER INFORMATION: Where n is a, c, g or t
<221> NAME/KEY: modified_base
<222> LOCATION: (761)
<223> OTHER INFORMATION: Where n is a, c, g or t
<221> NAME/KEY: modified_base
<222> LOCATION: (762)
<223> OTHER INFORMATION: Where n is a, c, g or t
<221> NAME/KEY: modified_base
<222> LOCATION: (769)
<223> OTHER INFORMATION: Where n is a, c, g or t
<221> NAME/KEY: modified_base
<222> LOCATION: (770)
<223> OTHER INFORMATION: Where n is a, c, g or t
<221> NAME/KEY: modified_base
<222> LOCATION: (778)
<223> OTHER INFORMATION: Where n is a, c, g or t
<221> NAME/KEY: modified_base
<222> LOCATION: (779)
<223> OTHER INFORMATION: Where n is a, c, g or t
<221> NAME/KEY: modified_base
<222> LOCATION: (781)
<223> OTHER INFORMATION: Where n is a, c, g or t
<221> NAME/KEY: modified_base
<222> LOCATION: (782)
<223> OTHER INFORMATION: Where n is a, c, g or t
<221> NAME/KEY: modified_base
<222> LOCATION: (785)
<223> OTHER INFORMATION: Where n is a, c, g or t
<221> NAME/KEY: modified_base
<222> LOCATION: (791)
<223> OTHER INFORMATION: Where n is a, c, g or t
<221> NAME/KEY: modified_base
<222> LOCATION: (802)
<223> OTHER INFORMATION: Where n is a, c, g or t
<221> NAME/KEY: modified_base
<222> LOCATION: (807)
<223> OTHER INFORMATION: Where n is a, c, g or t
<221> NAME/KEY: modified_base
<222> LOCATION: (808)
<223> OTHER INFORMATION: Where n is a, c, g or t
<221> NAME/KEY: modified_base
<222> LOCATION: (812)
<223> OTHER INFORMATION: Where n is a, c, g or t
<221> NAME/KEY: modified_base
<222> LOCATION: (815)
<223> OTHER INFORMATION: Where n is a, c, g or t
<221> NAME/KEY: modified_base
<222> LOCATION: (820)
<223> OTHER INFORMATION: Where n is a, c, g or t
<221> NAME/KEY: modified_base
<222> LOCATION: (827)
<223> OTHER INFORMATION: Where n is a, c, g or t
<221> NAME/KEY: modified_base
<222> LOCATION: (828)
<223> OTHER INFORMATION: Where n is a, c, g or t
<221> NAME/KEY: modified_base
<222> LOCATION: (838)
<223> OTHER INFORMATION: Where n is a, c, g or t
<221> NAME/KEY: modified_base
<222> LOCATION: (841)
<223> OTHER INFORMATION: Where n is a, c, g or t
<221> NAME/KEY: modified_base
<222> LOCATION: (844)
<223> OTHER INFORMATION: Where n is a, c, g or t
<221> NAME/KEY: modified_base
<222> LOCATION: (851)
<223> OTHER INFORMATION: Where n is a, c, g or t
<221> NAME/KEY: modified_base
<222> LOCATION: (857)
<223> OTHER INFORMATION: Where n is a, c, g or t
<221> NAME/KEY: modified_base
<222> LOCATION: (864)

-continued

<223> OTHER INFORMATION: Where n is a, c, g or t
<221> NAME/KEY: modified_base
<222> LOCATION: (866)
<223> OTHER INFORMATION: Where n is a, c, g or t
<221> NAME/KEY: modified_base
<222> LOCATION: (869)
<223> OTHER INFORMATION: Where n is a, c, g or t
<221> NAME/KEY: modified_base
<222> LOCATION: (872)
<223> OTHER INFORMATION: Where n is a, c, g or t

<400> SEQUENCE: 210
agcgtggtcg cggccgaggt ccactagagg tctgtgtgcc attgcccagg cagagtctct 60
gcgttacaaa ctcctaggag ggcttgctgt gcggagggcc tgctatggtg tgctgcggtt 120
catcatggag agtggggcca aaggctgcga ggttgtggtg tctgngaaac tccnaggaca 180
ngagggctaa attccatgaa gtttgtggat ggcctgatga tccacaatcg gagaccctgt 240
taactactac cgtctnaccn cctgctgtnc ncccccnttt ctgctnaana catngggntn 300
ntncttgncc ntccttgggt ngaanatnna atngcctncc cnttcntanc nctactngnt 360
ccananttgg cctttaaana atccnccttg ccttnnncac tgttcanntn tttnntcgta 420
aaccctatna nttnnattan atnntnnnnn nctcaccccc ctcntcattn anccnatang 480
ctnnnaantc cttnanncct cccncccnnt ncnctcntac tnantncttc tnncccatta 540
cnnagctctt tcntttaana taatgnngcc nngctctnca tntctacnat ntgnnnaatn 600
cccccncccc cnancgnntt tttgacctnn naacctcctt tcctcttccc tncnnaaatt 660
ncnnanttcc ncnttccnnc ntttcggntn ntcccatnct ttccannnct tcantctanc 720
ncnctncaac ttattttcct ntcatccctt nttctttaca nncccccctnn tctactcnnc 780 nnttncatta natttgaaac tnccacnnct anttncctcn ctctacnntt ttattttncg 840
ntcnctctac ntaatanttt aatnanttnt cn 872

<210> SEQ ID NO 211
<211> LENGTH: 517
<212> TYPE: DNA
<213> ORGANISM: Homo sapiens
<220> FEATURE:
<221> NAME/KEY: modified_base
<222> LOCATION: (462)
<223> OTHER INFORMATION: Where n is a, c, g or t
<221> NAME/KEY: modified_base
<222> LOCATION: (464)
<223> OTHER INFORMATION: Where n is a, c, g or t
<221> NAME/KEY: modified_base
<222> LOCATION: (506)
<223> OTHER INFORMATION: Where n is a, c, g or t

<400> SEQUENCE: 211
tcgagcggcc gcccgggcag gtctgccaag gagaccctgt tatgctgtgg ggactggctg 60
gggcatggca ggcggctctg gcttcccacc cttctgttct gagatggggg tggtgggcag 120
tatctcatct ttgggttcca caatgctcac gtggtcaggc aggggcttct tagggccaat 180
cttaccagtt gggtcccagg gcagcatgat cttcaccttg atgcccagca caccctgtct 240
gagcaacacg tggcgcacaa gcagtgtcaa cgtagtaagt taacagggtc tccgctgtgg 300
atcatcaggc catccacaaa cttcatggat ttagccctct gtcctcggag tttcccagac 360
accacaacct cgcagccttt ggccccactc tccatgatga accgcagcac accatagcag 420
gccctccgca caagcaagcc ctcctaagaa tttgtaacgc ananactctg ctggcaatgg 480
cacacaaacc tctagtggac ctcggncgcg accacgc 517

-continued

<210> SEQ ID NO 212
<211> LENGTH: 695
<212> TYPE: DNA
<213> ORGANISM: Homo sapiens
<220> FEATURE:
<221> NAME/KEY: modified_base
<222> LOCATION: (432)
<223> OTHER INFORMATION: Where n is a, c, g or t
<221> NAME/KEY: modified_base
<222> LOCATION: (476)
<223> OTHER INFORMATION: Where n is a, c, g or t
<221> NAME/KEY: modified_base
<222> LOCATION: (522)
<223> OTHER INFORMATION: Where n is a, c, g or t
<221> NAME/KEY: modified_base
<222> LOCATION: (547)
<223> OTHER INFORMATION: Where n is a, c, g or t
<221> NAME/KEY: modified_base
<222> LOCATION: (621)
<223> OTHER INFORMATION: Where n is a, c, g or t
<221> NAME/KEY: modified_base
<222> LOCATION: (624)
<223> OTHER INFORMATION: Where n is a, c, g or t
<221> NAME/KEY: modified_base
<222> LOCATION: (647)
<223> OTHER INFORMATION: Where n is a, c, g or t
<221> NAME/KEY: modified_base
<222> LOCATION: (679)
<223> OTHER INFORMATION: Where n is a, c, g or t

<400> SEQUENCE: 212
tcgagcggcc gcccgggcag gtctggtcca ggatagcctg cgagtcctcc tactgctact 60
ccagacttga catcatatga atcatactgg ggagaatagt tctgaggacc agtagggcat 120
gattcacaga ttccaggggg gccaggagaa ccaggggacc ctggttgtcc tggaatacca 180
gggtcaccat ttctcccagg aataccagga gggcctggat ctcccttggg gccttgaggt 240
ccttgaccat taggagggcg agtaggagca gttggaggct gtgggcaaac tgcacaacat 300
tctccaaatg gaatttctgg gttggggcag tctaattctt gatccgtcac atattatgtc 360
atcgcagaga acggatcctg agtcacagac acatatttgg catggttctg gcttccagac 420
atctctatcc gncataggac tgaccaagat gggaacatcc tccttcaaca agcttnctgt 480
tgtgccaaaa ataatagtgg gatgaagcag accgagaagt anccagctcc cctttttgca 540
caaagcntca tcatgtctaa atatcagaca tgagacttct ttgggcaaaa aaggagaaaa 600
agaaaaagca gttcaaagta nccnccatca agttggttcc ttgcccnttc agcacccggg 660
ccccgttata aaacacctng ggccggaccc ccctt 695

<210> SEQ ID NO 213
<211> LENGTH: 804
<212> TYPE: DNA
<213> ORGANISM: Homo sapiens
<220> FEATURE:
<221> NAME/KEY: modified_base
<222> LOCATION: (552)
<223> OTHER INFORMATION: Where n is a, c, g or t
<221> NAME/KEY: modified_base
<222> LOCATION: (555)
<223> OTHER INFORMATION: Where n is a, c, g or t
<221> NAME/KEY: modified_base
<222> LOCATION: (592)
<223> OTHER INFORMATION: Where n is a, c, g or t
<221> NAME/KEY: modified_base
<222> LOCATION: (624)
<223> OTHER INFORMATION: Where n is a, c, g or t
<221> NAME/KEY: modified_base
<222> LOCATION: (629)
<223> OTHER INFORMATION: Where n is a, c, g or t
<221> NAME/KEY: modified_base -continued

```
<222> LOCATION: (633)
<223> OTHER INFORMATION: Where n is a, c, g or t
<221> NAME/KEY: modified_base
<222> LOCATION: (658)
<223> OTHER INFORMATION: Where n is a, c, g or t
<221> NAME/KEY: modified_base
<222> LOCATION: (695)
<223> OTHER INFORMATION: Where n is a, c, g or t
<221> NAME/KEY: modified_base
<222> LOCATION: (697)
<223> OTHER INFORMATION: Where n is a, c, g or t
<221> NAME/KEY: modified_base
<222> LOCATION: (698)
<223> OTHER INFORMATION: Where n is a, c, g or t
<221> NAME/KEY: modified_base
<222> LOCATION: (700)
<223> OTHER INFORMATION: Where n is a, c, g or t
<221> NAME/KEY: modified_base
<222> LOCATION: (702)
<223> OTHER INFORMATION: Where n is a, c, g or t
<221> NAME/KEY: modified_base
<222> LOCATION: (745)
<223> OTHER INFORMATION: Where n is a, c, g or t
<221> NAME/KEY: modified_base
<222> LOCATION: (753)
<223> OTHER INFORMATION: Where n is a, c, g or t
<221> NAME/KEY: modified_base
<222> LOCATION: (755)
<223> OTHER INFORMATION: Where n is a, c, g or t
<221> NAME/KEY: modified_base
<222> LOCATION: (762)
<223> OTHER INFORMATION: Where n is a, c, g or t
<221> NAME/KEY: modified_base
<222> LOCATION: (773)
<223> OTHER INFORMATION: Where n is a, c, g or t
<221> NAME/KEY: modified_base
<222> LOCATION: (786)
<223> OTHER INFORMATION: Where n is a, c, g or t
<221> NAME/KEY: modified_base
<222> LOCATION: (788)
<223> OTHER INFORMATION: Where n is a, c, g or t
<221> NAME/KEY: modified_base
<222> LOCATION: (793)
<223> OTHER INFORMATION: Where n is a, c, g or t
<221> NAME/KEY: modified_base
<222> LOCATION: (795)
<223> OTHER INFORMATION: Where n is a, c, g or t

<400> SEQUENCE: 213

agcgtggtcg cggccgaggt gttttatgac gggcccggtg ctgaagggca gggaacaact     60

tgatggtgct actttgaact gcttttcttt tctccttttt gcacaaagag tctcatgtct    120

gatatttaga catgatgagc tttgtgcaaa aggggagctg gctacttctc gctctgcttc    180

atcccactat tattttggca caacaggaag ctgttgaagg aggatgttcc catcttggtc    240

agtcctatgc ggatagagat gtctggaagc cagaaccatg ccaaatatgt gtctgtgact    300

caggatccgt tctctgcgat gacataatat gtgacgatca agaattagac tgccccaacc    360

cagaaattcc atttggagaa tgttgtgcag tttgcccaca gcctccaact gctcctactc    420

gccctcctaa tggtcaagga cctcaaggcc ccaagggaga tccaggccct cctggtattc    480

ctgggagaaa tggtgaccct ggtattccag gacaaccagg gtcccctggt tctcctggcc    540

cccctggaat cnggngaatc atgccctact ggtcctcaaa ctattctccc anatgattca    600

tatgatgtca agtctgggat agcnagtang ganggactcg caggctattc tggaccanac    660

ctgccggggg ggcgttcgaa agcccgaatc tgcananntn cnttcacact ggcggccgtc    720

gagctgcttt aaaagggcca ttccnccttt agngngggg antacaatta ctnggcggcg    780

ttttanancg cgngnctggg aaat                                           804
```

-continued

<210> SEQ ID NO 214
<211> LENGTH: 594
<212> TYPE: DNA
<213> ORGANISM: Homo sapiens
<220> FEATURE:
<221> NAME/KEY: modified_base
<222> LOCATION: (452)
<223> OTHER INFORMATION: Where n is a, c, g or t
<221> NAME/KEY: modified_base
<222> LOCATION: (509)
<223> OTHER INFORMATION: Where n is a, c, g or t
<221> NAME/KEY: modified_base
<222> LOCATION: (585)
<223> OTHER INFORMATION: Where n is a, c, g or t

<400> SEQUENCE: 214

```
agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacacgc aggtctcacc    180

agtctccatg ttgcagaaga ctttgatggc atccaggttg cagccttggt tggggtcaat    240

ccagtactct ccactcttcc agtcagagtg gcacatcttg aggtcacggc aggtgcgggc    300

ggggttcttg cggctgccct ctgggctccg gatgttctcg atctgctggc tcaggctctt    360

gagggtggtg tccacctcga ggtcacggtc acgaaccaca ttggcatcat cagcccggta    420

gtagcggcca ccatcgtgag ccttctcttg angtggctgg ggcaggaact gaagtcgaaa    480

ccagcgctgg gaggaccagg gggaccaana ggtccaggaa gggcccgggg gggaccaaca    540

ggaccagcat caccaagtgc gacccgcgag aacctgcccg gccgnccgct cgaa          594
```

<210> SEQ ID NO 215
<211> LENGTH: 590
<212> TYPE: DNA
<213> ORGANISM: Homo sapiens
<220> FEATURE:
<221> NAME/KEY: modified_base
<222> LOCATION: (8)
<223> OTHER INFORMATION: Where n is a, c, g or t
<221> NAME/KEY: modified_base
<222> LOCATION: (9)
<223> OTHER INFORMATION: Where n is a, c, g or t

<400> SEQUENCE: 215

```
tcgagcgnnc gcccgggcag gtctcgcggt cgcactggtg atgctggtcc tgttggtccc     60

cccggccctc ctggacctcc tggtccccct ggtcctccca gcgctggttt cgacttcagc    120

ttcctgcccc agccacctca agagaaggct cacgatggtg gccgctacta ccgggctgat    180

gatgccaatg tggttcgtga ccgtgacctc gaggtggaca ccaccctcaa gagcctgagc    240

cagcagatcg agaacatccg gagcccagag ggcagccgca agaaccccgc ccgcacctgc    300

cgtgacctca agatgtgcca ctctgactgg aagagtggag agtactggat tgaccccaac    360

caaggctgca acctggatgc catcaaagtc ttctgcaaca tggagactgg tgagacctgc    420

gtgtacccca ctcagcccag tgtggcccag aagaactggt acatcagcaa gaaccccaag    480

gacaagaggc atgtctggtt cggcgagagc atgaccgatg gattccagtt cgagtatggc    540

ggccagggct cccaccctgc cgatgtggac ctccggccgc gaccaccctt               590
```

<210> SEQ ID NO 216
<211> LENGTH: 801
<212> TYPE: DNA
<213> ORGANISM: Homo sapiens
<220> FEATURE:
<221> NAME/KEY: modified_base -continued
<222> LOCATION: (2)
<223> OTHER INFORMATION: Where n is a, c, g or t
<221> NAME/KEY: modified_base
<222> LOCATION: (22)
<223> OTHER INFORMATION: Where n is a, c, g or t
<221> NAME/KEY: modified_base
<222> LOCATION: (25)
<223> OTHER INFORMATION: Where n is a, c, g or t
<221> NAME/KEY: modified_base
<222> LOCATION: (26)
<223> OTHER INFORMATION: Where n is a, c, g or t
<221> NAME/KEY: modified_base
<222> LOCATION: (328)
<223> OTHER INFORMATION: Where n is a, c, g or t
<221> NAME/KEY: modified_base
<222> LOCATION: (373)
<223> OTHER INFORMATION: Where n is a, c, g or t
<221> NAME/KEY: modified_base
<222> LOCATION: (385)
<223> OTHER INFORMATION: Where n is a, c, g or t
<221> NAME/KEY: modified_base
<222> LOCATION: (440)
<223> OTHER INFORMATION: Where n is a, c, g or t
<221> NAME/KEY: modified_base
<222> LOCATION: (473)
<223> OTHER INFORMATION: Where n is a, c, g or t
<221> NAME/KEY: modified_base
<222> LOCATION: (534)
<223> OTHER INFORMATION: Where n is a, c, g or t
<221> NAME/KEY: modified_base
<222> LOCATION: (571)
<223> OTHER INFORMATION: Where n is a, c, g or t
<221> NAME/KEY: modified_base
<222> LOCATION: (572)
<223> OTHER INFORMATION: Where n is a, c, g or t
<221> NAME/KEY: modified_base
<222> LOCATION: (573)
<223> OTHER INFORMATION: Where n is a, c, g or t
<221> NAME/KEY: modified_base
<222> LOCATION: (582)
<223> OTHER INFORMATION: Where n is a, c, g or t
<221> NAME/KEY: modified_base
<222> LOCATION: (587)
<223> OTHER INFORMATION: Where n is a, c, g or t
<221> NAME/KEY: modified_base
<222> LOCATION: (589)
<223> OTHER INFORMATION: Where n is a, c, g or t
<221> NAME/KEY: modified_base
<222> LOCATION: (593)
<223> OTHER INFORMATION: Where n is a, c, g or t
<221> NAME/KEY: modified_base
<222> LOCATION: (600)
<223> OTHER INFORMATION: Where n is a, c, g or t
<221> NAME/KEY: modified_base
<222> LOCATION: (605)
<223> OTHER INFORMATION: Where n is a, c, g or t
<221> NAME/KEY: modified_base
<222> LOCATION: (617)
<223> OTHER INFORMATION: Where n is a, c, g or t
<221> NAME/KEY: modified_base
<222> LOCATION: (633)
<223> OTHER INFORMATION: Where n is a, c, g or t
<221> NAME/KEY: modified_base
<222> LOCATION: (642)
<223> OTHER INFORMATION: Where n is a, c, g or t
<221> NAME/KEY: modified_base
<222> LOCATION: (653)
<223> OTHER INFORMATION: Where n is a, c, g or t
<221> NAME/KEY: modified_base
<222> LOCATION: (672)
<223> OTHER INFORMATION: Where n is a, c, g or t
<221> NAME/KEY: modified_base
<222> LOCATION: (681)
<223> OTHER INFORMATION: Where n is a, c, g or t
<221> NAME/KEY: modified_base
<222> LOCATION: (685)
<223> OTHER INFORMATION: Where n is a, c, g or t
<221> NAME/KEY: modified_base
<222> LOCATION: (696)

```
<223> OTHER INFORMATION: Where n is a, c, g or t
<221> NAME/KEY: modified_base
<222> LOCATION: (699)
<223> OTHER INFORMATION: Where n is a, c, g or t
<221> NAME/KEY: modified_base
<222> LOCATION: (709)
<223> OTHER INFORMATION: Where n is a, c, g or t
<221> NAME/KEY: modified_base
<222> LOCATION: (715)
<223> OTHER INFORMATION: Where n is a, c, g or t
<221> NAME/KEY: modified_base
<222> LOCATION: (717)
<223> OTHER INFORMATION: Where n is a, c, g or t
<221> NAME/KEY: modified_base
<222> LOCATION: (726)
<223> OTHER INFORMATION: Where n is a, c, g or t
<221> NAME/KEY: modified_base
<222> LOCATION: (731)
<223> OTHER INFORMATION: Where n is a, c, g or t
<221> NAME/KEY: modified_base
<222> LOCATION: (739)
<223> OTHER INFORMATION: Where n is a, c, g or t
<221> NAME/KEY: modified_base
<222> LOCATION: (742)
<223> OTHER INFORMATION: Where n is a, c, g or t
<221> NAME/KEY: modified_base
<222> LOCATION: (745)
<223> OTHER INFORMATION: Where n is a, c, g or t
<221> NAME/KEY: modified_base
<222> LOCATION: (758)
<223> OTHER INFORMATION: Where n is a, c, g or t
<221> NAME/KEY: modified_base
<222> LOCATION: (769)
<223> OTHER INFORMATION: Where n is a, c, g or t
<221> NAME/KEY: modified_base
<222> LOCATION: (772)
<223> OTHER INFORMATION: Where n is a, c, g or t
<221> NAME/KEY: modified_base
<222> LOCATION: (778)
<223> OTHER INFORMATION: Where n is a, c, g or t
<221> NAME/KEY: modified_base
<222> LOCATION: (780)
<223> OTHER INFORMATION: Where n is a, c, g or t
<221> NAME/KEY: modified_base
<222> LOCATION: (788)
<223> OTHER INFORMATION: Where n is a, c, g or t
<221> NAME/KEY: modified_base
<222> LOCATION: (789)
<223> OTHER INFORMATION: Where n is a, c, g or t
<221> NAME/KEY: modified_base
<222> LOCATION: (791)
<223> OTHER INFORMATION: Where n is a, c, g or t
<221> NAME/KEY: modified_base
<222> LOCATION: (793)
<223> OTHER INFORMATION: Where n is a, c, g or t
<221> NAME/KEY: modified_base
<222> LOCATION: (796)
<223> OTHER INFORMATION: Where n is a, c, g or t

<400> SEQUENCE: 216

tngagcggcc gcccgggcag gntgnnaacg ctggtcctgc tggtcctcct ggcaaggctg      60

gtgaagatgg tcaccctgga aaacccggac gacctggtga gagaggagtt gttggaccac     120

agggtgctcg tggtttccct ggaactcctg gacttcctgg cttcaaaggc attaggggac     180

acaatggtct ggatggattg aagggacagc ccggtgctcc tggtgtgaag ggtgaacctg     240

gtgcccctgg tgaaaatgga actccaggtc aaacaggagc ccgtgggctt cctggtgaga     300

gaggaccgtg ttggtgcccc tggcccanac ctcggccgcg accacgctaa gcccgaattt     360

ccagcacact ggnggccgtt actantggat ccgagctcgg taccaagctt ggcgtaatca     420

tggtcatagc tgtttcctgn gtgaaattgt tatccgctca caatttcaca cancatacga     480

agccggaaag cataaagtgt aaagccttgg ggtgctaatg agtgagctaa ctcncattaa     540
```

-continued attgcgttgc gctcactgcc cgcttttcca nnngggaaac cntggcntng ccngcttgcn 600
ttaantgaaa tccgccnacc cccggggaaa agncggtttg cngtattggg gcncttttttc 660 cctttcctcg gnttacttga nttantgggc tttggncgnt tcgggttgng gcgancnggt 720
tcaacntcac nccaaaggng gnaanacggt tttcccanaa tccgggggnt ancccaangn 780
aaaacatnng ncnaangggc t 801

<210> SEQ ID NO 217
<211> LENGTH: 349
<212> TYPE: DNA
<213> ORGANISM: Homo sapiens
<220> FEATURE:
<221> NAME/KEY: modified_base
<222> LOCATION: (10)
<223> OTHER INFORMATION: Where n is a, c, g or t
<221> NAME/KEY: modified_base
<222> LOCATION: (157)
<223> OTHER INFORMATION: Where n is a, c, g or t
<221> NAME/KEY: modified_base
<222> LOCATION: (170)
<223> OTHER INFORMATION: Where n is a, c, g or t

<400> SEQUENCE: 217
agcgtggttn gcggccgagg tctgggccag gggcaccaac acgtcctctc tcaccaggaa 60
gcccacgggc tcctgtttga cctggagttc cattttcacc aggggcacca ggttcaccct 120
tcacaccagg agcaccgggc tgtcccttca atccatncag accattgtgn cccctaatgc 180
ctttgaagcc aggaagtcca ggagttccag ggaaaccacc gagcaccctg tggtccaaca 240
actcctctct caccaggtcg tccgggtttt ccagggtgac catcttcacc agccttgcca 300
ggaggaccag caggaccagc gttaccaacc tgcccgggcg gccgctcga 349

<210> SEQ ID NO 218
<211> LENGTH: 372
<212> TYPE: DNA
<213> ORGANISM: Homo sapiens

<400> SEQUENCE: 218
tcgagcggcc gcccgggcag gtccattttc tccctgacgg tcccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ttgacagagt tgcccacggt aacaacctct tcccgaacct tatgcctctg 300
ctggtctttc agtgcctcca ctatgatgtt gtaggtggca cctctggtga ggacctcggc 360
cgcgaccacg ct 372

<210> SEQ ID NO 219
<211> LENGTH: 374
<212> TYPE: DNA
<213> ORGANISM: Homo sapiens

<400> SEQUENCE: 219
agcgtggtcg cggccgaggt cctcaccaga ggtgccacct acaacatcat agtggaggca 60
ctgaaagacc agcagaggca taaggttcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttaggct ttggaagtgg tcatttcaag atgtgattca tctagatggt gccatgacaa 300
tggtgtgaac tacaagattg gagagaagtg ggaccgtcag ggagaaaatg gacctgcccg 360
ggccggccgc tcga 374

<210> SEQ ID NO 220
<211> LENGTH: 828
<212> TYPE: DNA
<213> ORGANISM: Homo sapiens
<220> FEATURE:
<221> NAME/KEY: modified_base
<222> LOCATION: (8)
<223> OTHER INFORMATION: Where n is a, c, g or t
<221> NAME/KEY: modified_base
<222> LOCATION: (9)
<223> OTHER INFORMATION: Where n is a, c, g or t
<221> NAME/KEY: modified_base
<222> LOCATION: (557)
<223> OTHER INFORMATION: Where n is a, c, g or t
<221> NAME/KEY: modified_base
<222> LOCATION: (571)
<223> OTHER INFORMATION: Where n is a, c, g or t
<221> NAME/KEY: modified_base
<222> LOCATION: (587)
<223> OTHER INFORMATION: Where n is a, c, g or t
<221> NAME/KEY: modified_base
<222> LOCATION: (588)
<223> OTHER INFORMATION: Where n is a, c, g or t
<221> NAME/KEY: modified_base
<222> LOCATION: (601)
<223> OTHER INFORMATION: Where n is a, c, g or t
<221> NAME/KEY: modified_base
<222> LOCATION: (642)
<223> OTHER INFORMATION: Where n is a, c, g or t
<221> NAME/KEY: modified_base
<222> LOCATION: (643)
<223> OTHER INFORMATION: Where n is a, c, g or t
<221> NAME/KEY: modified_base
<222> LOCATION: (647)
<223> OTHER INFORMATION: Where n is a, c, g or t
<221> NAME/KEY: modified_base
<222> LOCATION: (654)
<223> OTHER INFORMATION: Where n is a, c, g or t
<221> NAME/KEY: modified_base
<222> LOCATION: (664)
<223> OTHER INFORMATION: Where n is a, c, g or t
<221> NAME/KEY: modified_base
<222> LOCATION: (681)
<223> OTHER INFORMATION: Where n is a, c, g or t
<221> NAME/KEY: modified_base
<222> LOCATION: (688)
<223> OTHER INFORMATION: Where n is a, c, g or t
<221> NAME/KEY: modified_base
<222> LOCATION: (698)
<223> OTHER INFORMATION: Where n is a, c, g or t
<221> NAME/KEY: modified_base
<222> LOCATION: (719)
<223> OTHER INFORMATION: Where n is a, c, g or t
<221> NAME/KEY: modified_base
<222> LOCATION: (720)
<223> OTHER INFORMATION: Where n is a, c, g or t
<221> NAME/KEY: modified_base
<222> LOCATION: (725)
<223> OTHER INFORMATION: Where n is a, c, g or t
<221> NAME/KEY: modified_base
<222> LOCATION: (734)
<223> OTHER INFORMATION: Where n is a, c, g or t
<221> NAME/KEY: modified_base
<222> LOCATION: (738)
<223> OTHER INFORMATION: Where n is a, c, g or t
<221> NAME/KEY: modified_base
<222> LOCATION: (743)
<223> OTHER INFORMATION: Where n is a, c, g or t
<221> NAME/KEY: modified_base
<222> LOCATION: (744)
<223> OTHER INFORMATION: Where n is a, c, g or t
<221> NAME/KEY: modified_base
<222> LOCATION: (757)

-continued

<223> OTHER INFORMATION: Where n is a, c, g or t
<221> NAME/KEY: modified_base
<222> LOCATION: (765)
<223> OTHER INFORMATION: Where n is a, c, g or t
<221> NAME/KEY: modified_base
<222> LOCATION: (773)
<223> OTHER INFORMATION: Where n is a, c, g or t
<221> NAME/KEY: modified_base
<222> LOCATION: (778)
<223> OTHER INFORMATION: Where n is a, c, g or t
<221> NAME/KEY: modified_base
<222> LOCATION: (780)
<223> OTHER INFORMATION: Where n is a, c, g or t
<221> NAME/KEY: modified_base
<222> LOCATION: (782)
<223> OTHER INFORMATION: Where n is a, c, g or t
<221> NAME/KEY: modified_base
<222> LOCATION: (783)
<223> OTHER INFORMATION: Where n is a, c, g or t
<221> NAME/KEY: modified_base
<222> LOCATION: (793)
<223> OTHER INFORMATION: Where n is a, c, g or t
<221> NAME/KEY: modified_base
<222> LOCATION: (798)
<223> OTHER INFORMATION: Where n is a, c, g or t
<221> NAME/KEY: modified_base
<222> LOCATION: (805)
<223> OTHER INFORMATION: Where n is a, c, g or t
<221> NAME/KEY: modified_base
<222> LOCATION: (809)
<223> OTHER INFORMATION: Where n is a, c, g or t
<221> NAME/KEY: modified_base
<222> LOCATION: (821)
<223> OTHER INFORMATION: Where n is a, c, g or t
<221> NAME/KEY: modified_base
<222> LOCATION: (827)
<223> OTHER INFORMATION: Where n is a, c, g or t

<400> SEQUENCE: 220
tcgagcgnnc gcccgggcag gtccagtagt gccttcggga ctgggttcac ccccaggtct 60
gcggcagttg tcacagcgcc agccccgctg gcctccaaag catgtgcagg agcaaatggc 120
accgagatat tccttctgcc actgttctcc tacgtggtat gtcttcccat catcgtaaca 180
cgttgcctca tgagggtcac acttgaattc tccttttccg ttcccaagac atgtgcagct 240
catttggctg gctctatagt ttggggaaag tttgttgaaa ctgtgccact gacctttact 300
tcctccttct ctactggagc tttcgtacct tccacttctg ctgttggtaa aatggtggat 360
cttctatcaa tttcattgac agtacccact tctcccaaac atccagggaa atagtgattt 420
cagagcgatt aggagaacca aattatgggg cagaaataag gggcttttcc acaggttttc 480
ctttggagga agatttcagt ggtgacttta aaagaatact caacagtgtc ttcatcccca 540
tagcaaaaga agaaacngta aatgatggaa ngcttctgga gatgccnnca tttaagggac 600
ncccagaact tcaccatcta caggacctac ttcagtttac annaagncac atantctgac 660
tcanaaagga cccaagtagc nccatggnca gcactttnag cctttcccct ggggaaaann 720
ttacnttctt aaancctngg ccnngacccc cttaagncca aattntggaa aanttccntn 780
cnnctggggg gcngttcnac atgcntttna agggcccaat tnccccnt 828

<210> SEQ ID NO 221
<211> LENGTH: 476
<212> TYPE: DNA
<213> ORGANISM: Homo sapiens

<400> SEQUENCE: 221
tcgagcggcc gcccgggcag gtgtcggagt ccagcacggg aggcgtggtc ttgtagttgt 60
tctccggctg cccattgctc tcccactcca cggcgatgtc gctgggatag aagcctttga 120

-continued

```
ccaggcaggt caggctgacc tggttcttgg tcatctcctc ccgggatggg ggcagggtgt    180

acacctgtgg ttctcggggc tgccctttgg ctttggagat ggttttctcg atgggggctg    240

ggagggcttt gttggagacc ttgcacttgt actccttgcc attcagccag tcctggtgca    300

ggacggtgag gacgctgacc acacggtacg tgctgttgta ctgctcctcc cgcggctttg    360

tcttggcatt atgcacctcc acgccgtcca cgtaccagtt gaacttgacc tcagggtctt    420

cgtggctcac gtccaccacc acgcatgtaa cctcagacct cggccgcgac cacgct        476
```

<210> SEQ ID NO 222
<211> LENGTH: 477
<212> TYPE: DNA
<213> ORGANISM: Homo sapiens

<400> SEQUENCE: 222

```
agcgtggtcg cggccgaggt ctgaggttac atgcgtggtg gtggacgtga gccacgaaga     60

ccctgaggtc aagttcaact ggtacgtgga cggcgtggag gtgcataatg ccaagacaaa    120

gccgcgggag gagcagtaca acagcacgta ccgtgtggtc agcgtcctca ccgtcctgca    180

ccaggactgg ctgaatggca aggagtacaa gtgcaaggtc tccaacaaag ccctcccagc    240

ccccatcgag aaaaccatct ccaaagccaa agggcaagcc ccgagaacca caggtgtaca    300

ccctgccccc atcccgggag gagatgacca agaaccaggt cagcctgacc tgcctggtca    360

aaggcttcta tcccagcgac atcgccgtgg agtgggagag caatgggcag ccggagaaca    420

actacaagac cacgcctccc gtgctggact ccgacacctg cccgggcggc cgctcga       477
```

<210> SEQ ID NO 223
<211> LENGTH: 361
<212> TYPE: DNA
<213> ORGANISM: Homo sapiens

<400> SEQUENCE: 223

```
tcgagcggcc gcccgggcag gttgaatggc tcctcgctga ccaccccggt gctggtggtg     60

ggtacagagc tccgatgggt gaaaccattg acatagagac tgtccctgtc cagggtgtag    120

gggcccagct cagtgatgcc gtgggtcagc tggctcagct tccagtacag ccgctctctg    180

tccagtccag ggcttttggg gtcaggacga tgggtgcaga cagcatccac tctggtggct    240

gccccatcct tctcaggcct gagcaaggtc agtctgcaac cagagtacag agagctgaca    300

ctggtgttct tgaacaaggg cataagcaga ccctgaagga cacctcggcc gcgaccacgc    360

t                                                                    361
```

<210> SEQ ID NO 224
<211> LENGTH: 361
<212> TYPE: DNA
<213> ORGANISM: Homo sapiens

<400> SEQUENCE: 224

```
agcgtggtcg cggccgaggt gtccttcagg gtctgcttat gcccttgttc aagaacacca     60

gtgtcagctc tctgtactct ggttgcagac tgaccttgct caggcctgag aaggatgggg    120

cagccaccag agtggatgct gtctgcaccc atcgtcctga ccccaaaagc cctggactgg    180

acagagagcg gctgtactgg aagctgagcc agctgaccca cggcatcact gagctgggcc    240

cctacaccct ggacagggac agtctctatg tcaatggttt cacccatcgg agctctgtac    300

ccaccaccag caccggggtg gtcagcgagg agccattcaa cctgcccggg cggccgctcg    360
```

-continued a 361

<210> SEQ ID NO 225
<211> LENGTH: 766
<212> TYPE: DNA
<213> ORGANISM: Homo sapiens
<220> FEATURE:
<221> NAME/KEY: modified_base
<222> LOCATION: (574)
<223> OTHER INFORMATION: Where n is a, c, g or t
<221> NAME/KEY: modified_base
<222> LOCATION: (610)
<223> OTHER INFORMATION: Where n is a, c, g or t
<221> NAME/KEY: modified_base
<222> LOCATION: (631)
<223> OTHER INFORMATION: Where n is a, c, g or t
<221> NAME/KEY: modified_base
<222> LOCATION: (643)
<223> OTHER INFORMATION: Where n is a, c, g or t
<221> NAME/KEY: modified_base
<222> LOCATION: (657)
<223> OTHER INFORMATION: Where n is a, c, g or t
<221> NAME/KEY: modified_base
<222> LOCATION: (660)
<223> OTHER INFORMATION: Where n is a, c, g or t
<221> NAME/KEY: modified_base
<222> LOCATION: (688)
<223> OTHER INFORMATION: Where n is a, c, g or t
<221> NAME/KEY: modified_base
<222> LOCATION: (712)
<223> OTHER INFORMATION: Where n is a, c, g or t
<221> NAME/KEY: modified_base
<222> LOCATION: (735)
<223> OTHER INFORMATION: Where n is a, c, g or t
<221> NAME/KEY: modified_base
<222> LOCATION: (747)
<223> OTHER INFORMATION: Where n is a, c, g or t

<400> SEQUENCE: 225
agcgtggtcg cggccgaggt cctgtcagag tggcactggt agaagttcca ggaaccctga 60
actgtaaggg ttcttcatca gtgccaacag gatgacatga aatgatgtac tcagaagtgt 120
cctggaatgg ggcccatgag atggttgtct gagagagagc ttcttgtcct acattcggcg 180
ggtatggtct tggcctatgc cttatggggg tggccgttgt gggcggtgtg gtccgcctaa 240
aaccatgttc ctcaaagatc atttgttgcc caacactggg ttgctgacca gaagtgccag 300
gaagctgaat accatttcca gtgtcatacc cagggtgggt gacgaaaggg gtcttttgaa 360
ctgtggaagg aacatccaag atctctggtc catgaagatt ggggtgtgga agggttacca 420
gttggggaag ctcgtctgtc tttttccttc caatcagggg ctcgctcttc tgattattct 480
tcagggcaat gacataaatt gtatattcgg tcccggttcc aggccagtaa tagtagcctc 540
tgtgacacca gggcggggcc gagggaccct tctnttggaa gagaccagct tctcatactt 600
gatgatgagn ccggtaatcc tggcacgtgg nggttgcatg atnccaccaa ggaaatnggn 660
gggggnggac ctgcccggcg gccgttcnaa agcccaattc cacacacttg gnggccgtac 720
tatggatccc actcngtcca acttggngga atatggcata actttt 766

<210> SEQ ID NO 226
<211> LENGTH: 364
<212> TYPE: DNA
<213> ORGANISM: Homo sapiens

<400> SEQUENCE: 226
tcgagcggcc gcccgggcag gtccttgacc ttttcagcaa gtgggaaggt gtaatccgtc 60
tccacagaca aggccaggac tcgtttgtac ccgttgatga tagaatgggg tactgatgca 120

-continued

```
acagttgggt agccaatctg cagacagaca ctggcaacat tgcggacacc ctccaggaag    180

cgagaatgca gagtttcctc tgtgatatca agcacttcag ggttgtagat gctgccattg    240

tcgaacacct gctggatgac cagcccaaag gagaaggggg agatgttgag catgttcagc    300

agcgtggctt cgctggctcc cactttgtct ccagtcttga tcagacctcg gccgcgacca    360

cgct                                                                 364


<210> SEQ ID NO 227
<211> LENGTH: 275
<212> TYPE: DNA
<213> ORGANISM: Homo sapiens

<400> SEQUENCE: 227

agcgtggtcg cggccgaggt ctgtcctaca gtcctcagga ctctactccc tcagcagcgt     60

ggtgaccgtg ccctccagca acttcggcac ccagacctac acctgcaacg tagatcacaa    120

gcccagcaac accaaggtgg acaagagagt tgagcccaaa tcttgtgaca aaactcacac    180

atgcccaccg tgcccagcac ctgaactcct ggggggaccg tcagtcttcc tcttcccccg    240

catccccctt ccaaacctgc ccgggcggcc gctcg                               275


<210> SEQ ID NO 228
<211> LENGTH: 275
<212> TYPE: DNA
<213> ORGANISM: Homo sapiens

<400> SEQUENCE: 228

cgagcggccg cccgggcagg tttggaaggg ggatgcgggg gaagaggaag actgacggtc     60

cccccaggag ttcaggtgct gggcacggtg ggcatgtgtg agttttgtca caagatttgg    120

gctcaactct cttgtccacc ttggtgttgc tgggcttgtg atctacgttg caggtgtagg    180

tctgggtgcc gaagttgctg gagggcacgg tcaccacgct gctgagggag tagagtcctg    240

aggactgtag gacagacctc ggccgcgacc acgct                               275


<210> SEQ ID NO 229
<211> LENGTH: 40
<212> TYPE: DNA
<213> ORGANISM: Homo sapiens
<220> FEATURE:
<221> NAME/KEY: modified_base
<222> LOCATION: (1)
<223> OTHER INFORMATION: Where n is a, c, g or t
<221> NAME/KEY: modified_base
<222> LOCATION: (4)
<223> OTHER INFORMATION: Where n is a, c, g or t
<221> NAME/KEY: modified_base
<222> LOCATION: (5)
<223> OTHER INFORMATION: Where n is a, c, g or t
<221> NAME/KEY: modified_base
<222> LOCATION: (13)
<223> OTHER INFORMATION: Where n is a, c, g or t
<221> NAME/KEY: modified_base
<222> LOCATION: (15)
<223> OTHER INFORMATION: Where n is a, c, g or t
<221> NAME/KEY: modified_base
<222> LOCATION: (17)
<223> OTHER INFORMATION: Where n is a, c, g or t
<221> NAME/KEY: modified_base
<222> LOCATION: (29)
<223> OTHER INFORMATION: Where n is a, c, g or t

<400> SEQUENCE: 229

nggnnggtcc ggncngncag gaccactcnt cttcgaaata                           40
```

-continued

<210> SEQ ID NO 230
<211> LENGTH: 208
<212> TYPE: DNA
<213> ORGANISM: Homo sapiens

<400> SEQUENCE: 230
agcgtggtcg cggccgaggt cctcacttgc ctcctgcaaa gcaccgatag ctgcgctctg 60
gaagcgcaga tctgttttaa agtcctgagc aatttctcgc accagacgct ggaagggaag 120
tttgcgaatc agaagttcag tggacttctg ataacgtcta atttcacgga gcgccacagt 180
accaggacct gcccgggcgg ccgctcga 208

<210> SEQ ID NO 231
<211> LENGTH: 208
<212> TYPE: DNA
<213> ORGANISM: Homo sapiens
<220> FEATURE:
<221> NAME/KEY: modified_base
<222> LOCATION: (33)
<223> OTHER INFORMATION: Where n is a, c, g or t

<400> SEQUENCE: 231
tcgagcggcc gcccgggcag gtcctggtac tgnggcgctc cgtgaaatta gacgttatca 60
gaagtccact gaacttctga ttcgcaaact tcccttccag cgtctggtgc gagaaattgc 120
tcaggacttt aaaacagatc tgcgcttcca gagcgcagct atcggtgctt tgcaggaggc 180
aagtgaggac ctcggccgcg accacgct 208

<210> SEQ ID NO 232
<211> LENGTH: 332
<212> TYPE: DNA
<213> ORGANISM: Homo sapiens

<400> SEQUENCE: 232
tcgagcggcc gcccgggcag gtccacatcg gcagggtcgg agccctggcc gccatactcg 60
aactggaatc catcggtcat gctctcgccg aaccagacat gcctcttgtc cttggggttc 120
ttgctgatgt accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagtcagag tggcacatct tgaggtcacg gcaggtgcgg 300
gcggggttct tgacctcggc cgcgaccacg ct 332

<210> SEQ ID NO 233
<211> LENGTH: 415
<212> TYPE: DNA
<213> ORGANISM: Homo sapiens
<220> FEATURE:
<221> NAME/KEY: modified_base
<222> LOCATION: (6)
<223> OTHER INFORMATION: Where n is a, c, g or t
<221> NAME/KEY: modified_base
<222> LOCATION: (15)
<223> OTHER INFORMATION: Where n is a, c, g or t
<221> NAME/KEY: modified_base
<222> LOCATION: (19)
<223> OTHER INFORMATION: Where n is a, c, g or t
<221> NAME/KEY: modified_base
<222> LOCATION: (21)
<223> OTHER INFORMATION: Where n is a, c, g or t

<400> SEQUENCE: 233
gtgggnttga acccntttna nctccgcttg gtaccgagct cggatccact agtaacggcc 60
gccagtgtgc tggaattcgg cttagcgtgg tcgcggccga ggtcaagaac cccgcccgca 120

-continued

```
cctgccgtga cctcaagatg tgccactctg actggaagag tggagagtac tggattgacc    180

ccaaccaagg ctgcaacctg gatgccatca aagtcttctg caacatggag actggtgaga    240

cctgcgtgta ccccactcag cccagtgtgg cccagaagaa ctggtacatc agcaagaacc    300

ccaaggacaa gaggcatgtc tggttcggcg agagcatgac cgatggattc cagttcgagt    360

atggcggcca gggctccgac cctgccgatg tggacctgcc cgggcggccg ctcga         415
```

```
<210> SEQ ID NO 234
<211> LENGTH: 776
<212> TYPE: DNA
<213> ORGANISM: Homo sapiens
<220> FEATURE:
<221> NAME/KEY: modified_base
<222> LOCATION: (505)
<223> OTHER INFORMATION: Where n is a, c, g or t
<221> NAME/KEY: modified_base
<222> LOCATION: (550)
<223> OTHER INFORMATION: Where n is a, c, g or t
<221> NAME/KEY: modified_base
<222> LOCATION: (574)
<223> OTHER INFORMATION: Where n is a, c, g or t
<221> NAME/KEY: modified_base
<222> LOCATION: (601)
<223> OTHER INFORMATION: Where n is a, c, g or t
<221> NAME/KEY: modified_base
<222> LOCATION: (604)
<223> OTHER INFORMATION: Where n is a, c, g or t
<221> NAME/KEY: modified_base
<222> LOCATION: (608)
<223> OTHER INFORMATION: Where n is a, c, g or t
<221> NAME/KEY: modified_base
<222> LOCATION: (612)
<223> OTHER INFORMATION: Where n is a, c, g or t
<221> NAME/KEY: modified_base
<222> LOCATION: (649)
<223> OTHER INFORMATION: Where n is a, c, g or t
<221> NAME/KEY: modified_base
<222> LOCATION: (656)
<223> OTHER INFORMATION: Where n is a, c, g or t
<221> NAME/KEY: modified_base
<222> LOCATION: (657)
<223> OTHER INFORMATION: Where n is a, c, g or t
<221> NAME/KEY: modified_base
<222> LOCATION: (680)
<223> OTHER INFORMATION: Where n is a, c, g or t
<221> NAME/KEY: modified_base
<222> LOCATION: (711)
<223> OTHER INFORMATION: Where n is a, c, g or t
<221> NAME/KEY: modified_base
<222> LOCATION: (750)
<223> OTHER INFORMATION: Where n is a, c, g or t
<221> NAME/KEY: modified_base
<222> LOCATION: (776)
<223> OTHER INFORMATION: Where n is a, c, g or t

<400> SEQUENCE: 234

agcgtggtcg cggccgaggt ctgggatgct cctgctgtca cagtgagata ttacaggatc     60

acttacggag aaacaggagg aaatagccct gtccaggagt tcactgtgcc tgggagcaag    120

tctacagcta ccatcagcgg ccttaaacct ggagttgatt ataccatcac tgtgtatgct    180

gtcactggcc gtggagacag ccccgcaagc agcaagccaa tttccattaa ttaccgaaca    240

gaaattgaca aaccatccca gatgcaagtg accgatgttc aggacaacag cattagtgtc    300

aagtggctgc cttcaagttc ccctgttact ggttacagag taaccaccac tcccaaaaat    360

ggaccaggac caacaaaaac taaaactgca ggtccagatc aaacagaaat gactattgaa    420

ggcttgcagc ccacagtgga gtatgtggtt aagtgtctat gctcagaatc caagcggaga    480

gaagtcagcc tctggttcag actgnaagta accaacattg atcgcctaaa ggactggcat    540
```

-continued

```
tcactgatgn ggatgccgat tccatcaaaa ttgnttggga aaacccacag gggcaagttt    600

ncangtcnag gnggacctac tcgagccctg aggatggaat ccttgactnt tccttnncct    660

gatggggaaa aaaaaccttn aaaacttgaa ggacctgccc gggcggccgt ncaaaaccca    720

attccacccc cttgggggcg ttctatgggn cccactcgga ccaaacttgg ggtaan        776
```

<210> SEQ ID NO 235
<211> LENGTH: 805
<212> TYPE: DNA
<213> ORGANISM: Homo sapiens
<220> FEATURE:
<221> NAME/KEY: modified_base
<222> LOCATION: (637)
<223> OTHER INFORMATION: Where n is a, c, g or t
<221> NAME/KEY: modified_base
<222> LOCATION: (684)
<223> OTHER INFORMATION: Where n is a, c, g or t
<221> NAME/KEY: modified_base
<222> LOCATION: (705)
<223> OTHER INFORMATION: Where n is a, c, g or t
<221> NAME/KEY: modified_base
<222> LOCATION: (724)
<223> OTHER INFORMATION: Where n is a, c, g or t
<221> NAME/KEY: modified_base
<222> LOCATION: (733)
<223> OTHER INFORMATION: Where n is a, c, g or t
<221> NAME/KEY: modified_base
<222> LOCATION: (756)
<223> OTHER INFORMATION: Where n is a, c, g or t
<221> NAME/KEY: modified_base
<222> LOCATION: (778)
<223> OTHER INFORMATION: Where n is a, c, g or t
<221> NAME/KEY: modified_base
<222> LOCATION: (793)
<223> OTHER INFORMATION: Where n is a, c, g or t
<221> NAME/KEY: modified_base
<222> LOCATION: (796)
<223> OTHER INFORMATION: Where n is a, c, g or t
<221> NAME/KEY: modified_base
<222> LOCATION: (804)
<223> OTHER INFORMATION: Where n is a, c, g or t

<400> SEQUENCE: 235

```
tcgagcggcc gcccgggcag gtccttgcag ctctgcagtg tcttcttcac catcaggtgc     60

agggaatagc tcatggattc catcctcagg gctcgagtag gtcaccctgt acctggaaac    120

ttgcccctgt gggctttccc aagcaatttt gatggaatcg gcatccacat cagtgaatgc    180

cagtccttta gggcgatcaa tgttggttac tgcagtctga accagaggct gactctctcc    240

gcttggattc tgagcataga cactaaccac atactccact gtgggctgca agccttcaat    300

agtcatttct gtttgatctg gacctgcagt tttagttttt gttggtcctg gtccattttt    360

gggagtggtg gttactctgt aaccagtaac aggggaactt gaaggcagcc acttgacact    420

aatgctgttg tcctgaacat cggtcacttg catctgggat ggtttgtcaa tttctgttcg    480

gtaattaatg gaaattggct tgctgcttgc ggggcttgtc tccacggcca gtgacagcat    540

acacagtgat ggtataatca actccaggtt taagccgctg atggtagctg aaactttgct    600

ccaggcacaa gtgaactcct gacagggcta tttcctnctg ttctccgtaa gtgatcctgt    660

aatatctcac tgggacagca ggangcattc caaaacttcg ggcgngaccc cctaagccga    720

attntgcaat atncatcaca ctggcgggcg ctcgancatt cattaaaagg cccaatcncc    780

cctataggga gtntantaca attng                                          805
```

<210> SEQ ID NO 236
<211> LENGTH: 262

-continued

<212> TYPE: DNA
<213> ORGANISM: Homo sapiens

<400> SEQUENCE: 236
tcgagcggcc gcccgggcag gtcacttttg gtttttggtc atgttcggtt ggtcaaagat 60
aaaaactaag tttgagagat gaatgcaaag gaaaaaaata ttttccaaag tccatgtgaa 120
attgtctccc attttttgg cttttgaggg ggttcagttt gggttgcttg tctgtttccg 180
ggttgggggg aaagttggtt gggtgggagg gagccaggtt gggatggagg gagtttacag 240
gaagcagaca gggccaacgt cg 262

<210> SEQ ID NO 237
<211> LENGTH: 372
<212> TYPE: DNA
<213> ORGANISM: Homo sapiens

<400> SEQUENCE: 237
agcgtggtcg cggccgaggt cctcaccaga ggtgccacct acaacatcat agtggaggca 60
ctgaaagacc agcagaggca taaggttcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttaggct ttggaagtgg tcatttcaga tgtgattcat ctagatggtg ccatgacaat 300
ggtgtgaact acaagattgg agagaagtgg gaccgtcagg gagaaaatgg acctgcccgg 360
gcggccgctc ga 372

<210> SEQ ID NO 238
<211> LENGTH: 372
<212> TYPE: DNA
<213> ORGANISM: Homo sapiens

<400> SEQUENCE: 238
tcgagcggcc gcccgggcag gtccattttc tccctgacgg tcccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ttgacagagt tgcccacggt aacaacctct tcccgaacct tatgcctctg 300
ctggtctttc agtgcctcca ctatgatgtt gtaggtggca cctctggtga ggacctcggc 360
cgcgaccacg ct 372

<210> SEQ ID NO 239
<211> LENGTH: 720
<212> TYPE: DNA
<213> ORGANISM: Homo sapiens
<220> FEATURE:
<221> NAME/KEY: modified_base
<222> LOCATION: (478)
<223> OTHER INFORMATION: Where n is a, c, g or t
<221> NAME/KEY: modified_base
<222> LOCATION: (557)
<223> OTHER INFORMATION: Where n is a, c, g or t
<221> NAME/KEY: modified_base
<222> LOCATION: (563)
<223> OTHER INFORMATION: Where n is a, c, g or t
<221> NAME/KEY: modified_base
<222> LOCATION: (566)
<223> OTHER INFORMATION: Where n is a, c, g or t
<221> NAME/KEY: modified_base
<222> LOCATION: (620)

-continued

<223> OTHER INFORMATION: Where n is a, c, g or t
<221> NAME/KEY: modified_base
<222> LOCATION: (660)
<223> OTHER INFORMATION: Where n is a, c, g or t
<221> NAME/KEY: modified_base
<222> LOCATION: (663)
<223> OTHER INFORMATION: Where n is a, c, g or t
<221> NAME/KEY: modified_base
<222> LOCATION: (672)
<223> OTHER INFORMATION: Where n is a, c, g or t
<221> NAME/KEY: modified_base
<222> LOCATION: (673)
<223> OTHER INFORMATION: Where n is a, c, g or t
<221> NAME/KEY: modified_base
<222> LOCATION: (684)
<223> OTHER INFORMATION: Where n is a, c, g or t
<221> NAME/KEY: modified_base
<222> LOCATION: (693)
<223> OTHER INFORMATION: Where n is a, c, g or t
<221> NAME/KEY: modified_base
<222> LOCATION: (695)
<223> OTHER INFORMATION: Where n is a, c, g or t

<400> SEQUENCE: 239
tcgagcggcc gcccgggcag gtccaccata agtcctgata caaccacgga tgagctgtca 60
ggagcaaggt tgatttcttt cattggtccg gtcttctcct tgggggtcac ccgcactcga 120
tatccagtga gctgaacatt gggtggtgtc cactgggcgc tcaggcttgt gggtgtgacc 180
tgagtgaact tcaggtcagt tggtgcagga atagtggtta ctgcagtctg aaccagaggc 240
tgactctctc cgcttggatt ctgagcatag acactaacca catactccac tgtgggctgc 300
aagccttcaa tagtcatttc tgtttgatct ggacctgcag ttttagtttt tgttggtcct 360
ggtccatttt tgggagtggt ggttactctg taaccagtaa caggggaact tgaaggcagc 420
cacttgacac taatgctgtt gtcctgaaca tcggtcactt gcatctggga tggtttgnca 480
atttctgttc ggtaattaat ggaaattggc ttgctgcttg cggggctgtc tccacggcca 540
gtgacagcat acacagngat ggnatnatca actccaagtt taaggccctg atggtaactt 600
taaacttgct cccagccagn gaacttccgg acagggtatt tcttctggtt ttccgaaagn 660
gancctggaa tnntctcctt ggancagaag gancntccaa aacttgggcc ggaacccctt 720

<210> SEQ ID NO 240
<211> LENGTH: 691
<212> TYPE: DNA
<213> ORGANISM: Homo sapiens
<220> FEATURE:
<221> NAME/KEY: modified_base
<222> LOCATION: (564)
<223> OTHER INFORMATION: Where n is a, c, g or t
<221> NAME/KEY: modified_base
<222> LOCATION: (582)
<223> OTHER INFORMATION: Where n is a, c, g or t
<221> NAME/KEY: modified_base
<222> LOCATION: (640)
<223> OTHER INFORMATION: Where n is a, c, g or t
<221> NAME/KEY: modified_base
<222> LOCATION: (651)
<223> OTHER INFORMATION: Where n is a, c, g or t
<221> NAME/KEY: modified_base
<222> LOCATION: (666)
<223> OTHER INFORMATION: Where n is a, c, g or t
<221> NAME/KEY: modified_base
<222> LOCATION: (669)
<223> OTHER INFORMATION: Where n is a, c, g or t
<221> NAME/KEY: modified_base
<222> LOCATION: (690)
<223> OTHER INFORMATION: Where n is a, c, g or t

<400> SEQUENCE: 240

-continued

```
agcgtggtcg cggccgaggt cctgtcagag tggcactggt agaagttcca ggaaccctga     60

actgtaaggg ttcttcatca gtgccaacag gatgacatga aatgatgtac tcagaagtgt    120

cctggaatgg ggcccatgag atggttgtct gagagagagc ttcttgtcct acattcggcg    180

ggtatggtct tggcctatgc cttatggggg tggccgttgt gggcggtgtg gtccgcctaa    240

aaccatgttc ctcaaagatc atttgttgcc caacactggg ttgctgacca gaagtgccag    300

gaagctgaat accatttcca gtgtcatacc cagggtgggt gacgaaaggg gtcttttgaa    360

ctgtggaagg aacatccaag atctctggtc catgaagatt ggggtgtgga agggttacca    420

gttggggaag ctcgtctgtc tttttccttc caatcagggg ctcgctcttc tgattattct    480

tcagggcaat gacataaatt gtatattcgg ttcccggttc caggccagta atagtagcct    540

cttgtgacac caggcggggc ccanggacca cttctctggg angagaccca gcttctcata    600

cttgatgatg taacccggta atcctgcacg tggcggctgn catgatacca ncaaggaatt    660

gggtgnggng gacctgcccg gcggccctcn a                                   691
```

```
<210> SEQ ID NO 241
<211> LENGTH: 808
<212> TYPE: DNA
<213> ORGANISM: Homo sapiens
<220> FEATURE:
<221> NAME/KEY: modified_base
<222> LOCATION: (680)
<223> OTHER INFORMATION: Where n is a, c, g or t
<221> NAME/KEY: modified_base
<222> LOCATION: (715)
<223> OTHER INFORMATION: Where n is a, c, g or t
<221> NAME/KEY: modified_base
<222> LOCATION: (721)
<223> OTHER INFORMATION: Where n is a, c, g or t
<221> NAME/KEY: modified_base
<222> LOCATION: (728)
<223> OTHER INFORMATION: Where n is a, c, g or t
<221> NAME/KEY: modified_base
<222> LOCATION: (735)
<223> OTHER INFORMATION: Where n is a, c, g or t
<221> NAME/KEY: modified_base
<222> LOCATION: (749)
<223> OTHER INFORMATION: Where n is a, c, g or t
<221> NAME/KEY: modified_base
<222> LOCATION: (757)
<223> OTHER INFORMATION: Where n is a, c, g or t
<221> NAME/KEY: modified_base
<222> LOCATION: (762)
<223> OTHER INFORMATION: Where n is a, c, g or t
<221> NAME/KEY: modified_base
<222> LOCATION: (772)
<223> OTHER INFORMATION: Where n is a, c, g or t
<221> NAME/KEY: modified_base
<222> LOCATION: (776)
<223> OTHER INFORMATION: Where n is a, c, g or t
<221> NAME/KEY: modified_base
<222> LOCATION: (779)
<223> OTHER INFORMATION: Where n is a, c, g or t
<221> NAME/KEY: modified_base
<222> LOCATION: (781)
<223> OTHER INFORMATION: Where n is a, c, g or t
<221> NAME/KEY: modified_base
<222> LOCATION: (792)
<223> OTHER INFORMATION: Where n is a, c, g or t
<221> NAME/KEY: modified_base
<222> LOCATION: (796)
<223> OTHER INFORMATION: Where n is a, c, g or t
<221> NAME/KEY: modified_base
<222> LOCATION: (800)
<223> OTHER INFORMATION: Where n is a, c, g or t
<221> NAME/KEY: modified_base
<222> LOCATION: (808)
<223> OTHER INFORMATION: Where n is a, c, g or t
```

-continued

<400> SEQUENCE: 241
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agcaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagag taaccaccac tcccaaaaat 360
ggaccaggac caacaaaaac taaaactgca ggtccagatc aaacagaaat gactattgaa 420
ggcttgcagc ccacagtgga gtatgtggtt agtgtctatg ctcagaatcc aagcggagag 480
agtcagcctc tggttcagac tgcagtaacc actattcctg caccaactga cctgaagttc 540
actcaggtca cacccacaag cctgagccgc cagtggacac cacccaatgt tcactcactg 600
gatatcgagt gcgggtgacc cccaaggaga agacccggac ccatgaaaga aatcaacctt 660
gctcctgaca gctcatccgn gggtgtatca ggacttatgg gggactgccc cggcnggccg 720
ntcgaaancg aattntgaaa tttccttcnc actgggnggc gnttcgagct tncttntana 780
nggcccaatt cncctntagn gggtcgtn 808

<210> SEQ ID NO 242
<211> LENGTH: 26
<212> TYPE: DNA
<213> ORGANISM: Homo sapiens
<220> FEATURE:
<221> NAME/KEY: modified_base
<222> LOCATION: (22)
<223> OTHER INFORMATION: Where n is a, c, g or t

<400> SEQUENCE: 242
agcgtggtcg cggccgaggt cnagga 26

<210> SEQ ID NO 243
<211> LENGTH: 697
<212> TYPE: DNA
<213> ORGANISM: Homo sapiens
<220> FEATURE:
<221> NAME/KEY: modified_base
<222> LOCATION: (496)
<223> OTHER INFORMATION: Where n is a, c, g or t
<221> NAME/KEY: modified_base
<222> LOCATION: (541)
<223> OTHER INFORMATION: Where n is a, c, g or t
<221> NAME/KEY: modified_base
<222> LOCATION: (624)
<223> OTHER INFORMATION: Where n is a, c, g or t
<221> NAME/KEY: modified_base
<222> LOCATION: (662)
<223> OTHER INFORMATION: Where n is a, c, g or t
<221> NAME/KEY: modified_base
<222> LOCATION: (679)
<223> OTHER INFORMATION: Where n is a, c, g or t
<221> NAME/KEY: modified_base
<222> LOCATION: (688)
<223> OTHER INFORMATION: Where n is a, c, g or t

<400> SEQUENCE: 243
tcgagcggcc gcccgggcag gtccaccaca cccaattcct tgctggtatc atggcagccg 60
ccacgtgcca ggattaccgg ctacatcatc aagtatgaga agcctgggtc tcctcccaga 120
gaagtggtcc ctcggccccg ccctggtgtc acagaggcta ctattactgg cctggaaccg 180
ggaaccgaat atacaattta tgtcattgcc ctgaagaata atcagaagag cgagcccctg 240

-continued attggaagga aaaagacaga cgagcttccc caactggtaa cccttccaca ccccaatctt 300
catggaccag agatcttgga tgttccttcc acagttcaaa agaccccttt cgtcacccac 360
cctgggtatg acactggaaa tggtattcag cttcctggca cttctggtca gcaacccagt 420
gttgggcaac aaatgatctt tgaggaacat ggttttaggc ggaccacacc gcccacaacg 480
ggcaccccca taaggnatag gccaagacca taccccgccg aatgtaggac aagaagctct 540
ntctcaacaa ccatctcatg ggccccattc caggacactt ctgagtacat catttcatgt 600
catcctggtg ggcacttgat gaanaaccct tacagttcag ggttcctgga acttctacca 660
gngccacttc tgacaggganc ttgggcgnga ccaccct 697

<210> SEQ ID NO 244
<211> LENGTH: 373
<212> TYPE: DNA
<213> ORGANISM: Homo sapiens

<400> SEQUENCE: 244
agcgtggtcg cggccgaggt ccattttctc cctgacggtc ccacttctct ccaatcttgt 60
agttcacacc attgtcatgg caccatctag atgaatcaca tctgaaatga ccacttccaa 120
agcctaagca ctggcacaac agtttaaagc ctgattcaga cattcgttcc cactcatctc 180
caacggcata atgggaaact gtgtaggggt caaagcacga gtcatccgta ggttggttca 240
agccttcgtt gacagagttg cccacggtaa caacctcttc ccgaacctta tgcctctgct 300
ggtctttcag tgcctccact atgatgttgt aggtggcacc tctggtgagg acctgcccgg 360
gcggcccgct cga 373

<210> SEQ ID NO 245
<211> LENGTH: 307
<212> TYPE: DNA
<213> ORGANISM: Homo sapiens

<400> SEQUENCE: 245
agcgtggtcg cggccgaggt gtgccccaga ccaggaattc ggcttcgacg ttggccctgt 60
ctgcttcctg taaactccct ccatcccaac ctggctccct cccacccaac caactttccc 120
cccaacccgg aaacagacaa gcaacccaaa ctgaaccccc tcaaaagcca aaaaaatggg 180
agacaatttc acatggactt tggaaaatat ttttttcctt tgcattcatc tctcaaactt 240
agtttttatc tttgaccaac cgaacatgac caaaaaccaa aagtgacctg cccgggcggc 300
cgctcga 307

<210> SEQ ID NO 246
<211> LENGTH: 372
<212> TYPE: DNA
<213> ORGANISM: Homo sapiens

<400> SEQUENCE: 246
tcgagcggcc gcccgggcag gtcctcacca gaggtgccac ctacaacatc atagtggagg 60
cactgaaaga ccagcagagg cataaggttc gggaagaggt tgttaccgtg ggcaactctg 120
tcaacgaagg cttgaaccaa cctacggatg actcgtgctt tgacccctac acagtttccc 180
attatgccgt tggagatgag tgggaacgaa tgtctgaatc aggctttaaa ctgttgtgcc 240
agtgcttagg ctttggaagt ggtcatttca gatgtgattc atctagatgg tgccatgaca 300
atggtgtgaa ctacaagatt ggagagaagt gggaccgtca gggagaaaat ggacctcggc 360
cgcgaccacg ct 372

-continued

<210> SEQ ID NO 247
<211> LENGTH: 348
<212> TYPE: DNA
<213> ORGANISM: Homo sapiens
<220> FEATURE:
<221> NAME/KEY: modified_base
<222> LOCATION: (284)
<223> OTHER INFORMATION: Where n is a, c, g or t
<221> NAME/KEY: modified_base
<222> LOCATION: (297)
<223> OTHER INFORMATION: Where n is a, c, g or t
<221> NAME/KEY: modified_base
<222> LOCATION: (299)
<223> OTHER INFORMATION: Where n is a, c, g or t
<221> NAME/KEY: modified_base
<222> LOCATION: (322)
<223> OTHER INFORMATION: Where n is a, c, g or t
<221> NAME/KEY: modified_base
<222> LOCATION: (325)
<223> OTHER INFORMATION: Where n is a, c, g or t
<221> NAME/KEY: modified_base
<222> LOCATION: (338)
<223> OTHER INFORMATION: Where n is a, c, g or t
<221> NAME/KEY: modified_base
<222> LOCATION: (342)
<223> OTHER INFORMATION: Where n is a, c, g or t
<221> NAME/KEY: modified_base
<222> LOCATION: (345)
<223> OTHER INFORMATION: Where n is a, c, g or t

<400> SEQUENCE: 247
tcgagcggcc gcccgggcag gtaccggggt ggtcagcgag gagccattca cactgaactt 60
caccatcaac aacctgcggt atgaggagaa catgcagcac cctggctcca ggaagttcaa 120
caccacggag agggtccttc agggcctgct caggtccctg ttcaagagca ccagtgttgg 180
ccctctgtac tctggctgca gactgacttt gctcagacct gagaaacatg ggcagccac 240 tggagtggac gccatctgca ccctccgcct tgatcccact ggtnctggac tggacanana 300
gcggctatac ttgggagctg anccnaacct ttggcggnga cnccnctt 348

<210> SEQ ID NO 248
<211> LENGTH: 304
<212> TYPE: DNA
<213> ORGANISM: Homo sapiens
<220> FEATURE:
<221> NAME/KEY: modified_base
<222> LOCATION: (125)
<223> OTHER INFORMATION: Where n is a, c, g or t

<400> SEQUENCE: 248
gaggactggc tcagctccca gtatagccgc tctctgtcca gtccaggacc agtgggatca 60
aggcggaggg tgcagatggc gtccactcca gtggctgccc catgtttctc aagtctgagc 120
aaagncagtc tgcagccaga gtacagaggg ccaacactgg tgctcttgaa cagggacctg 180
agcaggccct gaaggaccct ctccgtggtg ttgaacttcc tggagccagg gtgctgcatg 240
ttctcctcat accgcaggtt gttgatggtg aagttcagtg tgaatggctc ctcgctgacc 300
accc 304

<210> SEQ ID NO 249
<211> LENGTH: 400
<212> TYPE: DNA
<213> ORGANISM: Homo sapiens
<220> FEATURE:
<221> NAME/KEY: modified_base
<222> LOCATION: (308)
<223> OTHER INFORMATION: Where n is a, c, g or t -continued
<221> NAME/KEY: modified_base
<222> LOCATION: (310)
<223> OTHER INFORMATION: Where n is a, c, g or t
<221> NAME/KEY: modified_base
<222> LOCATION: (312)
<223> OTHER INFORMATION: Where n is a, c, g or t
<221> NAME/KEY: modified_base
<222> LOCATION: (320)
<223> OTHER INFORMATION: Where n is a, c, g or t
<221> NAME/KEY: modified_base
<222> LOCATION: (331)
<223> OTHER INFORMATION: Where n is a, c, g or t
<221> NAME/KEY: modified_base
<222> LOCATION: (336)
<223> OTHER INFORMATION: Where n is a, c, g or t
<221> NAME/KEY: modified_base
<222> LOCATION: (383)
<223> OTHER INFORMATION: Where n is a, c, g or t
<221> NAME/KEY: modified_base
<222> LOCATION: (392)
<223> OTHER INFORMATION: Where n is a, c, g or t
<221> NAME/KEY: modified_base
<222> LOCATION: (396)
<223> OTHER INFORMATION: Where n is a, c, g or t

<400> SEQUENCE: 249
agcgtggtcg cggccgaggt ccaccacacc caattccttg ctggtatcat ggcagccgcc 60
acgtgccagg attaccggct acatcatcaa gtatgagaag cctgggtctc ctcccagaga 120
agtggtccct cggccccgcc ctggtgtcac agaggctact attactggcc tggaaccggg 180
aaccgaatat acaatttatg tcattgccct gaagaataat cagaagagcg agcccctgat 240
tggaaggaaa aagacagacg agcttcccca actggtaacc cttccacacc ccaatcttca 300
tggaccanan ancttggatn gtcctttcac nggttnaaaa aacccttttc gcccccccac 360
cttggggatt aaccttggga aanggggatt tnaccnttcc 400

<210> SEQ ID NO 250
<211> LENGTH: 400
<212> TYPE: DNA
<213> ORGANISM: Homo sapiens
<220> FEATURE:
<221> NAME/KEY: modified_base
<222> LOCATION: (338)
<223> OTHER INFORMATION: Where n is a, c, g or t
<221> NAME/KEY: modified_base
<222> LOCATION: (357)
<223> OTHER INFORMATION: Where n is a, c, g or t
<221> NAME/KEY: modified_base
<222> LOCATION: (361)
<223> OTHER INFORMATION: Where n is a, c, g or t
<221> NAME/KEY: modified_base
<222> LOCATION: (369)
<223> OTHER INFORMATION: Where n is a, c, g or t
<221> NAME/KEY: modified_base
<222> LOCATION: (388)
<223> OTHER INFORMATION: Where n is a, c, g or t
<221> NAME/KEY: modified_base
<222> LOCATION: (394)
<223> OTHER INFORMATION: Where n is a, c, g or t

<400> SEQUENCE: 250
tcgagcggcc gcccgggcag gtcctgtcag agtggcactg gtagaagttc caggaaccct 60
gaactgtaag ggttcttcat cagtgccaac aggatgacat gaaatgatgt actcagaagt 120
gtcctggaat ggggcccatg agatggttgt ctgagagaga gcttcttgtc ctacattcgg 180
cgggtatggt cttggcctat gccttatggg ggtggccgtt gtgggcggtg tggtccgcct 240
aaaaccatgt tcctcaaaga tcatttgttg cccaacactg ggttgctgac cagaagtgcc 300
aggaagctga ataccatttc cagtgtcata cccagggngg gtgaccaaag ggggtcnttt 360

-continued ngacctggng aaaggaacca tccaaaanct ctgncccatg 400

<210> SEQ ID NO 251
<211> LENGTH: 514
<212> TYPE: DNA
<213> ORGANISM: Homo sapiens
<220> FEATURE:
<221> NAME/KEY: modified_base
<222> LOCATION: (8)
<223> OTHER INFORMATION: Where n is a, c, g or t
<221> NAME/KEY: modified_base
<222> LOCATION: (107)
<223> OTHER INFORMATION: Where n is a, c, g or t
<221> NAME/KEY: modified_base
<222> LOCATION: (312)
<223> OTHER INFORMATION: Where n is a, c, g or t
<221> NAME/KEY: modified_base
<222> LOCATION: (338)
<223> OTHER INFORMATION: Where n is a, c, g or t
<221> NAME/KEY: modified_base
<222> LOCATION: (351)
<223> OTHER INFORMATION: Where n is a, c, g or t
<221> NAME/KEY: modified_base
<222> LOCATION: (352)
<223> OTHER INFORMATION: Where n is a, c, g or t
<221> NAME/KEY: modified_base
<222> LOCATION: (357)
<223> OTHER INFORMATION: Where n is a, c, g or t
<221> NAME/KEY: modified_base
<222> LOCATION: (363)
<223> OTHER INFORMATION: Where n is a, c, g or t
<221> NAME/KEY: modified_base
<222> LOCATION: (366)
<223> OTHER INFORMATION: Where n is a, c, g or t
<221> NAME/KEY: modified_base
<222> LOCATION: (373)
<223> OTHER INFORMATION: Where n is a, c, g or t
<221> NAME/KEY: modified_base
<222> LOCATION: (380)
<223> OTHER INFORMATION: Where n is a, c, g or t
<221> NAME/KEY: modified_base
<222> LOCATION: (405)
<223> OTHER INFORMATION: Where n is a, c, g or t
<221> NAME/KEY: modified_base
<222> LOCATION: (421)
<223> OTHER INFORMATION: Where n is a, c, g or t
<221> NAME/KEY: modified_base
<222> LOCATION: (424)
<223> OTHER INFORMATION: Where n is a, c, g or t
<221> NAME/KEY: modified_base
<222> LOCATION: (508)
<223> OTHER INFORMATION: Where n is a, c, g or t

<400> SEQUENCE: 251
agcgtggncg cggccgaggt ctgaggatgt aaactcttcc caggggaagg ctgaagtgct 60
gaccatggtg ctactgggtc cttctgagtc agatatgtga ctgatgngaa ctgaagtagg 120
tactgtagat ggtgaagtct gggtgtccct aaatgctgca tctccagagc cttccatcat 180
taccgtttct tcttttgcta tgggatgaga cactgttgag tattctctaa agtcaccact 240
gaaatcttcc tccaaaggaa aacctgtgga aaagcccctt atttctgccc cataatttgg 300
ttctcctaat cnctctgaaa tcactatttc cctggaangt ttgggaaaaa nngggcnacc 360
tgncantgga aantggatan aaagatccca ccattttacc caacnagcag aaagtgggaa 420
nggtaccgaa aagctccaag taanaaaaag gagggaagta aaggtcaagt gggcaccagt 480
ttcaaacaaa actttcccca aactatanaa ccca 514

<210> SEQ ID NO 252
<211> LENGTH: 501
<212> TYPE: DNA

-continued

<213> ORGANISM: Homo sapiens
<220> FEATURE:
<221> NAME/KEY: modified_base
<222> LOCATION: (20)
<223> OTHER INFORMATION: Where n is a, c, g or t
<221> NAME/KEY: modified_base
<222> LOCATION: (21)
<223> OTHER INFORMATION: Where n is a, c, g or t
<221> NAME/KEY: modified_base
<222> LOCATION: (25)
<223> OTHER INFORMATION: Where n is a, c, g or t
<221> NAME/KEY: modified_base
<222> LOCATION: (44)
<223> OTHER INFORMATION: Where n is a, c, g or t
<221> NAME/KEY: modified_base
<222> LOCATION: (343)
<223> OTHER INFORMATION: Where n is a, c, g or t
<221> NAME/KEY: modified_base
<222> LOCATION: (347)
<223> OTHER INFORMATION: Where n is a, c, g or t
<221> NAME/KEY: modified_base
<222> LOCATION: (356)
<223> OTHER INFORMATION: Where n is a, c, g or t
<221> NAME/KEY: modified_base
<222> LOCATION: (362)
<223> OTHER INFORMATION: Where n is a, c, g or t
<221> NAME/KEY: modified_base
<222> LOCATION: (387)
<223> OTHER INFORMATION: Where n is a, c, g or t
<221> NAME/KEY: modified_base
<222> LOCATION: (391)
<223> OTHER INFORMATION: Where n is a, c, g or t
<221> NAME/KEY: modified_base
<222> LOCATION: (398)
<223> OTHER INFORMATION: Where n is a, c, g or t
<221> NAME/KEY: modified_base
<222> LOCATION: (409)
<223> OTHER INFORMATION: Where n is a, c, g or t
<221> NAME/KEY: modified_base
<222> LOCATION: (428)
<223> OTHER INFORMATION: Where n is a, c, g or t
<221> NAME/KEY: modified_base
<222> LOCATION: (430)
<223> OTHER INFORMATION: Where n is a, c, g or t
<221> NAME/KEY: modified_base
<222> LOCATION: (453)
<223> OTHER INFORMATION: Where n is a, c, g or t
<221> NAME/KEY: modified_base
<222> LOCATION: (494)
<223> OTHER INFORMATION: Where n is a, c, g or t

<400> SEQUENCE: 252
aagcggccgc ccgggcaggn ncagnagtgc cttcgggact gggntcaccc ccaggtctgc 60
ggcagttgtc acagcgccag ccccgctggc ctccaaagca tgtgcaggag caaatggcac 120
cgagatattc cttctgccac tgttctccta cgtggtatgt cttcccatca tcgtaacacg 180
ttgcctcatg agggtcacac ttgaattctc cttttccgtt cccaagacat gtgcagctca 240
tttggctggc tctatagttt ggggaaagtt tgttgaaact gtgccactga cctttacttc 300
ctccttctct actggagctt tccgtacctt ccacttctgc tgntggnaaa aagggnggaa 360
cntcttatca atttcattgg acagtanccc nctttctncc caaaacatnc aagggaaaat 420
attgattncn agagcggatt aaggaacaac ccnaattatg ggggccagaa ataaaggggg 480
cttttccaca ggtnttttcc t 501

<210> SEQ ID NO 253
<211> LENGTH: 226
<212> TYPE: DNA
<213> ORGANISM: Homo sapiens

<400> SEQUENCE: 253

-continued

```
tcgagcggcc gcccgggcag gtctgcaggc tattgtaagt gttctgagca catatgagat     60

aacctgggcc aagctatgat gttcgatacg ttaggtgtat taaatgcact tttgactgcc    120

atctcagtgg atgacagcct tctcactgac agcagagatc ttcctcactg tgccagtggg    180

caggagaaag agcatgctgc gactggacct cggccgcgac cacgct                   226


<210> SEQ ID NO 254
<211> LENGTH: 226
<212> TYPE: DNA
<213> ORGANISM: Homo sapiens

<400> SEQUENCE: 254

agcgtggtcg cggccgaggt ccagtcgcag catgctcttt ctcctgccca ctggcacagt     60

gaggaagatc tctgctgtca gtgagaaggc tgtcatccac tgagatggca gtcaaaagtg    120

catttaatac acctaacgta tcgaacatca tagcttggcc caggttatct catatgtgct    180

cagaacactt acaatagcct gcagacctgc ccgggcggcc gctcga                   226


<210> SEQ ID NO 255
<211> LENGTH: 427
<212> TYPE: DNA
<213> ORGANISM: Homo sapiens
<220> FEATURE:
<221> NAME/KEY: modified_base
<222> LOCATION: (327)
<223> OTHER INFORMATION: Where n is a, c, g or t
<221> NAME/KEY: modified_base
<222> LOCATION: (403)
<223> OTHER INFORMATION: Where n is a, c, g or t

<400> SEQUENCE: 255

cgagcggccg cccgggcagg tccagactcc aatccagaga accaccaagc cagatgtcag     60

aagctacacc atcacaggtt tacaaccagg cactgactac aagatctacc tgtacacctt    120

gaatgacaat gctcggagct cccctgtggt catcgacgcc tccactgcca ttgatgcacc    180

atccaacctg cgtttcctgg ccaccacacc caattccttg ctggtatcat ggcagccgcc    240

acgtgccagg attaccggct acatcatcaa gtatgagaag cctgggtctc ctcccagaga    300

agtggtccct cggccccgcc ctggtgncac agaagctact attactggcc tggaaccggg    360

aaccgaatat acaatttatg tcattgccct gaagaataat canaagagcg agcccctgat    420

tggaagg                                                              427


<210> SEQ ID NO 256
<211> LENGTH: 535
<212> TYPE: DNA
<213> ORGANISM: Homo sapiens
<220> FEATURE:
<221> NAME/KEY: modified_base
<222> LOCATION: (347)
<223> OTHER INFORMATION: Where n is a, c, g or t
<221> NAME/KEY: modified_base
<222> LOCATION: (456)
<223> OTHER INFORMATION: Where n is a, c, g or t
<221> NAME/KEY: modified_base
<222> LOCATION: (475)
<223> OTHER INFORMATION: Where n is a, c, g or t

<400> SEQUENCE: 256

agcgtggtcg cggccgaggt cctgtcagag tggcactggt agaagttcca ggaaccctga     60

actgtaaggg ttcttcatca gtgccaacag gatgacatga aatgatgtac tcagaagtgt    120

cctggaatgg ggcccatgag atggttgtct gagagagagc ttcttgtcct gtctttttcc    180
```

-continued

```
ttccaatcag gggctcgctc ttctgattat tcttcagggc aatgacataa attgtatatt    240

cggttcccgg ttccaggcca gtaatagtag cctctgtgac accagggcgg ggccgaggga    300

ccacttctct gggaggagac ccaggcttct catacttgat gatgtanccg gtaatcctgg    360

caccgtggcg gctgccatga taccagcaag gaattgggtg tggtggccaa gaaacgcagg    420

ttggatggtg catcaatggc agtggaggcg tcgatnacca caggggagct ccgancattg    480

tcattcaagg tggacaggta gaatcttgta atcaggtgcc tggtttgtaa acctg         535
```

<210> SEQ ID NO 257
<211> LENGTH: 544
<212> TYPE: DNA
<213> ORGANISM: Homo sapiens
<220> FEATURE:
<221> NAME/KEY: modified_base
<222> LOCATION: (495)
<223> OTHER INFORMATION: Where n is a, c, g or t
<221> NAME/KEY: modified_base
<222> LOCATION: (511)
<223> OTHER INFORMATION: Where n is a, c, g or t

<400> SEQUENCE: 257

```
tcgagcggcc gcccgggcag gtttcgtgac cgtgacctcg aggtggacac caccctcaag     60

agcctgagcc agcagatcga gaacatccgg agcccagagg gcagccgcaa gaaccccgcc    120

cgcacctgcc gtgacctcaa gatgtgccac tctgactgga agagtggaga gtactggatt    180

gaccccaacc aaggctgcaa cctggatgcc atcaaagtct tctgcaacat ggagactggt    240

gagacctgcg tgtaccccac tcagcccagt gtggcccaga agaactggta catcagcaag    300

aaccccaagg acaagaagca tgtctggttc ggcgaaagca tgaccgatgg attccagttc    360

gagtatggcg gccagggctc cgaccctgcc gatgtggacc tcggccgcga ccacgctaag    420

cccgaattcc agcacactgg cggccgttac tagtgggatc cgagcttcgg taccaagctt    480

ggcgtaatca tgggncatag ctgtttcctg ngtgaaaatg gtattccgct tcacaatttc    540

ccac                                                                 544
```

<210> SEQ ID NO 258
<211> LENGTH: 418
<212> TYPE: DNA
<213> ORGANISM: Homo sapiens

<400> SEQUENCE: 258

```
agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacacgc aggtctcacc    180

agtctccatg ttgcagaaga ctttgatggc atccaggttg cagccttggt tggggtcaat    240

ccagtactct ccactcttcc agtcagagtg gcacatcttg aggtcacggc aggtgcgggc    300

ggggttcttg cggctgccct ctgggctccg gatgttctcg atctgctggc tcaagctctt    360

gaagggtggt gtccacctcg aggtcacggt cacgaaacct gcccgggcgg ccgctcga      418
```

<210> SEQ ID NO 259
<211> LENGTH: 377
<212> TYPE: DNA
<213> ORGANISM: Homo sapiens
<220> FEATURE:
<221> NAME/KEY: modified_base
<222> LOCATION: (320)
<223> OTHER INFORMATION: Where n is a, c, g or t
<221> NAME/KEY: modified_base -continued
<222> LOCATION: (326)
<223> OTHER INFORMATION: Where n is a, c, g or t
<221> NAME/KEY: modified_base
<222> LOCATION: (342)
<223> OTHER INFORMATION: Where n is a, c, g or t
<221> NAME/KEY: modified_base
<222> LOCATION: (352)
<223> OTHER INFORMATION: Where n is a, c, g or t

<400> SEQUENCE: 259
agcgtggtcg cggccgaggt caagaacccc gcccgcacct gccgtgacct caagatgtgc 60
cactctgact ggaagagtgg agagtactgg attgacccca accaaggctg caacctggat 120
gccatcaaag tcttctgcaa catggagact ggtgagacct gcgtgtaccc cactcagccc 180
agtgtggccc agaagaactg gtacatcagc aagaacccca aggacaagag gcatgtctgg 240
ttcggcgaga gcatgaccga tggattccag ttcgagtatg gcggccaggg ctccgaccct 300
gccgatgtgg acctgcccgn gccggnccgc tcgaaaagcc cnaatttcca gncacacttg 360
gccggccgtt actactg 377

<210> SEQ ID NO 260
<211> LENGTH: 332
<212> TYPE: DNA
<213> ORGANISM: Homo sapiens

<400> SEQUENCE: 260
tcgagcggcc gcccgggcag gtccacatcg gcagggtcgg agccctggcc gccatactcg 60
aactggaatc catcggtcat gctctcgccg aaccagacat gcctcttgtc cttggggttc 120
ttgctgatgt accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagtcagag tggcacatct tgaggtcacg gcaggtgcgg 300
gcggggttct tgacctcggc cgcgaccacg ct 332

<210> SEQ ID NO 261
<211> LENGTH: 94
<212> TYPE: DNA
<213> ORGANISM: Homo sapiens

<400> SEQUENCE: 261
cgagcggccg cccgggcagg tcccccccct tttttttttt tttttttttt tttttttttt 60
tttttttttt tttttttttt tttttttttt tttt 94

<210> SEQ ID NO 262
<211> LENGTH: 650
<212> TYPE: DNA
<213> ORGANISM: Homo sapiens
<220> FEATURE:
<221> NAME/KEY: modified_base
<222> LOCATION: (412)
<223> OTHER INFORMATION: Where n is a, c, g or t
<221> NAME/KEY: modified_base
<222> LOCATION: (582)
<223> OTHER INFORMATION: Where n is a, c, g or t
<221> NAME/KEY: modified_base
<222> LOCATION: (612)
<223> OTHER INFORMATION: Where n is a, c, g or t
<221> NAME/KEY: modified_base
<222> LOCATION: (641)
<223> OTHER INFORMATION: Where n is a, c, g or t
<221> NAME/KEY: modified_base
<222> LOCATION: (646)
<223> OTHER INFORMATION: Where n is a, c, g or t -continued

<400> SEQUENCE: 262
agcgtggtcg cggccgaggt ctggcattcc ttcgacttct ctccagccga gcttcccaga 60
acatcacata tcactgcaaa aatagcattg catacatgga tcaggccagt ggaaatgtaa 120
agaaggccct gaagctgatg gggtcaaatg aaggtgaatt caaggctgaa ggaaatagca 180
aattcaccta cacagttctg gaggatggtt gcacgaaaca cactggggaa tggagcaaaa 240
cagtctttga atatcgaaca cgcaaggctg tgagactacc tattgtagat attgcaccct 300
atgacattgg tggtcctgat caagaatttg gtgtggacgt tggccctgtt tgctttttat 360
aaaccaaact ctatctgaaa tcccaacaaa aaaaatttaa ctccatatgt gntcctcttg 420
ttctaatctt ggcaaccagt gcaagtgacc gacaaaattc cagttattta tttccaaaat 480
gtttggaaac agtataattt gacaaagaaa aaaggatact tctctttttt tggctggtcc 540
accaaataca attcaaaagg ctttttggtt ttattttttt anccaattcc aatttcaaaa 600
tgtctcaatg gngcttataa taaaataaac tttcaccctt nttttntgat 650

<210> SEQ ID NO 263
<211> LENGTH: 573
<212> TYPE: DNA
<213> ORGANISM: Homo sapiens
<220> FEATURE:
<221> NAME/KEY: modified_base
<222> LOCATION: (453)
<223> OTHER INFORMATION: Where n is a, c, g or t
<221> NAME/KEY: modified_base
<222> LOCATION: (458)
<223> OTHER INFORMATION: Where n is a, c, g or t
<221> NAME/KEY: modified_base
<222> LOCATION: (544)
<223> OTHER INFORMATION: Where n is a, c, g or t

<400> SEQUENCE: 263
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agcaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagaa gtaaccacca ctcccaaaaa 360
tggaccagga ccaacaaaaa ctaaaactgc aggtccagat caaacagaaa atggactatt 420
gaaggcttgc agcccacagt ggaagtatgt ggntaggngt ctatgctcag aatcccaagc 480
cggagaaagt cagccttctg gtttagactg cagtaaccaa cattgatcgc cctaaaggac 540
tggncattca cttggatggt ggatgtccaa ttc 573

<210> SEQ ID NO 264
<211> LENGTH: 550
<212> TYPE: DNA
<213> ORGANISM: Homo sapiens
<220> FEATURE:
<221> NAME/KEY: modified_base
<222> LOCATION: (39)
<223> OTHER INFORMATION: Where n is a, c, g or t
<221> NAME/KEY: modified_base
<222> LOCATION: (174)
<223> OTHER INFORMATION: Where n is a, c, g or t
<221> NAME/KEY: modified_base
<222> LOCATION: (352)
<223> OTHER INFORMATION: Where n is a, c, g or t
<221> NAME/KEY: modified_base
<222> LOCATION: (526)

-continued

<223> OTHER INFORMATION: Where n is a, c, g or t

<400> SEQUENCE: 264
tcgagcggcc gcccgggcag gtccttgcag ctctgcagng tcttcttcac catcaggtgc 60
agggaatagc tcatggattc catcctcagg gctcgagtag gtcaccctgt acctggaaac 120
ttgcccctgt gggctttccc aagcaatttt gatggaatcg acatccacat cagngaatgc 180
cagtccttta gggcgatcaa tgttggttac tgcagtctga accagaggct gactctctcc 240
gcttggattc tgagcataga cactaaccac atactccact gtgggctgca agccttcaat 300
agtcatttct gtttgatctg gacctgcagt tttaagtttt tggtggtcct gncccatttt 360
tgggaagtgg ggggttactc tgtaaccagt aacaggggaa cttgaaggca gccacttgac 420
actaatgctg ttgtcctgaa catcggtcac ttgcatctgg ggatggtttt gacaatttct 480
ggttcggcaa attaatggaa attggcttgc tgcttggcgg ggctgnctcc acgggccagt 540
gacagcatac 550

<210> SEQ ID NO 265
<211> LENGTH: 596
<212> TYPE: DNA
<213> ORGANISM: Homo sapiens
<220> FEATURE:
<221> NAME/KEY: modified_base
<222> LOCATION: (347)
<223> OTHER INFORMATION: Where n is a, c, g or t
<221> NAME/KEY: modified_base
<222> LOCATION: (352)
<223> OTHER INFORMATION: Where n is a, c, g or t
<221> NAME/KEY: modified_base
<222> LOCATION: (353)
<223> OTHER INFORMATION: Where n is a, c, g or t
<221> NAME/KEY: modified_base
<222> LOCATION: (534)
<223> OTHER INFORMATION: Where n is a, c, g or t
<221> NAME/KEY: modified_base
<222> LOCATION: (555)
<223> OTHER INFORMATION: Where n is a, c, g or t
<221> NAME/KEY: modified_base
<222> LOCATION: (587)
<223> OTHER INFORMATION: Where n is a, c, g or t

<400> SEQUENCE: 265
tcgagcggcc gcccgggcag gtccttgcag ctctgcagtg tcttcttcac catcaggtgc 60
agggaatagc tcatggattc catcctcagg gctcgagtag gtcaccctgt acctggaaac 120
ttgcccctgt gggctttccc aagcaatttt gatggaatcg acatccacat cagtgaatgc 180
cagtccttta gggcgatcaa tgttggttac tgcagtctga accagaggct gactctctcc 240
gcttggattc tgagcataga cactaaccac atactccact gtgggctgca agccttcaat 300
agtcatttct gtttgatctg gacctgcagt tttaagtttt tgttggncct gnnccatttt 360
tggggaaggg gtggttactc ttgtaaccag taacagggga acttgaagca gccacttgac 420
actaatgctg gtggcctgaa catcggtcac ttgcatctgg gatggtttgg tcaatttctg 480
ttcggtaatt aatgggaaat tggcttactg gcttgcgggg gctgtctcca cggncagtga 540
caagcataca caggngatgg gtataatcaa ctccaggttt aaggccnctg atggta 596

<210> SEQ ID NO 266
<211> LENGTH: 506
<212> TYPE: DNA
<213> ORGANISM: Homo sapiens
<220> FEATURE:
<221> NAME/KEY: modified_base
<222> LOCATION: (393)

-continued

<223> OTHER INFORMATION: Where n is a, c, g or t
<221> NAME/KEY: modified_base
<222> LOCATION: (473)
<223> OTHER INFORMATION: Where n is a, c, g or t

<400> SEQUENCE: 266
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agtaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagag taaccaccac tcccaaaaat 360
gggaccagga ccaacaaaaa actaaaactg canggtccag atcaaacaga aatgactatt 420
gaaggcttgc agcccacagt ggagtatgtg ggttagtgtc tatgctcaga atnccaagcg 480
gagagagtca gcctctggtt cagact 506

<210> SEQ ID NO 267
<211> LENGTH: 548
<212> TYPE: DNA
<213> ORGANISM: Homo sapiens
<220> FEATURE:
<221> NAME/KEY: modified_base
<222> LOCATION: (346)
<223> OTHER INFORMATION: Where n is a, c, g or t
<221> NAME/KEY: modified_base
<222> LOCATION: (358)
<223> OTHER INFORMATION: Where n is a, c, g or t
<221> NAME/KEY: modified_base
<222> LOCATION: (432)
<223> OTHER INFORMATION: Where n is a, c, g or t
<221> NAME/KEY: modified_base
<222> LOCATION: (510)
<223> OTHER INFORMATION: Where n is a, c, g or t
<221> NAME/KEY: modified_base
<222> LOCATION: (512)
<223> OTHER INFORMATION: Where n is a, c, g or t

<400> SEQUENCE: 267
tcgagcggcc gcccgggcag gtcagcgctc tcaggacgtc accaccatgg cctgggctct 60
gctcctcctc accctcctca ctcagggcac agggtcctgg gcccagtctg ccctgactca 120
gcctccctcc gcgtccgggt ctcctggaca gtcagtcacc atctcctgca ctggaaccag 180
cagtgacgtt ggtgcttatg aatttgtctc ctggtaccaa caacacccag gcaaggcccc 240
caaactcatg atttctgagg tcactaagcg gccctcaggg gtccctgatc gcttctctgg 300
ctccaagtct ggcaacacgg cctccctgac cgtctctggg ctccangctg aggatgangc 360
tgattattac tggaagctca tatgcaggca acaacaattg ggtgttcggc ggaagggacc 420
aagctgaccg tnctaaggtc aagcccaagg cttgcccccc tcggtcactc tgttcccacc 480
ctcctctgaa gaagctttca agccaacaan gncacactgg gtgtgtctca taagtggact 540
ttctaccc 548

<210> SEQ ID NO 268
<211> LENGTH: 584
<212> TYPE: DNA
<213> ORGANISM: Homo sapiens
<220> FEATURE:
<221> NAME/KEY: modified_base
<222> LOCATION: (98)
<223> OTHER INFORMATION: Where n is a, c, g or t
<221> NAME/KEY: modified_base -continued
<222> LOCATION: (380)
<223> OTHER INFORMATION: Where n is a, c, g or t
<221> NAME/KEY: modified_base
<222> LOCATION: (421)
<223> OTHER INFORMATION: Where n is a, c, g or t
<221> NAME/KEY: modified_base
<222> LOCATION: (454)
<223> OTHER INFORMATION: Where n is a, c, g or t
<221> NAME/KEY: modified_base
<222> LOCATION: (495)
<223> OTHER INFORMATION: Where n is a, c, g or t
<221> NAME/KEY: modified_base
<222> LOCATION: (506)
<223> OTHER INFORMATION: Where n is a, c, g or t
<221> NAME/KEY: modified_base
<222> LOCATION: (512)
<223> OTHER INFORMATION: Where n is a, c, g or t
<221> NAME/KEY: modified_base
<222> LOCATION: (561)
<223> OTHER INFORMATION: Where n is a, c, g or t
<221> NAME/KEY: modified_base
<222> LOCATION: (565)
<223> OTHER INFORMATION: Where n is a, c, g or t
<221> NAME/KEY: modified_base
<222> LOCATION: (579)
<223> OTHER INFORMATION: Where n is a, c, g or t

<400> SEQUENCE: 268
agcgtggtcg cggccgaggt ctgtagcttc tgtgggactt ccactgctca ggcgtcaggc 60
tcaggtagct gctggccgcg tacttgttgt tgctttgntt ggagggtgtg gtggtctcca 120
ctcccgcctt gacggggctg ctatctgcct tccaggccac tgtcacggct cccgggtaga 180
agtcacttat gagacacacc agtgtggcct tgttggcttg aagctcctca gaggagggtg 240
ggaacagagt gaccgagggg gcagccttgg gctgacctag gacggtcagc ttggtccctc 300
cgccgaacac ccaattgttg ttgcctgcat atgagctgca gtaataatca gcctcatcct 360
cagcctggag cccagagacn gtcaagggag gcccgtgttt gccaagactt ggaagccaga 420
naagcgatca gggacccctg agggccgctt tacngacctc aaaaaatcat gaatttgggg 480
ggcctttgcc tgggngttgg ttggtnacca gnaaaacaaa atttcataaa gcaccaacgt 540
cactgctggt ttccagtgca ngaanatggt gaactgaant gtcc 584

<210> SEQ ID NO 269
<211> LENGTH: 368
<212> TYPE: DNA
<213> ORGANISM: Homo sapiens
<220> FEATURE:
<221> NAME/KEY: modified_base
<222> LOCATION: (265)
<223> OTHER INFORMATION: Where n is a, c, g or t
<221> NAME/KEY: modified_base
<222> LOCATION: (329)
<223> OTHER INFORMATION: Where n is a, c, g or t

<400> SEQUENCE: 269
agcgtggtcg cggccgaggt ccagcatcag gagccccgcc ttgccggctc tggtcatcgc 60
ctttcttttt gtggcctgaa acgatgtcat caattcgcag tagcagaact gccgtctcca 120
ctgctgtctt ataagtctgc agcttcacag ccaatggctc ccatatgccc agttccttca 180
tgtccaccaa agtacccgtc tcaccattta caccccaggt ctcacagttc tcctgggtgt 240
gcttggcccg aagggaggta agtanacgga tggtgctggt cccacagttc tggatcaggg 300
tacgaggaat gacctctagg gcctgggcna caagccctgt atggacctgc ccgggcgggc 360
ccgctcga 368

<210> SEQ ID NO 270
<211> LENGTH: 368
<212> TYPE: DNA
<213> ORGANISM: Homo sapiens
<220> FEATURE:
<221> NAME/KEY: modified_base
<222> LOCATION: (54)
<223> OTHER INFORMATION: Where n is a, c, g or t
<221> NAME/KEY: modified_base
<222> LOCATION: (163)
<223> OTHER INFORMATION: Where n is a, c, g or t
<221> NAME/KEY: modified_base
<222> LOCATION: (219)
<223> OTHER INFORMATION: Where n is a, c, g or t
<221> NAME/KEY: modified_base
<222> LOCATION: (229)
<223> OTHER INFORMATION: Where n is a, c, g or t
<221> NAME/KEY: modified_base
<222> LOCATION: (316)
<223> OTHER INFORMATION: Where n is a, c, g or t

<400> SEQUENCE: 270

```
tcgagcggcc gcccgggcag gtccatacag ggctgttgcc caggccctag aggncattcc     60

ttgtaccctg atccagaact gtgggaccag caccatccgt ctacttacct cccttcgggc    120

caagcacacc caggagaact gtgagacctg gggtgtaaat ggngagacgg gtactttggt    180

ggacatgaag gaactgggca tatgggagcc attggctgng aagctgcana cttataagac    240

agcagtggag acggcagttc tgctactgcg aattgatgac atcgtttcag gccacaaaaa    300

gaaaggcgat gaccanagcc ggcaaggcgg ggcttcctga tgctggacct cggccgccga    360

ccacgctt                                                             368
```

<210> SEQ ID NO 271
<211> LENGTH: 424
<212> TYPE: DNA
<213> ORGANISM: Homo sapiens
<220> FEATURE:
<221> NAME/KEY: modified_base
<222> LOCATION: (279)
<223> OTHER INFORMATION: Where n is a, c, g or t
<221> NAME/KEY: modified_base
<222> LOCATION: (329)
<223> OTHER INFORMATION: Where n is a, c, g or t
<221> NAME/KEY: modified_base
<222> LOCATION: (362)
<223> OTHER INFORMATION: Where n is a, c, g or t
<221> NAME/KEY: modified_base
<222> LOCATION: (384)
<223> OTHER INFORMATION: Where n is a, c, g or t
<221> NAME/KEY: modified_base
<222> LOCATION: (400)
<223> OTHER INFORMATION: Where n is a, c, g or t

<400> SEQUENCE: 271

```
agcgtggtcg cggccgaggt ccactagagg tctgtgtgcc attgcccagg cagagtctct     60

gcgttacaaa ctcctaggag ggcttgctgt gcggagggcc tgctatggtg tgctgcggtt    120

catcatggag agtggggcca aaggctgcga ggttgtggtg tctgggaaac tccgaggaca    180

gagggctaaa tccatgaagt ttgtggatgg cctgatgatc cacagcggag accctgttaa    240

ctactacgtt gacactgctg tgcgccacgt gttgctcana cagggtgtgc tgggcatcaa    300

ggtgaagatc atgctgccct gggacccanc tggcaaaaat ggcccttaaa aaccccttgc    360

cntgaccacg tgaaccattt gtgngaaccc caagatgaan atacttgccc accaccccc    420

attc                                                                 424
```

<210> SEQ ID NO 272

<211> LENGTH: 541
<212> TYPE: DNA
<213> ORGANISM: Homo sapiens
<220> FEATURE:
<221> NAME/KEY: modified_base
<222> LOCATION: (422)
<223> OTHER INFORMATION: Where n is a, c, g or t
<221> NAME/KEY: modified_base
<222> LOCATION: (442)
<223> OTHER INFORMATION: Where n is a, c, g or t
<221> NAME/KEY: modified_base
<222> LOCATION: (510)
<223> OTHER INFORMATION: Where n is a, c, g or t
<221> NAME/KEY: modified_base
<222> LOCATION: (513)
<223> OTHER INFORMATION: Where n is a, c, g or t
<221> NAME/KEY: modified_base
<222> LOCATION: (515)
<223> OTHER INFORMATION: Where n is a, c, g or t
<221> NAME/KEY: modified_base
<222> LOCATION: (525)
<223> OTHER INFORMATION: Where n is a, c, g or t

<400> SEQUENCE: 272
tcgagcggcc gcccgggcag gtctgccaag gagaccctgt tatgctgtgg ggactggctg 60
gggcatggca ggcggctctg gcttcccacc cttctgttct gagatggggg tggtgggcag 120
tatctcatct ttgggttcca caatgctcac gtggtcaggc aggggcttct tagggccaat 180
cttaccagtt gggtcccagg gcagcatgat cttcaccttg atgcccagca caccctgtct 240
gagcaacacg tggcgcacag cagtgtcaac gtagtagtta acagggtctc cgctgtggat 300
catcaggcca tccacaaact tcatggattt agccctctgt cctcggagtt tcccaaaaca 360
ccacaacctc gccagccttt gggccccact tcttcatgaa tgaaaccgca gcacaccatt 420
ancaaggccc ttccgcacag gnaagccctt cctaaggagt tttgtaaacg caaaaaactc 480
ttgcctgggg caaatgggca cacagacctn tantnggacc ttggnccgcg aaccaccgct 540
t 541

<210> SEQ ID NO 273
<211> LENGTH: 579
<212> TYPE: DNA
<213> ORGANISM: Homo sapiens
<220> FEATURE:
<221> NAME/KEY: modified_base
<222> LOCATION: (223)
<223> OTHER INFORMATION: Where n is a, c, g or t
<221> NAME/KEY: modified_base
<222> LOCATION: (265)
<223> OTHER INFORMATION: Where n is a, c, g or t
<221> NAME/KEY: modified_base
<222> LOCATION: (277)
<223> OTHER INFORMATION: Where n is a, c, g or t
<221> NAME/KEY: modified_base
<222> LOCATION: (308)
<223> OTHER INFORMATION: Where n is a, c, g or t
<221> NAME/KEY: modified_base
<222> LOCATION: (329)
<223> OTHER INFORMATION: Where n is a, c, g or t
<221> NAME/KEY: modified_base
<222> LOCATION: (346)
<223> OTHER INFORMATION: Where n is a, c, g or t
<221> NAME/KEY: modified_base
<222> LOCATION: (360)
<223> OTHER INFORMATION: Where n is a, c, g or t
<221> NAME/KEY: modified_base
<222> LOCATION: (366)
<223> OTHER INFORMATION: Where n is a, c, g or t
<221> NAME/KEY: modified_base
<222> LOCATION: (429)
<223> OTHER INFORMATION: Where n is a, c, g or t
<221> NAME/KEY: modified_base -continued
<222> LOCATION: (448)
<223> OTHER INFORMATION: Where n is a, c, g or t
<221> NAME/KEY: modified_base
<222> LOCATION: (517)
<223> OTHER INFORMATION: Where n is a, c, g or t
<221> NAME/KEY: modified_base
<222> LOCATION: (524)
<223> OTHER INFORMATION: Where n is a, c, g or t
<221> NAME/KEY: modified_base
<222> LOCATION: (531)
<223> OTHER INFORMATION: Where n is a, c, g or t
<221> NAME/KEY: modified_base
<222> LOCATION: (578)
<223> OTHER INFORMATION: Where n is a, c, g or t

<400> SEQUENCE: 273

```
agcgtggtcg cggccgaggt ctggccctcc tggcaaggct ggtgaagatg gtcaccctgg     60

aaaacccgga cgacctggtg agagaggagt tgttggacca cagggtgctc gtggtttccc    120

tggaactcct ggacttcctg gcttcaaagg cattagggga cacaatggtc tggatggatt    180

gaagggacag cccggtgctc ctggtgtgaa gggtgaacct ggngcccctg gtgaaaatgg    240

aactccaggt caaacaggag cccgngggct tcctggngag agaggacgtg ttggtgcccc    300

tggcccanac ctgcccgggc ggccgctcna aaagccgaaa tccagnacac tggcggccgn    360

tactantgga atccgaactt cggtaccaaa gcttggccgt aatcatggcc atagcttgtt    420

ccctggggng gaaattggta ttccgctncc aattccacac aacataccga acccggaaag    480

cattaaagtg taaaagccct ggggggggcct aaatgangtg agcntaactc ncatttaatt    540

ggcgttgcgc ttcactgccc cgcttttcca gtccgggna                           579
```

<210> SEQ ID NO 274
<211> LENGTH: 330
<212> TYPE: DNA
<213> ORGANISM: Homo sapiens
<220> FEATURE:
<221> NAME/KEY: modified_base
<222> LOCATION: (171)
<223> OTHER INFORMATION: Where n is a, c, g or t

<400> SEQUENCE: 274

```
tcgagcggcc gcccgggcag gtctgggcca ggggcaccaa cacgtcctct ctcaccagga     60

agcccacggg ctcctgtttg acctggagtt ccattttcac caggggcacc aggttcaccc    120

ttcacaccag gagcaccggg ctgtcccttc aatccatcca gaccattgtg ncccctaatg    180

cctttgaagc caggaagtcc aggagttcca gggaaaccac gagcaccctg tggtccaaca    240

actcctctct caccaggtcg tccgggtttt ccagggtgac catcttcacc agccttgcca    300

ggagggccag acctcggccg cgaccacgct                                     330
```

<210> SEQ ID NO 275
<211> LENGTH: 97
<212> TYPE: DNA
<213> ORGANISM: Homo sapiens
<220> FEATURE:
<221> NAME/KEY: modified_base
<222> LOCATION: (2)
<223> OTHER INFORMATION: Where n is a, c, g or t
<221> NAME/KEY: modified_base
<222> LOCATION: (35)
<223> OTHER INFORMATION: Where n is a, c, g or t
<221> NAME/KEY: modified_base
<222> LOCATION: (72)
<223> OTHER INFORMATION: Where n is a, c, g or t

<400> SEQUENCE: 275

-continued

```
ancgtggtcg cggccgaggt cctcaccaga ggtgncacct acaacatcat agtggaggca     60

ctgaaagacc ancagaggca taaggttcgg gaagagg                              97


<210> SEQ ID NO 276
<211> LENGTH: 610
<212> TYPE: DNA
<213> ORGANISM: Homo sapiens
<220> FEATURE:
<221> NAME/KEY: modified_base
<222> LOCATION: (358)
<223> OTHER INFORMATION: Where n is a, c, g or t
<221> NAME/KEY: modified_base
<222> LOCATION: (360)
<223> OTHER INFORMATION: Where n is a, c, g or t
<221> NAME/KEY: modified_base
<222> LOCATION: (363)
<223> OTHER INFORMATION: Where n is a, c, g or t
<221> NAME/KEY: modified_base
<222> LOCATION: (382)
<223> OTHER INFORMATION: Where n is a, c, g or t
<221> NAME/KEY: modified_base
<222> LOCATION: (424)
<223> OTHER INFORMATION: Where n is a, c, g or t
<221> NAME/KEY: modified_base
<222> LOCATION: (453)
<223> OTHER INFORMATION: Where n is a, c, g or t
<221> NAME/KEY: modified_base
<222> LOCATION: (464)
<223> OTHER INFORMATION: Where n is a, c, g or t
<221> NAME/KEY: modified_base
<222> LOCATION: (468)
<223> OTHER INFORMATION: Where n is a, c, g or t
<221> NAME/KEY: modified_base
<222> LOCATION: (477)
<223> OTHER INFORMATION: Where n is a, c, g or t
<221> NAME/KEY: modified_base
<222> LOCATION: (491)
<223> OTHER INFORMATION: Where n is a, c, g or t
<221> NAME/KEY: modified_base
<222> LOCATION: (499)
<223> OTHER INFORMATION: Where n is a, c, g or t
<221> NAME/KEY: modified_base
<222> LOCATION: (511)
<223> OTHER INFORMATION: Where n is a, c, g or t
<221> NAME/KEY: modified_base
<222> LOCATION: (558)
<223> OTHER INFORMATION: Where n is a, c, g or t
<221> NAME/KEY: modified_base
<222> LOCATION: (584)
<223> OTHER INFORMATION: Where n is a, c, g or t
<221> NAME/KEY: modified_base
<222> LOCATION: (588)
<223> OTHER INFORMATION: Where n is a, c, g or t
<221> NAME/KEY: modified_base
<222> LOCATION: (590)
<223> OTHER INFORMATION: Where n is a, c, g or t

<400> SEQUENCE: 276

tcgagcggcc gcccgggcag gtccattttc tccctgacgg tcccacttct ctccaatctt     60

gtagttcaca ccattgtcat ggcaccatct agatgaatca catctgaaat gaccacttcc    120

aaagcctaag cactggcaca acagtttaaa gcctgattca gacattcgtt cccactcatc    180

tccaacggca taatgggaaa ctgtgtaggg gtcaaagcac gagtcatccg taggttggtt    240

caagccttcg ttgacagagt tgtccacggt aacaacctct tcccgaacct tatgcctctg    300

ctggtctttc agtgcctcca ctatgatgtt gtaggtggca cctctggtga ggacctcngn    360

ccngaacaac gcttaagccc gnattctgca gaataatccc atcacacttg gcggccgctt    420

cgancatgca tcntaaaagg ggccccaatt tccccccttat aagngaaccc gtatttncca    480

atttcactgg ncccgccgnt tttacaaacg ncggtgaact ggggaaaaac cctggcggtt    540
```

```
acccaacttt aatcgccntt ggcagcacaa tccccccttt tcgnccancn tgggcgtaaa    600

taaccgaaaa                                                          610
```

<210> SEQ ID NO 277
<211> LENGTH: 38
<212> TYPE: DNA
<213> ORGANISM: Homo sapiens
<220> FEATURE:
<221> NAME/KEY: modified_base
<222> LOCATION: (2)
<223> OTHER INFORMATION: Where n is a, c, g or t
<221> NAME/KEY: modified_base
<222> LOCATION: (5)
<223> OTHER INFORMATION: Where n is a, c, g or t
<221> NAME/KEY: modified_base
<222> LOCATION: (18)
<223> OTHER INFORMATION: Where n is a, c, g or t
<221> NAME/KEY: modified_base
<222> LOCATION: (21)
<223> OTHER INFORMATION: Where n is a, c, g or t
<221> NAME/KEY: modified_base
<222> LOCATION: (31)
<223> OTHER INFORMATION: Where n is a, c, g or t

<400> SEQUENCE: 277

```
ancgnggtcg cggccgangt nttttttctt ntttttttt                            38
```

<210> SEQ ID NO 278
<211> LENGTH: 443
<212> TYPE: DNA
<213> ORGANISM: Homo sapiens
<220> FEATURE:
<221> NAME/KEY: modified_base
<222> LOCATION: (156)
<223> OTHER INFORMATION: Where n is a, c, g or t
<221> NAME/KEY: modified_base
<222> LOCATION: (212)
<223> OTHER INFORMATION: Where n is a, c, g or t
<221> NAME/KEY: modified_base
<222> LOCATION: (233)
<223> OTHER INFORMATION: Where n is a, c, g or t
<221> NAME/KEY: modified_base
<222> LOCATION: (245)
<223> OTHER INFORMATION: Where n is a, c, g or t
<221> NAME/KEY: modified_base
<222> LOCATION: (327)
<223> OTHER INFORMATION: Where n is a, c, g or t
<221> NAME/KEY: modified_base
<222> LOCATION: (331)
<223> OTHER INFORMATION: Where n is a, c, g or t
<221> NAME/KEY: modified_base
<222> LOCATION: (336)
<223> OTHER INFORMATION: Where n is a, c, g or t
<221> NAME/KEY: modified_base
<222> LOCATION: (361)
<223> OTHER INFORMATION: Where n is a, c, g or t
<221> NAME/KEY: modified_base
<222> LOCATION: (364)
<223> OTHER INFORMATION: Where n is a, c, g or t
<221> NAME/KEY: modified_base
<222> LOCATION: (381)
<223> OTHER INFORMATION: Where n is a, c, g or t
<221> NAME/KEY: modified_base
<222> LOCATION: (391)
<223> OTHER INFORMATION: Where n is a, c, g or t
<221> NAME/KEY: modified_base
<222> LOCATION: (397)
<223> OTHER INFORMATION: Where n is a, c, g or t
<221> NAME/KEY: modified_base
<222> LOCATION: (419)
<223> OTHER INFORMATION: Where n is a, c, g or t
<221> NAME/KEY: modified_base
<222> LOCATION: (437)
<223> OTHER INFORMATION: Where n is a, c, g or t -continued

<400> SEQUENCE: 278
agcgtggtcg cggccgaggt ctgaggttac atgcgtggtg gtggacgtga gccacgaaga 60
ccctgaggtc aagttcaact ggtacgtgga cggcgtggag gtgcataatg ccaagacaaa 120
gccgcgggag gagcagtaca acagcacgta ccgggnggtc agcgtcctca ccgtcctgca 180
ccagaattgg ttgaatggca aggagtacaa gngcaaggtt tccaacaaag ccntcccagc 240
ccccntcgaa aaaaccattt ccaaagccaa agggcagccc cgagaaccac aggtgtacac 300 cctgcccca tcccgggagg aaaagancaa naaccnggtt cagccttaac ttgcttggtc 360
naangctttt tatcccaacg nacttccccc ntggaantgg gaaaaaccaa tgggccaanc 420
cgaaaaacaa ttacaanaac ccc 443

<210> SEQ ID NO 279
<211> LENGTH: 348
<212> TYPE: DNA
<213> ORGANISM: Homo sapiens
<220> FEATURE:
<221> NAME/KEY: modified_base
<222> LOCATION: (219)
<223> OTHER INFORMATION: Where n is a, c, g or t
<221> NAME/KEY: modified_base
<222> LOCATION: (256)
<223> OTHER INFORMATION: Where n is a, c, g or t
<221> NAME/KEY: modified_base
<222> LOCATION: (291)
<223> OTHER INFORMATION: Where n is a, c, g or t
<221> NAME/KEY: modified_base
<222> LOCATION: (297)
<223> OTHER INFORMATION: Where n is a, c, g or t
<221> NAME/KEY: modified_base
<222> LOCATION: (307)
<223> OTHER INFORMATION: Where n is a, c, g or t
<221> NAME/KEY: modified_base
<222> LOCATION: (314)
<223> OTHER INFORMATION: Where n is a, c, g or t
<221> NAME/KEY: modified_base
<222> LOCATION: (317)
<223> OTHER INFORMATION: Where n is a, c, g or t

<400> SEQUENCE: 279
tcgagcggcc gcccgggcag gtgtcggagt ccagcacggg aggcgtggtc ttgtagttgt 60
tctccggctg cccattgctc tcccactcca cggcgatgtc gctgggatag aagcctttga 120
ccaggcaggt caggctgacc tggttcttgg tcatctcctc ccgggatggg ggcagggtga 180
acacctgggg ttctcggggc ttgccctttg gttttgaana tggttttctc gatgggggct 240
ggaagggctt tgttgnaaac cttgcacttg actccttgcc attcacccag ncctggngca 300
ggacggngag gacnctnacc acacggaacc gggctggtgg actgctcc 348

<210> SEQ ID NO 280
<211> LENGTH: 149
<212> TYPE: DNA
<213> ORGANISM: Homo sapiens
<220> FEATURE:
<221> NAME/KEY: modified_base
<222> LOCATION: (18)
<223> OTHER INFORMATION: Where n is a, c, g or t
<221> NAME/KEY: modified_base
<222> LOCATION: (34)
<223> OTHER INFORMATION: Where n is a, c, g or t
<221> NAME/KEY: modified_base
<222> LOCATION: (51)
<223> OTHER INFORMATION: Where n is a, c, g or t
<221> NAME/KEY: modified_base
<222> LOCATION: (118)
<223> OTHER INFORMATION: Where n is a, c, g or t
<221> NAME/KEY: modified_base -continued
<222> LOCATION: (120)
<223> OTHER INFORMATION: Where n is a, c, g or t
<221> NAME/KEY: modified_base
<222> LOCATION: (140)
<223> OTHER INFORMATION: Where n is a, c, g or t

<400> SEQUENCE: 280
agcgtggtcg cggacgangt cctgtcagag tggnactggt agaagttcca ngaaccctga 60
actgtaaggg ttcttcatca gtgccaacag gatgacatga aatgatgtac tcagaagngn 120
cctggaatgg ggcccatgan atggttgcc 149

<210> SEQ ID NO 281
<211> LENGTH: 404
<212> TYPE: DNA
<213> ORGANISM: Homo sapiens
<220> FEATURE:
<221> NAME/KEY: modified_base
<222> LOCATION: (383)
<223> OTHER INFORMATION: Where n is a, c, g or t
<221> NAME/KEY: modified_base
<222> LOCATION: (386)
<223> OTHER INFORMATION: Where n is a, c, g or t
<221> NAME/KEY: modified_base
<222> LOCATION: (388)
<223> OTHER INFORMATION: Where n is a, c, g or t
<221> NAME/KEY: modified_base
<222> LOCATION: (393)
<223> OTHER INFORMATION: Where n is a, c, g or t

<400> SEQUENCE: 281
tcgagcggcc gcccgggcag gtccaccaca cccaattcct tgctggtatc atggcagccg 60
ccacgtgcca ggattaccgg ctacatcatc aagtatgaga agcctgggtc tcctcccaga 120
gaagtggtcc ctcggccccg ccctggtgtc acagaggcta ctattactgg cctggaaccg 180
ggaaccgaat atacaattta tgtcattgcc ctgaagaata atcagaagag cgagcccctg 240
attggaagga aaaagacaga cgagcttccc caactggtaa cccttccaca ccccaatctt 300
catggaccag agatcttgga tgttccttcc acagttcaaa agaccccttt cggcaccccc 360
cctgggtatg aacctgggaa aanggnantt aanctttcct ggca 404

<210> SEQ ID NO 282
<211> LENGTH: 507
<212> TYPE: DNA
<213> ORGANISM: Homo sapiens
<220> FEATURE:
<221> NAME/KEY: modified_base
<222> LOCATION: (320)
<223> OTHER INFORMATION: Where n is a, c, g or t
<221> NAME/KEY: modified_base
<222> LOCATION: (341)
<223> OTHER INFORMATION: Where n is a, c, g or t
<221> NAME/KEY: modified_base
<222> LOCATION: (424)
<223> OTHER INFORMATION: Where n is a, c, g or t
<221> NAME/KEY: modified_base
<222> LOCATION: (450)
<223> OTHER INFORMATION: Where n is a, c, g or t
<221> NAME/KEY: modified_base
<222> LOCATION: (459)
<223> OTHER INFORMATION: Where n is a, c, g or t
<221> NAME/KEY: modified_base
<222> LOCATION: (487)
<223> OTHER INFORMATION: Where n is a, c, g or t
<221> NAME/KEY: modified_base
<222> LOCATION: (498)
<223> OTHER INFORMATION: Where n is a, c, g or t

<400> SEQUENCE: 282

-continued agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agcaagccaa tttccattaa ttaccgaaca 240
gaaattgaca aaccatccca gatgcaagtg accgatgttc aggacaacag cattagtgtc 300
aagtggctgc cttcaaggtn ccctggtact gggttacaga ntaaccacca ctcccaaaaa 360
tggaccagga accacaaaaa cttaaactgc agggtccaga tcaaaacaga aatgactatt 420
gaangcttgc agcccacagt gggagtatgn gggtagtgnc tatgcttcag aatccaagcg 480
gaaaaangtc aagccttntg ggttcaa 507

<210> SEQ ID NO 283
<211> LENGTH: 325
<212> TYPE: DNA
<213> ORGANISM: Homo sapiens
<220> FEATURE:
<221> NAME/KEY: modified_base
<222> LOCATION: (216)
<223> OTHER INFORMATION: Where n is a, c, g or t
<221> NAME/KEY: modified_base
<222> LOCATION: (292)
<223> OTHER INFORMATION: Where n is a, c, g or t
<221> NAME/KEY: modified_base
<222> LOCATION: (303)
<223> OTHER INFORMATION: Where n is a, c, g or t
<221> NAME/KEY: modified_base
<222> LOCATION: (304)
<223> OTHER INFORMATION: Where n is a, c, g or t

<400> SEQUENCE: 283
tcgagcggcc gcccgggcag gtccttgcag ctctgcagtg tcttcttcac catcaggtgc 60
agggaatagc tcatggattc catcctcagg gctcgagtag gtcaccctgt acctggaaac 120
ttgcccctgt gggctttccc aagcaatttt gatggaatcg acatccacat cagtgaatgc 180
cagtccttta gggcgatcaa tgttggttac tgcagnctga accagaggct gactctctcc 240
gcttggattc tgagcataga cactaaccac atactccact gtgggctgca anccttcaat 300
aanncatttc tgtttgatct ggacc 325

<210> SEQ ID NO 284
<211> LENGTH: 331
<212> TYPE: DNA
<213> ORGANISM: Homo sapiens
<220> FEATURE:
<221> NAME/KEY: modified_base
<222> LOCATION: (54)
<223> OTHER INFORMATION: Where n is a, c, g or t
<221> NAME/KEY: modified_base
<222> LOCATION: (59)
<223> OTHER INFORMATION: Where n is a, c, g or t
<221> NAME/KEY: modified_base
<222> LOCATION: (63)
<223> OTHER INFORMATION: Where n is a, c, g or t
<221> NAME/KEY: modified_base
<222> LOCATION: (121)
<223> OTHER INFORMATION: Where n is a, c, g or t
<221> NAME/KEY: modified_base
<222> LOCATION: (312)
<223> OTHER INFORMATION: Where n is a, c, g or t
<221> NAME/KEY: modified_base
<222> LOCATION: (327)
<223> OTHER INFORMATION: Where n is a, c, g or t

<400> SEQUENCE: 284
tcgagcggcc gcccgggcag gtctggtggg gtcctggcac acgcacatgg gggngttgnt 60

-continued ctnatccagc tgcccagccc ccattggcga gtttgagaag gtgtgcagca atgacaacaa 120
naccttcgac tcttcctgcc acttctttgc cacaaagtgc accctggagg gcaccaagaa 180
gggccacaag ctccacctgg actacatcgg gccttgcaaa tacatccccc cttgcctgga 240
ctctgagctg accgaattcc cccttgcgca tgcgggactg gctcaagaac cgtcctggca 300
cccttgtatg anagggatga agacacnacc c 331

<210> SEQ ID NO 285
<211> LENGTH: 509
<212> TYPE: DNA
<213> ORGANISM: Homo sapiens
<220> FEATURE:
<221> NAME/KEY: modified_base
<222> LOCATION: (316)
<223> OTHER INFORMATION: Where n is a, c, g or t
<221> NAME/KEY: modified_base
<222> LOCATION: (319)
<223> OTHER INFORMATION: Where n is a, c, g or t
<221> NAME/KEY: modified_base
<222> LOCATION: (327)
<223> OTHER INFORMATION: Where n is a, c, g or t
<221> NAME/KEY: modified_base
<222> LOCATION: (329)
<223> OTHER INFORMATION: Where n is a, c, g or t
<221> NAME/KEY: modified_base
<222> LOCATION: (339)
<223> OTHER INFORMATION: Where n is a, c, g or t
<221> NAME/KEY: modified_base
<222> LOCATION: (344)
<223> OTHER INFORMATION: Where n is a, c, g or t
<221> NAME/KEY: modified_base
<222> LOCATION: (357)
<223> OTHER INFORMATION: Where n is a, c, g or t
<221> NAME/KEY: modified_base
<222> LOCATION: (384)
<223> OTHER INFORMATION: Where n is a, c, g or t
<221> NAME/KEY: modified_base
<222> LOCATION: (398)
<223> OTHER INFORMATION: Where n is a, c, g or t
<221> NAME/KEY: modified_base
<222> LOCATION: (427)
<223> OTHER INFORMATION: Where n is a, c, g or t
<221> NAME/KEY: modified_base
<222> LOCATION: (443)
<223> OTHER INFORMATION: Where n is a, c, g or t
<221> NAME/KEY: modified_base
<222> LOCATION: (450)
<223> OTHER INFORMATION: Where n is a, c, g or t
<221> NAME/KEY: modified_base
<222> LOCATION: (478)
<223> OTHER INFORMATION: Where n is a, c, g or t

<400> SEQUENCE: 285
agcgtggtcg cggccgaggt ctgtcctaca gtcctcagga ctctactccc tcagcagcgt 60
ggtgaccgtg ccctccagca acttcggcac ccagacctac acctgcaacg tagatcacaa 120
gcccagcaac accaaggtgg acaagagagt tgagcccaaa tcttgtgaca aaactcacac 180
atgcccaccg tgcccagcac ctgaactcct ggggggaccg tcagtcttcc tcttcccccg 240
catccccctt ccaaacctgc ccgggcggcc gctcgaaagc cgaattccag cacactggcg 300
gccggtacta gtgganccna acttggnanc caacctggng gaantaatgg gcataanctg 360
tttctggggg gaaattggta tccngtttac aattcccnca caacatacga gccggaagca 420
taaaagngta aaagcctggg ggnggcctan tgaagtgaag ctaaactcac attaattngc 480
gttgccgctc actggcccgc ttttccagc 509

<210> SEQ ID NO 286

-continued

<211> LENGTH: 336
<212> TYPE: DNA
<213> ORGANISM: Homo sapiens
<220> FEATURE:
<221> NAME/KEY: modified_base
<222> LOCATION: (188)
<223> OTHER INFORMATION: Where n is a, c, g or t
<221> NAME/KEY: modified_base
<222> LOCATION: (251)
<223> OTHER INFORMATION: Where n is a, c, g or t
<221> NAME/KEY: modified_base
<222> LOCATION: (267)
<223> OTHER INFORMATION: Where n is a, c, g or t

<400> SEQUENCE: 286
tcgagcggcc gcccgggcag gtttggaagg gggatgcggg ggaagaggaa gactgacggt 60
ccccccagga gttcaggtgc tgggcacggt gggcatgtgt gagttttgtc acaagatttg 120
ggctcaactc tcttgtccac cttggtgttg ctgggcttgt gatctacgtt gcaggtgtag 180
gtctgggngc cgaagttgct ggagggcacg gtcaccacgc tgctgaggga gtagagtcct 240
gaggactgta ngacagacct cggccgngac cacgctaagc cgaattctgc agatatccat 300
cacactggcg gccgctccga gcatgcattt tagagg 336

<210> SEQ ID NO 287
<211> LENGTH: 30
<212> TYPE: DNA
<213> ORGANISM: Homo sapiens
<220> FEATURE:
<221> NAME/KEY: modified_base
<222> LOCATION: (8)
<223> OTHER INFORMATION: Where n is a, c, g or t
<221> NAME/KEY: modified_base
<222> LOCATION: (18)
<223> OTHER INFORMATION: Where n is a, c, g or t

<400> SEQUENCE: 287
agcgtggncg cggacganga caacaacccc 30

<210> SEQ ID NO 288
<211> LENGTH: 316
<212> TYPE: DNA
<213> ORGANISM: Homo sapiens
<220> FEATURE:
<221> NAME/KEY: modified_base
<222> LOCATION: (22)
<223> OTHER INFORMATION: Where n is a, c, g or t
<221> NAME/KEY: modified_base
<222> LOCATION: (130)
<223> OTHER INFORMATION: Where n is a, c, g or t

<400> SEQUENCE: 288
tcgagcggcc gcccgggcag gnccacatcg gcagggtcgg agccctggcc gccatactcg 60
aactggaatc catcggtcat gctcttgccg aaccagacat gcctcttgtc cttggggttc 120
ttgctgatgn accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagtcagag tggcacatct tgaggtcacg gcaggtgcgg 300
gcggggttct tgacct 316

<210> SEQ ID NO 289
<211> LENGTH: 308
<212> TYPE: DNA
<213> ORGANISM: Homo sapiens
<220> FEATURE:
<221> NAME/KEY: modified_base -continued
<222> LOCATION: (36)
<223> OTHER INFORMATION: Where n is a, c, g or t
<221> NAME/KEY: modified_base
<222> LOCATION: (165)
<223> OTHER INFORMATION: Where n is a, c, g or t
<221> NAME/KEY: modified_base
<222> LOCATION: (191)
<223> OTHER INFORMATION: Where n is a, c, g or t
<221> NAME/KEY: modified_base
<222> LOCATION: (195)
<223> OTHER INFORMATION: Where n is a, c, g or t
<221> NAME/KEY: modified_base
<222> LOCATION: (218)
<223> OTHER INFORMATION: Where n is a, c, g or t
<221> NAME/KEY: modified_base
<222> LOCATION: (235)
<223> OTHER INFORMATION: Where n is a, c, g or t

<400> SEQUENCE: 289
agcgtggtcg cggccgaggt ccagcctgga gataanggtg aaggtggtgc ccccggactt 60
ccaggtatag ctggacctcg tggtagccct ggtgagagag gtgaaactgg ccctccagga 120
cctgctggtt tccctggtgc tcctggacag aatggtgaac ctggnggtaa aggagaaaga 180
ggggctccgg ntganaaagg tgaaggaggc cctcctgnat tggcaggggc cccangactt 240
agaggtggag ctggcccccc tggccccgaa ggaggaaagg gtgctgctgg tcctcctggg 300
ccacctgg 308

<210> SEQ ID NO 290
<211> LENGTH: 324
<212> TYPE: DNA
<213> ORGANISM: Homo sapiens
<220> FEATURE:
<221> NAME/KEY: modified_base
<222> LOCATION: (184)
<223> OTHER INFORMATION: Where n is a, c, g or t

<400> SEQUENCE: 290
tcgagcggcc gcccgggcag gtctgggcca ggaggaccaa taggaccagt aggacccctt 60
gggccatctt tccctgggac accatcagca cctggaccgc ctggttcacc cttgtcaccc 120
tttggaccag gacttccaag acctcctctt tctccaggca ttccttgcag accaggagta 180
ccancagcac caggtggccc aggaggacca gcagcaccct ttcctccttc gggaccaggg 240
ggaccagctc cacctctaag tcctggggcc cctgccaatc caggagggcc tccttcacct 300
ttctcacccg gagcccctct ttct 324

<210> SEQ ID NO 291
<211> LENGTH: 278
<212> TYPE: DNA
<213> ORGANISM: Homo sapiens
<220> FEATURE:
<221> NAME/KEY: modified_base
<222> LOCATION: (249)
<223> OTHER INFORMATION: Where n is a, c, g or t
<221> NAME/KEY: modified_base
<222> LOCATION: (267)
<223> OTHER INFORMATION: Where n is a, c, g or t

<400> SEQUENCE: 291
tcgagcggcc gcccgggcag gtccaccggg atattcgggg gtctggcagg aatgggaggc 60
atccagaacg agaaggagac catgcaaagc ctgaacgacc gcctggcctc ttacctggac 120
agagtgagga gcctggagac cgacaaccgg aggctggaga gcaaaatccg ggagcacttg 180
gagaagaagg gaccccaggt cagagactgg agccattact tcaagatcat cgaggacctg 240

-continued agggctcana tcttcgcaaa tactgcngac aatgcccg 278

<210> SEQ ID NO 292
<211> LENGTH: 299
<212> TYPE: DNA
<213> ORGANISM: Homo sapiens
<220> FEATURE:
<221> NAME/KEY: modified_base
<222> LOCATION: (6)
<223> OTHER INFORMATION: Where n is a, c, g or t
<221> NAME/KEY: modified_base
<222> LOCATION: (19)
<223> OTHER INFORMATION: Where n is a, c, g or t
<221> NAME/KEY: modified_base
<222> LOCATION: (25)
<223> OTHER INFORMATION: Where n is a, c, g or t
<221> NAME/KEY: modified_base
<222> LOCATION: (51)
<223> OTHER INFORMATION: Where n is a, c, g or t
<221> NAME/KEY: modified_base
<222> LOCATION: (53)
<223> OTHER INFORMATION: Where n is a, c, g or t
<221> NAME/KEY: modified_base
<222> LOCATION: (61)
<223> OTHER INFORMATION: Where n is a, c, g or t
<221> NAME/KEY: modified_base
<222> LOCATION: (63)
<223> OTHER INFORMATION: Where n is a, c, g or t
<221> NAME/KEY: modified_base
<222> LOCATION: (70)
<223> OTHER INFORMATION: Where n is a, c, g or t
<221> NAME/KEY: modified_base
<222> LOCATION: (109)
<223> OTHER INFORMATION: Where n is a, c, g or t
<221> NAME/KEY: modified_base
<222> LOCATION: (136)
<223> OTHER INFORMATION: Where n is a, c, g or t
<221> NAME/KEY: modified_base
<222> LOCATION: (157)
<223> OTHER INFORMATION: Where n is a, c, g or t
<221> NAME/KEY: modified_base
<222> LOCATION: (241)
<223> OTHER INFORMATION: Where n is a, c, g or t
<221> NAME/KEY: modified_base
<222> LOCATION: (276)
<223> OTHER INFORMATION: Where n is a, c, g or t

<400> SEQUENCE: 292
atgcgnggtc gcggccgang accanctctg gctcatactt gactctaaag ncntcaccag 60
nanttacggn cattgccaat ctgcagaacg atgcgggcat tgtccgcant atttgcgaag 120
atctgagccc tcaggncctc gatgatcttg aagtaanggc tccagtctct gacctggggt 180
cccttcttct ccaagtgctc ccggattttg ctctccagcc tccggttctc ggtctccaag 240
ncttctcact ctgtccagga aaagaggcca ggcggncgat cagggctttt gcatggact 299

<210> SEQ ID NO 293
<211> LENGTH: 101
<212> TYPE: DNA
<213> ORGANISM: Homo sapiens

<400> SEQUENCE: 293
agcgtggtcg cggccgaggt tgtacaagct tttttttttt tttttttttt tttttttttt 60
tttttttttt tttttttttt tttttttttt tttttttttt t 101

<210> SEQ ID NO 294
<211> LENGTH: 285
<212> TYPE: DNA
<213> ORGANISM: Homo sapiens
<220> FEATURE:
<221> NAME/KEY: modified_base -continued
<222> LOCATION: (64)
<223> OTHER INFORMATION: Where n is a, c, g or t
<221> NAME/KEY: modified_base
<222> LOCATION: (103)
<223> OTHER INFORMATION: Where n is a, c, g or t
<221> NAME/KEY: modified_base
<222> LOCATION: (110)
<223> OTHER INFORMATION: Where n is a, c, g or t
<221> NAME/KEY: modified_base
<222> LOCATION: (237)
<223> OTHER INFORMATION: Where n is a, c, g or t
<221> NAME/KEY: modified_base
<222> LOCATION: (282)
<223> OTHER INFORMATION: Where n is a, c, g or t

<400> SEQUENCE: 294
tcgagcggcc gcccgggcag gtctgccaac accaagattg gcccccgccg catccacaca 60
gttngtgtgc ggggaggtaa caagaaatac cgtgccctga ggntggacgn ggggaatttc 120
tcctggggct cagagtgttg tactcgtaaa acaaggatca tcgatgttgt ctacaatgca 180
tctaataacg agctggttcg taccaagacc ctggtgaaga attgcatcgt gctcatngac 240
agcacaccgt accgacagtg ggtaccgaag tcccactatg cncct 285

<210> SEQ ID NO 295
<211> LENGTH: 216
<212> TYPE: DNA
<213> ORGANISM: Homo sapiens

<400> SEQUENCE: 295
tcgagcggcc gcccgggcag gtccaccaca cccaattcct tgctggtatc atggcagccg 60
ccacgtgcca ggattaccgg ctacatcatc aagtatgaga agcctgggtc tcctcccaga 120
gaagtggtcc ctcggccccg ccctggtgtc acagaggcta ctattactgg cctggaaccg 180
ggaaccgaat atacaattta tgtcattgcc ctgaag 216

<210> SEQ ID NO 296
<211> LENGTH: 414
<212> TYPE: DNA
<213> ORGANISM: Homo sapiens
<220> FEATURE:
<221> NAME/KEY: modified_base
<222> LOCATION: (7)
<223> OTHER INFORMATION: Where n is a, c, g or t
<221> NAME/KEY: modified_base
<222> LOCATION: (10)
<223> OTHER INFORMATION: Where n is a, c, g or t
<221> NAME/KEY: modified_base
<222> LOCATION: (33)
<223> OTHER INFORMATION: Where n is a, c, g or t
<221> NAME/KEY: modified_base
<222> LOCATION: (61)
<223> OTHER INFORMATION: Where n is a, c, g or t
<221> NAME/KEY: modified_base
<222> LOCATION: (62)
<223> OTHER INFORMATION: Where n is a, c, g or t
<221> NAME/KEY: modified_base
<222> LOCATION: (63)
<223> OTHER INFORMATION: Where n is a, c, g or t
<221> NAME/KEY: modified_base
<222> LOCATION: (88)
<223> OTHER INFORMATION: Where n is a, c, g or t
<221> NAME/KEY: modified_base
<222> LOCATION: (109)
<223> OTHER INFORMATION: Where n is a, c, g or t
<221> NAME/KEY: modified_base
<222> LOCATION: (122)
<223> OTHER INFORMATION: Where n is a, c, g or t
<221> NAME/KEY: modified_base
<222> LOCATION: (255)
<223> OTHER INFORMATION: Where n is a, c, g or t -continued
<221> NAME/KEY: modified_base
<222> LOCATION: (298)
<223> OTHER INFORMATION: Where n is a, c, g or t
<221> NAME/KEY: modified_base
<222> LOCATION: (307)
<223> OTHER INFORMATION: Where n is a, c, g or t
<221> NAME/KEY: modified_base
<222> LOCATION: (340)
<223> OTHER INFORMATION: Where n is a, c, g or t
<221> NAME/KEY: modified_base
<222> LOCATION: (355)
<223> OTHER INFORMATION: Where n is a, c, g or t
<221> NAME/KEY: modified_base
<222> LOCATION: (386)
<223> OTHER INFORMATION: Where n is a, c, g or t
<221> NAME/KEY: modified_base
<222> LOCATION: (393)
<223> OTHER INFORMATION: Where n is a, c, g or t

<400> SEQUENCE: 296
agcgtgntcn cggccgagga tggggaagct cgnctgtctt tttccttcca atcaggggct 60
nnntcttctg attattcttc agggcaanga cataaattgt atattcggnt cccggttcca 120
gnccagtaat agtagcctct gtgacaccag ggcggggccg agggaccact tctctgggag 180
gagacccagg cttctcatac ttgatgatga agccggtaat cctggcacgt gggcggctgc 240
catgatacca ccaangaatt gggtgtggtg gacctgcccg ggcgggccgc tcgaaaancc 300
gaattcntgc aagaatatcc atcacacttg ggcgggccgn tcgaaccatg catcntaaaa 360
gggccccaat ttccccccta ttaggngaag ccncatttaa caaattccac ttgg 414

<210> SEQ ID NO 297
<211> LENGTH: 376
<212> TYPE: DNA
<213> ORGANISM: Homo sapiens
<220> FEATURE:
<221> NAME/KEY: modified_base
<222> LOCATION: (312)
<223> OTHER INFORMATION: Where n is a, c, g or t
<221> NAME/KEY: modified_base
<222> LOCATION: (326)
<223> OTHER INFORMATION: Where n is a, c, g or t
<221> NAME/KEY: modified_base
<222> LOCATION: (335)
<223> OTHER INFORMATION: Where n is a, c, g or t
<221> NAME/KEY: modified_base
<222> LOCATION: (361)
<223> OTHER INFORMATION: Where n is a, c, g or t

<400> SEQUENCE: 297
tcgagcggcc gcccgggcag gtctcgcggt cgcactggtg atgctggtcc tgttggtccc 60
cccggccctc ctggacctcc tggtccccct ggtcctccca gcgctggttt cgacttcagc 120
ttcctgcccc agccacctca agagaaggct cacgatggtg gccgctacta ccgggctgat 180
gatgccaatg tggttcgtga ccgtgacctc gaggtggaca ccaccctcaa gagccttgag 240
ccagcagaat cgaaaacatt cggaacccaa gaagggcaag cccgcaaaga aaccccgccc 300
gcacctggcc gngaacctcc aagaangtgc ccacntcttg actgggaaaa aaagggaaaa 360
ntacttggaa ttggac 376

<210> SEQ ID NO 298
<211> LENGTH: 357
<212> TYPE: DNA
<213> ORGANISM: Homo sapiens
<220> FEATURE:
<221> NAME/KEY: modified_base
<222> LOCATION: (345)
<223> OTHER INFORMATION: Where n is a, c, g or t -continued
<221> NAME/KEY: modified_base
<222> LOCATION: (346)
<223> OTHER INFORMATION: Where n is a, c, g or t

<400> SEQUENCE: 298
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacacgc aggtctcacc 180
agtctccatg ttgcagaaga ctttgatggc atccaggttg cagccttggt tggggtcaat 240
ccagtactct ccactcttcc agtcagaagt ggcacatctt gaggtcacgg cagggtgcgg 300
gcggggttct tgcgggctgc ccttctgggc tcccggaatg ttctnngaac ttgctgg 357

<210> SEQ ID NO 299
<211> LENGTH: 307
<212> TYPE: DNA
<213> ORGANISM: Homo sapiens
<220> FEATURE:
<221> NAME/KEY: modified_base
<222> LOCATION: (281)
<223> OTHER INFORMATION: Where n is a, c, g or t
<221> NAME/KEY: modified_base
<222> LOCATION: (285)
<223> OTHER INFORMATION: Where n is a, c, g or t
<221> NAME/KEY: modified_base
<222> LOCATION: (306)
<223> OTHER INFORMATION: Where n is a, c, g or t

<400> SEQUENCE: 299
agcgtggtcg cggccgaggt ccactagagg tctgtgtgcc attgcccagg cagagtctct 60
gcgttacaaa ctcctaggag ggcttgctgt gcggagggcc tgctatggtg tgctgcggtt 120
catcatggag agtggggcca aaggctgcga ggttgtggtg tctgggaaac tccgaggaca 180
gagggctaaa tccatgaagt ttgtggatgg cctgatgatc cacagcggag accctgttaa 240
ctactacgtt gacacttgct tgtgcgccac gtgttgctca nacangggtg ggctgggcat 300 caaggng 307

<210> SEQ ID NO 300
<211> LENGTH: 351
<212> TYPE: DNA
<213> ORGANISM: Homo sapiens

<400> SEQUENCE: 300
tcgagcggcc gcccgggcag gtctgccaag gagaccctgt tatgctgtgg ggactggctg 60
gggcatggca ggcggctctg gcttcccacc cttctgttct gagatggggg tggtgggcag 120
tatctcatct ttgggttcca caatgctcac gtggtcaggc aggggcttct tagggccaat 180
cttaccagtt gggtcccagg gcagcatgat cttcaccttg atgcccagca caccctgtct 240
gagcaacacg tggcgcacag caagtgtcaa cgtaagtaag ttaacagggt ctccgctgtg 300
gatcatcagg ccatccacaa acttcatgga tttaaccctc tgtcctcgga g 351

<210> SEQ ID NO 301
<211> LENGTH: 330
<212> TYPE: DNA
<213> ORGANISM: Homo sapiens

<400> SEQUENCE: 301
tcgagcggcc gcccgggcag gtgtttcaga ggttccaagg tccactgtgg aggtcccagg 60
agtgctggtg gtgggcacag aggtccgatg ggtgaaacca ttgacataga gactgttcct 120

-continued

```
gtccagggtg taggggccca gctctttgat gccattggcc agttggctca gctcccagta    180

cagccgctct ctgttgagtc cagggctttt ggggtcaaga tgatggatgc agatggcatc    240

cactccagtg gctgctccat ccttctcgga cctgagagag gtcagtctgc agccagagta    300

cagagggcca acactggtgt tctttgaata                                     330
```

<210> SEQ ID NO 302
<211> LENGTH: 317
<212> TYPE: DNA
<213> ORGANISM: Homo sapiens
<220> FEATURE:
<221> NAME/KEY: modified_base
<222> LOCATION: (129)
<223> OTHER INFORMATION: Where n is a, c, g or t
<221> NAME/KEY: modified_base
<222> LOCATION: (295)
<223> OTHER INFORMATION: Where n is a, c, g or t

<400> SEQUENCE: 302

```
agcgtggtcg cggccgaggt ctgtactggg agctaagcaa actgaccaat gacattgaag     60

agctgggccc ctacaccctg gacaggaaca gtctctatgt caatggtttc acccatcaga    120

gctctgtgnc caccaccagc actcctggga cctccacagt ggatttcaga acctcaggga    180

ctccatcctc cctctccagc cccacaatta tggctgctgg ccctctcctg gtaccattca    240

ccctcaactt caccatcacc aacctgcagt atggggagga catgggtcac cctgnctcca    300

ggaagttcaa caccaca                                                   317
```

<210> SEQ ID NO 303
<211> LENGTH: 283
<212> TYPE: DNA
<213> ORGANISM: Homo sapiens
<220> FEATURE:
<221> NAME/KEY: modified_base
<222> LOCATION: (139)
<223> OTHER INFORMATION: Where n is a, c, g or t
<221> NAME/KEY: modified_base
<222> LOCATION: (146)
<223> OTHER INFORMATION: Where n is a, c, g or t
<221> NAME/KEY: modified_base
<222> LOCATION: (195)
<223> OTHER INFORMATION: Where n is a, c, g or t

<400> SEQUENCE: 303

```
tcgagcggcc gcccggacag gtctgggcgg atagcaccgg gcatattttg gaatggatga     60

ggtctggcac cctgagcagt ccagcgagga cttggtctta gttgagcaat ttggctagga    120

ggatagtatg cagcacggnt ctgagnctgt gggatagctg ccatgaagta acctgaagga    180

ggtgctggct ggtangggtt gattacaggg ttgggaacag ctcgtacact tgccattctc    240

tgcatatact ggttagtgag gtgagcctgg ccctcttctt ttg                      283
```

<210> SEQ ID NO 304
<211> LENGTH: 72
<212> TYPE: DNA
<213> ORGANISM: Homo sapiens
<220> FEATURE:
<221> NAME/KEY: modified_base
<222> LOCATION: (59)
<223> OTHER INFORMATION: Where n is a, c, g or t

<400> SEQUENCE: 304

```
agcgtggtcg cggccgaggt gagccacagg tgaccggggc tgaagctggg gctgctggnc     60

ctgctggtcc tg                                                         72
```

<210> SEQ ID NO 305
<211> LENGTH: 245
<212> TYPE: DNA
<213> ORGANISM: Homo sapiens
<220> FEATURE:
<221> NAME/KEY: modified_base
<222> LOCATION: (5)
<223> OTHER INFORMATION: Where n is a, c, g or t
<221> NAME/KEY: modified_base
<222> LOCATION: (11)
<223> OTHER INFORMATION: Where n is a, c, g or t
<221> NAME/KEY: modified_base
<222> LOCATION: (22)
<223> OTHER INFORMATION: Where n is a, c, g or t
<221> NAME/KEY: modified_base
<222> LOCATION: (98)
<223> OTHER INFORMATION: Where n is a, c, g or t
<221> NAME/KEY: modified_base
<222> LOCATION: (102)
<223> OTHER INFORMATION: Where n is a, c, g or t

<400> SEQUENCE: 305
cagcngctcc nacggggcct gngggaccaa caacaccgtt ttcaccctta ggccctttgg 60
ctcctctttc tcctttagca ccaggttgac cagcagcncc ancaggacca gcaaatccat 120
tggggccagc aggaccgacc tcaccacgtt caccagggct tccccgagga ccagcaggac 180
cagcaggacc agcagcccca gcttcgcccc ggtcacctgt ggctcacctc ggccgcgacc 240
acgct 245

<210> SEQ ID NO 306
<211> LENGTH: 246
<212> TYPE: DNA
<213> ORGANISM: Homo sapiens
<220> FEATURE:
<221> NAME/KEY: modified_base
<222> LOCATION: (144)
<223> OTHER INFORMATION: Where n is a, c, g or t
<221> NAME/KEY: modified_base
<222> LOCATION: (159)
<223> OTHER INFORMATION: Where n is a, c, g or t

<400> SEQUENCE: 306
tcgagcggtc gcccgggcag gtccaccggg atagccgggg gtctggcagg aatgggaggc 60
atccagaacg agaaggagac catgcaaagc ctgaacgacc gcctggcctc ttacctggac 120
agagtgagga gcctggagac cganaaccgg aggctggana gcaaaatccg ggagcacttg 180
gagaagaagg gaccccaggt caagagactg gagccattac ttcaagatca tcgagggacc 240
tggagg 246

<210> SEQ ID NO 307
<211> LENGTH: 333
<212> TYPE: DNA
<213> ORGANISM: Homo sapiens
<220> FEATURE:
<221> NAME/KEY: modified_base
<222> LOCATION: (5)
<223> OTHER INFORMATION: Where n is a, c, g or t

<400> SEQUENCE: 307
agcgnggtcg cggccgaggt ccagctctgt ctcatacttg actctaaagt catcagcagc 60
aagacgggca ttgtcaatct gcagaacgat gcgggcattg tccgcagtat ttgcgaagat 120
ctgagccctc aggtcctcga tgatcttgaa gtaatggctc cagtctctga cctggggtcc 180
cttcttctcc aagtgctccc ggattttgct ctccagcctc cggttctcgg tctccaggct 240

-continued

```
cctcactctg tccaggtaag aaggcccagg cggtcgttca ggctttgcat ggtctccttc    300

tcgttctgga tgcctcccat tcctgccaga ccc                                 333


<210> SEQ ID NO 308
<211> LENGTH: 310
<212> TYPE: DNA
<213> ORGANISM: Homo sapiens

<400> SEQUENCE: 308

tcgagcggcc gcccgggcag gtcaggaagc acattggtct tagagccact gcctcctgga     60

ttccacctgt gctgcggaca tctccaggga gtgcagaagg gaagcaggtc aaactgctca    120

gatcagtcag actggctgtt ctcagttctc acctgagcaa ggtcagtctg cagccagagt    180

acagagggcc aacactggtg ttcttgaaca agggcttgag cagaccctgc agaaccctct    240

tccgtggtgt tgaacttcct ggaaaccagg gtgttgcatg tttttcctca taatgcaagg    300

ttggtgatgg                                                           310


<210> SEQ ID NO 309
<211> LENGTH: 429
<212> TYPE: DNA
<213> ORGANISM: Homo sapiens

<400> SEQUENCE: 309

agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacaccg caggtctcac    180

cagtctccat gttgcagaag actttgatgg catccaggtt gcagccttgg ttggggtcaa    240

tccagtactc tccactcttc cagtcagaag tgggcacatc ttgaggtcac cggcaggtgc    300

cgggccgggg gttcttgcgg cttgccctct gggctccgga tgttctcgat ctgcttggct    360

caggctcttg agggtgggtg tccacctcga ggtcacggtc accgaaacct gcccgggcgg    420

cccgctcga                                                            429


<210> SEQ ID NO 310
<211> LENGTH: 430
<212> TYPE: DNA
<213> ORGANISM: Homo sapiens
<220> FEATURE:
<221> NAME/KEY: modified_base
<222> LOCATION: (342)
<223> OTHER INFORMATION: Where n is a, c, g or t

<400> SEQUENCE: 310

tcgagcggtc gcccgggcag gtttcgtgac cgtgacctcg aggtggacac caccctcaag     60

agcctgagcc agcagatcga gaacatccgg agcccagagg gcagccgcaa gaaccccgcc    120

cgcacctgcc gtgacctcaa gatgtgccac tctgactgga agagtggaga gtactggatt    180

gaccccaacc aaggctgcaa cctggatgcc atcaaagtct tctgcaacat ggagactggt    240

gagacctgcg tgtaccccac tcagcccagt gtgggcccag aagaaactgg tacatcagca    300

aggaacccca aggacaagag gcattgtctt ggttcggcga gnagcatgac ccgatggatt    360

ccagtttcga gtattggcgg ccagggcttc ccgacccttg ccgatgtgga cctcggccgc    420

gaccaccgct                                                           430
```

COMPOSITIONS AND METHODS FOR THERAPY OF OVARIAN CANCER

TECHNICAL FIELD

The present invention relates generally to ovarian cancer therapy. The invention is more specifically related to polypeptides comprising at least a portion of an ovarian carcinoma protein, and to polynucleotides encoding such polypeptides, as well as antibodies and immune system cells that specifically recognize such polypeptides. Such polypeptides, polynucleotides antibodies and cells may be used in vaccines and pharmaceutical compositions for treatment of ovarian cancer.

BACKGROUND OF THE INVENTION

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

Immunotherapies have the potential to substantially improve cancer treatment and survival. Such therapies may involve the generation or enhancement of an immune response to an ovarian carcinoma antigen. However, to date, relatively few ovarian carcinoma antigens are known and the generation of an immune response against such antigens has not been shown to be therapeutically beneficial.

Accordingly, there is a need in the art for improved methods for identifying ovarian tumor antigens and for using such antigens in the therapy of ovarian cancer. The present invention fulfills these needs and further provides other related advantages.

SUMMARY OF THE INVENTION

Briefly stated, this invention provides compositions and methods for the therapy of cancer, such as ovarian cancer. In one aspect, the present invention provides polypeptides comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished. Within certain embodiments, the polypeptide comprises a sequence that is encoded by a polynucleotide sequence selected from the group consisting of SEQ ID NOs:1–81, and complements of such polynucleotides.

The present invention further provides polynucleotides that encode a polypeptide as described above or a portion thereof, expression vectors comprising such polynucleotides and host cells transformed or transfected with such expression vectors.

Within other aspects, the present invention provides pharmaceutical compositions and vaccines. Pharmaceutical compositions may comprise a physiologically acceptable carrier or excipient in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein- specific antisera is not substantially diminished, wherein the ovarian carcinoma protein comprises an amino acid sequence encoded by a polynucleotide that comprises a sequence recited in any one of SEQ ID NOs: 1–81; (ii) a polynucleotide encoding such a polypeptide; (iii) an antibody that specifically binds to such a polypeptide; (iv) an antigen-presenting cell that expresses such a polypeptide and/or (v) a T cell that specifically reacts with such a polypeptide. Vaccines may comprise a non-specific immune response enhancer in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs: 1–81, (ii) a polynucleotide encoding such a polypeptide; (iii) an anti-idiotypic antibody that is specifically bound by an antibody that specifically binds to such a polypeptide; (iv) an antigen-presenting cell that expresses such a polypeptide and/or (v) a T cell that specifically reacts with such a polypeptide.

The present invention further provides, in other aspects, fusion proteins that comprise at least one polypeptide as described above, as well as polynucleotides encoding such fusion proteins.

Within related aspects, pharmaceutical compositions comprising a fusion protein or polynucleotide encoding a fusion protein in combination with a physiologically acceptable carrier are provided.

Vaccines are further provided, within other aspects, comprising a fusion protein or polynucleotide encoding a fusion protein in combination with a non-specific immune response enhancer.

Within further aspects, the present invention provides methods for inhibiting the development of a cancer in a patient, comprising administering to a patient a pharmaceutical composition or vaccine as recited above.

The present invention further provides, within other aspects, methods for stimulating and/or expanding T cells, comprising contacting T cells with (a) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs: 1–310; (b) a polynucleotide encoding such a polypeptide and/or (c) an antigen presenting cell that expresses such a polypeptide under conditions and for a time sufficient to permit the stimulation and/or expansion of T cells. Such polypeptide, polynucleotide and/or antigen presenting cell(s) may be present within a pharmaceutical composition or vaccine, for use in stimulating and/or expanding T cells in a mammal.

Within other aspects, the present invention provides methods for inhibiting the development of ovarian cancer in a patient, comprising administering to a patient T cells prepared as described above.

Within further aspects, the present invention provides methods for inhibiting the development of ovarian cancer in a patient, comprising the steps of: (a) incubating $CD4^+$ and/or $CD8^+$ T cells isolated from a patient with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs: 1–310; (ii) a polynucleotide encoding such a polypeptide; or (iii) an antigen-presenting cell that expresses such a polypeptide; such that T cells proliferate; and (b) administering to the patient an effective amount of the proliferated T cells, and thereby inhibiting the development of ovarian cancer in the patient. The proliferated cells may be cloned prior to administration to the patient.

The present invention also provides, within other aspects, methods for identifying secreted tumor antigens. Such methods comprise the steps of: (a) implanting tumor cells in an immunodeficient mammal; (b) obtaining serum from the immunodeficient mammal after a time sufficient to permit secretion of tumor antigens into the serum; (c) immunizing an immunocompetent mammal with the serum; (d) obtaining antiserum from the immunocompetent mammal; and (e) screening a tumor expression library with the antiserum, and therefrom identifying a secreted tumor antigen. A preferred method for identifying a secreted ovarian carcinoma antigen comprises the steps of: (a) implanting ovarian carcinoma cells in a SCID mouse; (b) obtaining serum from the SCID mouse after a time sufficient to permit secretion of ovarian carcinoma antigens into the serum; (c) immunizing an immunocompetent mouse with the serum; (d) obtaining antiserum from the immunocompetent mouse; and (e) screening an ovarian carcinoma expression library with the antiserum, and therefrom identifying a secreted ovarian carcinoma antigen.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1A–1S (SEQ ID NOs:1–71) depict partial sequences of polynucleotides encoding representative secreted ovarian carcinoma antigens.

FIGS. 2A–2C depict full insert sequences for three of the clones of FIG. 1. FIG. 2A shows the sequence designated O7E (11731; SEQ ID NO:72), FIG. 2B shows the sequence designated O9E (11785; SEQ ID NO:73) and FIG. 2C shows the sequence designated O8E (13695; SEQ ID NO:74).

FIG. 3 presents results of microarray expression analysis of the ovarian carcinoma sequence designated O8E.

FIG. 4 presents a partial sequence of a polynucleotide (designated 3g; SEQ ID NO:75) encoding an ovarian carcinoma sequence that is a splice fusion between the human T-cell leukemia virus type I oncoprotein TAX and osteonectin.

FIG. 5 presents the ovarian carcinoma polynucleotide designated 3f (SEQ ID NO:76).

FIG. 6 presents the ovarian carcinoma polynucleotide designated 6b (SEQ ID NO:77).

FIGS. 7A and 7B present the ovarian carcinoma polynucleotides designated 8e (SEQ ID NO:78) and 8h (SEQ ID NO:79).

FIG. 8 presents the ovarian carcinoma polynucleotide designated 12c (SEQ ID NO:80).

FIG. 9 presents the ovarian carcinoma polynucleotide designated 12h (SEQ ID NO:81).

FIG. 10 depicts results of microarray expression analysis of the ovarian carcinoma sequence designated 3f.

FIG. 11 depicts results of microarray expression analysis of the ovarian carcinoma sequence designated 6b.

FIG. 12 depicts results of microarray expression analysis of the ovarian carcinoma sequence designated 8e.

FIG. 13 depicts results of microarray expression analysis of the ovarian carcinoma sequence designated 12c.

FIG. 14 depicts results of microarray expression analysis of the ovarian carcinoma sequence designated 1 2h.

FIGS. 15A–15EEE depict partial sequences of additional polynucleotides encoding representative secreted ovarian carcinoma antigens (SEQ ID NOs:82–310).

DETAILED DESCRIPTION OF THE INVENTION

As noted above, the present invention is generally directed to compositions and methods for the therapy of cancer, such as ovarian cancer. The compositions described herein may include immunogenic polypeptides, nucleic acid sequences encoding such polypeptides, binding agents such as antibodies that bind to a polypeptide and/or immune system cells (e.g., T cells).

Polypeptides of the present invention generally comprise at least an immunogenic portion of an ovarian carcinoma protein or a variant thereof. Certain ovarian carcinoma proteins have been identified using an immunoassay technique, and are referred to herein as ovarian carcinoma antigens. An "ovarian carcinoma antigen" is a protein that is expressed by ovarian tumor cells (preferably human cells) and that reacts detectably (within an immunoassay, such as an ELISA or Western blot) with antisera generated against serum from an immunodeficient animal implanted with a human ovarian tumor. Such ovarian carcinoma antigens are shed or secreted from an ovarian tumor into the sera of the immunodeficient animal. Accordingly, ovarian carcinoma antigens provided herein are generally secreted antigens. Certain nucleic acid sequences of the subject invention generally comprise a DNA or RNA sequence that encodes all or a portion of such a polypeptide, or that is complementary to such a sequence.

The present invention further provides ovarian carcinoma sequences that are identified using techniques to evaluate altered expression within an ovarian tumor. Such sequences may be polynucleotide or protein sequences. Ovarian carcinoma sequences are generally expressed in an ovarian tumor at a level that is at least two fold, and preferably at least five fold, greater than the level of expression in normal ovarian tissue, as determined using a representative assay provided herein. Certain ovarian carcinoma partial polynucleotide sequences are presented in FIGS. 4–9 as well as SEQ ID NOs:75–81. Proteins encoded by genes comprising such polynucleotide sequences (or complements thereof) are also considered ovarian carcinoma proteins.

Antibodies are generally immune system proteins, or antigen-binding fragments thereof, that are capable of binding to a portion of a polypeptide as described above. T cells that may be employed within such compositions are generally T cells (e.g., $CD4^+$ and/or $CD8^+$) that are specific for a polypeptide as described above. Certain methods described herein further employ antigen-presenting cells that express an ovarian carcinoma polypeptide as provided herein.

Ovarian Carcinoma Polynucleotides

Any polynucleotide that encodes an ovarian carcinoma protein or a portion or other variant thereof as described herein is encompassed by the present invention. Preferred polynucleotides comprise at least 15 consecutive nucleotides, and preferably at least 30 consecutive nucleotides, that encode a portion of an ovarian carcinoma protein. More preferably, a polynucleotide encodes an immunogenic portion of an ovarian carcinoma protein, such as an ovarian carcinoma antigen. Polynucleotides complementary to any such sequences are also encompassed by the present invention. Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an ovarian carcinoma protein or a portion thereof) or may comprise a variant of such a sequence. Polynucleotide variants may contain one or more substitutions, additions, deletions and/or insertions such that the immunogenicity of the encoded polypeptide is not diminished, relative to a native ovarian carcinoma protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native ovarian carcinoma protein or a portion thereof. The percent identity may be readily determined by comparing sequences using computer algorithms well known to those of ordinary skill in the art, such as Megalign, using default parameters. Certain variants are substantially homologous to a native gene, or a portion or complement thereof. Such polynucleotide variants are capable of hybridizing under moderately stringent conditions to a naturally occurring DNA sequence encoding a native ovarian carcinoma sequence (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS).

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention.

Polynucleotides may be prepared using any of a variety of techniques. For example, an ovarian carcinoma polynucleotide may be identified, as described in more detail below, by screening a late passage ovarian tumor expression library with antisera generated against sera of immunocompetent mice after injection of such mice with sera from SCID mice implanted with late passage ovarian tumors. Ovarian carcinoma polynucleotides may also be identified using any of a variety of techniques designed to evaluate differential gene expression. Alternatively, polypeptides may be amplified from cDNA prepared from ovarian tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., an ovarian carcinoma cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning. A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nuci. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of ovarian carcinoma antigens are provided in FIGS. 1A . 1S (SEQ ID NOS:1 to 71) and FIGS. 15A to 15EEE (SEQ ID NOs:82 to 310). These polynucleotides were isolated by serological screening of an ovarian tumor cDNA expression library, using a technique designed to identify secreted tumor antigens. Briefly, a late passage ovarian tumor expression library was prepared from a SCID-derived human ovarian tumor (OV9334) in the vector λ-screen (Novagen). The sera used for screening were obtained by injecting immunocompetent mice with sera from SCID mice implanted with one late passage ovarian tumors. This technique permits the identification of cDNA molecules that encode immunogenic portions of secreted tumor antigens. The polynucleotides recited herein, as well as full length polynucleotides comprising such sequences, other portions of such full length polynucleotides, and sequences complementary to all or a portion of such full length molecules, are specifically encompassed by the present invention. It will be apparent to those of ordinary skill in the art that this technique can also be applied to the identification of antigens that are secreted from other types of tumors.

The sequences provided in FIGS. 1A–1S appear to be novel. For sequences in FIGS. 15A–15EEE, database searches revealed matches having substantial identity.

Other nucleic acid sequences of cDNA molecules encoding portions of ovarian carcinoma proteins are provided in FIGS. 4–9 (SEQ ID NOs:75–81). These sequences were identified by screening a microarray of cDNAs for tumor-associated expression (i.e., expression that is at least five fold greater in an ovarian tumor than in normal ovarian tissue, as determined using a representative assay provided herein). Such screens were performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997).

Any of a variety of well known techniques may be used to evaluate tumor-associated expression of a cDNA. For example, hybridization techniques using labeled polynucleotide probes may be employed. Alternatively, or in addition, amplification techniques such as real-time PCR may be used (see Gibson et al., *Genome Research* 6:995–1001, 1996; Heid et al., *Genome Research* 6:986–994, 1996). Real-time PCR is a technique that evaluates the level of PCR product accumulation during amplification. This technique permits quantitative evaluation of mRNA levels in multiple samples. Briefly, mRNA is extracted from tumor and normal tissue and cDNA is prepared using standard techniques. Real-time PCR may be performed, for example, using a Perkin Elmer/Applied Biosystems (Foster City, Calif.) 7700 Prism instrument. Matching primers and fluorescent probes may be designed for genes of interest using, for example, the primer express program provided by Perkin Elmer/Applied Biosystems (Foster City, Calif.). Optimal concentrations of primers and probes may be initially determined by those of ordinary skill in the art, and control (e.g., β-actin) primers and probes may be obtained commercially from, for example, Perkin Elmer/Applied Biosystems (Foster City, Calif.). To quantitate the amount of specific RNA in a sample, a standard curve is generated alongside using a plasmid containing the gene of interest. Standard curves may be generated using the Ct values determined in the real-time PCR, which are related to the initial cDNA concentration used in the assay. Standard dilutions ranging from $10$–$10^6$ copies of the gene of interest are generally sufficient. In addition, a standard curve is generated for the control sequence. This permits standardization of initial RNA content of a tissue sample to the amount of control for comparison purposes.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding an ovarian carcinoma antigen, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo.

A portion of a sequence complementary to a coding sequence (i.e., an antisense polynucleotide) may also be used as a probe or to modulate gene expression. cDNA constructs that can be transcribed into antisense RNA may also be introduced into cells or tissues to facilitate the production of antisense RNA. An antisense polynucleotide may be used, as described herein, to inhibit expression of an ovarian carcinoma protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994). Alternatively, an antisense molecule may be designed to hybridize with a control region of a gene (e.g., promoter, enhancer or transcription initiation site), and block transcription of the gene; or to block translation by inhibiting binding of a transcript to ribosomes.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g, avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Ovarian Carcinoma Polypeptides

Within the context of the present invention, polypeptides may comprise at least an immunogenic portion of an ovarian carcinoma protein or a variant thereof, as described herein. As noted above, certain ovarian carcinoma proteins are ovarian carcinoma antigens that are expressed by ovarian tumor cells and react detectably within an immunoassay (such as an ELISA) with antisera generated against serum from an immunodeficient animal implanted with an ovarian tumor. Other ovarian carcinoma proteins are encoded by ovarian carcinoma polynucleotides recited herein. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of an antigen that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of an ovarian carcinoma protein or a variant thereof. Preferred immunogenic portions are encoded by cDNA molecules isolated as described herein. Further immunogenic portions may generally be identified using well known techniques, such as those summarized in Paul, *Fundamental Immunology,* 3rd ed., 243–247 (Raven Press, 1993) and references cited therein. Such techniques include screening polypeptides for the ability to react with ovarian carcinoma protein-specific antibodies, antisera and/or T-cell lines or clones. As used herein, antisera and antibodies are "ovarian carcinoma protein-specific" if they specifically bind to an ovarian carcinoma protein (i.e., they react with the ovarian carcinoma protein in an ELISA or other immunoassay, and do not react detectably with unrelated proteins). Such antisera, antibodies and T cells may be prepared as described herein, and using well known techniques. An immunogenic portion of a native ovarian carcinoma protein is a portion that reacts with such antisera, antibodies and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length protein. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native ovarian carcinoma protein. A polypeptide "variant," as used herein, is a polypeptide that differs from a native ovarian carcinoma protein in one or more substitutions, deletions, additions and/or insertions, such that the immunogenicity of the polypeptide is not substantially diminished. In other words, the ability of a variant to react with ovarian carcinoma protein-specific antisera may be enhanced or unchanged, relative to the native ovarian carcinoma protein, or may be diminished by less than 50%, and preferably less than 20%, relative to the native ovarian carcinoma protein. Such variants may generally be identified by modifying one of the above polypeptide sequences and evaluating the reactivity of the modified polypeptide with ovarian carcinoma protein-specific antibodies or antisera as described herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is Lcommercially available from suppliers such as Applied BioSystems, Inc. (Foster City, Calif.), and may be operated according to the manufacturer's instructions.

Within certain specific embodiments, a polypeptide may be a fusion protein that comprises multiple polypeptides as described herein, or that comprises one polypeptide as described herein and a known tumor antigen, such as an ovarian carcinoma protein or a variant of such a protein. Fusion proteins may generally be prepared using standard techniques. For example, a fusion protein may be prepared recombinantly. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad Sci*. USA 83:8258–8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86–91, 1997).

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to an ovarian carcinoma protein. As used herein, an antibody, or antigen-binding fragment thereof, is said to "specifically bind" to an ovarian carcinoma protein if it reacts at a detectable level (within, for example, an ELISA) with an ovarian carcinoma protein, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant maybe determined using methods well known in the art.

Any agent that satisfies the above requirements may be a binding agent. For example, a binding agent may be a ribosome, with or without a peptide component, and RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of manuals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies. A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.). by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g, U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Also provided herein are anti-idiotypic antibodies that mimic an immunogenic portion of an ovarian carcinoma protein. Such antibodies may be raised against an antibody, or antigen-binding fragment thereof, that specifically binds to an immunogenic portion of an ovarian carcinoma protein, using well known techniques. Anti-idiotypic antibodies that mimic an immunogenic portion of an ovarian carcinoma protein are those antibodies that bind to an antibody, or antigen-binding fragment thereof, that specifically binds to an immunogenic portion of an ovarian carcinoma protein, as described herein.

T Cells

Immunotherapeutic compositions may also, or alternatively, comprise T cells specific for an ovarian carcinoma protein. Such cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system, such as the CEPRATE™ system, available from CellPro Inc., Bothell Wash. (see also U.S. Pat. Nos. 5,240,856; 5,215,926; WO 89/06280; WO 91/16116 and WO 92/07243). Alternatively, T cells may be derived from related or unrelated humans, non-human animals, cell lines or cultures.

T cells may be stimulated with an ovarian carcinoma polypeptide, polynucleotide encoding an ovarian carcinoma polypeptide and/or an antigen presenting cell (APC) that expresses such a polypeptide. Such stimulation is performed under conditions and for a time sufficient to permit the generation of T cells that are specific for the polypeptide. Preferably, an ovarian carcinoma polypeptide or polynucleotide is present within a delivery vehicle, such as a microsphere, to facilitate the generation of specific T cells.

T cells are considered to be specific for an ovarian carcinoma polypeptide if the T cells kill target cells coated with an ovarian carcinoma polypeptide or expressing a gene encoding such a polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with an ovarian carcinoma polypeptide (200 ng/ml–100 $\mu$g/ml, preferably 100 ng/ml–25 $\mu$g/ml) for 3–7 days should result in at least a two fold increase in proliferation of the T cells and/or contact as described above for 2–3 hours should result in activation of the T cells, as measured using standard cytokine assays in which a two fold increase in the level of cytokine release (e.g., TNF or IFN-$\gamma$) is indicative of T cell activation (see Coligan et al., Current Protocols in Immunology, vol. 1, Wiley Interscience (Greene 1998). T cells that have been activated in response to an ovarian carcinoma polypeptide, polynucleotide or ovarian carcinoma polypeptide-expressing APC may be $CD4^-$ and/or $CD8^+$. Ovarian carcinoma polypeptide-specific T cells may be expanded using standard techniques. Within preferred embodiments, the T cells are derived from a patient or a related or unrelated donor and are administered to the patient following stimulation and expansion.

For therapeutic purposes, $CD4^+$ or $CD8^+$ T cells that proliferate in response to an ovarian carcinoma polypeptide, polynucleotide or APC can be expanded in number either in vitro or in vivo. Proliferation of such T cells in vitro may be accomplished in a variety of ways. For example, the T cells can be re-exposed to an ovarian carcinoma polypeptide, with or without the addition of T cell growth factors, such as interleukin-2, and/or stimulator cells that synthesize an ovarian carcinoma polypeptide. Alternatively, one or more T cells that proliferate in the presence of an ovarian carcinoma polypeptide can be expanded in number by cloning. Methods for cloning cells are well known in the art, and include limiting dilution.

Pharmaceutical Compositions and Vaccines

Within certain aspects, polypeptides, polynucleotides, binding agents and/or immune system cells as described herein may be incorporated into pharmaceutical compositions or vaccines. Pharmaceutical compositions comprise one or more such compounds or cells and a physiologically acceptable carrier. Vaccines may comprise one or more such compounds or cells and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Cancer Therapy

In further aspects of the present invention, the compositions described herein may be used for immunotherapy of cancer, such as ovarian cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. Within certain preferred embodiments, a patient is afflicted with ovarian cancer. Such cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immuno response-modifying agents (such as tumor vaccines, bacterial adjuvants and/or cytokines).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T lymphocytes (such as $CD8^-$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

The polypeptides provided herein may also be used to generate and/or isolate tumor-reactive T cells, which can then be administered to a patient. In one such technique, antigen-specific T cell lines may be generated by in vivo immunization with short peptides corresponding to immunogenic portions of the disclosed polypeptides. The resulting antigen-specific $CD8^+$ CTL clones may be isolated from the patient, expanded using standard tissue culture techniques and returned to the patient.

Polypeptides may also be used for ex vivo treatment of a cancer, such as ovanan cancer. For example, cells of the immune system, such as T cells, may be isolated from the peripheral blood of a patient, using a commercially available cell separation system, such as CellPro Incorporated's (Bothell, Wash.) CEPRATE™ system (see U.S. Pat. Nos. 5,240,856; 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is them expanded using standard techniques and the cells may be administered back to the patient as described, for example, by Chang et al., *Crit. Rev. Oncol. Hematol.* 22:213, 1996.

Within another embodiment, syngeneic or autologous dendritic-cells may be pulsed with peptides corresponding to at least an immunogenic portion of a polypeptide disclosed herein. The resulting antigen-specific dendritic cells may either be transferred into a patient or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al., *Immunological Reviews* 157:177, 1997.

Alternatively, a vector expressing a polypeptide recited herein may be introduced into stem cells taken from a patient and clonally propagated in vitro for autologous transplant back into the same patient.

Routes and frequency of administration, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration), orally or in the bed of a resected tumor. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to an ovarian carcinoma antigen generally correlate with an improved clinical outcome. Such immune responses may generally be evaluated using standard proliferation, cytotoxicity or cytokine assays, which may be performed using samples obtained from a patient before and after treatment.

Screens for Identifying Secreted Ovarian Carcinoma Antigens

The present invention provides methods for identifying secreted tumor antigens. Within such methods, tumors are implanted into immunodeficient animals such as SCID mice and maintained for a time sufficient to permit secretion of tumor antigens into serum. In general, tumors may be implanted subcutaneously or within the gonadal fat pad of an immunodeficient animal and maintained for 1–9 months, preferably 1–4 months. Implantation may generally be performed as described in WO 97/18300. The serum containing secreted antigens is then used to prepare antisera in immunocompetent mice, using standard techniques and as described herein. Briefly, 50–100 $\mu$L of sera (pooled from three sets of immunodeficient mice, each set bearing a different SCID-derived human ovarian tumor) may be mixed 1:1 (vol:vol) with an appropriate adjuvant, such as RIBI-MPL or MPL+TDM (Sigma Chemical Co., St. Louis, Mo.) and injected intraperitoneally into syngeneic immunocompetent animals at monthly intervals for a total of 5 months. Antisera from animals immunized in such a manner may be obtained by drawing blood after the third, fourth and fifth immunizations. The resulting antiserum is generally precleared of *E. coli* and phage antigens and used (generally following dilution, such as 1:200) in a serological expression screen.

The library is typically an expression library containing cDNAs from one or more tumors of the type that was implanted into SCID mice. This expression library may be prepared in any suitable vector, such as λ-screen (Novagen). cDNAs that encode a polypeptide that reacts with the antiserum may be identified using standard techniques, and sequenced. Such cDNA molecules may be further characterized to evaluate expression in tumor and normal tissue, and to evaluate antigen secretion in patients.

The methods provided herein have advantages over other methods for tumor antigen discovery. In particular, all antigens identified by such methods should be secreted or released through necrosis of the tumor cells. Such antigens may be present on the surface of tumor cells for an amount of time sufficient to permit targeting and killing by the immune system, following vaccination.

The following Examples are offered by way of illustration and not by way of limitation.

EXAMPLES

Example 1

Identification of Representative Ovarian Carcinoma Antigen cDNAs

This Example illustrates the identification of cDNA molecules encoding ovarian carcinoma antigens.

Anti-SCID mouse sera (generated against sera from SCID mice carrying late passage ovarian carcinoma) was precleared of *E. coli* and phage antigens and used at a 1:200 dilution in a serological expression screen. The library screened was made from a SCID-derived human ovarian tumor (OV9334) using a directional RH oligo(dT) priming cDNA library construction kit and the λScreen vector (Novagen). A bacteriophage lambda screen was employed. Approximately 400,000 pfu of the amplified OV9334 library were screened.

196 positive clones were isolated. Certain sequences-that appear to be novel are provided in FIGS. 1A–1S and SEQ ID NOs:1 to 71. Three complete insert sequences are shown in FIGS. 2A–2C (SEQ ID NOs:72 to 74). Other clones having known sequences are presented in FIGS. 15A–15EEE (SEQ ID NOs:82 to 310). Database searches identified the following sequences that were substantially identical to the sequences presented in FIGS. 15A–15EEE.

These clones were further characterized using microarray technology to determine mRNA expression levels in a variety of tumor and normal tissues. Such analyses were performed using a Synteni (Palo Alto, Calif.) microarray, according to the manufacturer's instructions. PCR amplification products were arrayed on slides, with each product occupying a unique location in the array. mRNA was extracted from the tissue sample to be tested, reverse transcribed and fluorescent-labeled cDNA probes were generated. The microarrays were probed with the labeled cDNA probes and the slides were scanned to measure fluorescence intensity. Data was analyzed using Synteni's provided GEMtools software. The results for one clone (13695, also referred to as O8E) are shown in FIG. 3.

Example 2

Identification of Ovarian Carcinoma cDNAs using Microarray Technology

This Example illustrates the identification of ovarian carcinoma polynucleotides by screening a microarray of cDNAs for ovarian tumor-specific expression. Such screens were performed using a Synteni (Palo Alto, Calif.) microarray, according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997).

cDNA was generated from ovarian tumor tissue and from normal ovarian tissue, and a subtracted cDNA library was prepared and arrayed on the chip. The chip was then probed with fluorescent probes generated from normal and tumor cDNA. The slides were scanned and the fluorescence intensity was measured, and the data were analyzed using Synteni's GEMtools software. In general, sequences showing at least a 5-fold increase in expression in tumor cells (relative to normal cells) were considered ovarian tumor antigens.

Using such assays, an ovarian tumor antigen was identified that is a splice fusion between the human T-cell leukemia virus type I oncoprotein TAX (see Jin et al., *Cell* 93:81–91, 1998) and an extracellular matrix protein called osteonectin. A splice junction sequence exists at the fusion point. The sequence of this clone is presented in FIG. 4 and SEQ ID NO:75. Osteonectin, unspliced and unaltered, was also identified from such assays independently.

Further clones identified by this methods are referred to herein as 3f, 6b, 8e, 8h, 12c and 12h. Sequences of these clones are shown in FIGS. 5 to 9 and SEQ ID NOs:76 to 81. Microarray analyses were performed as described above, and are presented in FIGS. 10 to 14.

From the foregoing it will be appreciated that, although specific embodiments of the invention have been described herein for purposes of illustration, various modifications may be made without deviating from the spirit and scope of the invention. Accordingly, the invention is not limited except as by the appended claims.

SUMMARY OF SEQUENCE LISTING

SEQ ID NOs:1–71 are ovarian carcinoma antigen polynucleotides shown in FIGS. 1A–1S.

SEQ ID NOs:72–74 are ovarian carcinoma antigen polynucleotides shown in FIGS. 2A–2C.

SEQ ID NO:75 is the ovarian carcinoma polynucleotide 3g (FIG. 4).

SEQ ID NO:76 is the ovarian carcinoma polynucleotide 3f (FIG. 5).

SEQ ID NO:77 is the ovarian carcinoma polynucleotide 6b (FIG. 6).

SEQ ID NO:78 is the ovarian carcinoma polynucleotide 8e (FIG. 7A).

SEQ ID NO:79 is the ovarian carcinoma polynucleotide 8h (FIG. 7B).

SEQ ID NO:80 is the ovarian carcinoma polynucleotide 2e (FIG. 8).

SEQ ID NO:81 is the ovarian carcinoma polynucleotide 12h (FIG. 9).

SEQ ID NOs:82–310 are ovarian carcinoma antigen polynucleotides shown in FIGS. 15A–15EEE.

What is claimed is:

1. An isolated polynucleotide comprising a sequence selected from the group consisting of SEQ ID NO:76, 77, 78, and 81.

2. An isolated polynucleotide consisting of a sequence selected from the group consisting of SEQ ID NO: 76, 77, 78, and 81.

3. An isolated polynucleotide useful in the detection of ovarian cancer comprising at least 30 contiguous nucleotide residues of SEQ ID NO:77.

4. An isolated polynucleotide useful in the detection of ovarian cancer consisting of at least 30 and not more than 361 contiguous nucleotide residues of SEQ ID NO:77.

5. An isolated polynucleotide fully complementary to a polynucleotide according to any one of claims 1, 2, 3, and 4.

6. A vector comprising a polynucleotide according to any one of claims 1, 2, 3, and 4.

7. An isolated host cell comprising a vector according to claim 6.

8. An isolated polynucleotide comprising SEQ ID NO: 74.

9. An isolated polynucleotide consisting SEQ ID NO: 74.

10. An isolated polynucleotide fully complementary to a polynucleotide according to any one of claims 8 and 9.

11. A vector comprising a polynucleotide according to any one of claims 8 and 9.

12. An isolated host cell comprising a vector according to claim 11.

* * * * *